US007501491B2

(12) United States Patent
Wild et al.

(10) Patent No.: US 7,501,491 B2
(45) Date of Patent: Mar. 10, 2009

(54) RECOMBINANT INFECTIOUS LARYNGOTRACHEITIS VIRUS AND USES THEREOF

(75) Inventors: Martha A. Wild, San Diego, CA (US); Mark D. Cochran, Carlsbad, CA (US)

(73) Assignee: Schering-Plough Animal Health Corp., Summit, NJ (US)

( * ) Notice: Subject to any disclaimer, the term of this patent is extended or adjusted under 35 U.S.C. 154(b) by 0 days.

(21) Appl. No.: 12/047,787

(22) Filed: Mar. 13, 2008

(65) Prior Publication Data

US 2008/0175859 A1  Jul. 24, 2008

Related U.S. Application Data

(60) Division of application No. 11/342,171, filed on Jan. 27, 2006, now Pat. No. 7,364,893, which is a division of application No. 10/836,383, filed on Apr. 30, 2004, now Pat. No. 7,045,598, which is a division of application No. 09/994,064, filed on Nov. 6, 2001, now Pat. No. 6,984,728, which is a division of application No. 08/468,190, filed on Jun. 6, 1995, now abandoned, which is a continuation of application No. 08/410,121, filed on Mar. 23, 1995, now abandoned, which is a continuation-in-part of application No. 08/126,597, filed on Sep. 24, 1993, now abandoned.

(51) Int. Cl.
*C07K 14/00* (2006.01)
*C07K 14/03* (2006.01)
*A61K 39/00* (2006.01)
*A61K 39/12* (2006.01)
*A61K 39/245* (2006.01)
*C12P 21/00* (2006.01)
*C12N 15/09* (2006.01)
*C12N 15/38* (2006.01)

(52) U.S. Cl. ............... 530/350; 424/184.1; 424/185.1; 424/186.1; 424/229.1; 435/69.1; 435/69.3

(58) Field of Classification Search .................. None
See application file for complete search history.

(56) References Cited

U.S. PATENT DOCUMENTS

| 4,769,331 | A | 9/1988 | Roizman et al. |
|---|---|---|---|
| 4,877,737 | A | 10/1989 | Shih |
| 4,980,162 | A | 12/1990 | Honda et al. |
| 5,047,237 | A | 9/1991 | Cochran et al. |
| 5,182,210 | A | 1/1993 | Binns et al. |
| 5,187,087 | A | 2/1993 | Sondermeijer et al. |
| 5,223,424 | A | 6/1993 | Cochran et al. |
| 5,231,023 | A | 7/1993 | Morgan |
| 5,240,703 | A | 8/1993 | Cochran et al. |
| 5,252,717 | A | 10/1993 | Velicer |
| 5,279,965 | A | 1/1994 | Keeler, Jr. |
| 5,310,671 | A | 5/1994 | Binns et al. |
| 5,869,312 | A | 2/1999 | Cochran et al. |
| 5,906,821 | A | 5/1999 | Griffin et al. |
| 5,928,648 | A | 7/1999 | Cochran |
| 5,965,138 | A * | 10/1999 | Cochran et al. .......... 424/199.1 |
| 6,033,904 | A | 3/2000 | Cochran et al. |
| 6,123,949 | A | 9/2000 | Cochran et al. |
| 6,221,361 | B1 | 4/2001 | Cochran et al. |
| 6,328,975 | B1 | 12/2001 | Cochran et al. |
| 6,497,882 | B1 | 12/2002 | Cochran et al. |

FOREIGN PATENT DOCUMENTS

| CA | 2050850 | 3/1992 |
|---|---|---|
| EP | 0 431 668 B1 | 6/1991 |
| EP | 0 473 210 B1 | 3/1992 |
| EP | 0 477 056 A1 | 3/1992 |
| WO | WO 87/04429 | 7/1987 |
| WO | WO 88/07088 | 9/1988 |
| WO | WO 89/01040 | 2/1989 |
| WO | WO90/02802 | 3/1990 |
| WO | WO 90/02803 | 3/1990 |
| WO | WO 91/02053 | 2/1991 |
| WO | WO 92/01040 | 1/1992 |
| WO | WO 92/02053 | 2/1992 |
| WO | WO 92/02802 | 2/1992 |
| WO | WO 92/03547 | 3/1992 |
| WO | WO 92/03554 | 3/1992 |
| WO | WO 93/14194 | 7/1993 |
| WO | WO 95/03070 | 2/1995 |

OTHER PUBLICATIONS

York et al., "Humoral and cell-mediated immune responses to the glycoproteins of infectious laryngotracheitis herpesvirus," Archives of Virology, vol. 115, pp. 289-297 (1990).*
Andreasen, J., et al., "Studies of infectious laryngotracheitis vaccines: Immunity in broilers," *Avian Diseases* 33:516-23 (1989).
Andreasen, J., et al., "Studies of infectious laryngotracheitis vaccines: Immunity in vayers," *Avian Diseases* 33:524-30 (1989).
Andreasen, J., et al., "Reproducibility of a virus-neutralization test for infections laryngotracheitis virus," *Avian Diseases* 34:185-194.
Andreasen, J., et al., "Differentiation of vaccine strains and Georgia field isolates of infectious laryngotracheitis virus by their restriction endonuclease fragment patterns," *Avian Diseases* 34:646-56(1990).
Cantello, J., et al., "Isolation of a Marek's Disease Virus (MDV) recombinant containing the lacZ gene of *Escherichia coli*," *J. Gen. Virology* 65:1584-1588.

(Continued)

*Primary Examiner*—Zachariah Lucas

(57) ABSTRACT

The present invention provides a recombinant, attenuated infectious laryngotracheitis virus comprising the infectious laryngotracheitis viral genome which contains a deletion in the glycoprotein gG gene. This attenuated virus is useful as a vaccine against infectious laryngotracheitis virus.

The present invention also provides a recombinant, attenuated infectious laryngotracheitis virus comprising the infectious laryngotracheitis viral genome which contains a deletion in the US2 gene, UL47-like gene, ORF4 gene or glycoprotein g60 gene.

The present invention also provides a method for distinguishing chickens or other poultry vaccinated with a recombinant infectious laryngotracheitis virus which produces no glycoprotein gG from those infected with a naturally-occurring infectious laryngotracheitis virus.

4 Claims, 35 Drawing Sheets

OTHER PUBLICATIONS

Colle, et al., "Open reading frames encoding a protein kinase, homolog of glycoprotein gX of pseudorabies virus and a novel glycoprotein map within the unique short segment of equine herpesvirus type 1.," *Virology* 188:545-57 (1992).

Davison, S., et al., "Laryngotracheitis in chickens: The length of the preinfectious periods," *Avian Diseases* 33:18-23 (1989).

Davison, S., et al., "Laryngotracheitis in chickens: Infections studies and the efficacy of a tissue-culture vaccine in chicks less than four weeks old," *Avian Diseases* 33:24-29 (1989).

Finkelstein, A., et al., "Live recombinant vaccines for poultry," *Trends in Biotechnology* 7:273-77 (1989).

Griffin, A., et al., "The neucleotide sequence of the glycoprotein gB gene of infectious laryntracheitis virus: Analysis and evolutionary relationship to the homologous gene from other herpesviruses," *J. Gen. Virology* 72:393-98 (1991).

Griffin, A., et al., The complete sequence of the capsid p40 gene from infectious laryngotracheitis virus, *Nucleic Acids Res.* 18:3664 (1991).

Griffin, A., et al., "Identification of 21 genes of infectious laryngotracheitis virus random sequencing of genomic DNA," *J. Gen. Virology* 70:3085-89 (1989).

Griffin, A., "Analysis of the nucleotide sequence of DNA from the region of the thymidine kinase gene of infectious laryngotracheitis virus: Potential evolutionary relationships between the herpesvirus subfamilies," *J. Gen. Virology* 71:841-50 (1990).

Griffin, H., "Attenuated *Salmonella* as live vaccines: Prospects for multivalent poultry vaccines," *World's Poultry Science Journal* 47:131-40 (1991).

Guo, et al., "Construction of recombinant avian infectious laryngotracheitis virus express the β-galactosidase gene and DNA sequencing of the insertion region," *Virology* 202:771-81 (1994).

Guy, J., et al., "Virulence of infectious laryngotracheitis viruses: Comparison of modified-live vaccine viruses and North Carolina field isolates," *Avian Diseases* 34:106-12 (1990).

Guy, J., et al., "Increased virulence of modified-live infections laryngotracheitis vaccine virus following bird-to-bird passage," *Avian Diseases* 35:348-55 (1991).

Guy, J., et al., "Restriction endonuclease analysis of infections laryngotracheitis viruses: Comparison of modified-live vaccine and North Carolina field isolates," *Avian Diseases* 33:316-23 (1989).

Hanson, et al., Disease of Poultry, Ninth Edition, M.S. Hofstad Ed., pp. 485-95, Iowa State University Press (1991).

Hughes, et al., "Latency and reactivation of infectious laryngotracheitis vaccine virus," *Arch. Virol.* 121:213-18 (1991).

Izuchi, et al., "Studies on a live virus vaccine against infectious laryngotracheitis of chickens, I. Biological properties of attenuated strain C7," *Avian Diseases* 27:918-926. (1983).

Johnson, M., et al., "Gallid herpesvirus 1 (infectious laryngotracheitis virus): Cloning and physical maps of the SA-2 strain," *Arch Virol.* 119:181-198 (1991).

Johnson, et al., "Sequence characteristics of a gene in infections laryngotracheitis virus homologous to glycoprotein D of herpes simplex virus," *The Journal of Sequencing and Mapping* 5:191-94 (1995).

Johnson, et al., "Nucleotide sequence of infectious laryngotracheitis virus (gallid herpesvirus 1) ICP4 gene," *Virus Research* 35:193-204 (1995).

Johnson, et al., "Molecular evolution of infectious laryngotracheitis virus (ILTV; gallid herpesvirus 1): An ancient example of the Alphaherpesviridae?" *Veterinary Microbiology* 46:221-31 (1995).

Keam, L., et al., "Detection of infectious laryngotracheitis virus in chickens using a non-radioactive DNA probe," *Avian Diseases* 35:257-262 (1991).

Keeler, C., et al., "Identification of the thymidine kinase gene of infectious laryngotracheitis virus," *Avian Diseases* 35:920-929 (1991).

Key, D., et al., Abstract From the 65th Northeast Conference on Avian Disease, Jun. 9-11, University of Delaware, Newark, Delaware (1993).

Kingsley, et al., Abstract From the 65th Northeastern Conference on Avian Diseases, Jun. 9-11, University of Delaware, Newark , Delaware (1993).

Kongsuwan, K., et al., "Nucleotide sequence of the gene encoding infectious laryngotracheitis virus glycoprotein B," *Virology* 184:404-410 (1991).

Kongsuwan, K., et al., "Use of lambda gtII and monoclonal antibodies to map the gene for the 60,000 Dalton glycoprotein of infectious laryngotracheitis virus," *Virus Genes* 7:297-303 (1993).

Kongsuwan, K., et al., "Identification on an infectious laryngotracheitis virus gene encoding an immunogenic protein with a predicted M(r) of 32 kilodaltons," *Virus Research* 29:125-140 (1993).

Kotiw, M., et al., "Differentiation of infectious laryngotracheitis virus strain using restriction endonucleases," *Avian Diseases* 26:718-731 (1982).

Kotiw, M., et al., "Differentiation between virulent and avirulent strains of infectious laryngotracheitis virus by DNA: DNA hybridization using a cloned DNA marker," *Vet. Microbiology* 11:319-330 (1986).

Leib, D. et al., "Restriction endonuclease patterns of some European and American isolates of avian infectious laryngotracheitis virus," *Avian Diseases* 30:835-837 (1986).

Leib, D., et al., "Genome isomerism in two alphaherpesviruses: Herpesvirus Saimiri-1 (Herpesvirus tamarinus) and avian infectious laryngotracheitis virus," *Arch Virology* 93:287-294 (1987).

Nazerian, et al., "Protection against Marek's disease by fowlpox virus recombinant expressing the glycoprotein B of Marek's disease virus," *J. Virology* 66(3):1409-1413 (1992).

NCBI Accession No. L31965 and Revision History 1996.

Petrovskis, et al., "DNA sequence of the gene for pseudorabies virus gp50, a glycoprotein gB gene by the polymerase chain reaction," *J. Virol.* 59(2):216-223 (1986).

Poulsen, D., et al., "Identification of the infectious laryngotracheitis virus glycoprotein gB gene by the polymerase chain reaction," *Virus Genes* 5:335-347 (1991).

Purves, et al., "Herpes simplex virus 1 protein kinase is encoded by open reading frame US3 which is not essential for virus growth in cell culture," *J. Virology* 61:2896-2901 (1987).

Prideaux, et al., "Infectious laryngotracheitis virus growth, DNA replication, and protein synthesis," *Arch. Virol.* 123:181-192 (1991).

Reilly, et al., "Cosmid library of the turkey herpesvirus genome constructed from nanogram quantities of viral DNA associated with an excess of cellular DNA," *Journal of Virological Methods* 41:323-332 (1993).

Ross, L., et al., "Properties and evolutionary relationships of the Marek's disease virus homologues of protein kinase, glycoprotein I of herpes simplex virus," *J. Gen. Virology* 72:939-947 (1991).

Ross, L., et al., "DNA sequence and organization of genes in a 5.5 kbp EcoRI fragment mapping in the short unique segment of Marek's disease virus (strain RB1B)," *J. Gen. Virology* 72:949-954 (1991).

Saif, et al., AVMA 130th Annual Meeting, Jul. 17/21, Minneapolis, MN. (1993).

Sakaguchi, et al., "Sequence determination and genetic content of an 8.9-kb restriction fragment in the short unique region and the internal inverted repeat of Marek's disease virus type 1 DNA," *Virus Genes* 6(4):365-378 (1992).

Sanchez-Martinez, et al., "Evaluation of a test based on baculovirus expressed glycoprotein G for detection of herpes simplex virus type specific antibodies," *J. of Infectious Disease* 164:1196-1199 (1991).

Schnitzlein, W. et al., "Generation of thymidine kinase-deficient mutant of infectious laryngotracheitis virus," *Virology* 209:304-314 (1995).

Sharma, et al., "A plaque system for study of infectious laryngotracheitis virus in aduit chicken kidney cultures," *Avian Diseases* 13:268-279 (1969).

Sheppard, et al., "Identification of an infectious laryngotracheitis virus equivalent to the herpes simplex virus type 2 major DNA binding protein (ICP8)," *Acta. Virol.* 34:443-448 (1990).

Shirley, et al., "Detection of DNA from infectious laryngotracheitis virus b colourimetric analysis of polymerase chain reactions," *J. Virological Methods* 30:251-260 (1990).

Van Zijl et al., "Regeneration of herpesviruses from molecularly cloned subgenomic fragments," *J. Virology* 62:2191-2195 (1988).

Wark, et al., "The development and evaluation of a cell vaccine against infectious laryngotracheitis virus," *Journal of Biological Standardization* 7:73-80 (1979).

Weber, et al., "Rapid identification of nonessential genes of herpes simplex virus type 1 by Tn5 mutagenesis," *Science* 236:576-579 (1987).

Wild et al., "A genomic map of infectious laryngotracheitis virus and the sequence and organization of genes present in the unique short and flanking regions," *Virus Genes* 12:107-116 (1996).

York, et al., "Immunogenic glycoproteins of infectious laryngotracheitis herpesvirus," *Virology* 161:340-347 (1990).

York, et al., "Humoral and cell-medicated immune responses to the glycoproteins of infections laryngotracheitis herpesvirus," *Arch. Viro.* 115:289-97 (1990).

Zelnik, et al., "The complete sequence and gene organization of the short unique region of herpesvirus of turkeys," *J. Gen. Virol.* 74:2151-62 (1993).

Altschul, et al., "Gapped BLAST and PSI-BLAST", *Nucleic Acids Res.* 25:3389-3402 (1997).

Barker et al. "Identification of three genes nonessential for growth in cell culture near the right terminus of the unique sequences of long component of herpes simplex virus 1", *Virology*, 177(2):684-91 (1990).

Cardona et al., "Characterization of a recombinant fowlpox virus expressing the native hexon of hemorrhagic enteritis virus," *Virus Genes*, Col. 22. No. 3, pp. 353-361 (Jun. 2001).

Grose, C. "Glycoproteins of varicella-zoster virus and their herpes simplex virus homologs", *Rev Infect Dis.*, 13 Suppl 11:S960-3 (1991).

Jucker et al., "Characterization of the haemorrhagic enteritis virus genome and the sequence of the putative penton bases and core protein genes", *Journal of General Virology*, 77:469-479 (1996).

Kongsuwan et al., "Nucleotide sequence analysis of an infectious laryngotracheitis virus gene corresponding to the US3 of HSV-1 and a unique gene encoding a 67 kDa protein", *Archives of Virology*, 140:27-39; © Springer-Verlag, Austria (1995).

Longnecker et al., "Clustering of Genes Dispensable for Growth in Culture in the S Component of the HSV-1 Genome", *Science*, 236(4801):573-576 (987).

Mettenleiter et al., "Isolation of a viable herpesvirus (pseudorabies virus) mutant specifically lacking all four known nonessential glycoproteins", *Virology*, 179(1):498-503 (1990).

Mutalib, A., "Studies on Transmissibility of a tissue-culture-modified larynotracheitis virus", *Journal of Veterinary Diagnostic Investigation*, 4(4):412-415 (1992).

\* cited by examiner

FIGURE 1A

```
CCCGTGCCCC TAAAGGCCGC CGAGAAAGCT AAGTCCAAAT GTGACGTCGG 50
AGGTCTCGAC ATGGTCGCCA ACCCTCCAAA TGCTACCCGC CGGCCCACGC 100
AACGCGGGCT TTTATAAAGA TGGCGCGCGA GACAATAACA CTTACTCATC 150
CGCGTACGCG TTTATTATTG TCAATATTTG TGTGGTTATT ATTACTGCTA 200
CCGCCCTTGT TTCTGCAAGG CCCTCGCCGC GGCCCAGGCC ACTATTCCGG 250
CAGCGGCCGC CGACGCGGCG AGCGTCGCCG CTAACGTCGG CGCCGCGGGG 300
AGCGGGGTTT CTTCGACTTA AATAGACTCC CGAGAAAAAA TTTTGGCTGC 350
CGTTCGCCAT CATCCGAGTC GGAAACACAG TATGCGGCCG AGTTAGGTTT 400
TACTTTTAAA AACTTTACCG TGCTGTACGG CCAGGGCGTT CTCAGGCTCG 450
AAGGGGCAAG AGTTGTCCAG ACTGATGGGT GACTCAGAGA CAGCGTTGTC 500
TTGTCTCCGT TTACCAAAAA TATTTCCACT CCTCTCTCAA AATTTTTACC 550
TCCGGTTTCG GTAATTAGGA AAGTTTTTGG CGCAGGGAGG TTTAAAGCTG 600
CCATGCATAT GTCAGCGGTA CCCAGCACCC ACAAATGGAA CTCTTTTGCG 650
GCATACGCGC CAGATGACAA ATGGTAAAAC CCTGCGTCCA AGCCGCTCCA 700
CTCGGGACTT ACTCCAGGCG GGTCGCCCCC CTCACCGAAC CGAATCACGG 750
GTCTGCACAT CCTGGGAAGG GAAAACAGCT CCCCGGAAAC TTCGTACAGA 800
GATGCCGGGC GCACGATTAC CGATAATGTA CTCGGACGAT CGTAACTCGC 850
CATAGTTTTC ACTGCGTGAA CCAATTCTTT CCATCCAGAA TCCGAGAGCT 900
CAAATCTAGA ATTAGGTAGT TTGTAGTGCG AATCGACCGC AGAAACTATA 950
GTCACTTTTA CAGGCGCCAT CGCCGCTCAG ACTCCACCCC GCTATGATGT 1000
CAGAAATATA ACGCTCTTAT TCTAGCAGAG TCAGGCCAAT ATATACAGCT 1050
TAGAGAAGAT GCGGTTTCGG CGCATCTGTT CACGCTCTAG GGCAGAAAAA 1100
CGAAGAAGAA CAACCGAGAA TCCGCTTACC TCAAAACGCG TTTGCGTATT 1150
GGATAGTTTC TCACGGACAA TGTCATTGCG CCCCTATGCA GAAATTTTGC 1200
CGACCGCGGA AGGCGTCGAG CGCCTCGCCG AACTTGTTAG TGTGACAATG 1250
ACAGAACGCG CGGAACCTGT GACAGAGAAT ACAGCTGTAA ACAGTATCCC 1300
CCCGGCTAAC GAGAACGGGC AGAACTTCGC ATATGCAGGC GATGGGCCCT 1350
CGACTACTGA AAAAGTTGAC GGCTCGCATA CAGACTTCGA TGAAGCATCG 1400
AGCGACTACG CCGGCCCTGT CCCGCTCGCG CAAACTAGAT TGAAGCATTC 1450
GGATGAATTT CTTCAGCACT TCCGAGTTTT AGACGATTTG GTGGAGGGGG 1500
CTTACGGGTT TATCTGCGGC GTCCGTCGCT ACACCGAGGA AGAGCAACGT 1550
CGAAGAGGGG TTAACAGTAC TAACCAGGGG AAATCAAAAT GTAAGCGCCT 1600
GATAGCTAAA TATGTGAAAA ATGGAACAAG GGCGGCCTCT CAGCTGGAAA 1650
ATGAAATTTT GGTTCTCGGG CGCCTAAATC ACGAGAATGT TCTCAAGATC 1700
CAGGAAATCC TTCGGTACCC GGATAATACG TACATGTTAA CGCAGAGGTA 1750
```

FIGURE 1B

```
TCAGTTCGAC TTGTACAGCT ACATGTACGA TGAAGCGTTC GACTGGAAAG 1800
ACAGTCCAAT GCTTAAACAG ACTAGACGCA TCATGAAGCA GCTCATGTCA 1850
GCGGTCTCGT ATATCCATTC AAAGAAACTG ATTCACAGGG ACATCAAACT 1900
CGAAAATATT TTCTTAAACT GCGACGGCAA GACAGTGCTG GGCGACTTTG 1950
GAACTGTCAC GCCTTTTGAA AATGAGCGGG AGCCCTTCGA ATATGGATGG 2000
GTGGGGACCG TGGCTACTAA CTCTCCCGAG ATACTCGCCA GGGATTCGTA 2050
CTGTGAAATT ACAGACATTT GGAGCTGCGG AGTAGTATTG CTGGAAATGG 2100
TAAGCCATGA ATTTTGCCCG ATCGGCGATG GCGGGGGAAA TCCGCACCAG 2150
CAATTGCTGA AAGTTATCGA CTCTCTCTCA GTTTGTGATG AAGAGTTCCC 2200
AGACCCCCCG TGTAATCTGT ACAATTATTT GCATTATGCG AGCATCGATC 2250
GCGCCGGACA TACGGTCCCG TCGCTCATAC GGAACCTCCA CCTTCCGGCG 2300
GATGTGGAAT ACCCTCTAGT TAAAATGCTT ACTTTTGACT GGCGTTTGAG 2350
ACCCAGCGCG GCCGAAGTAT TGGCAATGCC ACTGTTTTCG GCTGAAGAGG 2400
AACGGACCAT AACAATTATT CATGGAAAAC ATAAACCCAT CCGACCCGAA 2450
ATCCGTGCGC GGGTGCCACG GTCCATGAGT GAAGGTTAAT AATAAAGGAC 2500
GGAGATAGAG AACTGAAGCG TCAGATTTTT TTAAAAAAAT AAATGATCGA 2550
GAACTTATGA TTTGTCTTTC TTGAATGACC TTGCCCCATC GATTAACGAA 2600
AAGACCTTTC GCGCGTCGAT TCTGCTCGGT CTTTGTGATA CATTATAGTG 2650
AGACTAAACT CGACCGATAT AACAAGACAA TGTTACTCTA TAGACCGGAC 2700
TCAACCATGC GGCATAGCGG AGGCGACGCA AATCACAGAG GGATAAGGCC 2750
GAGGCGGAAA TCTATTGGAG CGTTTAGCGC GCGCGAAAAG ACTGGAAAAC 2800
GAAATGCGCT GACGGAAAGC AGCTCCTCCT CCGACATGCT AGATCCGTTT 2850
TCCACGGATA AGGAATTTGG CGGTAAGTGG ACGGTAGACG GACCTGCCGA 2900
CATTACTGCC GAGGTCCTTT CTCAGGCATG GGACGTTCTC CAATTAGTGA 2950
AGCATGAAGA TGCGGAGGAG GAGAGAGTGA CTTATGAGTC CAAACCGACC 3000
CCGATACAGC CGTTCAATGC CTGGCCGGAC GGGCCGAGTT GGAACGCGCA 3050
GGATTTTACT CGAGCGCCAA TAGTTTATCC CTCTGCGGAG GTATTGGACG 3100
CAGAGGCGTT GAAAGTAGGG GCATTCGTTA GCCGAGTTTT ACAATGTGTA 3150
CCGTTCACGC GATCAAAGAA AAGCGTTACG GTGCGGGATG CGCAGTCGTT 3200
TTTGGGGGAC TCGTTCTGGA GAATAATGCA GAACGTTTAC ACGGTTTGCT 3250
TACGACAGCA CATAACTCGA CTCAGGCACC CTTCCAGCAA AAGCATTGTT 3300
AACTGCAACG ACCCTCTATG GTACGCCTAC GCGAATCAAT TCACTGGAG 3350
AGGAATGCGC GTGCCGTCGC TTAAATTAGC CTCTCCCCCG GAGGAGAATA 3400
TTCAACACGG CCCAATGGCC GCCGTTTTTA GAAACGCGGG GGCTGGTCTG 3450
TTCCTGTGGC CTGCCATGCG CGCAGCCTTT GAAGAGCGCG ACAAGCGACT 3500
```

FIGURE 1C

```
GTTAAGAGCA TGCCTGTCTT CACTCGATAT CATGGACGCA GCCGTCCTCG 3550
CGTCGTTTCC ATTTTACTGG CGCGGCGTCC AAGACACCTC GCGCTTCGAG 3600
CCTGCGCTGG GCTGTTTGTC AGAGTACTTT GCACTAGTGG TGTTACTGGC 3650
CGAGACGGTC TTAGCGACCA TGTTCGACCA CGCACTGGTA TTCATGAGGG 3700
CGCTGGCAGA CGGCAATTTC GATGACTATG ACGAAACTAG ATATATAGAC 3750
CCCGTTAAAA ACGAGTACCT GAACGGAGCC GAGGGTACTC TGTTACGGGG 3800
CATAGTGGCC TCCAACACCG CTCTGGCGGT GGTTTGCGCA AACACCTATT 3850
CGACGATAAG AAAACTCCCG TCCGTGGCAA CTAGCGCGTG CAATGTTGCC 3900
TACAGGACCG AAACGCTGAA AGCGAGGCGC CCTGGCATGA GCGACATATA 3950
CCGGATATTA CAAAAAGAGT TTTTCTTTTA CATTGCGTGG CTCCAGAGGG 4000
TTGCAACACA CGCAAATTTC TGTTTAAACA TTCTGAAGAG AAGCGTGGAT 4050
ACGGGCCCCC GCCATTTTTG TTCAGGGCCA GCTCGGAGAA GCGGCTGCAG 4100
CAGTTAAATA AAATGCTCTG CCCCCTTCTC GTGCCGATTC AATATGAAGA 4150
CTTTTCGAAG GCCATGGGGT CTGAGCTCAA GAGGGAAAAG TTAGAGACAT 4200
TCGTTAAAGC TATTTCCAGC GACAGGGACC CGAGGGGGTC CTTAAGATTT 4250
CTCATTTCGG ACCATGCAAG GGAAATTATT GCAGACGGAG TACGGTTTAA 4300
GCCGGTGATA GACGAGCCGG TTCGGGCTTC AGTTGCGCTG AGTACCGCTG 4350
CCGCTGGGAA AGTGAAAGCG CGACGCTTAA CCTCAGTTCG CGCGCCCGTA 4400
CCGCCCGCAG GCGCCGTTTC CGCGCGCCGG AAATCGGAAA TATGATAAAA 4450
ATGCTTGGCA TTTGCGGGCG AAGAGGCGTG ATCTGAAGGG CTCCACAATG 4500
ACGTAACTGA GCTACGCATC CCTATAAAGT GTACSCGCTG ACCGCTAGCC 4550
CATACAGTGT TACAGGAGGG GAGAGAGACA ACTTCAGCTC GAAGTCTGAA 4600
GAGACATCAT GAGCGGCTTC AGTAACATAG GATCGATTGC CACCGTTTCC 4650
CTAGTATGCT CGCTTTTGTG CGCATCTGTA TTAGGGGCGC CGGTACTGGA 4700
CGGGCTCGAG TCGAGCCCTT TCCCGTTCGG GGGCAAAATT ATAGCCCAGG 4750
CGTGCAACCG CACCACGATT GAGGTGACGG TCCCGTGGAG CGACTACTCT 4800
GGTCGCACCG AAGGAGTGTC AGTCGAGGTG AAATGGTTCT ACGGGAATAG 4850
TAATCCCGAA AGCTTCGTGT TCGGGGTGGA TAGCGAAACG GGCAGTGGAC 4900
ACGAGGACCT GTCTACGTGC TGGGCTCTAA TCCATAATCT GAACGCGTCT 4950
GTGTGCAGGG CGTCTGACGC CGGGATACCT GATTTCGACA AGCAGTGCGA 5000
AAAAGTGCAG AGAAGACTGC GCTCCGGGGT GGAACTTGGT AGTTACGTGT 5050
CTGGCAATGG ATCCCTGGTG CTGTACCCAG GGATGTACGA TGCCGGCATC 5100
TACGCCTACC AGCTCTCAGT GGGTGGGAAG GGATATACCG GGTCTGTTTA 5150
TCTAGACGTC GGACCAAACC CCGGATGCCA CGACCAGTAT GGGTACACCT 5200
ATTACAGCCT GGCCGACGAG GCGTCAGACT TATCATCTTA TGACGTAGCC 5250
```

FIGURE 1D

```
TCGCCCGAAC TCGACGGTCC TATGGAGGAA GATTATTCCA ATTGTCTAGA 5300
CATGCCCCCG CTACGCCCAT GGACAACCGT TTGTTCGCAT GACGTCGAGG 5350
AGCAGGAAAA CGCCACGGAC GAGCTTTACC TATGGGACGA GGAATGCGCC 5400
GGTCCGCTGG ACGAGTACGT CGACGAAAGG TCAGAGACGA TGCCCAGGAT 5450
GGTTGTCTTT TCACCGCCCT CTACGCTCCA GCAGTAGCCA CCCGAGAGTG 5500
TTTTTTGTGA GCGCCCACGC AACATACCTA ACTGCTTCAT TTCTGATCAA 5550
TTATTGCGTA TTGAATAAAT AAACAGTACA AAAGCATCAG GTGTGGTTTG 5600
CGTGTCTGTG CTAAACCATG GCGTGTGCGG GTGAAAcCGT AAATTACGTG 5650
ATAATAAATA GCATAGGAGT TGGCGTGCAG CGTATTTCGC CGAGAGATGG 5700
GGACAATGTT AGTGTTGCGC CTTTTCCTAC TTGCAGTAGC GGACGCGGCG 5750
TTGCCGACCG GCAGATTCTG CCGAGTTTGG AAGGTGCCTC CGGGAGGAAC 5800
CATCCAAGAG AACCTGGCGG TGCTCGCGGA ATCGCCGGTC ACGGACACG 5850
CGACATATCC GCCGCCTGAA GGCGCCGTCA GCTTTCAGAT TTTTGCGGAC 5900
ACCCCTACTT TGCGCATTCG CTACGGGCCT ACGGAGGACG AACTTGCACT 5950
GGAGCGCGGG ACGTCCGCCT CAGACGCGGA CAACGTGACA TTTTCGCTGT 6000
CATATCGCCC GCGCCCAGAA ATTCACGGAG CATACTTCAC CATAGGGGTA 6050
TTCGCTACTG GCCAGAGCAC GGAAAGCAGC TATTCGGTCA TCAGTCGGGT 6100
CTTAGTTAAC GCCTCTCTGG AACGGTCCGT GCGCCTGGAA ACGCCGTGCG 6150
ATGAAAATTT TTTGCAGAAC GAGCCTACAT GGGGCTCGAA GCGTTGGTTA 6200
GGCCCCCCGT CGCCTTATGT GCGAGATAAC GATGTCGCCG TGTTGACAAA 6250
AGCGCAGTAC ATTGGGGAGT GCTACTCCAA CTCGGCGGCC CAGACGGGGC 6300
TCACGTCTCT CAACATGACC TTTTTCTATT CGCCTAAAAG AATAGTAAAC 6350
GTCACGTGGA CAACCGGCGG CCCCTCCCCC TCGCGCATAA CGGTATACTC 6400
GTCGCGGGAG AACGGGCAGC CCGTGTTGAG GAACGTTTCT GACGGGTTCT 6450
TGGTTAAGTA CACTCCCGAC ATTGACGGCC GGGCCATGAT AAACGTTATT 6500
GCCAATTATT CGCCGGCGGA CTCCGGCAGC GTCCTCGCGT TTACGGCCTT 6550
TAGGGAAGGA AAACTCCCAT CCGCGATTCA ACTGCACCGG ATAGATATGT 6600
CCGGGACTGA GCCGCCGGGG ACTGAAACGA CCTTCGACTG TCAAAAAATG 6650
ATAGAAACCC CGTACCGAGC GCTCGGGAGC AATGTTCCCA GGGACGACTC 6700
TATCCGTCCG GGGGCCACTC TGCCTCCGTT CGATACCGCA GCACCTGATT 6750
TCGATACAGG TACTTCCCCG ACCCCACTA CCGTGCCAGA GCCAGCCATT 6800
ACTACACTCA TACCGCGCAG CACTAGCGAT ATGGGATTCT TCTCCACGGC 6850
ACGTGCTACC GGATCAGAAA CTCTTTCGGT ACCCGTCCAG GAAACGGATA 6900
GAACTCTTTC GACAACTCCT CTTACCCTTC CACTGACTCC CGGTGAGTCA 6950
GAAAATACAC TGTTTCCTAC GACCGCGCCG GGGATTTCTA CCGAGACCCC 7000
```

FIGURE 1E

```
GAGCGCGGCA CATGAAACTA CACAGACCCA GAGTGCAGAA ACGGTGGTCT 7050
TTACTCAGAG TCCGAGTACC GAGTCGGAAA CCGCGCGGTC CCAGAGTCAG 7100
GAACCGTGGT ATTTTACTCA GACTCCGAGT ACTGAACAGG CGGCTCTTAC 7150
TCAGACGCAG ATCGCAGAAA CGGAGGCGTT GTTTACTCAG ACTCCGAGTG 7200
CTGAACAGAT GACTTTTACT CAGACTCCGG GTGCAGAAAC CGAGGCACCT 7250
GCCCAGACCC CGAGCACGAT ACCCGAGATA TTTACTCAGT CTCGTAGCAC 7300
GCCCCCCGAA ACCGCTCGCG CTCCGAGCGC GGCGCCGGAG GTTTTTACAC 7350
AGAGTTCGAG TACGGTAACG GAGGTGTTTA CTCAGACCCC GAGCACGGTA 7400
CCGAAAACTA CTCTGAGTTC GAGTACTGAA CCGGCGATTT TTACTCGGAC 7450
TCAGAGCGCG GGAACTGAGG CCTTTACTCA GACTTCGAGT GCCGAGCCGG 7500
ACACTATGCG AACTCAGAGT ACTGAAACAC ACTTTTTCAC TCAGGCCCCG 7550
AGTACGGTAC CGAAAGCTAC TCAGACTCCG AGTACAGAGC CGGAGGTGTT 7600
GACTCAGAGT CCGAGTACCG AACCTGTGCC TTTCACCCGG ACTCTGGGCG 7650
CAGAGCCGGA AATTACTCAG ACCCCGAGCG CGGCACCGGA GGTTTATACT 7700
CGGAGTTCGA GTACGATGCC AGAAACTGCA CAGAGCACAC CCCTGGCCTC 7750
GCAAAACCCT ACCAGTTCGG GAACCGGGAC GCATAATACT GAACCGAGGA 7800
CTTATCCAGT GCAAACGACA CCACATACCC AGAAACTCTA CACAGAAAAT 7850
AAGACTTTAT CGTTTCCTAC TGTTGTTTCA GAATTCCATG AGATGTCGAC 7900
GGCAGAGTCG CAGACGCCCC TATTGGACGT CAAAATTGTA GAGGTGAAGT 7950
TTTCAAACGA TGGCGAAGTA ACGGCGACTT GCGTTTCCAC CGTCAAATCT 8000
CCCTATAGGG TAGAAACTAA TTGGAAAGTA GACCTCGTAG ATGTAATGGA 8050
TGAAATTTCT GGGAACAGTC CCGCCGGGGT TTTTAACAGT AATGAGAAAT 8100
GGCAGAAACA GCTGTACTAC AGAGTAACCG ATGGAAGAAC ATCGGTCCAG 8150
CTAATGTGCC TGTCGTGCAC GAGCCATTCT CCGGAACCTT ACTGTCTTTT 8200
CGACACGTCT CTTATAGCGA GGGAAAAAGA TATCGCGCCA GAGTTATACT 8250
TTACCTCTGA TCCGCAAACG GCATACTGCA CAATAACTCT GCCGTCCGGC 8300
GTTGTTCCGA GATTCGAATG GAGCCTTAAT AATGTTTCAC TGCCGGAATA 8350
TTTGACGGCC ACGACCGTTG TTTCGCATAC CGCTGGCCAA AGTACAGTGT 8400
GGAAGAGCAG CGCGAGAGCA GGCGAGGCGT GGATTTCTGG CCGGGGAGGC 8450
AATATATACG AATGCACCGT CCTCATCTCA GACGGCACTC GCGTTACTAC 8500
GCGAAAGGAG AGGTGCTTAA CAAACACATG GATTGCGGTG GAAAACGGTG 8550
CTGCTCAGGC GCAGCTGTAT TCACTCTTTT CTGGACTTGT GTCAGGATTA 8600
TGCGGGAGCA TATCTGCTTT GTACGCAACG CTATGGACCG CCATTTATTT 8650
TTGAGGAATG CTTTTTGGAC TATCGTACTG CTTTCTTCCT TCGCTAGCCA 8700
GAGCACCGCC GCCGTCACGT ACGACTACAT TTTAGGCCGT CGCGCGCTCG 8750
```

FIGURE 1F

```
ACGCGCTAAC CATACCGGCG GTTGGCCCGT ATAACAGATA CCTCACTAGG 8800
GTATCAAGAG GCTGCGACGT TGTCGAGCTC AACCCGATTT CTAACGTGGA 8850
CGACATGATA TCGGCGGCCA AAGAAAAAGA GAAGGGGGGC CCTTTCGAGG 8900
CCTCCGTCGT CTGGTTCTAC GTGATTAAGG GCGACGACGG CGAGGACAAG 8950
TACTGTCCAA TCTATAGAAA AGAGTACAGG GAATGTGGCG ACGTACAACT 9000
GCTATCTGAA TGCGCCGTTC AATCTGCACA GATGTGGGCA GTGGACTATG 9050
TTCCTAGCAC CCTTGTATCG CGAAATGGCG CGGGACTGAC TATATTCTCC 9100
CCCACTGCTG CGCTCTCTGG CCAATACTTG CTGACCCTGA AAATCGGGAG 9150
ATTTGCGCAA ACAGCTCTCG TAACTCTAGA AGTTAACGAT CGCTGTTTAA 9200
AGATCGGGTC GCAGCTTAAC TTTTTACCGT CGAAATGCTG GACAACAGAA 9250
CAGTATCAGA CTGGATTTCA AGGCGAACAC CTTTATCCGA TCGCAGACAC 9300
CAATACACGA CACGCGGACG ACGTATATCG GGGATACGAA GATATTCTGC 9350
AGCGCTGGAA TAATTTGCTG AGGAAAAAGA ATCCTAGCGC GCCAGACCCT 9400
CGTCCAGATA GCGTCCCGCA AGAAATTCCC GCTGTAACCA AGAAAGCGGA 9450
AGGGCGCACC CCGGACGCAG AAAGCAGCGA AAAGAAGGCC CCTCCAGAAG 9500
ACTCGGAGGA CGACATGCAG GCAGAGGCTT CTGGAGAAAA TCCTGCCGCC 9550
CTCCCCGAAG ACGACGAAGT CCCCGAGGAC ACCGAGCACG ATGATCCAAA 9600
CTCGGATCCT GACTATTACA ATGACATGCC CGCCGTGATC CCGGTGGAGG 9650
AGACTACTAA AAGTTCTAAT GCCGTCTCCA TGCCCATATT CGCGGCGTTC 9700
GTAGCCTGCG CGGTCGCGCT CGTGGGGCTA CTGGTTTGGA GCATCGTAAA 9750
ATGCGCGCGT AGCTAATCGA GCCTAGAATA GGTGGTTTCT TCCTACATGC 9800
CACGCCTCAC GCTCATAATA TAAATCACAT GGAATAGCAT ACCAATGCCT 9850
ATTCATTGGG ACGTTCGAAA AGCATGGCAT CGCTACTTGG AACTCTGGCT 9900
CTCCTTGCCG CGACGCTCGC ACCCTTCGGC GCGATGGGAA TCGTGATCAC 9950
TGGAAATCAC GTCTCCGCCA GGATTGACGA CGATCACATC GTGATCGTCG 10000
CGCCTCGCCC CGAAGCTACA ATTCAACTGC AGCTATTTTT CATGCCTGGC 10050
CAGAGACCCC ACAAACCCTA CTCAGGAACC GTCCGCGTCG CGTTTCGGTC 10100
TGATATAACA AACCAGTGCT ACCAGGAACT TAGCGAGGAG CGCTTTGAAA 10150
ATTGCACTCA TCGATCGTCT TCTGTTTTTG TCGGCTGTAA AGTGACCGAG 10200
TACACGTTCT CCGCCTCGAA CAGACTAACC GGACCTCCAC ACCCGTTTAA 10250
GCTCACTATA CGAAATCCTC GTCCGAACGA CAGCGGGATG TTCTACGTAA 10300
TTGTTCGGCT AGACGACACC AAAGAACCCA TTGACGTCTT CGCGATCCAA 10350
CTATCGGTGT ATCAATTCGC GAACACCGCC GCGACTCGCG GACTCTATTC 10400
CAAGGCTTCG TGTCGCACCT TCGGATTACC TACCGTCCAA CTTGAGGCCT 10450
ATCTCAGGAC CGAGGAAAGT TGGCGCAACT GGCAAGCGTA CGTTGCCACG 10500
```

FIGURE 1G

```
GAGGCCACGA CGACCAGCGC CGAGGCGACA ACCCCGACGC CGTCACTGC  10550
AACCAGCGCC TCCGAACTTG AAGCGGAACA CTTTACCTTT CCCTGGCTAG  10600
AAAATGGCGT GGATCATTAC GAACCGACAC CCGCAAACGA AAATTCAAAC  10650
GTTACTGTCC GTCTCGGGAC AATGAGCCCT ACGCTAATTG GGGTAACCGT  10700
GGCTGCCGTC GTGAGCGCAA CGATCGGCCT CGTCATTGTA ATTTCCATCG  10750
TCACCAGAAA CATGTGCACC CCGCACCGAA AATTAGACAC GGTCTCGCAA  10800
GACGACGAAG AACGTTCCCA AACTAGAAGG GAATCGCGAA AATTTGGACC  10850
CATGGTTGCG TGCGAAATAA ACAAGGGCGC TGACCAGGAT AGTGAACTTG  10900
TGGAACTGGT TGCGATTGTT AACCCGTCTG CGCTAAGCTC GCCCGACTCA  10950
ATAAAAATGT GATTAAGTCT GAATGTGGCT CTCCAATCAT TTCGATTCTC  11000
TAATCTCCCA ATCCTCTCAA AAGGGGCAGT ATCGGACACG GACTGGGAGG  11050
GGCGTACTAC ACGATAGTTA TATGGTACAG CAGAGGCCTC TGAACACTTA  11100
GGAGGAGAAT TCAGCCGGGG AGAGCCCCTG TTGAGTAGGC TTGGGAGCAT  11150
ATTGCAGGAT GAACATGTTA GTGATAGTTC TCGCCTCTTG TCTTGCGCGC  11200
CTAACTTTTG CGACGCGACA CGTCCTCTTT TTGGAAGGCA CTCAGGCTGT  11250
CCTCGGGGAA GATGATCCCA GAAACGTTCC GGAAGGGACT GTAATCAAAT  11300
GGACAAAAGT CCTGCGGAAC GCGTGCAAGA TGAAGGCGGC CGATGTCTGC  11350
TCTTCGCCTA ACTATTGCTT TCATGATTTA ATTTACGACG GAGGAAAGAA  11400
AGACTGCCCG CCCGCGGGAC CCCTGTCTGC AAACCTGGTA ATTTTACTAA  11450
AGCGCGGCGA AAGCTTCGTC GTGCTGGGTT CTGGGCTACA CAACAGCAAT  11500
ATAACTAATA TCATGTGGAC AGAGTACGGA GGCCTGCTCT TTGATCCTGT  11550
AACTCGTTCG GACGAGGGAA TCTATTTTCG ACGGATCTCT CAGCCAGATC  11600
TGGCCATGGA AACTACATCG TACAACGTCA GCGTTCTTTC GCACGTAGAC  11650
GAGAAGGCTC CAGCACCGCA CGAGGTGGAG ATAGACACCA TCAAGCCGTC  11700
AGAGGCCCAC GCGCACGTGG AATTACAAAT GCTGCCGTTT CATGAACTCA  11750
ACGACAACAG CCCCACCTAT GTGACCCCTG TTCTTAGAGT CTTCCCACCG  11800
ACCGAGCACG TAAAATTTAA CGTTACGTAT TCGTGGTATG GGTTTGATGT  11850
CAAAGAGGAG TGCGAAGAAG TGAAACTGTT CGAGCCGTGC GTATACCATC  11900
CTACAGACGG CAAATGTCAG TTTCCCGCAA CCAACCAGAG ATGCCTCATA  11950
GGATCTGTCT TGATGGCGGA ATTCTTGGGC GCGGCCTCTT TGCTGGATTG  12000
TTCCCGCGAT ACTCTAGAAG ACTGCCACGA AAATCGCGTG CCGAACCTAC  12050
GGTTCGATTC GCGACTCTCC GAGTCACGCG CAGGCCTGGT GATCAGTCCT  12100
CTTATAGCCA TCCCCAAAGT TTTGATTATA GTCGTTTCCG ACGGAGACAT  12150
TTTGGGATGG AGCTACACGG TGCTCGGGAA ACGTAACAGT CCGCGCGTAG  12200
TAGTCGAAAC GCACATGCCC TCGAAGGTCC CGATGAACAA AGTAGTAATT  12250
```

FIGURE 1H

```
GGCAGTCCCG GACCAATGGA CGAAACGGGT AACTATAAAA TGTACTTCGT 12300
CGTCGCGGGG GTGGCCGCGA CGTGCGTAAT TCTTACATGC GCTCTGCTTG 12350
TGGGGAAAAA GAAGTGCCCC GCGCACCAAA TGGGTACTTT TTCCAAGACC 12400
GAACCATTGT ACGCGCCGCT CCCCAAAAAC GAGTTTGAGG CCGGCGGGCT 12450
TACGGACGAT GAGGAAGTGA TTTATGACGA AGTATACGAA CCCCTATTTC 12500
GCGGCTACTG TAAGCAGGAA TTCCGCGAAG ATGTGAATAC CTTTTTCGGT 12550
GCGGTCGTGG AGGGAGAAAG GGCCTTAAAC TTTAAATCCG CCATCGCATC 12600
AATGGCAGAT CGCATCCTGG CAAATAAAAG CGGCAGAAGG AATATGGATA 12650
GCTATTAGTT GGTCATGCCT TTTAAGACCA GAGGGGCCGA AGACGCGGCC 12700
GCGGGCAAGA ACAGGTTTAA GAAATCGAGA AATCGGGAAA TCTTACCGAC 12750
CAGACTGCGT GGCACCGGTA AGAAAACTGC CGGATTGTCC AATTATACCC 12800
AGCCTATTCC CTGGAACCCT AAATTCTGCA GCGCGCGCGG GGAATCTGAC 12850
AACCACGCGT GTAAAGACAC TTTTTATCGC AGGACGTGCT GCGCATCGCG 12900
CTCTACCGTT TCCAGTCAAC CCGATTCCCC CCACACACCC ATGCCTACTG 12950
AGTATGGGCG CGTGCCCTCC GCAAAGCGCA AAAAACTATC ATCTTCAGAC 13000
TSSGAGGGCG CGCACCAACC CCTAGTATCC TGTAAACTTC CGGATTCTCA 13050
AGCAGCACCG GCGCGAACCT ATAGTTCTGC GCAAAGATAT ACTGTTGACG 13100
AGGTTTCGTC GCCAACTCCG CCAGGCGTCG ACGCTGTTGC GGACTTAGAA 13150
ACGCGCGCGG AACTTCCTGG CGCTACGACG GAACAAACGG AAAGTAAAAA 13200
TAAGCTCCCC AACCAACAAT CGCGCCTGAA GCCGAAACCC ACAAACGAGC 13250
ACGTCGGAGG GGAGCGGTGC CCCTCCGAAG GCACGGTCGA GGCGCCATCG 13300
CTCGGCATCC TCTCGCGCGT CGGGGCAGCG ATAGCAAACG AGCTGGCTCG 13350
TATGCGGAGG GCGTGTCTTC CGCTCGCCGC GTCGGCGGCC GCTGCCGGAA 13400
TAGTGGCCTG GGCCGCGGCG AGGGCCTTGC AGAAACAAGG GCGGTAGCAG 13450
TAATAATAAC CACACAAATA TTG 13473
```

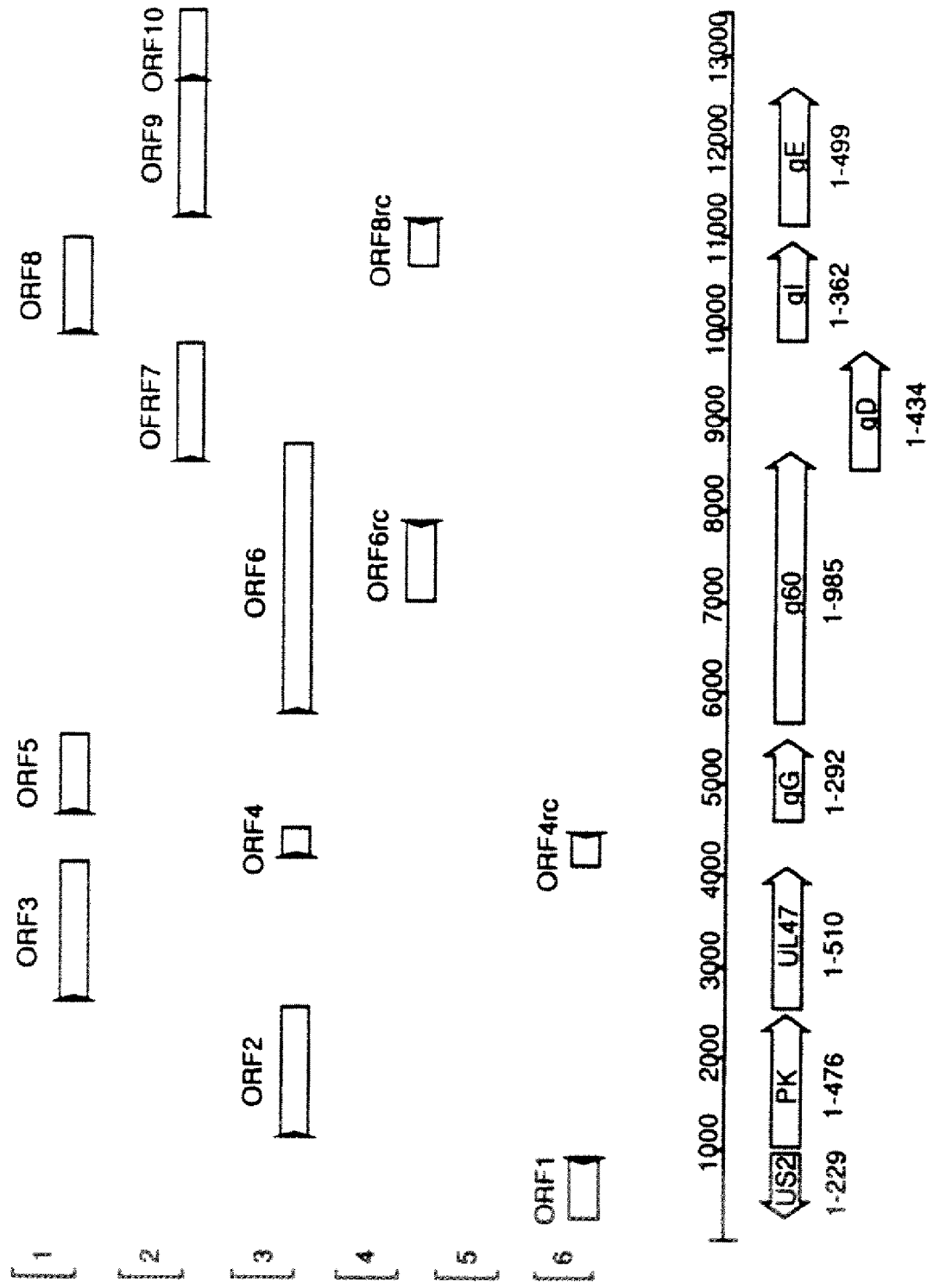

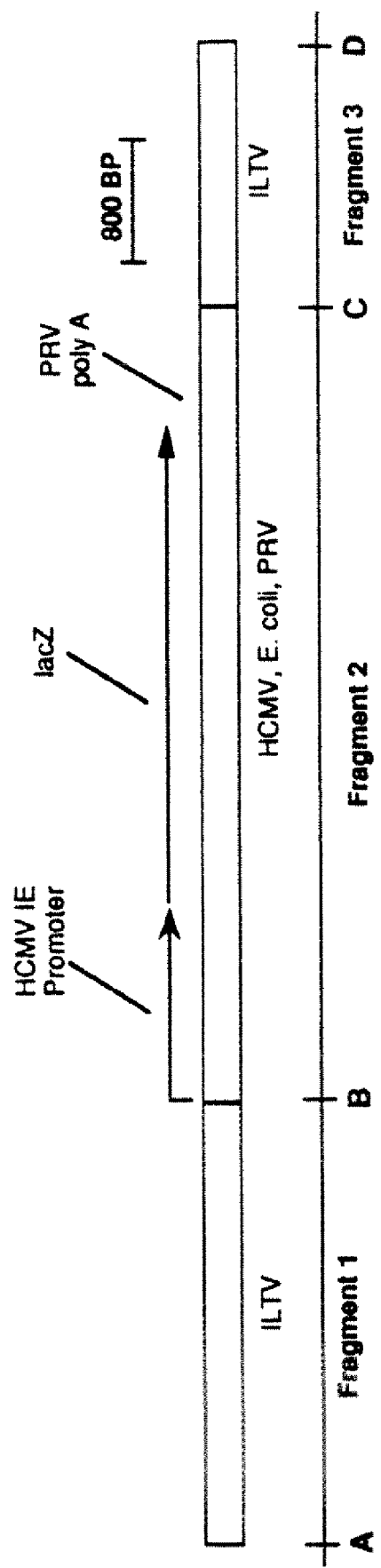

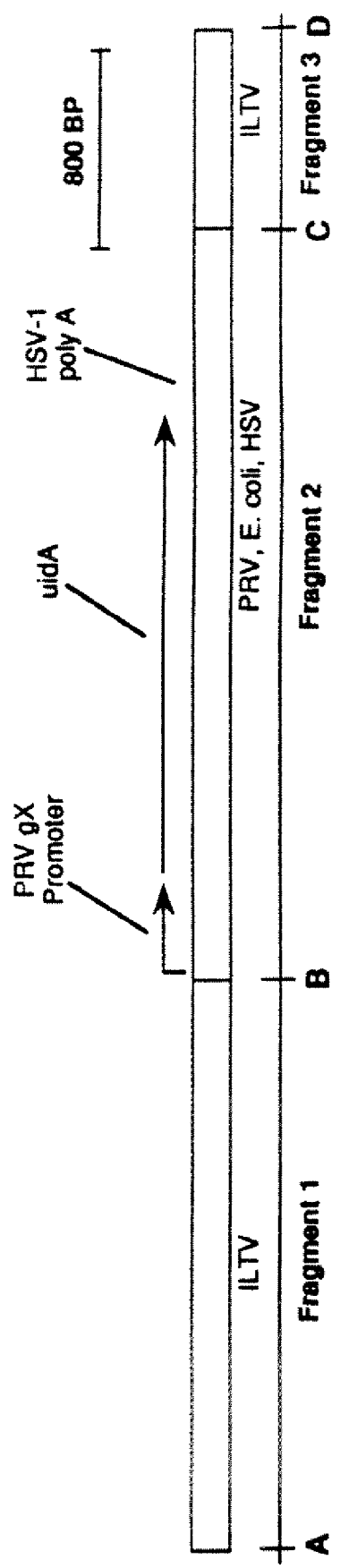

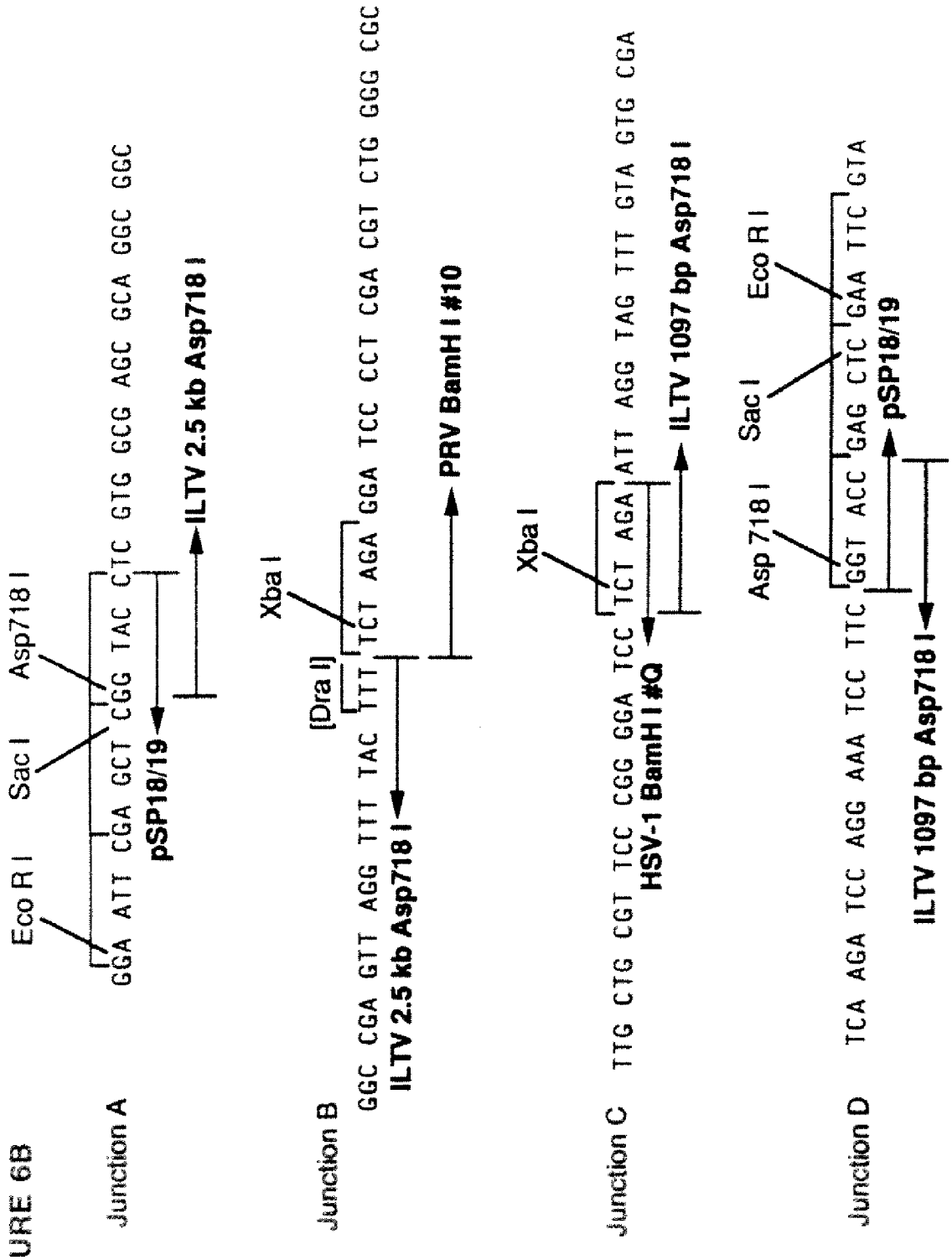

| DNA | Origin | Sites | Size |
|---|---|---|---|
| Vector | pUC19 | Asp718 I—Hind III | ~2647 BP |
| Fragment 1 | ILTV 8.0 kb Asp718 I | Asp718 I—Xba I | ~1619 BP |
| Fragment 2 | ILTV 8.0 kb Asp718 I | Xba I—Xho I† | ~691 BP |
| Fragment 3 | HSV-1, E. coli, PRV | Sal I—Sal I | ~3051 BP |
| Fragment 4 | ILTV 8.0 kb Asp718 I | Xho I†—Hind III | ~624 BP |
| Fragment 5 | ILTV 8.0 kb Asp718 I | Hind III—Hind III | ~2700 BP |

† Restriction enzyme site introduced by PCR cloning

| FIGURE 7A |
| FIGURE 7B |
| FIGURE 7C |

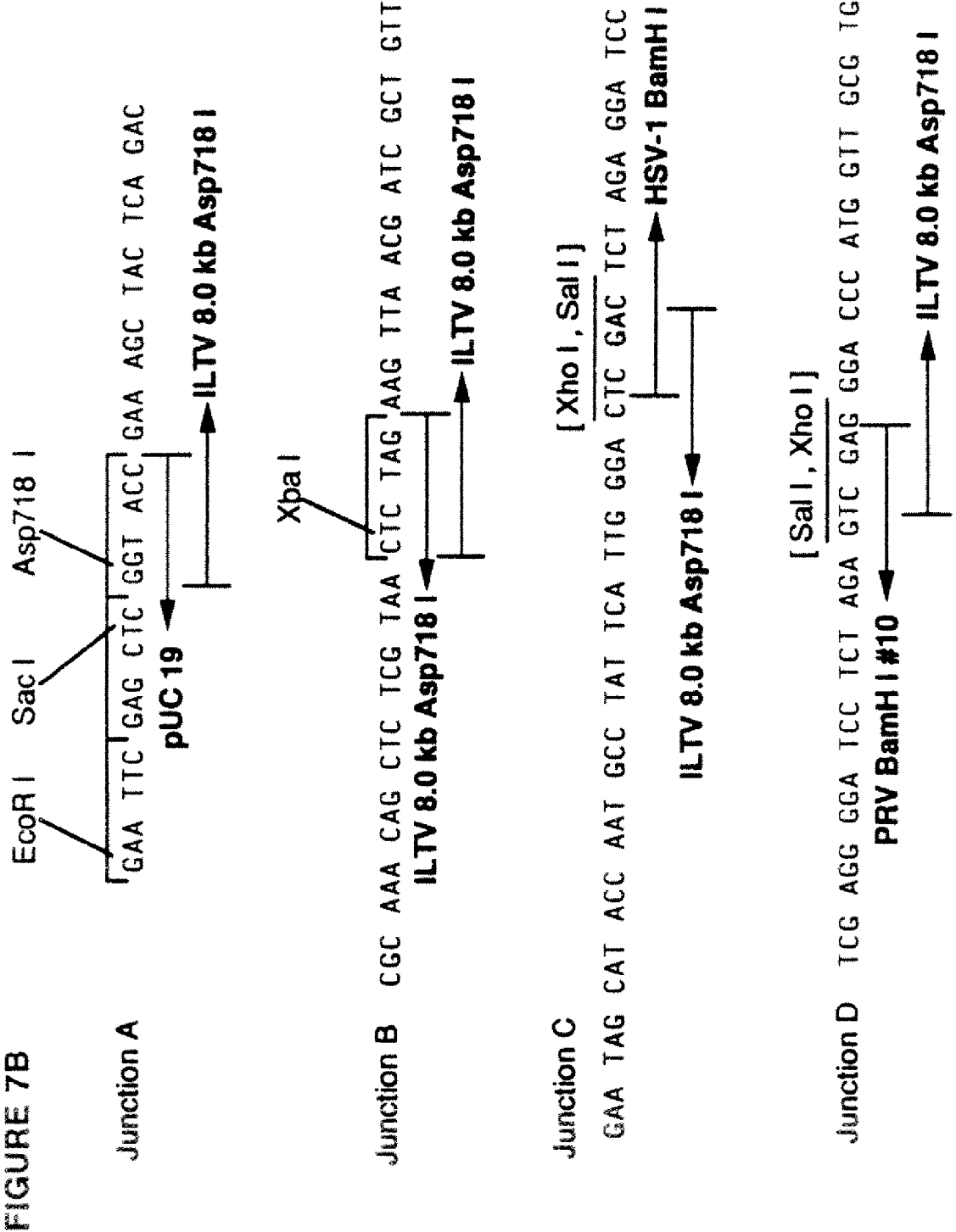

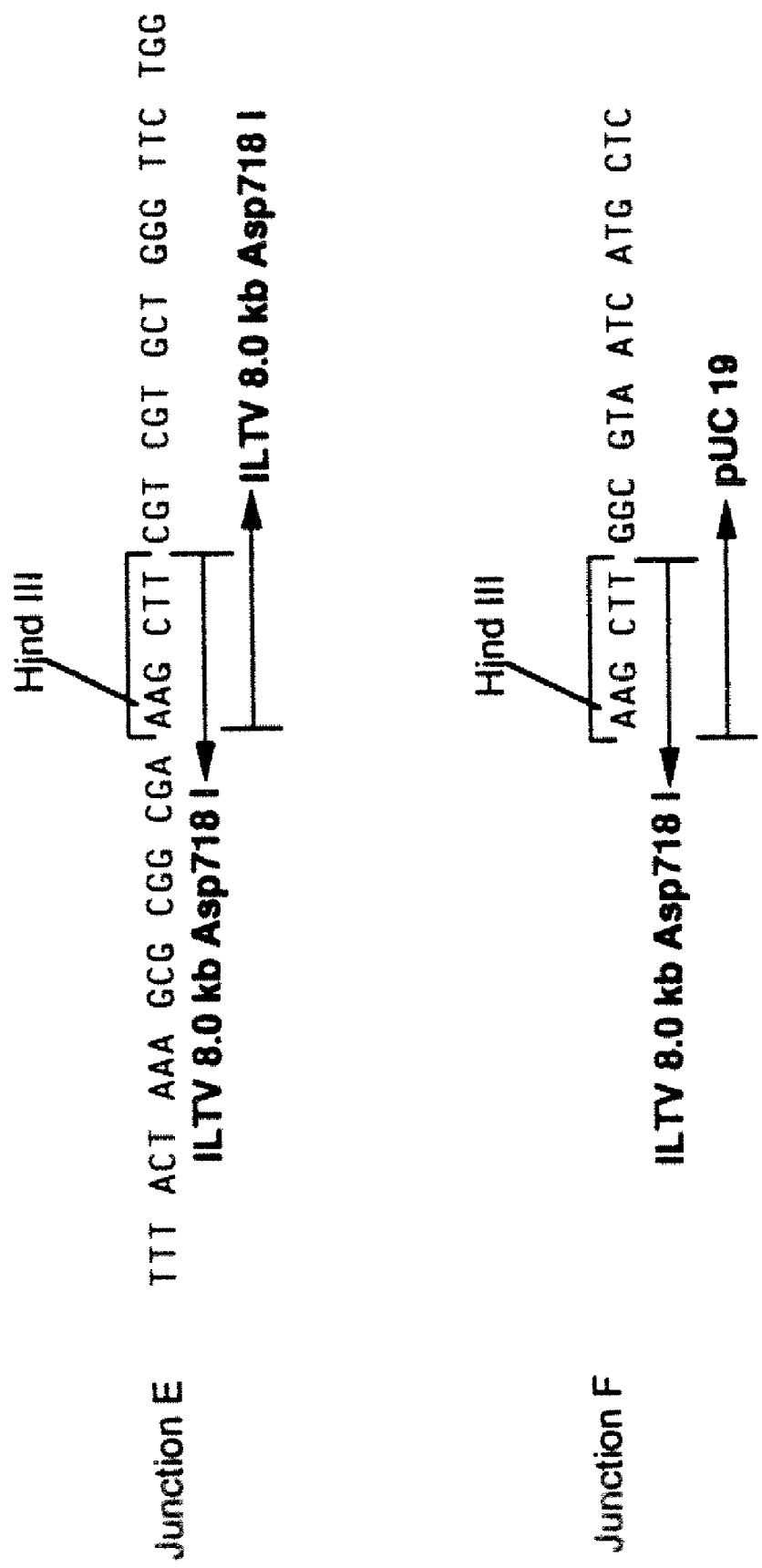

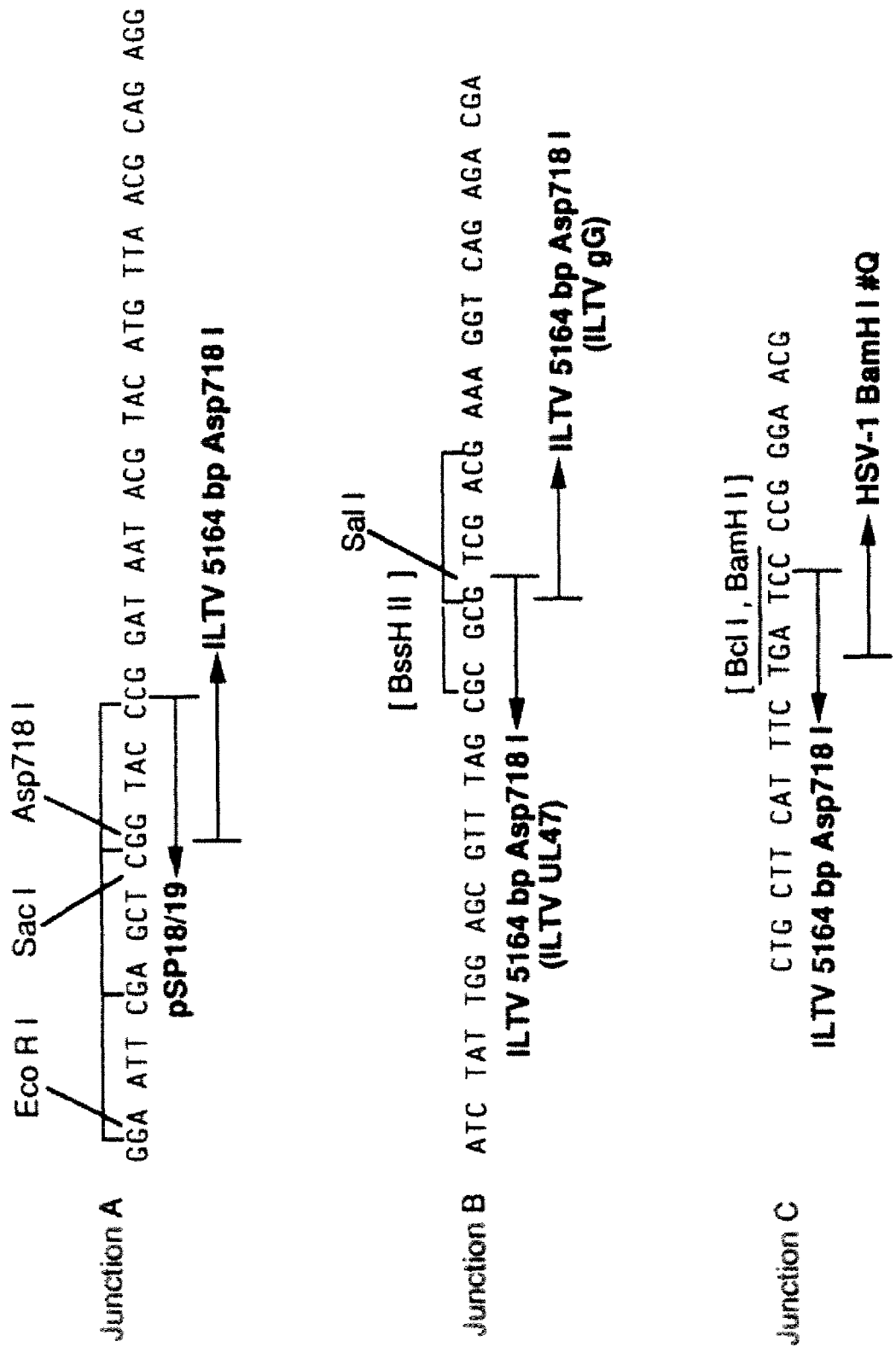

| DNA | Origin | Sites | Size |
| --- | --- | --- | --- |
| Vector | pUC19 | Asp718 I—BamH I | ~2677 BP |
| Fragment 1 | ILTV 5164 bp Asp718I | Asp718 I—Nhe I | ~2830 BP |
| Fragment 2 | PRV, E. coli, HSV-1 | Sal I—Sal I | ~3051 BP |
| Fragment 3 | ILTV 4545 bp BamH I | Sal I—BamH I | ~1709 BP |

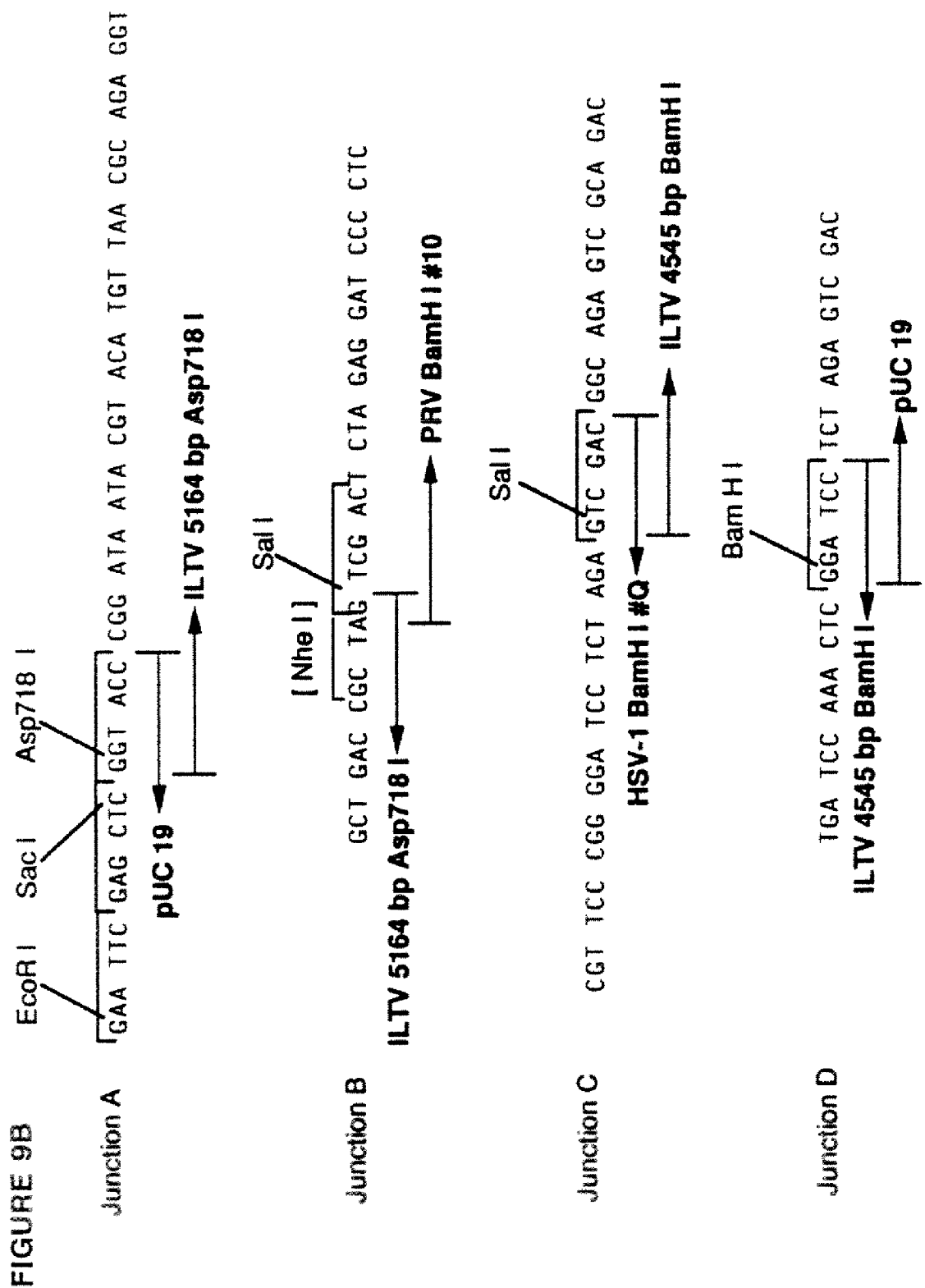

| DNA | Origin | Sites | Size |
|---|---|---|---|
| Vector | pSP 71 | Xma I—Sma I | ~3066 BP |
| Fragment 1 | PRV BamH I #10 | Sal I—EcoR I† | ~ 422 BP |
| Fragment 2 | pRAJ 260 | EcoR I†—Xma I† | ~1826 BP |
| Fragment 3 | HSV-1 BamH I #Q | Xma I—Xma I | ~ 784 BP |

†Restriction enzyme site introduced by PCR cloning

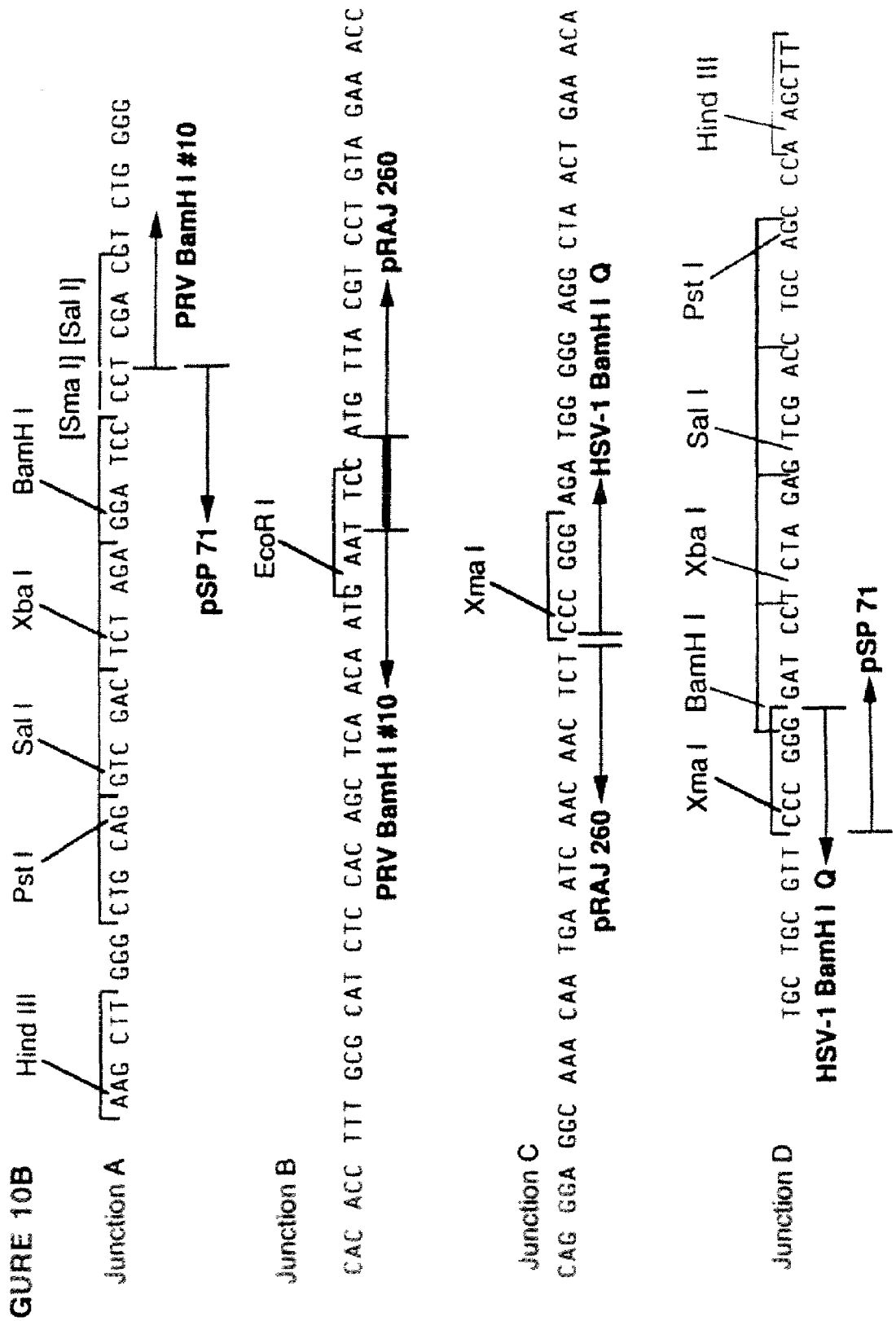

| DNA | Origin | Sites | Size |
|---|---|---|---|
| Vector | pSP 72 | Pst I—Pst I | ~3076 BP |
| Fragment 1 | HCMV 2.1 kb Pst I | Pst I—Ava II | ~1154 BP |
| Fragment 2 | pJF 751 | BamH I—Pvu II | ~3010 BP |
| Fragment 3 | PRV BamH I #7 | Nde I—Sal I | ~ 750 BP |

FIGURE 17

```
ILT 277  QHGPMAAVFRNAGAGLFLWPAMRAAFEERDKRLLRACLSSLDIMDAAVLASF
              | ||||||::  :::|:  |::::||  ::   ..:|:||.|
HSV 351  QSGPDAAVFRSSLGSLLYWPGVRALLDRDCRVAARYAGRMTYLATGALLARF
         ..:|:|||||: ::|||::::  :||||:::.:    ::  ||.|  |||||
EHV 531  LRTPNSAVFRAFFGSLVYWAELRLALRDPASINCRYVGFHLQTSEIYLLARA
         :|.|  ::: ||  :|||||.|||  ||  |:   ::   |:. :|||||||  :|
MDV 472  MRDPMASAARASYGSLAYWPELRCALGSENKRIVRYAIVAMLQAEIYLLTRI
```

RECOMBINANT INFECTIOUS LARYNGOTRACHEITIS VIRUS AND USES THEREOF

This application is a divisional of U.S. Ser. No. 11/342,171, filed on Jan. 27, 2006, now U.S. Pat. No. 7,364,893, which is a divisional of U.S. Ser. No. 10/836,383, filed on Apr. 30, 2004, now U.S. Pat. No. 7,045,598, which is a divisional of U.S. Ser. No. 09/994,064 filed Nov. 6, 2001, now U.S. Pat. No. 6,984,728, which is a divisional of U.S. Ser. No. 08/468,190 filed Jun. 6, 1995, now abandoned, which is a continuation of U.S. Ser. No. 08/410,121 filed Mar. 23, 1995, now abandoned, which is a continuation-in-part of U.S. Ser. No. 08/126,597 filed Sep. 24, 1993, now abandoned, the contents of all of which are hereby incorporated by reference in their entireties into this application.

Within this application several publications are referenced by arabic numerals within parentheses. Full citations for these publications may be found at the end of the specification preceding the claims. The disclosures of these publications are hereby incorporated by reference into this application in order to more fully describe the state of the art to which this invention pertains.

BACKGROUND OF THE INVENTION

Infectious laryngotracheitis virus is a herpesvirus that causes a respiratory illness of varying virulence in chickens. Live attenuated ILTV vaccines are available to protect against the disease, but several reports have implicated vaccine viruses in the possible recurrence and spread of the disease (65 and 72), limiting vaccination to use in uninfected birds early in an outbreak. In order to design a more efficacious, attenuated vaccine, the genomic organization of the ILTV virus has been studied.

The ability to isolate viral DNA and clone this isolated DNA into bacterial plasmids has greatly expanded the approaches available to make viral vaccines. The methods used to make the present invention involve modifying cloned viral DNA sequences by insertions, deletions and single or multiple base changes. The modified DNA is then reinserted into the viral genome to render the virus non-pathogenic. The resulting live virus may then be used in a vaccine to elicit an immune response in a host animal and to protect the animal against a disease.

One group of animal viruses, the herpesviruses or Herpetoviridae, is an example of a class of viruses amenable to this approach. These viruses contain 100,000 to 200,000 base pairs of DNA as their genetic material. Importantly, several regions of the genome have been identified that are nonessential for the replication of virus in vitro in cell culture. Modifications in these regions of the DNA may lower the pathogenicity of the virus, i.e., attenuate the virus. For example, inactivation of the thymidine kinase gene renders human herpes simplex virus non-pathogenic (1), and pseudorabies virus of swine non-pathogenic (2).

Removal of part of the repeat region renders human herpes simplex virus non-pathogenic (3, 4). A repeat region has been identified in Marek's disease virus that is associated with viral oncogenicity (5). A region in herpesvirus saimiri has similarly been correlated with oncogenicity (6). Removal of part of the repeat region renders pseudorabies virus non-pathogenic (U.S. Pat. No. 4,877,737, issued Oct. 31, 1989). A region in pseudorabies virus has been shown to be deleted in naturally-occurring vaccine strains (7, 8) and it has been shown that these deletions are at least partly responsible for the lack of pathogenicity of these strains.

It is generally agreed that herpesviruses contain non-essential regions of DNA in various parts of the genome. Some of these regions are associated with virulence of the virus, and modification of them leads to a less-pathogenic virus, from which a vaccine may be derived.

Infectious laryngotracheitis virus (ILTV), an alpha herpesvirus (9), is an important pathogen of poultry in the USA, Europe, and Australia, responsible for egg production losses and death (10). It causes an acute disease of chickens which is characterized by respiratory depression, gasping and expectoration of bloody exudate. Viral replication is limited to cells of the respiratory tract wherein infection of the trachea gives rise to tissue erosion and hemorrhage. In chickens, no drug has been effective in reducing the degree of lesion formation or in decreasing clinical signs. Vaccination of birds with various modified forms of de ILT virus derived by cell passage and/or tedious regimes of administration have been used to confer acceptable protection in susceptible chickens. Due to the limited degree of attenuation of current ILTV vaccines care must be taken to assure that the correct level of virus is maintained: enough to provide protection, but not enough to cause disease in the flock (11-21). Furthermore, these viruses may revert back to virulence, causing disease rather than providing protection against it.

ILTV has been analyzed at the molecular level. Restriction maps of the ILTV genome have been reported (22-26). The DNA sequence of several genes have been identified, i.e., thymidine kinase (27, 28), glycoprotein gB (27, 29, 30), ribonucleotide reductase (27, 31), capsid p40 (31, 32).

Furthermore, Shepard, et al. (53) disclosed that several genes located in the unique long region of the infectious laryngotracheitis virus genomic DNA are non-essential for viral replication.

Applicants have unexpectedly found that the unique short region of the ILT virus genomic DNA contains genes that are associated with ILTV virulence and that a deletion in those genes leads to an attenuated ILTV. Particularly, it was found that a deletion in the glycoprotein G (gG) gene of the ILT virus results in an attenuated virus, which is useful as a vaccine against subsequent attack by a virulent ILTV strains.

Applicants also found that a deletion in the glycoprotein I (gI) gene of the unique short region also attenuates the ILTV. Furthermore, it is contemplated that a deletion in the US2 gene, the UL-47 like gene, and the glycoprotein g60 gene of the unique short region will also attenuate the ILTV.

ILTV can become latent in healthy animals which makes term potential carriers of the virus. For this reason, it is clearly advantageous to be able to distinguish animals vaccinated with non-virulent virus from animals infected with disease-causing wild-type or naturally-occurring virus. The development of differential vaccines and companion diagnostic tests has proven valuable in the management of pseudorabies disease (55). A similar differential marker vaccine would be of great value in the management of ILTV caused disease. The construction of differential diagnostics has focused on the deletion of glycoproteins. Theoretically, the glycoprotein chosen to be the diagnostic marker should have the following characteristics: (1) the glycoprotein and its gene should be non-essential for the production of infectious virus in tissue culture; (2) the glycoprotein should elicit a major serological response in the animal; and (3) the glycoprotein should not be one that makes a significant contribution to the protective immunity.

The ILT virus has been shown to specify at least four major glycoproteins as identified by monoclonal antibodies ($M_r$=205K, 115K, 90K and 60K). Three glycoproteins seem to be antigenically related ($M_r$=205K, 115K, and 90K) (34-36).

Three major ILT virus glycoproteins, gB (29, 30), gC (27, 51), and g60 (34, 53) have been described in the literature. These three genes have been sequenced and two of the ILTV genes have been shown to be homologous to the HSV glycoproteins gB, and gC.

Of these, it is known that the ILTV gB gene is an essential gene and would not be appropriate as deletion marker genes. Furthermore, the gC gene of herpesviruses has been shown to make a significant contribution to protective immunity as a target of neutralizing antibody (56) and as a target of cell-mediated immunity (57). Therefore, the gC gene is not desirable as a deletion marker gene.

As to other glycoprotein encoding genes cited above, it is not known whether or not they would be suitable candidates for deletion in order to construct a recombinant ILT virus which can be used as a diagnostic vaccine.

Applicants have unexpectedly found that there are two glycoprotein encoding genes located within the unique short region of the ILT viral genome which could be safely deleted in order to construct a recombinant ILT virus that can be used as a diagnostic vaccine. These are the glycoprotein gG gene and the glycoprotein gI gene. By genetically engineering an ILT virus with a deletion in the glycoprotein G gene or the glycoprotein I gene, a ILT virus is produced which does not express any glycoprotein G or glycoprotein I. None of the prior arts teach or suggest that these two genes in the unique short region of the virus are appropriate candidates for deletion in order to create a diagnostic ILT virus vaccine. Although several of the herpesviruses have been genetically engineered, no examples of recombinant ILTV have been reported.

The ability to engineer DNA viruses with large genomes, such as vaccinia virus and the herpesviruses, has led to the finding that these recombinant viruses can be used as vectors to deliver vaccine antigens and therapeutic agents for animals. The herpesviruses are attractive candidates for development as vectors because their host range is primarily limited to a single target species (37) and they have the capacity for establishing latent infection (38) that could provide for stable in vivo expression of a foreign gene. Although several herpesvirus species have been engineered to express foreign gene products, recombinant infectious laryngotracheitis viruses expressing foreign gene products have not been constructed. The infectious laryngotracheitis viruses described above may be used as vectors for the delivery of vaccine antigens from microorganisms causing important poultry diseases. Other viral antigens which may be included in a multivalent vaccine with an ILTV vector include infectious bronchitis virus (IBV), Newcastle disease virus (NDV), infectious bursal disease virus (IBDV), and Marek's disease virus (MDV). Such multivalent recombinant viruses would protect against ILT disease as well as other diseases. Similarly the infectious laryngotracheitis viruses may be used as vectors for the delivery of therapeutic agents. The therapeutic agent that is delivered by a viral vector of the present invention must be a biological molecule that is a by-product of ILTV replication. This limits the therapeutic agent in the first analysis to either DNA, RNA or protein. There are examples of therapeutic agents from each of these classes of compounds in the form of anti-sense DNA, anti-sense RNA (39) ribozymes (40), suppressor tRNAs (41), interferon-inducing double stranded RNA and numerous examples of protein therapeutics from hormones, e.g., insulin, to lymphokines, e.g., interferons and interleukins, to natural opiates. The discovery of these therapeutic agents and the elucidation of their structure and function does not necessarily allow one to use them in a viral vector delivery system, however, because of the experimentation necessary to determine whether an appropriate insertion site exists.

ILTV is classified as an alpha herpesvirus with a type D genome (78) composed of a unique long region and a unique short region flanked by inverted repeats. A genomic restriction map of an Australian ILTV isolate (SA-2) was described by Johnson et al. (66). Using this map, Guo et al. (62) isolated and sequenced a DNA fragment from the USDA challenge strain which appeared to be derived from the unique short region. Applicants map the USDA challenge strain of ILTV, and reports characteristics of the putative genes present in the unique short region. The map disclosed herewith indicates that the sequence identified by Guo et al. (62) is part of the short repeat sequence, and is not from the unique short. Other reports (69 and 70) describe the sequences of two genes, one homologous to PRV gG and the other unlike other reported herpesvirus genes. These two genes were mapped to the unique long region of SA-2. However, these sequences are identical to sequences identified in this application as being from the unique short region. The data in this application indicate that the overall organization of the short region of ILTV is similar to other herpesviruses.

SUMMARY OF THE INVENTION

The present invention provides a recombinant attenuated infectious laryngotracheitis virus comprising the infectious laryngotracheitis viral genome which contains a deletion in the glycoprotein gG gene. This attenuated virus is useful as a vaccine against infectious laryngotracheitis virus.

The present invention also provides a recombinant, attenuated infectious laryngotracheitis virus comprising the infectious laryngotracheitis viral genome which contains a deletion in the US2 gene, UL47-like gene, ORF4 gene or glycoprotein g60 gene.

The present invention also provides a method for distinguishing chickens or other poultry vaccinated with a recombinant infectious laryngotracheitis virus which produces no glycoprotein gG from those infected with a naturally-occurring infectious laryngotracheitis virus.

BRIEF DESCRIPTION OF THE FIGURES

FIGS. 1A-1H: The nucleotide sequence of 13,473 base pairs of contiguous DNA from the unique short region of the ILT virus. This sequence contains the entire 13,098 base pair unique short region as well as 273 base pairs of repeat region at one end and 102 base pairs of repeat region at the other end. The nucleotide sequences of FIGS. 1A-1H begin with the internal repeat sequence and end within the terminal repeat sequence. The unique short region begins at base pair 274 of this Figure. Sequence ID NO:59 contains the nucleotide sequence of 18,912 base pairs of contiguous DNA from the unique short and repeat regions of the ILT virus. This sequence contains the entire 13,094 base pair unique short region as well as 2909 base pairs of internal repeat region and 2909 base pairs of short terminal repeat region. The nucleotide sequences begin with the internal repeat sequence and end within the terminal repeat sequence. The unique short region begins at base pair 2910.

FIG. 17: The relationship of herpesvirus UL47 proteins to each other and to the ILTV UL47 homolog in a conserved region. Amino acids shared between ILTV UL47 and the other UL47 proteins are in boldface type. Pairwise comparisons have been made between the sequences as shown. A vertical bar indicates an identical amino acid, two dots indicate a positive probable acceptable mutation rate and one dot indicates a neutral probable acceptable mutation rate (60).

DETAILED DESCRIPTION OF THE INVENTION

Figure 2:
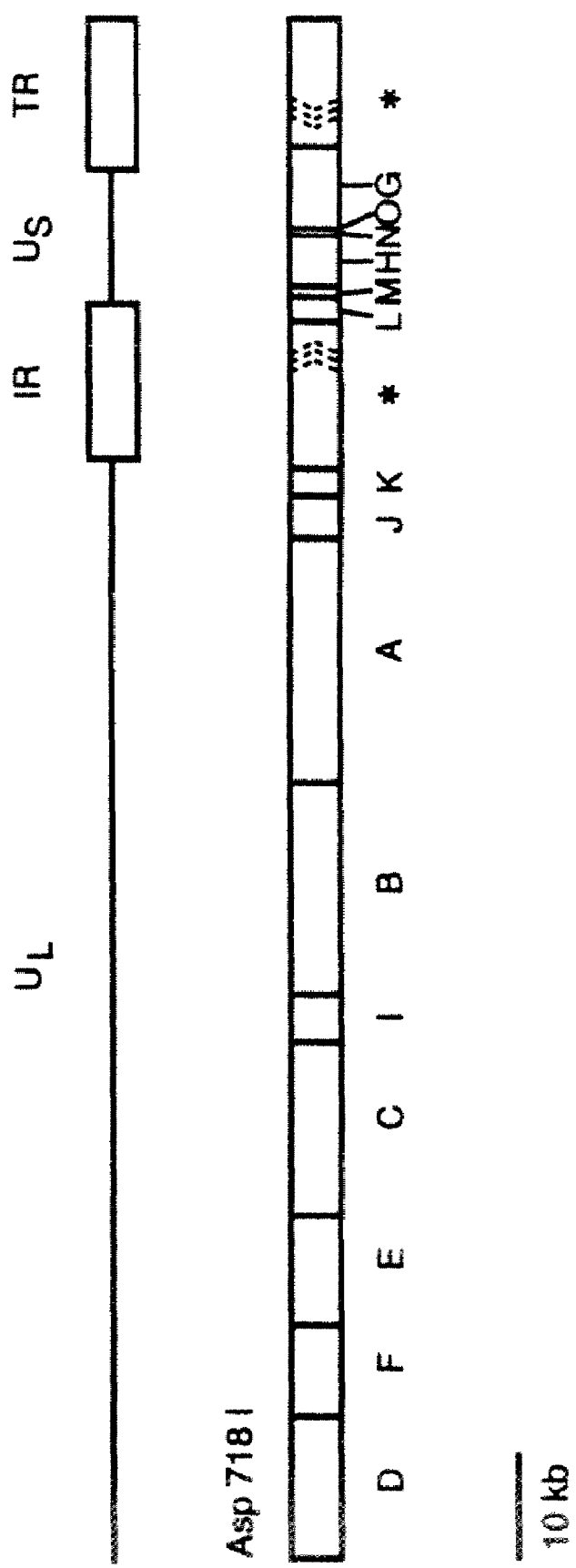
FIG. 2: Asp718 I restriction enzyme map of the infectious laryngotracheitis virus (ILTV) USDA 83-2 genome. The upper diagram identifies the unique long ($U_L$) internal repeat (IR), unique short ($U_S$), and terminal repeat (TR) sections found in the ILTV genome. A map of the Asp718 I restriction endonuclease sites in the ILTV genome is shown below. Letters A through O identify Asp718 I restriction endonuclease fragments with "A" representing the largest fragment. Fragment "L" is the 2.5 kb Asp718 I fragment, fragment "H" is the 5164 bp Asp718 I fragment, and fragment "G" is the 8.0 kb Asp718 I fragment. The fragments marked with asterisks cont tion of DNA fragments assembled in plasmid 544-39.13. The origin of each fragment is indicated in the table. The sequences located at each of the junctions between fragments are also shown (SEQ ID NO's: 47, 48, 49 and 50). The restriction sites used to generate each fragment as well as the synthetic linker sequences which were used to join the fragments are described for each junction. The synthetic linker sequences are underlined by a heavy bar. The location of several gene coding regions and regulatory elements is also given. Restriction sites in brackets [ ] indicate the remnants of sites which were destroyed during construction. The following abbreviations are used, pseudorabies virus (PRV), β-glucuronidase gene (uidA), *Escherichia coli* (*E. coli*), herpes simplex virus type 1 (HSV-1), polyadenylation signal (poly A), and base pairs (BP).
Figure 4B:
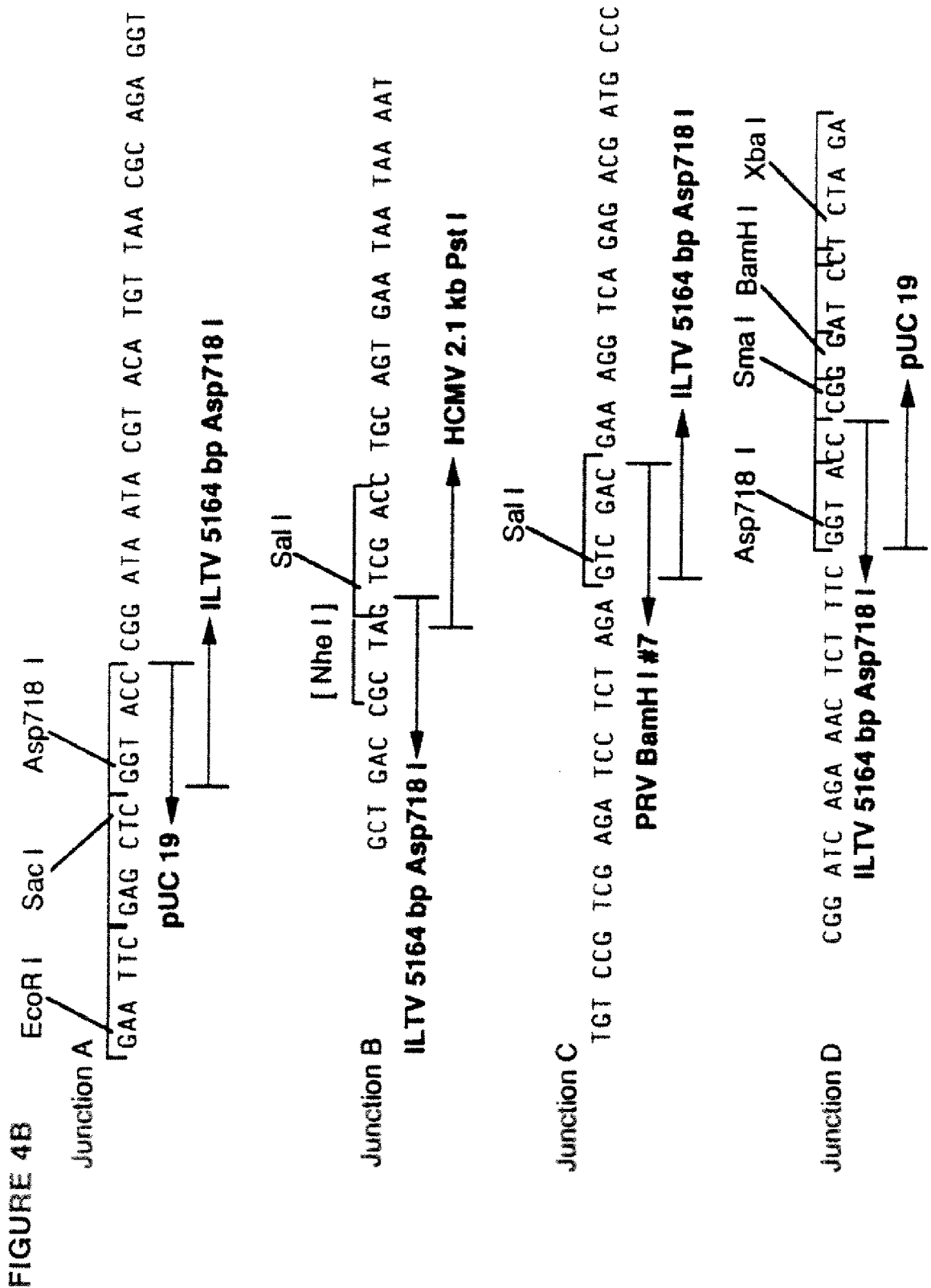
Figure 5A:
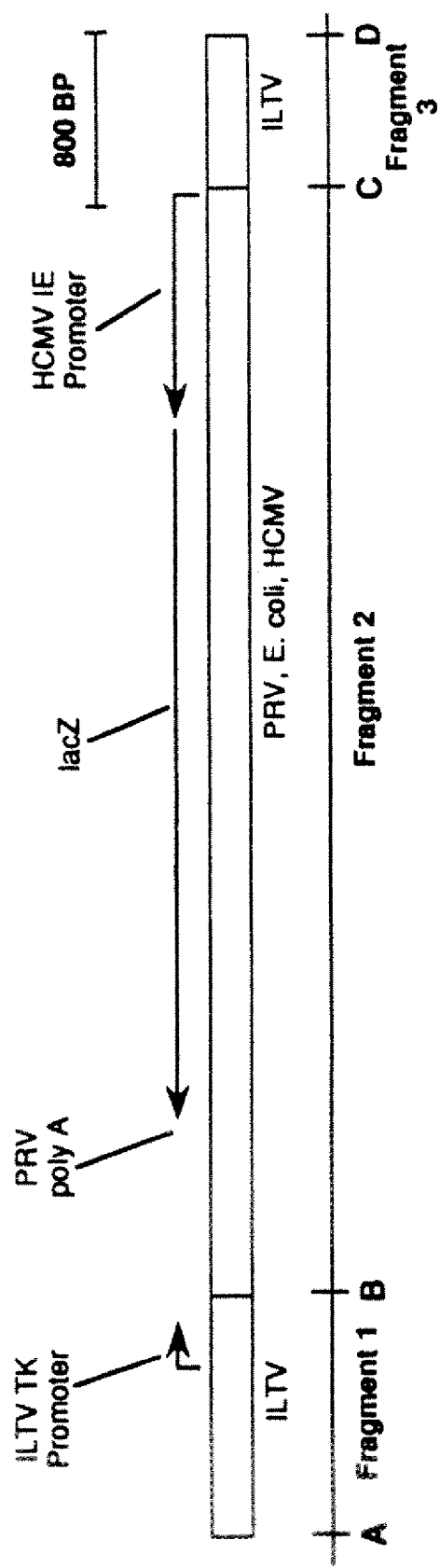
Figure 5B:
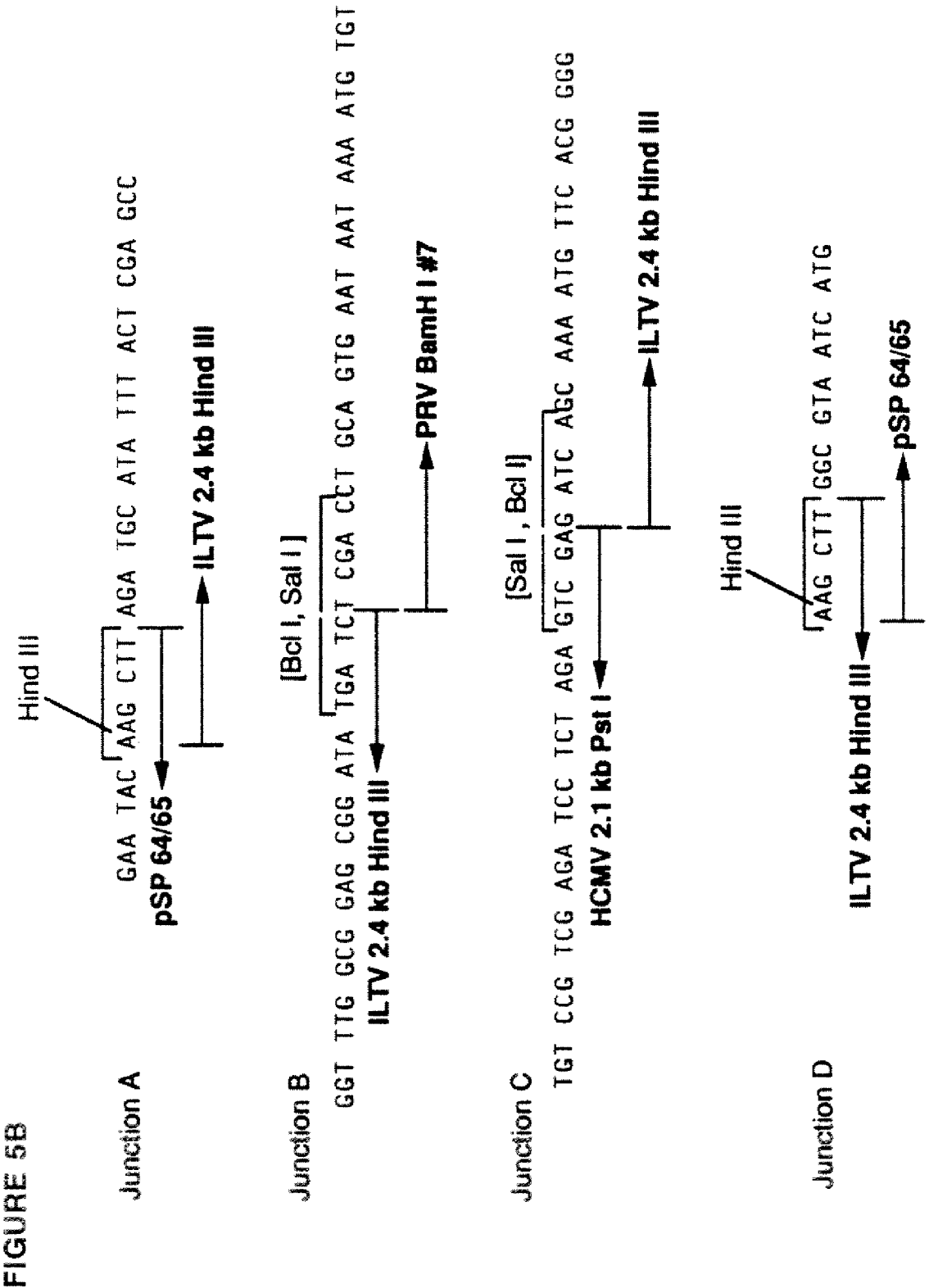
Figure 7A:
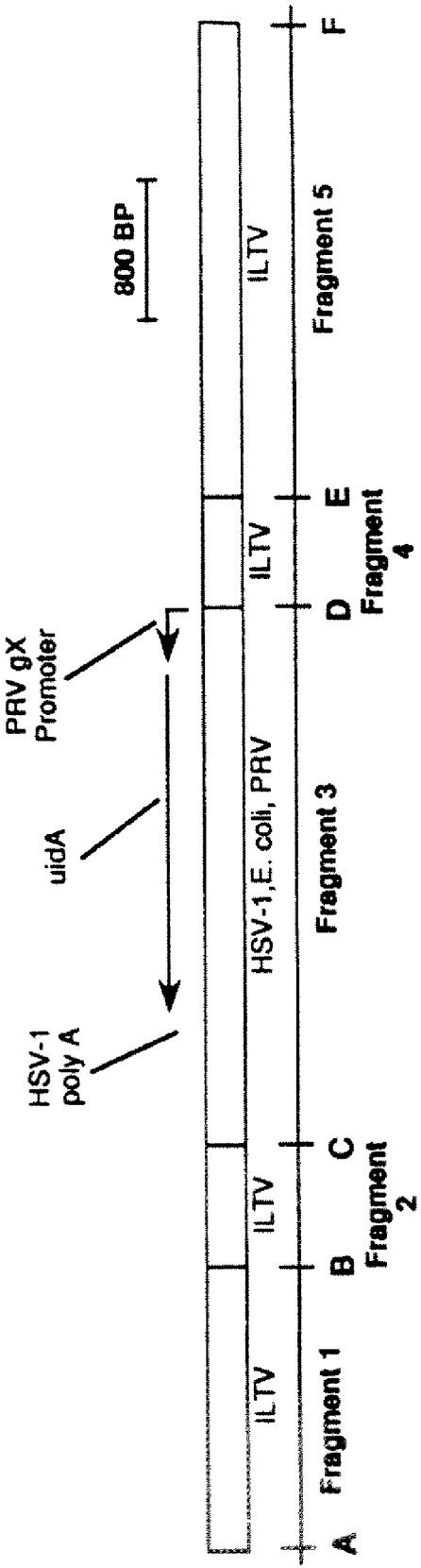
Figure 8A:
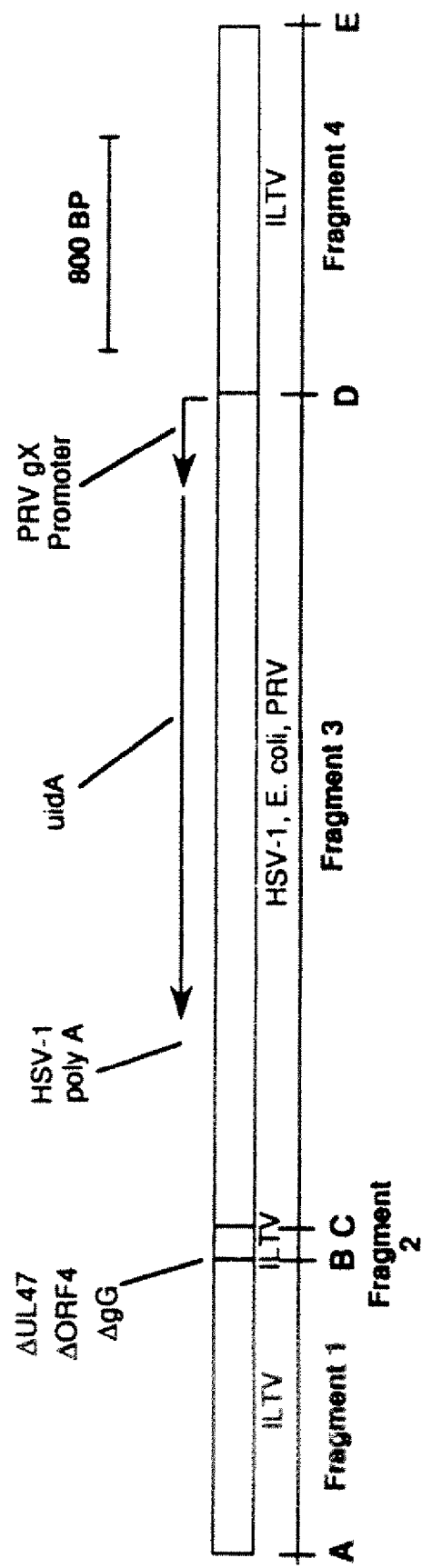
Figure 8C:
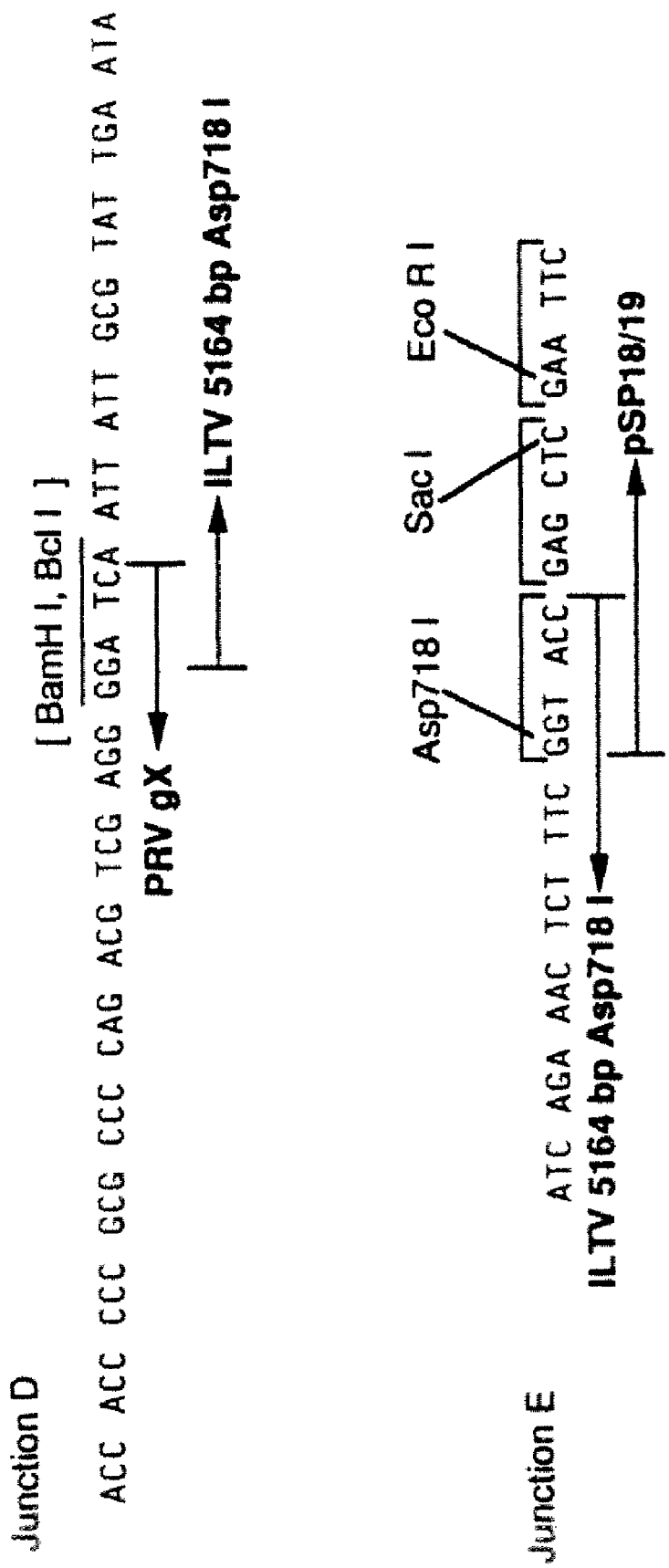
Figures 9A, 9B:
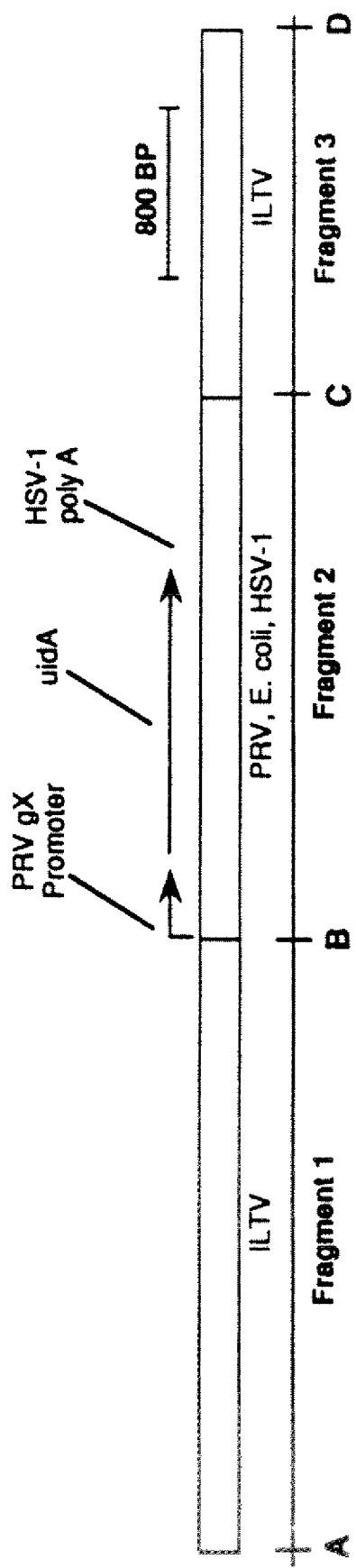
Figure 10A:
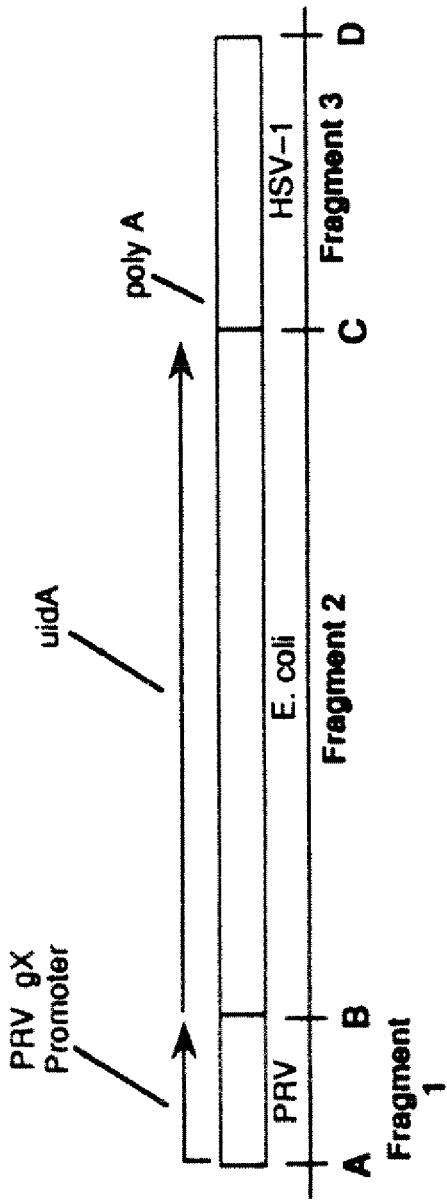
Figure 11A:
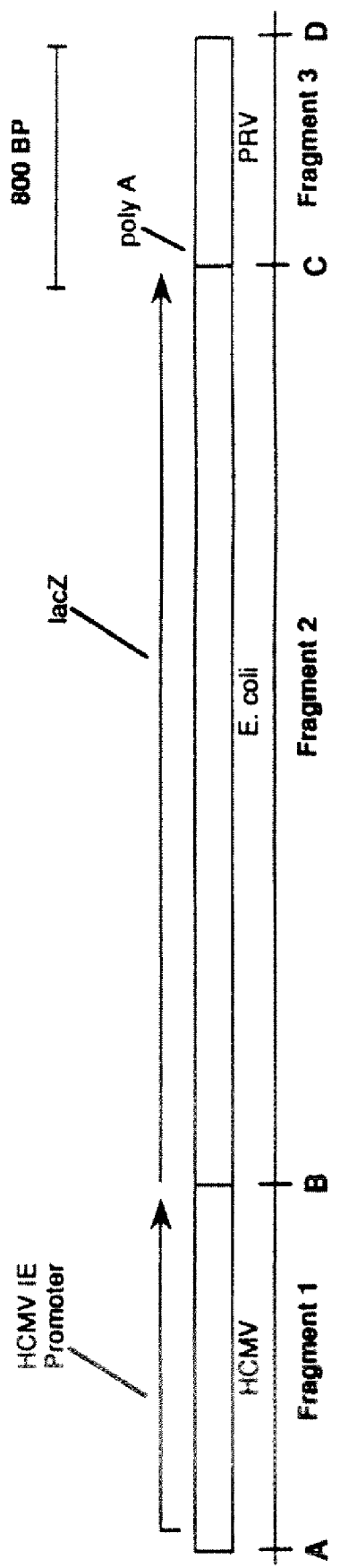
FIGS. 11A-11C: Detailed description of the DNA insertion in Plasmid Vector 388-65.2. Diagram showing the orientation of DNA fragments assembled in plasmid 388-65.2. The origin of each fragment is indicated in the table. The sequences located at each of the junctions between fragments are also shown (SEQ ID NO's: 51, 52, 53, and 54). The restriction sites used to generate each fragment as well as the synthetic linker sequences which were used to join the fragments are described for each junction. The synthetic linker sequences are underlined by a heavy bar. The location of several gene coding regions and regulatory elements is also given. Restriction sites in brackets [ ] indicate the remnants of sites which were destroyed during construction. The following abbreviations are used, human cytomegalovirus immediate early (HCMV IE), lactose operon Z gene (lacZ), *Escherichia coli* (*E. coli*), pseudorabies virus (PRV), polyadenylation signal (poly A), and base pairs (BP).
Figure 11B:
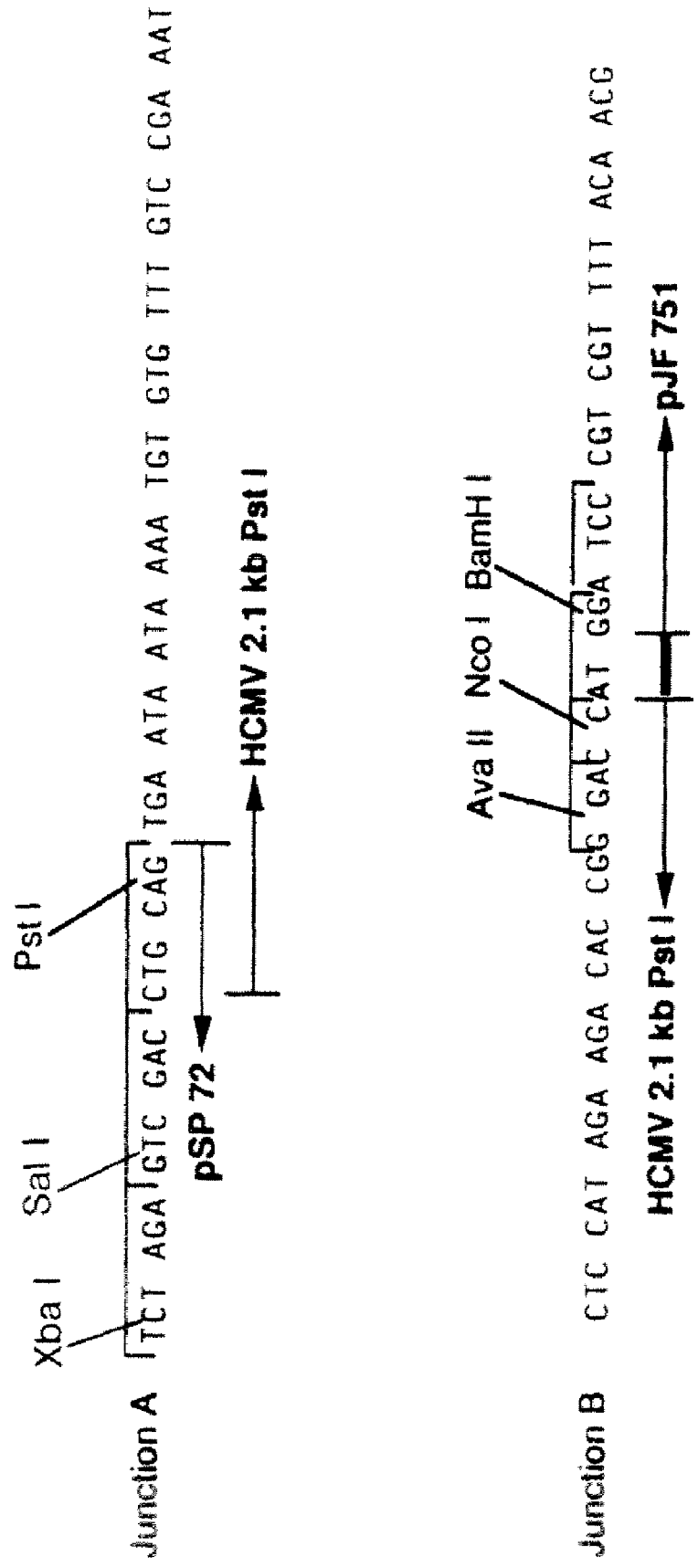
Figure 11C:
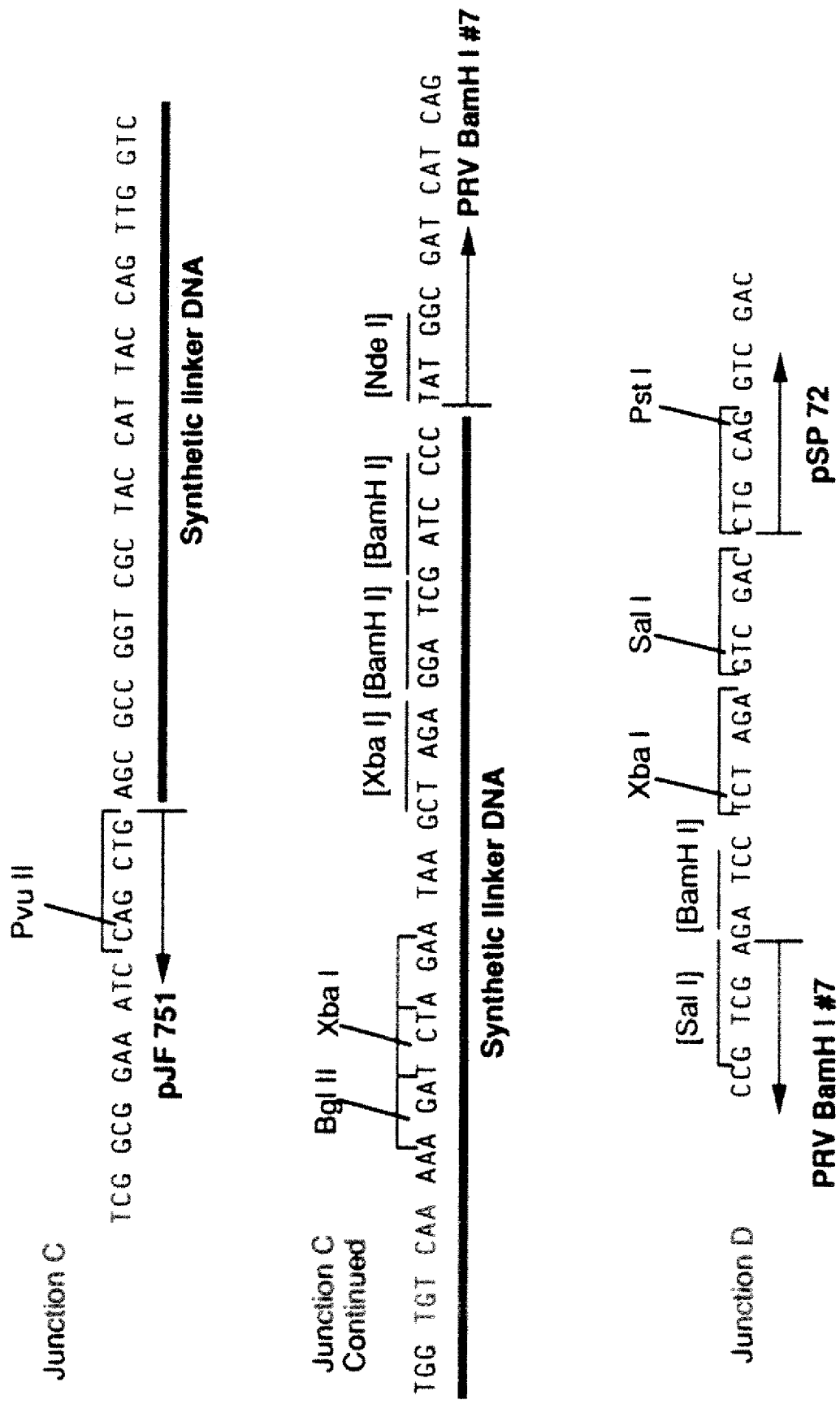

The present invention provides a recombinant infectious laryngotracheitis virus comprising the infectious laryngotracheitis viral genome which contains a deletion in the unique short region of the viral genome, wherein the deletion is in the glycoprotein gG gene. Said deletion attenuates the virus, rendering it suitable for use as a vaccine against infectious laryngotracheitis virus. A preferred embodiment of this invention is a recombinant infectious laryngotracheitis designated S-ILT-014 (ATCC Accession No, 2427). The S-ILT-014 virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. on Sep. 22, 1993 under ATCC Accession No. 2427). Another preferred embodiment of this invention is a recombinant infectious laryngotracheitis virus designated S-ILT-002.

For purposes of this invention, "a recombinant infectious laryngotracheitis virus" is a live infectious laryngotracheitis virus which has been generated by the recombinant methods well known to those of skill in the art, e.g., the methods set forth in DNA TRANSFECTION FOR GENERATING RECOMBINANT ILT VIRUS in Materials and Methods, and the virus has not had genetic material essential for the replication of the infectious laryngotracheitis virus deleted.

The present invention further provides a recombinant infectious laryngotracheitis virus comprising the infectious laryngotracheitis viral genome which contains a deletion in the glycoprotein gG gene and a deletion in the US2 gene. One preferred embodiment of this invention is a recombinant infectious laryngotracheitis virus designated S-ILT-009.

The present invention further provides a recombinant laryngotracheitis virus comprising the infectious laryngotracheitis viral genome which contains a deletion in the glycoprotein gG gene and a deletion in the ORF4 gene.

The present invention further provides a recombinant infectious laryngotracheitis virus which comprises the infectious laryngotracheitis viral genome which contains a deletion in the glycoprotein gG gene and a deletion in the UL47-like gene.

The present invention further provides a recombinant infectious laryngotracheitis virus which comprises the infectious laryngotracheitis viral genome which contains a deletion in the glycoprotein gG gene, a deletion in the ORF4 gene, and a deletion in the UL47-like gene. A preferred embodiment of this invention is a recombinant infectious laryngotracheitis virus designated S-ILT-015.

The present invention further provides a recombinant infectious laryngotracheitis virus which comprises the infectious laryngotracheitis viral genome which contains a deletion in the glycoprotein gG gene and a deletion in the glycoprotein g60 gene. A preferred embodiment of this invention is a recombinant infectious laryngotracheitis virus designated S-ILT-017.

The present invention further provides a recombinant infectious laryngotracheitis virus comprising the infectious laryngotracheitis viral genome which contains a deletion in the glycoprotein gG gene and a deletion in the glycoprotein gI gene.

The present invention further provides a recombinant infectious laryngotracheitis virus which comprises the infectious laryngotracheitis viral genome containing a deletion in the glycoprotein gG gene and a deletion in the thymidine kinase (TK) gene.

The present invention further provides a recombinant infectious laryngotracheitis virus comprising the infectious laryngotracheitis virus genome which contains a deletion in the unique short region of the viral genomic wherein the deletion in the glycoprotein gG gene and which also contains an insertion of a foreign gene. The foreign gene is inserted into a non-essential site of the infectious laryngotracheitis viral genome in such a way that it is capable of being expressed in a recombinant infectious laryngotracheitis infected host cell.

For purposes of this invention, "a non-essential site" of the infectious laryngotracheitis viral genome is a region of the viral genome which is not necessary for viral infection and replication.

The following non-essential sites of the infectious laryngotracheitis viral genome are preferred sites for inserting a foreign gene into the virus: the thymidine kinase (TK) gene, the US2 gene, the UL47-like gene, the ORF4 gene, the glycoprotein gG gene, the glycoprotein g60 gene, and the glycoprotein gI gene.

The foreign gene, which is inserted into a non-essential site in the infectious laryngotracheitis viral genome, may encode a screenable marker, such as *E. coli* B-galactosidase or *E. coli* B-glucuronidase.

The foreign gene which is inserted into a non-essential site in the infectious laryngotracheitis viral genome, may encode an antigenic polypeptide which, when introduced into the host cell, induces production of protective antibodies against an avian disease causing agent from which the antigen is derived or derivable. Antigenic polypeptide which includes, but is not limited to: marek's disease virus (MDV) gA, marek's disease virus gB, marek's disease virus gD, Newcastle disease virus (NDV), HN, Newcastle disease virus F, infectious laryngotracheitis virus (ILT) gB, infectious laryngotracheitis virus gI, infectious laryngotracheitis virus gD, infectious bursal disease virus (IBDV) VP2, infectious bursal disease virus VP3, infectious bursal disease virus VP4, infectious bursal disease virus polyprotein, infectious bronchitis virus (IBV) spike, infectious bronchitis virus matrix, avian encephalomyelitis virus, avian reovirus, avian paramyxovirus, avian influenza virus, avian adenovirus, fowl pox virus, avian coronavirus, avian rotavirus, chick anemia virus. *Salmonella* spp. *E. coli, Pasteurella* spp., *Bordetella* spp., *Eimeria* spp., *Histomonas* spp., *Trichomonas* spp. Poultry nematodes, cestodes, trematodes, poultry mites/lice and poultry protozoa.

In one embodiment of the recombinant infectious laryngotracheitis virus the foreign DNA sequence encodes a cytokine. In another embodiment the cytokine is chicken myelomonocytic growth factor (cMGF) or chicken interferon (cIFN). Cytokines include, but are not limited to: transforming growth factor beta, epidermal growth factor family fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropietin, interferon, interferon gamma, leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian. Recombinant ILT virus expressing cytokines is useful to enhance immune response when combined with vaccines containing antigens of disease causing microorganisms.

Recombinant infectious laryngotracheitis virus expressing cytokines is used to enhance the immune response either alone or when combined with vaccines containing cytokines or antigen genes of disease causing microorganisms.

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), *Bordetella pertussis*, Diptheria, *Rickettsia prowazekii, Borrelia berfdorferi*, Tetanus toxoid, malignant tumor antigens.

The antigenic polypeptide of an equine pathogen is derived from equine influenza virus, or equine herpesvirus. In one embodiment the antigenic polypeptide is equine influenza neuraminidase or hemagglutinin. Examples of such antigenic polypeptide are: equine influenza virus type A/Alaska 91 neuraminidase and hemagglutinin, equine influenza virus type A/Prague 56 neuraminidase and hemagglutinin, equine influenza virus type A/Miami 63 neuraminidase, equine influenza virus type A/Kentucky 81 neuraminidase and hemagglutinin, equine herpesvirus type 1 glycoprotein B, and equine herpesvirus type 1 glycoprotein D, *Streptococcus equi*, equine infectious anemia virus, equine encephalitis virus, equine rhinovirus and equine rotavirus.

The antigenic polypeptide of an equine pathogen is derived from bovine respiratory syncytial virus or bovine parainfluenza virus, and is capable of being expressed in a host infected by the recombinant infectious bovine rhinotracheitis virus. For example, the antigenic polypeptide is derived from bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

The foreign gene may be put under control of an endogenous upstream infectious laryngotracheitis virus promoter, or it may be put under control of a heterologous upstream promoter. The heterologous upstream promoter mat be derived from the HCMV IE promoter, the PRV gX promoter, and BHV-1.1 VP8 promoter.

The present invention further provides a recombinant infectious laryngotracheitis virus comprising the infectious laryngotracheitis viral genome which contains a deletion or other alteration in the unique short region of the viral genome, wherein the deletion or alteration is in the glycoprotein gG gene, so that upon replication the recombinant virus produces no glycoprotein gG. The following recombinant viruses are preferred embodiments of this invention: A recombinant infectious laryngotracheitis virus designated S-ILT-002, S-ILT-014, S-ILT-009, S-ILT-015, and S-ILT-017.

The present invention further provides a recombinant infectious laryngotracheitis virus comprising the infectious laryngotracheitis viral genome which contains a deletion or other alteration in the unique short region of the viral genome, wherein the deletion or alteration is in the glycoprotein gI gene so that upon replication, the recombinant virus produces no glycoprotein gI.

The present invention further provides a recombinant infectious laryngotracheitis virus comprising the infectious laryngotracheitis viral genome which contains a deletion or other alteration in the unique short region of the viral genome, wherein the deletion or alteration is in the glycoprotein gG gene and in the glycoprotein gI gene, so that upon replication the recombinant virus produces no glycoprotein gG and no glycoprotein gI.

The present invention further provides a recombinant infectious laryngotracheitis virus comprising the infectious laryngotracheitis viral genome which contains a deletion in the unique short region of the viral genome, wherein the deletion is in the US2 gene, UL47-like gene glycoprotein g60 gene. It is contemplated that a deletion in any one of these genes will attenuate the virus, rendering it suitable to be used as a vaccine against infectious laryngotracheitis virus.

The present invention further provides a recombinant infectious laryngotracheitis virus which comprises a foreign gene inserted within the unique short region of the infectious laryngotracheitis viral genome, provided, however, that the insertion is not in the protein kinase gene, the glycoprotein gD gene, the glycoprotein gE gene and the ORF10 gene. The foreign gene is inserted in such a way that it is capable of being expressed in the recombinant infectious laryngotracheitis virus infected host cell. Preferred insertion sites are the US2 gene, the UL47-like gene, the ORF4 gene and the glycoprotein g60 gene.

A foreign gene may be inserted within any one of these sites in such a way that it may be expressed in a host cell which is infected which the recombinant infectious laryngotracheitis virus of the present invention.

The foreign gene thus inserted may encode a screenable marker, such as *E. coli* β-galactosidase or *E. coli* β-glucuronidase.

The foreign gene thus inserted may encode an antigenic polypeptide which, when introduced into the host cell, induces production of protective antibodies against an avian disease causing agent from which the antigen is derived or derivable. Such antigenic polypeptide may be derived or derivable from infectious bronchitis virus, Newcastle disease virus, infectious bursal disease virus, and Marek's disease virus. Such antigenic polypeptide may also be derived or derivable from avian encephalomyelitis virus, avian reovirus, avian paramyxovirus, avian influenza virus, avian adenovirus, fowl pox virus, avian coronavirus, avian rotavirus, chick anemia agent, *Salmonella* spp. *E. coli, Pasteurella* spp, *Bordetella* spp. *Eimeria* spp. *Histomonas* spp., *Trichomonas* spp, Poultry nematodes, cestodes, trematodes, poultry; mites/lice, poultry protozoa.

The foreign gene thus inserted may be put under control of an endogenous upstream infectious laryngotracheitis virus promoter, or it may be put under control of a heterologous upstream promoter. The heterologous upstream promoter may be the HCMV IE promoter, the PRV gX promoter or BHV-1.1 VP8 promoter.

The present invention further provides a vaccine for infectious laryngotracheitis virus which comprises a suitable carrier and an effective immunizing amount of any of the recombinant infectious laryngotracheitis virus of the present invention. This vaccine may contain either inactivated or live recombinant virus.

Suitable carriers for the recombinant virus are well knows in the art and include proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilizing, hydrolyzed proteins. Preferably, the inactivated vaccine uses tissue culture fluids directly after inactivation of the virus.

The present invention further provides a vaccine which comprises a suitable carrier and an effective immunizing amount of a recombinant infectious laryngotracheitis virus comprising the infectious laryngotracheitis viral genome which contains a deletion in the unique short region of the viral genome, wherein the deletion is in the glycoprotein gG gene. A preferred embodiment of this invention is a vaccine which comprises a suitable carrier and an effective immunizing amount of any one of the following viruses: recombinant infectious laryngotracheitis viruses designated S-ILT-014, S-ILT-002, S-ILT-009, S-ILT-015 and S-ILT-017.

The present invention further provides a multivalent vaccine for infectious laryngotracheitis virus and for one or more of other avian diseases which comprises an effective immunizing amount of a recombinant virus comprising the infectious laryngotracheitis viral genome which contains a deletion in the unique short region wherein the deletion is in the glycoprotein gG gene, and an insertion of a foreign gene into a non-essential site of the viral genome.

The foreign gene encodes an antigenic polypeptide which induces host cell production of protective antibodies against an avian disease causing agent from which the antigen is derived or derivable.

The foreign gene may be derived or derivable from infectious bronchitis virus, Newcastle disease virus, infectious bursal disease virus, and Marek's disease virus, avian encephalomyelitis virus, avian reovirus, avian paramyxovirus, avian influenza virus, avian adenovirus, fowl pox virus, avian coronavirus, avian rotavirus, chick anemia agent, *Salmonella* spp., *E. coli, Pasteurella* spp., *Bordetella* spp., *Eimeria* spp., *Histomonas* spp., *Trichomonas* spp., poultry nematodes, cestodes, trematodes, poultry mites/lice, poultry protozoa.

The present invention further provides a vaccine which comprises a suitable carrier and an effective immunizing amount of a recombinant infectious laryngotracheitis virus comprising the infectious laryngotracheitis viral genome containing a deletion or other alteration in the unique short region of the viral genome, wherein the deletion or alteration is in the glycoprotein gG gene, so that upon replication, the recombinant virus produces no glycoprotein gG. A preferred embodiment of this invention is a vaccine which comprises a suitable carrier and an effective immunizing amount of any one of the following viruses: recombinant infectious laryngotracheitis viruses designated S-ILT-014, S-ILT-002, S-ILT-009, S-ILT-015 and S-ILT-017.

The present invention further provides a vaccine which comprises a suitable carrier and an effective immunizing amount of a recombinant infectious laryngotracheitis virus comprising the infectious laryngotracheitis viral genome which contains a deletion or other alteration in the unique short region of the viral genome, wherein the deletion or alteration is in the glycoprotein gI gene so that upon replication, the recombinant virus produces no glycoprotein gI.

The present invention further provides a vaccine which comprises a suitable carrier and an effective immunizing amount of a recombinant infectious laryngotracheitis virus comprising the infectious laryngotracheitis viral genome which contains a deletion or other alteration in the unique short region of the viral genome, wherein the deletion or alteration is in the glycoprotein gG gene and the glycoprotein gI gene so that upon replication, the recombinant virus produces no glycoprotein gG and glycoprotein gI.

The present invention further provides a vaccine which comprises a suitable carrier and an effective immunizing amount of a recombinant infectious laryngotracheitis virus comprising the infectious laryngotracheitis viral genome which contains a deletion in the unique short region of the viral genome, wherein the deletion is in the US2 gene, UL47-like gene, or glycoprotein g60 gene.

The present invention further provides a vaccine which comprises a suitable carrier and an effective immunizing amount of a recombinant infectious laryngotracheitis virus comprising the infectious laryngotracheitis viral genome which contains a deletion in the unique short region of the viral genome, wherein the deletion is in the US2 gene, ORF4 gene, UL47-like gene, or glycoprotein g60 gene, and insertion of a foreign gene into a non-essential site in the viral genome.

The foreign gene encodes an antigenic polypeptide which induces host cell production of protective antibodies against an avian disease causing agent from which the antigen is derived or derivable.

The foreign gene may be derived or derivable from infectious bronchitis virus, Newcastle disease virus, infectious bursal disease virus, and Marek's disease virus, avian encephalomyelitis virus, avian reovirus, avian paramyxovirus, avian influenza virus, avian adenovirus, fowl pox virus, avian coronavirus, avian rotavirus, chick anemia agent, *Salmonella* spp., *E. coli, Pasteurella* spp., *Bordetella* spp., *Eimeria* spp., *Histomonas* spp., *Trichomonas* spp., poultry nematodes, cestodes, trematodes, poultry mites/lice, poultry protozoa.

The present invention further provides a vaccine which comprises a suitable carrier and an effective immunizing amount of a recombinant infectious laryngotracheitis virus comprising the infectious laryngotracheitis viral genome which contains an insertion of a foreign gene into a non-essential site in the viral genome. The foreign gene encodes an antigenic polypeptide which induces host cell production of protective antibodies against an avian disease causing agent from which the antigen is derived or derivable.

The foreign gene may be derived or derivable from infectious bronchitis virus, Newcastle disease virus, infectious bursal disease virus, and Marek's disease virus, avian encephalomyelitis virus, avian reovirus, avian paramyxovirus, avian influenza virus, avian adenovirus, fowl pox virus, avian coronavirus, avian rotavirus, chick anemia agent *Salmonella* spp., *E. coli, Pasterurella* spp., *Bordetella* spp., *Eimeria* spp., *Histomonas* spp., *Trichomonas* spp, Poultry nematodes, cestodes, trematodes, poultry mites/lice, poultry protozoa.

The present invention further provides a method of immunizing an animal against infectious laryngotracheitis virus which comprises administering to chickens or other poultry an effective immunizing dose of any of the vaccines of the present invention.

The present invention further provides a method for distinguishing chickens or other poultry which are vaccinated with an effective immunizing amount of a recombinant virus which produces no glycoprotein gG from those which are infected with a naturally-occurring infectious laryngotracheitis virus. This method comprises analyzing a sample of body fluid from the chickens or other poultry for the presence of glycoprotein gG of the infectious laryngotracheitis virus and at least one other antigen normally expressed in chickens or other poultry infected by a naturally-occurring infectious laryngotracheitis virus. The presence of antigen which is normally expressed in chickens or other poultry infected by a naturally-occurring infectious laryngotracheitis virus and the absence of glycoprotein gG in the body fluid is indicative of being vaccinated with the recombinant vaccine and not infected with a naturally-occurring infectious laryngotracheitis virus. The presence of glycoprotein gG and the antigen in the body fluid may be determined by detecting in the body fluid antibodies specific for the antigen and glycoprotein gG.

The present invention further provides a method for distinguishing chickens or other poultry which are vaccinated with an effective immunizing amount of a recombinant infectious laryngotracheitis virus which produces no glycoprotein gI from those which are infected with a naturally-occurring infectious laryngotracheitis virus. This method comprises analyzing a sample of body fluid from the chickens or other poultry for the presence of glycoprotein gI of the infectious laryngotracheitis virus and at least one other antigen normally expressed in chickens or other poultry infected by a naturally-occurring infectious laryngotracheitis virus. The presence of the antigen which is normally expressed in chickens or other poultry infected by a naturally-occurring infectious laryngotracheitis virus and the absence of glycoprotein gI in the body fluid is indicative of being vaccinated with the recombinant vaccine and not infected with a naturally-occurring infectious laryngotracheitis virus. The presence of the antigen and glycoprotein gI in the body fluid may be determined by detecting in the body fluid antibodies specific for the antigen and glycoprotein gI.

The present invention further provides a method for distinguishing chickens or other poultry which are vaccinated with an effective immunizing amount of a recombinant virus which produces no glycoprotein gG ad no glycoprotein gI from those which are infected with a naturally-occurring infectious laryngotracheitis virus. This method comprises analyzing a sample of body fluid from the chickens or other poultry for the presence of glycoprotein gG and gI of the infectious laryngotracheitis virus and at least one other antigen normally expressed in an animal infected by a naturally-occurring infectious laryngotracheitis virus. The presence of the antigen which is normally-expressed in chickens or other poultry by a naturally-occurring, infectious laryngotracheitis virus and the absence of glycoprotein gG and gI in the body fluid is indicative of being vaccinated with the vaccine and not infected with a naturally-occurring infectious laryngotracheitis virus. The presence of the antigen and glycoprotein gG and gI in the body fluid may be determined by detecting in the body fluid antibodies specific for the antigen and glycoprotein gG and gI.

The present invention further provides a homology vector for producing a recombinant infectious laryngotracheitis virus by inserting a foreign DNA into the unique short region of the infectious laryngotracheitis genomic DNA, which comprises a double-stranded DNA molecule consisting essentially of a double-stranded foreign gene, which is flanked on either side by the double-stranded DNA homologous to the DNA located in the unique short region of the genomic DNA, provided, however, that the flanking sequences are not homologous to the glycoprotein gD gene, the glycoprotein gE gene, the protein kinase gene, and the ORF10 gene. The foreign gene may encode a screenable marker, such as *E. coli* B-galactosidase or *E. coli* B-glucuronidase.

The present invention further provides a homology vector for producing a recombinant infectious laryngotracheitis virus by deleting DNA which encodes a screenable marker, which has been inserted into the infectious laryngotracheitis virus genomic DNA, which comprises a double stranded DNA molecule consisting essentially of a double-stranded DNA to be deleted, which is flanked on each side by a double stranded DNA homologous to the infectious laryngotracheitis virus glycoprotein G gene, glycoprotein gI gene, US2 gene, or UL-47 like gene. Preferred embodiments of this invention are the homology vectors designated Homology Vector 544-55.12, Homology Vector 562-61.1F. Homology Vector 472-73.27, Homology Vector 560-52.F1 and Homology Vector 579-14.G2.

This invention provides an isolated nucleic acid molecule encoding a US10 gene (SEQ ID NOS:60 and 70), AvSp gene (SEQ ID NOS: 61 and 71), US2 gene (SEQ ID NO:62), PK gene (SEQ ID NO:63), UL47 gene (SEQ ID NO:64), gG gene (SEQ ID NO:65), ORF5 gene (SEQ ID NO: 66), gD gene (SEQ ID NO:67), gI gene (SEQ ID NO:68), gE gene (SEQ ID NO:69), or ORF9 gene (SEQ ID NO:70).

This invention provides an isolated polypeptide encoded by the US10 gene (SEQ ID NOs:60 and 70), AvSp gene (SEQ ID NOS: 61 and 71), US2 gene (SEQ ID NO:62), PK gene (SEQ ID NO:63), UL47 gene (SEQ ID NO:64), gG gene (SEQ ID NO:65), ORF5 gene (SEQ ID NO:66), gD gene (SEQ ID NO:67), gI gene (SEQ ID NO:68), gE gene (SEQ ID NO:69), or ORF9 gene (SEQ ID NO:70).

EXPERIMENTAL DETAILS

Materials and Methods

PREPARATION OF INFECTIOUS LARYNGOTRACHEITIS VIRUS STOCK SAMPLES. Infectious laryngotracheitis virus stock samples were prepared by infecting primary chicken embryo kidney cells (CEK: obtained from Spafas, Inc.) or primary chicken kidney cells (CK; obtained from chicks hatched from fertile eggs supplied by Hyac) (50) in 225 $cm^2$ flasks with 0.5 ml of viral stock containing $10^5$-$10^6$ pfu in 1× Eagle's Basal Medium (modified) with Hank's salts (BME), 10% bromoethylamine(BEI)-treated fetal bovine serum (FBS), 1% glutamine stock, 2% penicillin/streptomycin (P/S) stock, and 1% sodium bicarbonate stock (these components are obtained from Irvine Scientific or an equivalent supplier, and hereafter the growth medium is referred to as complete BME medium). Viral stocks were then harvested 4-5 days later. Infected media and cells were resuspended in complete medium containing 20% sterile whole milk and stored frozen at −70° C.

PREPARATION OF INFECTIOUS LARYNGOTRACHEITIS VIRUS DNA. Four to five days after viral infection, cells and media were scraped from each flask into 1 ml conical centrifuge tubes and pelleted at 1700×g for 5 minutes at 4° C. Because as much as 50% of the virus may be in the media, the supernatants were saved and treated as will be described below. The cell pellets were resuspended in 1 ml PBS per tube, combined and centrifuged again at 1700×g for 5 minutes. The pellets were resuspended in 1 ml/flask of a buffer containing 10 mM Tris-HCl pH 7.5, 1 mM EDTA, and 1.5 mM $MgCl_2$ and were incubated for 15 minutes at 4° C. Twenty five μls of 20% NP40 per flask was added, and the mixture was then homogenized in a dounce homogenizer using an A pestle. The preparation was centrifuged at 1700×g for 10 minutes at 4° C. and the supernatant was retained. Ten μl of 0.5 M EDTA, 50 μl of 20% SDS, and 25 μl of 10 mg/l proteinase K was added to the supernatant (per original ask). In some cases, is was then combined with virus obtained from the cell media supernatants (see above). The mixture was then treated at 65° C. for 1-16 hours, followed by two extractions with phenol saturated with 100 mM Tris-HCl pH 8. DNA in the aqueous phase was then precipitated with added 3 M sodium acetate (1/10 th volume) and 2.5 vols of 100% ethanol.

To obtain virus from the media, the cell media supernatants were centrifuged at 23,500×g for 30 minutes, and drained well. The pellet was resuspended in the above proteinase K-containing mixture as described. The DNA pellets were resuspended in 20 μl TE/flask and could be used at this point for further experiments or treated further to remove RNA with pancreatic RNase A, followed by phenol extraction and ethanol precipitation to obtain the DNA.

To prepare viral DNA minipreps, infected 10 cm. dishes were scraped into conical centrifuge tubes and centrifuged 5 minutes at 1000×g. Cell media supernatants were kept and treated as above. The cell pellets were each resuspended in 0.5 ml of 10 mM Tris-HCl pH 7.5, 1 mM EDTA, 0.5% NP40, and incubated 10 minutes at room temperature. Ten μl of 10 mg/ml RNase A was added, and the preparation was centrifuged 5 minutes at 1000×g. Twenty-five μl of 20% SDS and 25 μl of 10 mg/ml proteinase K was added to the supernatant, and the entire preparation was added to the viral pellet from the cell media if it was used. The mixture was incubated at 55-65° C. for one hour, extracted with buffer-saturated phenol and precipitated by the addition of 1 ml of ethanol. The DNA pellet was resuspended in 20 μl of TE and stored at 4° C.

POLYMERASE FILL-IN REACTION. DNA was resuspended in buffer containing 50 mM Tris pH 74, 50 mM KCl, 5 mM $MgCl_2$, and 400 micromolar each of the four deoxyribonucleotides. Ten units of Klenow DNA polymerase (Gibco BRL) were added and the reaction was allowed to proceed for 15 minutes at room temperature. The DNA was phenol extracted and ethanol precipitated as above.

DNA SEQUENCING. Sequencing was performed using the Sequenase Kit (US Biochemicals) and $\alpha^{35}$S-dATP (New England Nuclear). Reactions using both the dGTP mixes and the dITP mixes were performed to clarify areas of compression. Alternatively, compressed areas were resolved on formamide cells. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with IBI MacVector. Superclone and Supersee Align programs from Coral Software.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described (42, 43). The polymerase chain reaction (PCR) was used to introduce restriction sites convenient for the manipulation of various DNAs (44). In general amplified fragments were less than 500 base pairs in size and critical regions of amplified fragments were confirmed by DNA sequencing. Except as noted, these techniques were used with minor variation.

SOUTHERN BLOTTING OF DNA. The general procedure for Southern blotting was taken from Maniatis et al. (1982) and Sambrook, et al. (1989) (42, 43). DNA was blotted to nylon membrane (Biorad Zetaprobe) in 0.4M NaH and prehybridized for 5 minutes in a solution containing 0.25 M $Na_2HPO_4$, pH 7.2, 1 mM EDTA, 7% SDS at 65° C. Labeled probe was added that had been labeled by random priming using a Genius™ non-radioactive labeling kit from Boehringer-Mannheim. Hybridization was overnight at 65° C. Filters were washed twice with 40 mM $Na_2HPO_4$, pH 7.2, 1 mM EDTA, 5% SDS ad then twice with 40 mM $Na_2HPO_4$, pH 7.2, 1 mM EDTA 1% SDS for 30 minutes each at 65° C. Detection of bound probe was performed using the Boehringer Manneim Genius™ non-radioactive detection kit.

DNA TRANSFECTION FOR GENERATING RECOMBINANT ILT VIRUS. The method is based upon the $CaCl_2$ procedure of Chen and Okayama (1987) (45) with the following modifications. Generation of recombinant ILT virus is dependent upon homologous recombination between ILT viral DNA and the plasmid homology vector containing the desired foreign DNA flanked by the appropriate herpesvirus cloned sequences. Plasmid DNA 10-40 mg) was added to 250 ml of a solution having a final concentration of 0.25 M $CaCl_2$. An equal volume of a buffer containing 50 mM MOPS (pH 6.95), 280 mM NaCl, and 1.5 mM $Na_2HPO_4$ was added to the DNA/$CaCl_2$ solution. After 10 minutes at room temperature, the mixture was added dropwise to a 6 cm dish of CEK cells on maintenance media, and placed at 39° C. for 4 to 5 hours. The cells were rinsed once with PBS, once with 20% glycerol in PBS for 2 minutes, rinsed again with PBS and fed with maintenance media. 1.5 ml of ILT viral stock was added to the media, and the cells were incubated overnight. The next day, fresh maintenance media was added, and the cells were incubated for two more days. The transfection stock was harvested, aliquoted, and frozen at −70° C.

PROCEDURE FOR GENERATING ILTV SUBGENOMIC DNA FRAGMENTS. The ability to generate herpesviruses by cotransfection of cloned overlapping subgenomic fragments has been demonstrated for pseudorabies virus (46). If deletions and/or insertions are engineered directly into the subgenomic fragments prior to the cotransfection, this procedure results in a high frequency of viruses containing the genomic alteration, greatly reducing the amount of screening required to purify the recombinant virus. The procedure of overlapping cosmids to map restriction enzyme sites was employed.

A library of subclones containing overlapping ILTV subgenomic fragments was generated as follows. USDA ILTV Strain 83-2 has been designated S-ILT-001. Approximately 20 μg ILTV DNA (obtained from S-ILT-001) in 0.5 ml of 10 mM Tris-HCl pH 8.0, 1 mM EDTA (TE) was sheared b, passing it twice through a 25 gauge needle as previously described (46). The DNA was centrifuged through a 15-40% glycerol gradient in 50 mM Tris-HCl pH 8.0, 1 mM EDTA, and 0.3 M NaCl for 5.5 hours at 274,000×g. Fractions were analyzed on a 0.3% agarose gel, and those containing DNA of 35-50 kb were pooled, diluted twofold with TE, and precipitated with one tenth volume of 3 M sodium acetate and 2.5 volumes of ethanol. The tubes were centrifuged for one hour at 109,000×g at 10° C. Pellets were resuspended, transferred to microfuge tubes, and precipitated with one tenth volume of 3 M sodium acetate and 2.5 volumes of ethanol. The DNA was resuspended in TE. DNA ends were made blunt ended by the POLYMERASE FILL-IN REACTION. The DNA was purified by extraction with both buffer saturated phenol and ether, precipitated with sodium acetate and ethanol as above, and resuspended in TE. Half of this material was ligated with 3 mg of vector, pSY1626, by the DNA ligation reaction. The vector used was pSY1626, which was made as follows. Cosmid pHC79 (Gibco BRL) was cut with HindIII and AvaI to remove the tetracycline gene, and the ends were filled in with Klenow polymerase (FILL IN REACTION). The polylinker from pWE15 (Stratagene) was ligated into this vector. The polylinker was isolated by digestion with EcoRI, the ends were filled in with Klenow polymerase (FILL IN REACTION), and the fragment was purified on a LMP-agarose gel. DNA ligation was performed in the presence of melted agarose. The resulting cosmid, pSY1005, was modified at the EcoRI site to create pSY1626 by blunt-ended insertion of a 1.5 kb HindIII-BamHI fragment from pNEO (P-L Biochemicals) containing the neomycin resistance gene. pSY1626 was cut and made blunt at the BamHI site, and ligated with sheared ILTV fragments as described above. The ligation mixture was packaged using Gigapack XL (Stratagene) according to the manufacturers instructions. The packaging mixture was added to AG1 cells (Stratagene) grown in the presence of maltose, and colonies were selected on LB plates containing kanamycin. Cosmid subclones containing ILTV DNA were identified by comparing restriction enzyme maps of individual cosmid clones to each other and to ILTV genomic DNA to obtain a contiguous sequence of ILTV genomic DNA.

SCREEN FOR RECOMBINANT ILTV EXPRESSING ENZYMATIC MARKER GENES. When the *E. coli* β-galactosidase or β-glucuronidase (uidA) marker gene was incorporated into a recombinant virus the plaques containing the recombinants were visualized by a simple assay. The enzymatic substrate was incorporated (300 μg/ml) into the agarose overlay during the plaque assay. For the lacZ marker gene the substrate Bluogal™ (halogenated indolyl-β-D-galactosidase. Gibco BRL) was used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plaques were then picked onto fresh cells and purified by mer blue plaque isolation. In recombinant virus strategies in which the enzymatic marker gene was removed, the assay involves plaque purifying white plaques from a background of parental blue plaques. Viruses were typically purified with five to ten rounds of plaque purification.

SCREEN FOR FOREIGN GENE EXPRESSION IN RECOMBINANT ILTV USING BLACK PLAQUE ASSAYS. To analyze expression of foreign antigens expressed by recombinant ILT viruses, monolayers of CEK cells were infected with recombinant ILT virus, overlaid with nutrient agarose media and incubated for 3-5 days at 39° C. Once plaques have developed, the agarose overlay was removed from the dish, the monolayer rinsed once with PBS, fixed with 100% methanol for 10 minutes at room temperature and the cells air dried. After re-hydrating the plate with PBS, the prima antibody was diluted to the appropriate dilution with PBS plus Blotto and incubated with the cell monolayer for 2 hours to overnight at room temperature. Unbound antibody was removed from the cells by washing four times with PBS at room temperature. The appropriate secondary antibody conjugate was diluted 1:500 with PBS and incubated with the cells for 2 hours at room temperature. Unbound secondary ant body was removed by washing the cells three times with PBS at room temperature. The monolayer was rinsed in color development buffer (100 mM Tris pH 9.5/100 mM NaCl/5 mM MgCl2), and incubated 10 minutes to overnight at room temperature with freshly prepared substrate solution (0.3 mg/ml nitro blue tetrazolium+0.15 mg/ml 5-bromo-4-chloro-3-indolyl phosphatase in color development buffer). The reaction was stopped by replacing the substrate solution with TE (10 mM Tris, pH7.5/1 mM EDTA). Plaques expressing the correct antigen stain black.

PURIFICATION OF ILTV gG FROM ILT VIRUS OR RECOMBINANT VIRUSES EXPRESSING ILTV gG. ILTV gG was purified from the media of cells infected with either wild type ILTV or with FPV or SPV vectors expressing ILTV gG. Cells were allowed to go to complete cytopathic effect (CPE), the media was poured off and cell debris was pelleted in a table-top centrifuge. The media was concentrated in an Amicon concentrator using a YM30 ultrafiltration membrane at 15 psi. The concentrate was dialyzed against 20 mM Tris-HCl, pH 7.0 and loaded onto a DEAE-Sephacel (Pharmacia) column equilibrated with the same buffer. The material was eluted using a salt gradient from 0 to 1.5 M NaCl in 20 mM Tris-HCl, pH 7.0. Three ml fractions were collected and assayed by Western blot. A peptide antibody against ILTV gG was used to identify fractions containing ILTV gG. Fractions were pooled and further concentrated in a Centricon-10 microconcentrator (Amicon).

GROWTH OF CHICKEN KIDNEY CELLS AND ILT VIRUS. An ILTV virus, designated fowl laryngotracheitis challenge virus, lot number 83-2, was obtained from the National Veterinary Services Laboratories, USDA/APHIS, Ames, Iowa. ILTV viruses were grown in primary chicken kidney cells (CK) obtained by dissection of kidneys from 6-9 day old SPF chicks, obtained from Hy-Vac Laboratory Eggs Co. Fresh kidney cells were minced and disassociated with 5 mg/ml trypsin and were then pelleted and resuspended at $1.3\times10^6$ cells/ml. Growth media (GM) was 1× Eagle's Basal Medium (modified) with Hank's salts, with added 10% binary ethyleneimine-treated fetal bovine serum (FBS), 2 M glutamine, 200 units/ml penicillin, 200 mg/ml streptomycin and 8.9 mM sodium bicarbonate (85). After resuspension, cells were plated and incubated at 39° C. Cells were rinsed and fed after 24 hours with maintenance media (MM), which is GM with 1% FBS. CKs were inoculated with ILTV at 0.01 to 0.1 MOI and viral stocks were harvested 4-5 days later by scraping and sonicating. Titers were typically $10^5$-$10^6$ pfu/ml.

PREPARATION OF VIRAL DNA. Cells and media from infected flasks were pelleted at 1700 g for 5' at 4° C. Supernatant and cell pellet were initially treated separately. Virion particles were centrifuged out of the supernatant at 23,500 g for 30 minutes. The original cell pellet was rinsed with PBS and spun again. This pellet was resuspended in 1 ml/flask of a buffer containing 10 mM Tris-HCl pH 7.5, 1 mM EDTA, and 1.5 mM $MgCl_2$ and incubated 15', 4° C. To this was added 25 μl/flask of 20% NP40, and the mixture was dounce homogenized using an A pestle. The preparation was centrifuged at 1700 g, 10', 4° C., and the supernatant was retained and the pellet discarded. To the supernatant was added (per original flask) 10 μl of 0.5 M EDTA, 50 μl of 20% SDS, and 25 μl of 10 mg/ml proteinase K. This mixture was used to resuspend the pellet of viral particles obtained by high speed centrifugation of the first supernatant. The mixture was treated at 65° C. for 1-16 hours, extracted twice with buffer-saturated phenol, and precipitated with added salt and ethanol. The resulting DNA pellet was resuspended in 100 μl TE/flask. This was treated further to remove RNA with pancreatic RNase A, followed by phenol extraction and ethanol precipitation to obtain the DNA.

CREATION OF THE COSMID LIBRARY. The cosmid library of ILTV DNA was created following the protocol of van Zijl et al., (83). Approximately 20 μg of ILTV DNA in 0.5 ml of 10 mM Tris-HCl, pH 8.0, 1 mM EDTA (TE) was sheared by passing it twice though a 25 gauge needle. The DNA was centrifuged through a 15-40% glycerol gradient in 50 mM Tris-HCl, pH 8.0, 1 mM EDTA, 0.3 M NaCl for 5.5 h at 274,000 g. Fractions were analyzed on a 0.3% agarose gel, and those containing DNA of 35-50 kb were pooled, diluted twofold with TE, precipitated with added salt aid ethanol. The tubes were spun 1 h at 10° C. and 109,000 g. Pellets were resuspended and reprecipitated with added salt and ethanol. The DNA was resuspended in TE and the ends were made blunt by treatment with T4 DNA polymerase for 2 h at 15° C., in the presence of appropriate buffer and 25 μM dNTP, followed by treatment with Klenow polymerase for 16 h at 15° C. using 0.25 mM dNTP. The DNA was extracted with phenol and then ether, precipitated with added salt and ethanol, and resuspended in TE. This material was ligated overnight with 3 μg of cosmid vector pSY1626. Cosmid pSY1626 was made by digesting cosmid pHC79 (BRL) with HindIII and AvaI to remove the tetracycline gene. The remaining fragment and the EcoRI digested polylinker from pWE15 (Stratagene) were filled in with Klenow polymerase and ligated together. The resulting cosmid vector, pSY1005, was modified at the EcoRI site to create pSY1626 by blunt-ended insertion of a 1.5 kb HindIII-BamHI fragment from pNEO (P-L Biochemicals) containing the kanamycin resistance gene. PSY1626 was cut and made blunt at the BamHI site for use as the cosmid vector. The ligation mixture was packaged using Gigapack XL (Stratagene) according to the manufacturer's directions. Colonies were selected on LB plates containing kanamycin.

SEQUENCING. Manual sequencing was performed using $^{35}$S-dATP (NEN) with the BRL Sequenase Kit which uses the dideoxyribonucleotide chain termination method described by Sanger et al. (80). Reactions using both dGTP and dITP mixes were performed to clarify areas of compression. Alternatively, compressed areas were resolved on 8% acrylamide gels that were 40% in formamide. Automatic fluorescence sequencing was performed using an Applied Biosystems (ABI) 373A DNA Sequencer. Subclones were made to facilitate sequencing. Internal primers were synthesized on an ABI 392 DNA synthesizer. Sequence was obtained for bot strands and was assembled using DNAstar software. Manipulation and comparison of sequences was performed with DNAstar programs, Superclone and Supersee programs from Coral Software. Comparisons with GenBank were performed at the NCBI using the BLAST network service (58).

HOMOLOGY VECTOR 501-94. The plasmid 501-94 was constructed for the purpose of deleting a portion of the thymidine kinase (TK) gene coding, region from the ILT virus (28). It incorporates the HCMV IE promoter and a screenable marker, the *E. coli* lacZ gene, flanked by ILT virus DNA. The HCMV IE promoter-*E. coli* lacZ gene is inserted in the opposite transcriptional orientation to the ILTV TK gene. Upstream of the marker gene is an approximately 1087 base pair fragment of ILTV DNA which includes the first 77 amino acid codons of the ILTV TK gene. Downstream of the lacZ gene is an approximately 675 base pair fragment of ILTV DNA which includes 80 amino acid codons at the 3' end of the ILTV TK gene. When this plasmid is used according to the DNA TRANSFECTION FOR GENERATING RECOMBINANT ILT VIRUS, it will replace the DNA coding for amino acids 78 to 285 of the ILTV TK gene with DNA coding for the lacZ gene. The lacZ marker gene is under the control of the human cytomegalovirus (HCMV) immediate early (IE) gene promoter and also contains the pseudorabies virus (PRV) gX gene polyadenylation signal at the 3' end of the gene. A detailed description of the plasmid is given in FIGS. 5A-5D. It was constructed from the indicated DNA sources utilizing standard recombinant DNA techniques (42, 43). The plasmid vector is derived from an approximately 3002 base pair HindIII fragment of pSP64/65 (Promega). Fragment 1 is an approximately 1087 base pair HindIII to BclI subfragment of the ILTV 2.4 kb HindIII fragment. Fragment 2 is an approximately 5017 base pair SalI to SalI fragment containing the HCMV IE promoter. β-galactosidase (lacZ) marker gene, and PRV gX polyadenylation signal (see FIGS. 5A-5D). Fragment 3 is an approximately 675 base pair BclI to HindIII subfragment of the ILTV 2.4 kb HindIII fragment.

HOMOLOGY VECTOR 544-55.12. The plasmid 544-55.12 was constructed for the purpose of deleting a portion of the US2 gene coding region from the ILT virus and inserting a foreign DNA. It incorporates a screenable marker, the *E. coli* uidA gene flanked by ILT virus DNA. The PRV gX promoter-*E. coli* uidA gene is inserted in the opposite transcriptional orientation to the ILTV US2 gene. Upstream of the uidA gene is an approximately 2300 base pair fragment of ILTV DNA which includes 41 amino acid codons at the 3' end of the US2 gene (SEQ ID NO 2: aa. 188-229). Downstream of the uidA gene is an approximately 809 base pair fragment of ILTV DNA which includes 22 amino acid codons at the 5' end of the US2 gene (SEQ ID NO 2: aa. 1-22). When this plasmid is used according to the DNA TRANSFECTION FOR GENERATING RECOMBINANT ILT VIRUS, it will replace the ILTV US2 DNA coding for amino acids 23 to 187 with DNA coding for the *E. coli* uidA gene. The uidA marker gene is under the control of the pseudorabies virus (PRV) gX promoter and also contains the herpes simplex virus type 1 thymidine kinase (HSV-1 TK) gene polyadenylation signal at the 3' end of the gene. A detailed description of the plasmid is given in FIGS. 6A-6D. It was constructed from the indicated DNA sources utilizing standard recombinant DNA techniques (42, 43). The plasmid vector is derived from an approximately 2958 base pair Asp718I restriction fragment of a pSP18/pSP19 fusion such that the multiple cloning site is EcoRI/SacI/Asp718I/SacI/EcoRI. Fragment 1 is an approximately 2300 base pair Asp718I to DraI subfragment (SEQ ID NO 1: Nucl. 1-405) of the ILTV 2.5 kb Asp718I fragment. Fragment 2 is an approximately 3039 base pair XbaI fragment containing the PRV gX promoter, the *E. coli* uidA gene, and the HSV-1 TK polyadenylation site (See FIGS. 6A-6D). Fragment 3 is an approximately 809 base pair au to Asp718I subfragment of the ILTV 1097 bp Asp718I fragment (SEQ ID NO 1: Nucl. 905-1714).

HOMOLOGY VECTOR 562-61.1F. The plasmid 562-61.1F was constructed for the purpose of deleting part of the gI gene from the ILT virus and inserting a foreign DNA. It incorporates a screenable marker, the *E. coli* uidA gene, flanked by ILT virus DNA. The PRV gX promoter-*E. coli* uidA gene is transcribed in the opposite direction to the ILTV gI gene promoter. The 983 base pair deletion begins 12 base pairs upstream of the translation initiation codon and deletes 324 of 36'-amino acid codons at the 5' end of the ILTV gI gene (SEQ ID NO 11: aa. 325-363). When this plasmid is used according to the DNA TRANSFECTION FOR GENERATING RECOMBINANT ILT VIRUS, it will replace the DNA coding for the ILTV gI gene with DNA coding for the *E. coli* uidA gene. A detailed description of the plasmid is given in FIGS. 7A-7D. It was constructed from the indicated DNA sources utilizing standard recombinant DNA techniques (42, 43). The plasmid vector is derived from an approximately 2647 base pair Asp718I to HindIII fragment of pUC19. Fragment 1 is an approximately 1619 base pair Asp7181 to AbaI subfragment of the ILTV 8.0 kb Asp718I fragment (SEQ ID NO 1: Nucl. 7556-9175). Fragment 2 is an approximately 691 base pair XbaI to XhoI fragment (SEQ ID NO 1: Nucl. 9175-9861) generated by the polymerase chain reaction (PCR). The template was the ILTV 8.0 kb Asp718I fragment. The upstream primer 92.09 (5'-CCTAGCACCCTTGTATCGCG-3'; SEQ ID NO. 55) sits down at a site 821 base pairs upstream of the ILTV gI gene and synthesizes DNA toward the 3' end of the gene. The downstream primer 92.11 (5'-CGCCTCGAGTCCCAATGAATAGGCATTGG-3'; SEQ ID NO. 56) sits do at a site 12 base pairs upstream of the translation start site of the ILTV gI gene and synthesizes DNA toward the 5' end of the gD gene. The product of the PCR reaction is 818 base pairs. This DNA fragment is digested with XbaI at the 5' end (a restriction enzyme site present in the ILTV DNA) and XhoI at the 3' end (a restriction enzyme site created in the PCR primer—see underlined sequence) to create an approximately 691 base pair XbaI to XhoI fragment. Fragment 3 is an approximately 3051 base pair SalI fragment containing the PRV gX promoter, the uidA gene, and the HSV-1 TK polyadenylation site (See FIGS. 6A-6D). Fragment 4 is an approximately 624 base pair XhoI to HindIII fragment generated by PCR (SEQ ID NO 1: Nucl. 10, 847-1161). The template was the ILTV 8.0 kb Asp718I fragment. The upstream primer 92.10 (5'-CGCCTCGAGGACCCATGGTTGCGTGCG-3'; SEQ ID NO. 57) sits down at a site 117 base pairs upstream from the translation termination codon within the ILTV gI gene. The downstream primer 92.08 (5'-CTCGTCCGACGAGTTACAG-3'; SEQ ID NO. 58) sits down at a site 604 base pairs downstream of the translation termination site of the ILTV gI gene and within the ILTV gE gene. The PCR product (729 base pairs) is digested with XhoI which is a unique site generated by the upstream PCR primer (underlined) and with HindIII at a site within the ILTV gE gene. Restriction endonuclease digestion with XhoI and HindIII creates an approximately 624 base pair Fragment 4. Fragment 5 is an approximately 2700 base pair HindIII subfragment of the ILTV 8.0 kb Asp718I fragment (SEQ ID NO 1: Nucl. 11,461-13,4473 plus unsequenced DNA).

HOMOLOGY VECTOR 472-73.27. The plasmid 472-73.27 was constructed for the purpose of deleting a portion of the glycoprotein G (gG) gene coding region from the ILT virus and inserting a foreign DNA. It incorporates a screenable marker, the *E. coli* lacZ gene, flanked by ILT virus DNA. The HCMV IE promoter-*E. coli* lacZ gene is transcribed in the same direction to the ILTV gG gene promoter. The 874 base pair deletion of the ILTV gG gene extends from 60 nucleotides upstream of the translation initiation site to 814 nucleotides into the amino acid coding sequence, removing the coding capacity of 271 of 292 amino acids of the gG protein (SEQ ID NO 7). When this plasmid is used according to the DNA TRANSFECTION FOR GENERATING RECOMBINANT ILT VIRUS, it will replace the DNA coding for amino acids 1 to 271 of the ILTV gG gene with DNA coding for the *E. coli* lacZ gene. A detailed description of the plasmid is given in FIGS. 4A-4D. It was constructed from the indicated DNA sources utilizing standard recombinant DNA techniques (42, 43). The plasmid vector is derived from an approximately 2686 base pair Asp718I restriction fragment of pUC 19 (Gibco, BRL). Fragment 1 is an approximately 2830 base pair Asp718I to NheI subfragment of the ILTV 5164 bp Asp718I fragment (SEQ ID NO 1: Nucl. 1714-4544). Fragment 2 is an approximately 5017 base pair SalI to SalI fragment containing the HCMV IE promoter, *E. coli* β-galactosidase (lacZ) marker gene, and PRV gX polyadenylation signal (see FIGS. 4A-4D). Fragment 3 is an approximately 1709 base pair SalI to Asp718I subfragment of the ILTV 5164 bp Asp718I fragment (SEQ ID NO 1: Nucl. 5419-6878).

HOMOLOGY VECTOR 560-52.F1. The plasmid 560-52.F1 was constructed for the purpose of deleting part of the UL47-like gene, all of ORF4, and part of the ILTV gG gene from the ILT virus and inserting a foreign DNA. It incorporates a screenable marker, the *E. coli* uidA gene, flanked by ILT virus DNA. The PRV gX promoter-*E. coli* uidA gene is transcribed in the opposite direction to the ILTV UL47-like, ORF4, and gG gene promoters. The 2640 base pair deletion removes 442 of 511 amino acid codons at the 3' end of the UL47-like gene (SEQ ID NO 4), the entire coding sequence of the ORF4 gene (SEQ ID NO 5) and 271 of 293 amino acid codons at the 5' end of the ILTV gG gene (SEQ ID NO 7). When this plasmid is used according to the DNA TRANSFECTION FOR GENERATING RECOMBINANT ILT VIRUS, it will replace the DNA coding for the ILTV UL47-like, ORF4 and gG genes with DNA coding for the PRV gX promoter-*E. coli* uidA gene. A detailed description of the plasmid is given in FIGS. 8A-8D. It was constructed from the indicated DNA sources utilizing standard recombinant DNA techniques (42, 43). The plasmid vector is derived from an approximately 2958 base pair Asp718I restriction fragment of pSP18/pSP19 such that the multiple cloning site is EcoRI/SacI/Asp718I/SacI/EcoRI. Fragment 1 is an approximately 1066 base pair Asp718I to BssHII subfragment of the ILTV 5164 bp Asp718I fragment (SEQ ID NO 1: Nucl. 1714-2777). Fragment 2 is an approximately 123 base pair SalI to BclI subfragment of the ILTV 5164 bp Asp718I fragment. Fragment 3 is an approximately 3027 base pair BamHI fragment containing the PRV gX promoter, the uidA gene, and the HSV-1 TK polyadenylation site (See FIGS. 8A-8D). Fragment 4 is an approximately 1334 base pair BclI to Asp718I subfragment of the ILTV 5164 bp Asp718I fragment (SEQ ID NO 1: Nucl. 5544-6878).

HOMOLOGY VECTOR 579-14.G2. The plasmid 579-14.G2 was constructed for the purpose of deleting the entire gG gene and a portion of the g60 gene from the ILT virus and inserting a foreign DNA. It incorporates a PRV gX promoter and a screenable marker, the *E. coli* uidA gene, flanked by ILT virus DNA. The PRV gX promoter-*E. coli* uidA gene is transcribed in the same direction to the ILTV gG and g60 gene promoters. The 3351 base pair deletion includes the entire coding sequence of the ILTV gG gene (SEQ ID NO 7) and 733 of 986 amino acid codons from the 5' end of the g60 gene (SEQ ID NO 8). When is plasmid is used according to the DNA TRANSFECTION FOR GENERATING RECOMBINANT ILT VIRUS, it will replace the DNA coding for the ILTV gG gene and amino acids 1 to 733 of the ILTV g60 gene with DNA coding for the *E. coli* uidA gene. A detailed description of the plasmid is given in FIGS. 9A-9D. It was constructed from the indicated DNA sources utilizing standard recombinant DNA techniques (42, 43). The plasmid vector pUC19 (Gibco BRL) is derived from an approximately 2677 base pair Asp718I to BamHI fragment. Fragment 1 is an approximately 2830 base pair Asp718I to NheI subfragment of the ILTV 5164 bp Asp7181 fragment (SEQ ID NO 1: Nucl. 1714-4544). Fragment 2 is an approximately 3051 base pair SalI fragment containing the PRV gX promoter. *E. coli* β-glucuronidase (uidA) marker gene, and an HSV-1 TK polyadenylation site (See FIGS. 9A-9D). Fragment 3 is an approximately 1709 base pair SalI to BamHI subfragment of the ILTV 4545 base pair BamHI fragment (SEQ ID NO 1: Nucl. 7895-9604).

PLASMID 544-39.13. Plasmid 544-39.13 contains the β-glucuronidase expression cassette consisting of the PRV gX promoter, *E. coli* β-glucuronidase (uidA) marker gene, and an HSV-1 TK polyadenylation site. A detailed description of the marker gene is given in FIGS. 10A-10D. It was constructed utilizing standard recombinant DNA techniques (42, 43) by joining restriction fragments from the following sources with the synthetic DNA sequences indicated in FIGS. 10A-10D. The plasmid vector pSP71 (Promega) is derived from a approximately 3066 base pair XmaI to SmaI fragment. Fragment 1 is an approximately 422 base pair SalI to EcoRI restriction subfragment of the PRV BamHI restriction fragment #10 (47). Note that the EcoRI site was introduced at the location indicated in FIGS. 12A-12D by PCR cloning. Fragment 2 is an approximately 1826 base pair EcoRI to SmaI fragment of the plasmid pRAJ260 (Clonetech). Note that the EcoRI and XmaI sites were introduced at the locations indicated in FIGS. 10A-10D by PCR cloning. Fragment 3 is an approximately 784 base pair XmaI subfragment of the HSV-1 BamHI restriction fragment Q (48). Note that this fragment is oriented such that the polyadenylation sequence (AATAAA) is located closest to the junction with the *E. coli* uidA gene.

PLASMID 388-65.2. Plasmid 388-65.2 contains the β-galactosidase expression cassette consisting of the HCMV immediate early (IE) promoter, the *E. coli* lacZ marker gene, and the PRV gX gene polyadenylation site. A detailed description of the β-galactosidase expression cassette is given in FIGS. 11A-11D. It was constructed utilizing standard recombinant DNA techniques (42, 43) by joining restriction fragments from the following sources with the synthetic DNA sequences indicated in FIGS. 11A-11D. The plasmid vector pSP72 (Promega) is derived from an approximately 3076 base pair PstI to PstI fragment. Fragment 1 is a 1154 base pair PstI to AvaII fragment derived from a HCMV 2.1 kb PstI fragment containing the HCMV IE promoter. Fragment 2 is a 3010 base pair BamHI to PvuII fragment derived from plasmid pJF751 (49) containing the *E. coli* lacZ gene. Fragment 3 is an approximately 750 base pair NdeI to SalI fragment derived from PRV BamHI #7 which contains the carboxy-terminal 19 amino acids and the polyadenylation signal of the PRV gX gene.

EXAMPLES

Example 1

Complete sequence of the unique short region of Infectious Laryngotracheitis Virus (ILTV): The sequence of 13,473 base pairs of contiguous DNA from the short region of the ILT virus (SEQ. ID. NO. 1) was determined. This sequence contains the entire 13,098 base pair unique short region as well as 273 base pairs of repeat region at one end and 102 base pairs of repeat region at the other end. The unique short region contains 13 methionine initiated open reading frames (ORF) of greater than or equal to 110 amino acids (excluding smaller nested ORFs). All 13 ORFs were aligned to the Entrez release 6.0 virus division of the Genbank DNA database utilizing the IBI MacVector Protein to DNA alignment option (default settings). Eight of the ORFs exhibited significant homology to one or more other virus genes (see Table I). The nucleotide sequence numbers referred to below begin within the internal repeat sequence and end within the terminal repeat sequence. The unique short region begins at base pair 274 of SEQUENCE ID NO. 1.

TABLE I

Sequence Homology between Infectious Laryngotracheitis Virus (ILTV) Open Reading Frames in the Unique Short Region and other Viral Proteins

| Open Reading Frame(ORF) | Start (BP) | End (BP) | Length (aa) | Genbank Allignment[a] |
|---|---|---|---|---|
| 1 (Rc)[b] | 970 | 281 | 229 | EHV-1 US2 |
| 2 | 1059 | 2489 | 476 | MDV PK |
| 3 | 2575 | 4107 | 510 | HSV-1 UL47 |

TABLE I-continued Sequence Homology between Infectious Laryngotracheitis Virus (ILTV) Open Reading Frames in the Unique Short Region and other Viral Proteins

| Open Reading Frame(ORF) | Start (BP) | End (BP) | Length (aa) | Genbank Allignment[a] |
|---|---|---|---|---|
| 4 | 4113 | 4445 | 110 | NS[c] |
| 4 (RC) | 4519 | 4139 | 126 | NS |
| 5 | 4609 | 5487 | 292 | PRV gX |
| 6 | 5697 | 8654 | 985 | ILTV g60 |
| 6 (RC) | 7826 | 6948 | 292 | HSV-2 UL39 |
| 7 | 8462 | 9766 | 434 | PRV g50 |
| 8 | 9874 | 10962 | 362 | VZV gI |
| 8 (RC) | 11150 | 10617 | 177 | NS |
| 9 | 11159 | 12658 | 499 | VZV gE |
| 10 | 12665 | 13447 | 260 | NS |

[a]Sequence allignment scored to the Entrez Release 6.0 of Genbank Virus Database.
[b]RC = Reverse Complement.
[c]NS = No score above 120 was found.
Other Abbreviations: EHV = Equine herpesvirus; MDV = Mareks disease virus; HSV-1 = Herpes Simplex virus 1; PRV = Pseudorabies virus; ILTV = Infectious laryngotracheitis virus; HSV-2 = Herpes Simplex virus 2; VZV = Varicella-Zoster virus; BP = base pairs; aa = amino acids.

US2 Gene

The US2 gene consists of 690 base pairs and codes for a protein 229 amino acids in length and molecular weight approximately 25,272 daltons (SEQ. ID. NO. 12, 13). The ILTV US2 is homologous to the Equine herpesvirus(EHV)-1 and EHV-4 US2 proteins. The US2 gene is transcribed from nucleotide 970 to 281 on the reverse complement strand of the ILTV unique short region (SEQ. ID. NO. 1). The function of the US2 gene product is unknown.

Protein Kinase Gene

The protein kinase gene consists of 1431 base pairs from nucleotide 1059 to 2489 and codes for a protein 476 amino acids in length and molecular weight approximately 54,316 daltons (SEQ. ID. NO. 2). The ILTV protein kinase is homologous to the protein kinases from Mareks disease virus (MDV). Equine herpesvirus(EHV)-1 and -4, Pseudorabies virus (PRV), Varicella-Zoster virus (VZV), Simian varicella virus (SVV), and Herpes Simplex virus (HSV)-1 and -2.

UL47-like Gene

The UL47-like gene is unique in its location within the unique short region of ILT virus. The UL47-like gene in all other known herpesviruses is located within the unique long sequence. The UL47-like gene consists of 1533 base pairs from nucleotide 2575 to 4107 and codes for a protein 510 amino acids in length and molecular weight approximately 57,615 daltons (SEQ. ID. NO. 3).

ORF4

ORF4 codes for a protein of unknown function. ORF4 consists of 333 base pairs from nucleotide 4113 to 4445 and codes for an open reading frame 110 amino acids in length and molecular weight approximately 12,015 daltons (SEQ. ID. NO. 4).

ORF4 Reverse Complement

ORF4Reverse Complement (RC) codes for a protein of unknown function. ORF4 RC consists of 380 base pairs from nucleotide 4519 to 4139 and codes for an open reading frame 126 amino acids in length and molecular weight approximately 13,860 daltons (SEQ. ID. NOS. 14, 15).

gG Gene

The gG gene consists of 879 base pairs from nucleotide 4609 to 5487 and codes for a glycoprotein 292 amino acids in length and molecular weight approximately 31.699 daltons (SEQ. ID. NO. 5). ILTV gG glycoprotein is homologous to PRV gX, Bovine herpesvirus(BHV)-1.3 gG. EHV-1 gG and EHV-4 gG. Recombinant ILTV gG protein produced in a Swinepox virus vector or a Fowlpox virus vector can be purified (see Materials and Methods) and reacts to peptide antisera to ILTV gG. The peptide antisera reacts to ILTV gG from wild type virus, but not to viruses deleted for the ILTV gG gene. Deletion of the gG gene results in an attenuated ILT virus that is useful as a vaccine against ILT disease in chickens (see table in Example 6) and also serves as a negative marker to distinguish vaccinated from infected animals.

g60 Gene

The g60 gene has been identified as glycoprotein 60 (33, 53). The g60 gene consists of 2958 base pairs from nucleotide 5697 to 8654 and codes for a glycoprotein 985 amino acids in length and molecular weight approximately 106,505 daltons (SEQ. ID. NO. 6).

ORF6 Reverse Complement

ORF6 RC consists of 878 base pairs from nucleotide 7826 to 6948 and codes for an open reading frame 292 amino acids in length and molecular weight approximately 32,120 daltons (SEQ. ID. NO. 16, 17). The ILTV ORF6 RC shares limited homology to portions of the HSV-1 and HSV-2 ribonucleotide reductase large subunit (UL39).

gD Gene

The expression of the gD glycoprotein in vectored fowlpox virus or herpesvirus of turkeys (33) is sufficient to raise a protective immune response in the chicken. The gD gene consists of 1305 base pairs from nucleotide 8462 to 9766 and codes for a glycoprotein 434 amino acids in length and molecular weight approximately 48,477 daltons (SEQ. ID. NO. 10, 11). The ILTV gD glycoprotein is homologous to the PRV g50, and the gD from HSV-1. MDV, IPV, and BHV-1.1. Monoclonal antibodies raised to ILT virus react specifically with gD protein from ILTV and also react to ILTV gD protein expressed in a Herpesvirus of Turkeys (HVT) virus vector. ILTV gD expressed in the HVT vector is useful as a subunit vaccine.

gI Gene

The gI gene consists of 1089 base pairs from nucleotide 9874 to 10,962 and codes for a glycoprotein 362 amino acids in length and molecular weight approximately 39,753 daltons (SEQ. ID. NO. 7). The ILTV gI glycoprotein is homologous to the VZV gI. Recombinant ILTV gI protein expressed in a swinepox virus vector reacts to convalescent sera from ILTV-infected chickens. Deletion of the gI gene results in an attenuated ILT virus that is useful as a vaccine against ILT disease in chickens. Recombinant viruses deleted for gI are safe in animal trials when vaccinated by a natural route directly into the respiratory tract, whereas parental virus causes lesions in 90% of the birds inoculated via the same route. Deletion of the gI gene serves as a negative marker to distinguish vaccinated from infected animals.

ORF8 Reverse Complement

ORF8 Reverse Complement codes for a protein of unknown function. ORF8 RC consists of 533 base pairs from nucleotide 11,150 to 10,617 and codes for an open reading frame 7 amino acids in length and molecular weight approximately 9,470 daltons (SEQ. ID. NO. 18, 19).

gE Gene

The gE gene consists of 1500 base pairs from nucleotide 11,159 to 12,658 and codes for a glycoprotein 499 amino acids in length and molecular weight approximately 55,397 daltons (SEQ. ID. NO. 8). The ILTV gE glycoprotein is homologous to the gE glycoproteins from VZV, Simian herpesvirus (SHV) EHV-1, HSV-1, and PRV. The ILTV gE is a neutralizing antigen useful as a subunit vaccine.

ORF10

ORF10 consists of 783 base pairs from nucleotide 12,665 to 13,447 and codes for a protein 261 amino acids in length and molecular weight approximately 27,898 daltons (SEQ. ID. NO. 9).

Example 2

S-ILT-004

S-ILT-004 is a infectious laryngotracheitis virus (ILTV) that has an approximately 620 base pair deletion of the thymidine kinase (TK) gene 28). The gene for E. coli β-galactosidase (lacZ) was inserted in the place of the TK gene and is under the control of the HCMV immediate early (IE) promoter. Transcription of the HCMV IE promoter-lac Z gene is in the opposite orientation to the TK promoter.

S-ILT-004 was constructed using homology vector 501-94 (see Materials and Methods) and S-ILT-001 (USDA ILTV Strain 83-2) in the DNA TRANSFECTION FOR GENERATING RECOMBINANT ILT VIRUS. The transfection stock was screened by the Bluogal™ SCREEN FOR RECOMBINANT HERPESVIRUS EXPRESSING ENZYMATIC MARKER GENES. The result of blue plaque purification was recombinant virus S-ILT-004. This virus was characterized by restriction mapping and the SOUTHERN BLOTTING OF DNA procedure. This analysis confirmed the presence of the β-galactosidase (lacZ) marker gene and the deletion of approximately 619 base pairs of the TK gene. The remaining TK gene sequence codes for protein including amino acids 1 to 77, and amino acids 286 to 363. The HCMV IE promoter-lacZ gene is in the opposite orientation to the TK gene transcription.

S-ILT-004 is attenuated by deletion of the ILTV TK gene, but retains other genes known to be involved in be immune response in chickens to ILT virus Therefore, S-ILT-004 may be useful as a killed vaccine to protect chickens from ILT disease.

Example 3

S-ILT-009

S-ILT-009 is an infectious laryngotracheitis virus (ILTV) that has an approximately 498 base pair deletion of the ILTV US2 gene and an approximately 874 base pair deletion of the ILTV gG acne. The gene for E. coli β-glucuronidase (uidA) was inserted in the place of the US2 gene and is under the control of the pseudorabies virus (PRV) gX promoter.

S-ILT-009 was constructed using homology vector 544-55.12 (see Materials and Methods) and S-ILT-002 in the DNA TRANSFECTION FOR GENERATING RECOMBINANT ILT VIRUS. S-ILT-002 was constructed as described in Example 5 (S-ILT-014). The transfection stock was screened by the X-Gluc SCREEN FOR RECOMBINANT HERPESVIRUS EXPRESSING ENZYMATIC MARKER GENES. The resulting purification of a blue plaque was recombinant virus S-ILT-009. This virus was characterized by restriction mapping and the SOUTHERN BLOTTING OF DNA procedure. This analysis confirmed the presence of the PRV gX promoter-β-glucuronidase (uidA) marker gene and the deletion of approximately 498 base pairs of the ILTV US2 gene and an approximately 874 base pair deletion of the ILTV gG gene. However, during the Bluogal™ SCREEN FOR RECOMBINANT HERPESVIRUS EXPRESSING ENZYMATIC OR GENES, a deletion of the HCMV IE promoter-lacZ gene was detected within the existing ILTV gG deletion. The remaining insert into the ILTV gG deletion contains approximately 2000 base pairs of DNA of which all of the lacZ gene and part of the PRV gX polyadenylation site are missing. The deletion was characterized by detailed restriction mapping and determined to be slightly different from the S-ILT-014 deletion (See Example 5).

S-ILT-009 is attenuated by deletion of the ILTV US2 and gG genes but retains other genes known to be involved in the immune response in chickens to ILT virus. Therefore, S-ILT-009 is useful as an attenuated live vaccine or as a killed vaccine to protect chickens from ILT disease as shown in the table. Since S-ILT-009 does not express the ILTV gG genes it is utilized as a negative marker to distinguish vaccinated animals from infected animals as described previously.

TABLE II

EFFICACY OF RECOMBINANT LIVE ILT VIRUS S-ILT-009 AGAINST VIRULENT INFECTIOUS LARYNGOTRACHEITIS VIRUS CHALLENGE

| Vaccine | Gene(s) Deleted | Dose | Route | Challenge[a] | Protection[b] |
|---|---|---|---|---|---|
| S-ILT-009 | gG-, US2- | $7.8 \times 10^3$ | IO[c] | OS[d] | 70% |
| S-ILT-009 | gG-, US2- | $1.56 \times 10^3$ | IO | OS | 77% |
| Controls | | | | OS | 0% |
| ASL embryo | | | IO | OS | 90% |

14 day old chicks
[a]USDA Challenge virus = $1.0 \times 10^{4.5}$ pfu
[b]Protection = # healthy birds/total (%).
[c]Intraocular
[d]Orbital Sinus Example 4

S-ILT-011

S-ILT-011 is an infectious laryngotracheitis virus (ILTV) that has an approximately 983 base pair deletion of the ILTV gI gene. The gene for E. coli β-glucuronidase (uidA) was inserted in the place of the gI gene and is under the control of the pseudorabies virus (PRV) gX promoter. The PRV gX promoter-uidA gene is in the opposite orientation to the direction of transcription of the ILTV gI promoter.

S-ILT-011 was constructed using homology vector 562-61.1F (see Materials and Methods) and S-ILT-001 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-011. This virus was characterized by restriction mapping and the SOUTHERN BLOTTING OF DNA procedure. This analysis confirmed the presence of the β-glucuronidase (uidA) marker gene and the deletion of approximately 983 base pairs of the ILTV gI gene which deletes 325 of 363 amino acid codons from the 5' end of the gI gene.

S-ILT-011 is attenuated and is useful as a killed vaccine to protect chickens from ILT disease. S-ILT-011 shows a small plaque phenotype in tissue culture which is indicative of slow viral growth and attenuation. Since S-ILT-011 does not express the ILTV gI gene, it may be utilized as a negative marker to distinguish vaccinated animals from infected animals. As indicated in Example 1, ILTV infected chickens make antibodies against ILTV gI protein.

Example 5

S-ILT-013

S-ILT-013 is an infectious laryngotracheitis virus (ILTV) that has an approximately 983 base pair deletion of the ILTV gI gene and an approximately 874 base pair deletion of the ILTV gG gene (and a deletion of the HCMV IE promoter lacZ marker gene making the lacZ gene nonfuctional). The gene for E. coli β-glucuronidase (uidA) was inserted in the place of the gI gene and is under the control of the pseudorabies virus (PRV) gX promoter.

S-ILT-013 was constructed using homology vector 562-61.1F (see Materials and Methods) and S-ILT-014 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-013. This virus was characterized by restriction mapping and the SOUTHERN BLOTTING OF DNA procedure. This analysis confirmed the presence of the β-glucuronidase (uidA) marker gene and the deletion of approximately 983 base pairs of the ILTV gI gene which removes 325 of 363 amino acid codons from the 5' end of the gI gene. This analysis also confirmed an approximately 874 base pair deletion of the ILTV gG gene and an approximately 1906 base pair insertion of a partial HCMV IE promoter-lacZ marker gene DNA, of which a portion of the HCMV IE promoter and almost none of the lacZ gene remains (see Example 6).

S-ILT-013 is attenuated and is useful as a killed vaccine to protect chickens from ILT disease. S-ILT-013 shows a small plaque phenotype in tissue culture which is indicative of slow viral growth and attenuation. Since S-ILT-013 does not express the ILTV gI or gG genes, ILTV gI and gG may be utilized as negative markers to distinguish vaccinated animals from infected animals.

Example 6

S-ILT-014

S-ILT-014 is an infectious laryngotracheitis virus (ILTV) that has an approximately 874 base pair deletion of the ILTV gG gene and a deletion of the inserted HCMV IE promoter lacZ marker gene making the lacZ gene nonfunctional. S-ILT-014 was derived from a purified S-ILT-002 virus stock in which a deletion of the HCMV IE promoter lacZ marker gene occurred.

S-ILT-002 was constructed using homology vector 472-73.27 (See Materials and Methods) and S-ILT-001 in the DNA TRANSFECTION FOR GENERATING RECOMBINANT ILT VIRUS. The virus S-ILT-002 has a 874 base pair deletion within the ILTV gG gene and an insertion of the E. coli β-galactosidase (lacZ) gene in place of the ILTV gG gene. However, during the Bluogal™ SCREEN FOR RECOMBINANT HERPESVIRUS EXPRESSING ENZYMATIC MARKER GENES, a white plaque was picked which contained a deletion of the lacZ gene within the ILTV gG deletion.

This virus, S-ILT-014, was characterized by restriction mapping, DNA SEQUENCING and the SOUTHERN BLOTTING OF DNA procedure. This analysis confirmed the presence of an approximately 874 base pair deletion of the ILTV gG gene and approximately 1956 base pair insertion of a partial HCMV IE promoter lacZ marker gene DNA (2958 base pairs deleted). The remaining HCMV IE promoter lacZ marker gene DNA consists of an approximately 686 base pair DNA fragment of the approximately 1154 base pair HCMV IE promoter and an approximately 1270 base pair DNA fragment containing approximately 520 base pairs of the 3010 base pair β-galactosidase (lacZ) marker gene and all of the approximately 750 base pair PRV gX polyadenylation signal.

S-ILT-014 is useful as an attenuated live vaccine or as a killed vaccine to protect chickens from ILT disease as indicated in the table below. Since S-ILT-014 does not express the ILTV gG gene and ILTV-infected chickens make antibodies to gG as indicated in Example 1, ILTV gG is utilized as a negative marker to distinguish vaccinated animals from infected animals,

TABLE III

EFFICACY OF RECOMBINANT LIVE ILT VIRUS S-ILT-014 AGAINST VIRULENT INFECTIOUS LARYNGOTRACHEITIS VIRUS CHALLENGE

| Vaccine | Gene(s) Deleted | Dose | Route | Challenge[a] | Protection[b] |
|---|---|---|---|---|---|
| S-ILT-014 | gG- | $1.08 \times 10^4$ | IO[c] | OS[d] | 97% |
| S-ILT-014 | gG- | $2.16 \times 10^3$ | IO | OS | 97% |
| Controls | | | | OS | 0% |
| ASL embryo | | | IO | OS | 90% |

14 day old chicks
[a]USDA Challenge virus = $1.0 \times 10^{4.5}$ pfu
[b]Protection = # healthy birds/total (%).
[c]Intraocular
[d]Orbitual Sinus Example 7

S-ILT-015

S-ILT-015 is an infectious laryngotracheitis virus (ILTV) that has an approximately 2640 base pair deletion of the UL47-like gene, the ORF4 gene, and ILTV gG gene. The gene for E. coli β-glucuronidase (uidA) was inserted in the place of the UL47-like, ORF4, and gG genes and is under the control of the pseudorabies virus (PRV) gX promoter. The PRV gX promoter-uidA gene is in the opposite orientation to the direction of transcription of the ILTV UL47-like, ORF4, and gG promoters.

S-ILT-015 was constructed using homology vector 560-52.F1 (see Materials and Methods) and S-ILT-001 in the DNA TRANSFECTION FOR GENERATING RECOMBINANT ILT VIRUS. The transfection stock was screened by the N-Gluc SCREEN FOR RECOMBINANT HERPESVIRUS EXPRESSING ENZYMATIC MARKER GENES. The result of blue plaque purification was recombinant virus S-ILT-015. This virus was characterized by restriction mapping and the SOUTHERN BLOTTING OF DNA procedure. These results confirmed the presence of a 2640 base pair deletion which includes 442 of a total 511 amino acid codons at the 3' end of the UL47-like gene, all of the ORF4 gene and 271 of 293 amino acid codons of the 5', end of the gG gene.

S-ILT-015 is useful as an attenuated live vaccine or as a killed vaccine to protect chickens from ILT disease as indicated in the table below. Since S-ILT-015 does not express the ILTV gG gene, ILTV gG is utilized as a negative marker to distinguish vaccinated animals from infected animals.

TABLE IV

EFFICACY OF RECOMBINANT LIVE ILT VIRUS
S-ILT-015 AGAINST VIRULENT INFECTIOUS
LARYNGOTRACHEITIS VIRUS CHALLENGE

| Vaccine | Gene(s) Deleted | Dose | Route | Challenge[a] | Protection[b] |
|---|---|---|---|---|---|
| S-ILT-015 | gG-, UL47-like | $1.0 \times 10^5$ | IO[c] | OS[d] | 70% |
| Controls | | | | OS | 0% |
| ASL embryo | | | IO | OS | 90% |

14 day old chicks
[a]USDA Challenge virus = $1.0 \times 10^{4.5}$ pfu
[b]Protection = # healthy birds/total (%).
[c]Intraocular
[d]Orbital Sinus

Example 8

S-ILT-017

S-ILT-017 is an infectious laryngotracheitis virus (ILTV) that has an approximately 3351 base pair deletion of the ILTV gG gene ORF4 gene and the g60 gene. The gene for *E. coli* β-glucuronidase (uidA) was inserted in the place of the ILTV gG and g60 genes and is under the control of the pseudorabies virus (PRV) gX promoter.

S-ILT-017 was constructed using homology vector 579-14.G2 (see Materials and Methods) and S-ILT-001 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-017.

S-ILT-017 is attenuated by deletion of the ILTV g60 and gG genes, but retains other genes known to be involved in the immune response in chickens to ILT virus. Therefore, S-ILT-017 may be used as a killed vaccine to protect chickens from ILT disease. Since S-ILT-017 does not express the ILTV gG or g60 genes, it is used as a negative marker to distinguish vaccinated animals from infected animals.

Example 9

Recombinant Infectious Laryngotracheitis Virus that Express Infectious Bronchitis Virus (IBV) Spike and Matrix Protein Genes A homology vector is used to generate ILT viruses containing the IBV Arkansas spike protein gene. The recombinant ILT virus contains a deletion of one or more ILTV genes, including gG, US2, UL47-like, and ORF4, and the insertion of to foreign genes: the *E. coli* β-glucuronidase gene (uidA) and the IBV Arkansas spike protein gene. The uidA gene is under the control of the PRV gX promoter and the IBV Arkansas spike protein gene is under the control of the HCMV IE promoter.

To construct a homology vector containing the foreign genes inserted into the ILT virus, a DNA fragment containing the HCMV-IE promoter, the IBV Arkansas spike protein and the HSV-1 TK polyadenylation signal is inserted into a restriction enzyme site at the position of the deletion of the ILTV gG gene in the ILTV homology vector. A DNA fragment containing the PRV gX promoter and the *E. coli* β-glucuronidase (uidA) gene is inserted into a unique restriction enzyme site within the ILTV homology vector. A recombinant virus is constructed by combining the final homology vector containing the IBV Arkansas spike gene and the *E. coli* β-glucuronidase (uidA) gene and S-ILT-001 in the DNA TRANSFECTION FOR GENERATING RECOMBINANT ILT VIRUS. The transfection stock is screened by the X-Gluc SCREEN FOR RECOMBINANT HERPESVIRUS EXPRESSING ENZYMATIC MARKER GENES to detect the presence of uidA gene and by the BLACK PLAQUE ASSAY FOR FOREIGN GENE EXPRESSION to detect the presence of the IBV Arkansas spike protein.

A similar strategy is used to construct recombinant ILT viruses carrying the IBV S1 protein from Arkansas, Massachusetts, or Connecticut serotypes IBV matrix protein from Arkansas Massachusetts, or Connecticut serotypes, and IBV nucleocapsid from Arkansas, Massachusetts, or Connecticut serotypes. The strategy is also used to construct recombinant ILT viruses carrying the Newcastle Disease virus (NDV) HN and F genes and the Infectious Bursal Disease virus (IBDV) polyprotein or portions thereof. The strategy is also used to construct recombinant ILT viruses carrying the Mareks Disease virus (MDV) gA, gD, ad gB genes.

Recombinant ILT virus carrying these antigens are valuable as a multivalent vaccine to protect chickens from diseases caused by ILTV and one or more of the viruses IBV, NDV, IBDV, or MDV. Since the ILTV vaccines described here do not express ILTV gG, it is useful as a negative marker to distinguish vaccinated animals from infected animals.

Example 10

Vaccines Utilizing ILTV to Express Antigens from Various Disease Causing Microorganisms Antigens from the following microorganisms are utilized to develop poultry vaccines: Chick anemia agent, Avian encephalomyelitis virus, Avian reovirus, Avian paramyxoviruses, Avian influenza virus, Avian adenovirus, Fowl pox virus, Avian coronavirus, Avian rotavirus, *Salmonella* spp., *E. coli*. *Pasteurella* spp., *Haemophilus* spp., *Chlamydia* spp., *Mycoplasma* spp., *Campylobacter* spp. *Bordetella* spp., Poultry nematodes, cestodes, trematodes. Poultry mites/lice, Poultry protozoa (*Eimeria* spp., *Histomonas* spp., *Trichomonas* spp.).

Example 11

Figure 12:
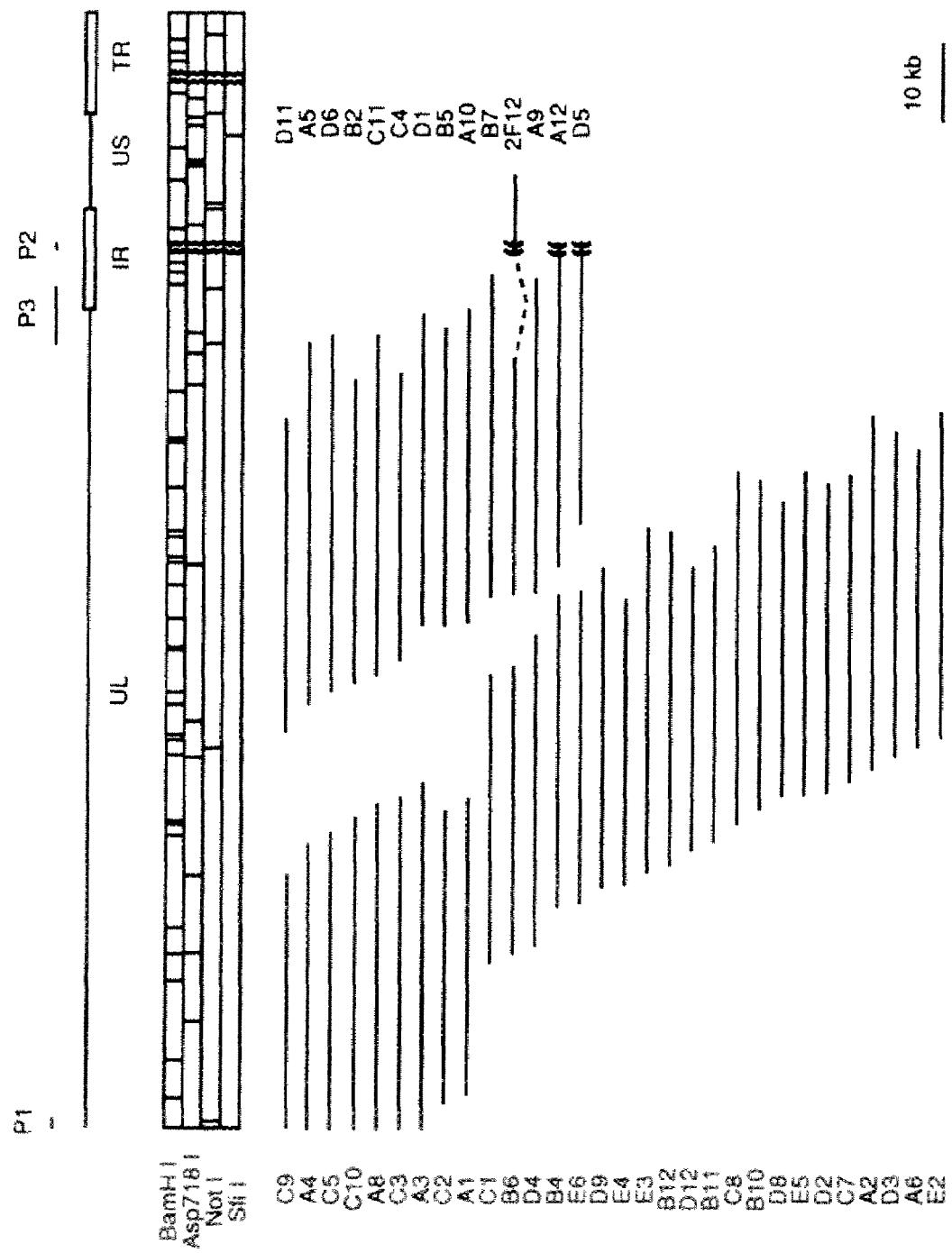
FIG. 12: The genome of the ILTV virus, identifying the unique long (UL), unique short (US), internal repeat (IR), and terminal repeat (TR) is shown. The BamHI, Asp718I, NotI, and SfiI restriction maps of the virus are drawn underneath, with the highly repetitive region of the short repeats indicated by a set of wavy lines. The position of the cosmids used to determine the map of ILTV are drawn beneath the restriction map. Note that cosmid 2F12 contains two non-continuous sections. Three probes used to characterize the ILTV genome are indicated as P1, P2, and P3, P1 is a 0.9 kb NotI fragment found at the terminus of the unique long region, P2 is the 856 bp HindIII fragment found in multiple copies within the short repeat, and P3 is a 6.6 kb NotI fragment used to identify the fragments at the end of the terminal repeat.

A Genomic Map of Infectious Laryngotracheitis Virus and the Sequence and Organization of Genes Present in the Unique Short Region A cosmid library of the ILTV genome was created to facilitate restriction endonuclease mapping. Forty-three overlapping cosmids were analyzed by digestion with Asp718I and NotI. Asp718I was known to cut the genome relatively infrequently (63), and it was found that NotI cut the genome less than ten times, which enabled cutting the vector away from the ILTV DNA insert. Comparison of these cosmid digests allowed the order of the Asp718I fragments covering 85% of the ILTV genome to be determined (FIG. 12). On the long end of the genome, seven cosmids were identified which all contained a NotI site 0.9 kb from the end of the cloned insert; all other cosmid inserts had heterogeneous ends from shearing. This 0.9 kb fragment was used as a probe (P1 in FIG. 12) to genomic ILTV digested with Asp718I, NotI, or BamHI: the sizes of the genomic fragments that hybridized were identical to the size of the fragments excised from the cloned cosmid insert, indicating that the cloned insert extended all the way or very close to the end of the unique long. The 0.9 kb fragment did not hybridize to other bands in the ILTV digest, consistent with previous reports that this virus resembles PRV, and contains no long repeat (66). Once the cosmid clones were ordered, the restriction sites for a more frequent cutting enzyme, BamHI, were mapped.

Figure 13:
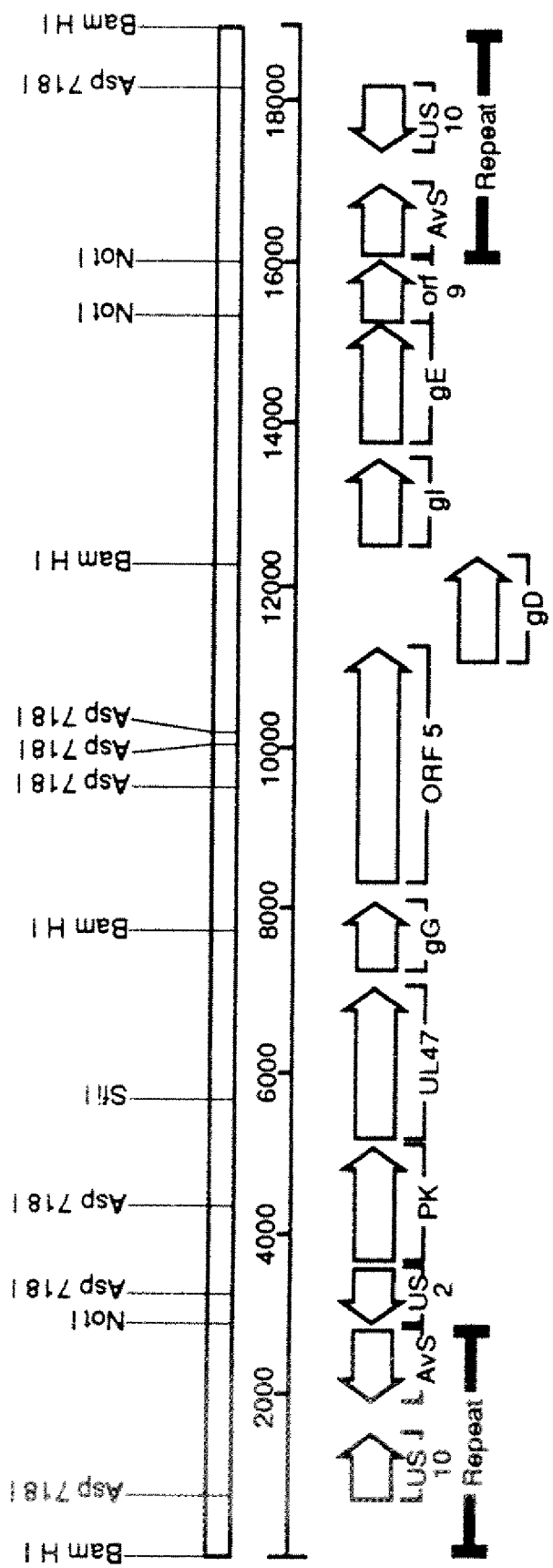
FIG. 13: The region sequenced, and the positions of the Asp718I, BamHI, NotI, and SfiI sites are shown. The and extent and orientation of the open reading frames found in the ILTV unique short and the flanking short repeat regions are indicated.

The resulting map indicated that the cosmid library did not include clones from the unique short portion of the genome. Cosmids spanning the unique short region of HVT (76) and PRV (83) have been found to be underrepresented in cosmid libraries. The Asp718I fragments found in the cosmid clones with an Asp718I digest of wild type ILTV and identified fragments of 8.0, 5.1, and 2.5 kb which were not represented in the cosmid library (FIG. 13) were compared. These fragments were cloned into plasmids ad hybridized to each other and to ILTV digested with BamHI. The Asp718I 2.5 and 8.0 kb fragments cross-hybridized, indicating that they contained sequence repeated in both clones. Fine mapping of the Asp718I 2.5 and 8.0 kb fragments showed them to contain 2.1 kb of identical sequence. Hybridization to ILTV digested with BamHI identified BamHI bands of 7.5, 6.5, and 4.5 kb which overlapped the Asp718I fragments. These BamHI fragments were cloned and analyzed by restriction digestion and hybridization. This allowed the map of the entire unique short region and some of the flanking short repeat to be elucidated (FIG. 13). Subclones of this region were made, and the entire unique short region was sequenced.

Figure 14:
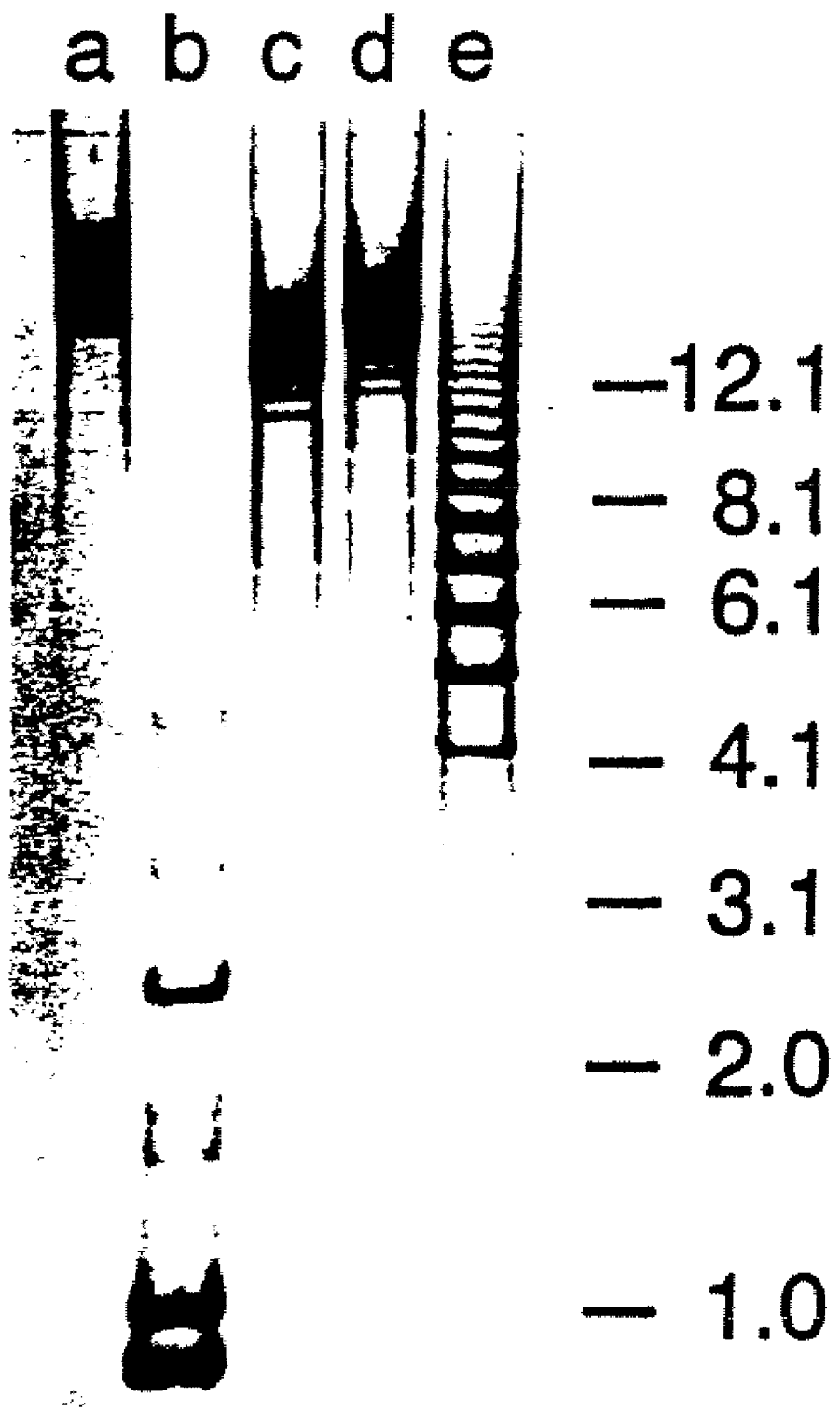
FIG. 14: Southern blot showing the repetition of an 856 bp element within the short repeat. Genomic ILTV DNA digested with SfiI (a), HindIII (b), NotI (c), Asp718I (d), or BamHI (e) was probed with an 856 bp HindIII fragment from the short repeat. Positions of molecular weight markers are indicated.
Figure 15:
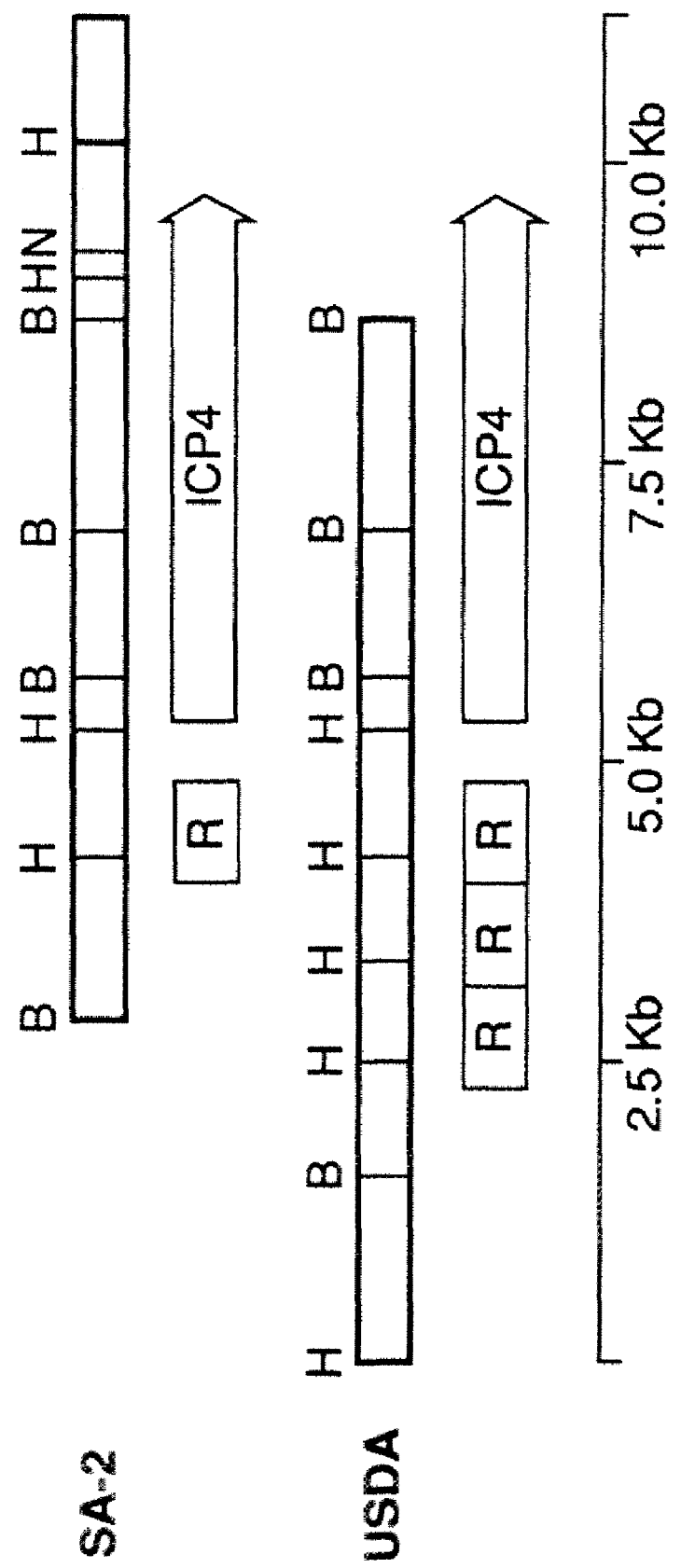
FIG. 15: Depiction of the position of the 856 bp repeat region in the USDA strain compared to the same region from the SA-2 strain as described by Johnson et al. Three repeats are arbitrarily shown in the USDA strain, the region is not repeated in SA-2. B=BamHI, H=HindIII, R=856 bp repeat.

To complete the genomic maps the map searched for an Asp718I or BamHI fragment that spanned the region between the short repeat sequences of the 8.0 or 2.5 kb Asp718I fragments mentioned above and the unique lone region identified in the cosmid map. A 10 kb NotI fragment from the rightmost end of cosmid D5 (FIG. 12) was hybridized to genomic ILTV digests on Southern blots. Interestingly ladders of hybridizing bands were seen when the enzymes BamHI, NotI and Asp718I were used. The bands corresponding to these ladders were not generally visible in ethidium bromide stained gels. Subsequent subcloning and mapping of the 10 kb D5 fragment indicated that it contained up to 5 repeats of an 856 bp segment and that the cosmid insert ended within a repeat motif. HindIII, which cuts once within the repeat, was used to clone the 856 bp fragment. When this fragment (FIG. 12, P2) was used to probe ILTV digested with SfiI, NotI, Asp718I, and BamHI, ladders of hybridization were again seen (FIG. 14). These ladders arise from varying numbers of the 856 bp repeat in different viral molecules. SfiI cuts only once in this ILTV strain, and a ladder at very high molecular weight can be seen. Because the unique short is expected to invert, two overlapping SfiI ladders containing the unique short and terminal repeat ($TR_s$) should be present; however, the bands are too large in this region to make this distinction. NotI and Asp718I cut further away from the repeat, generating ladders beginning at 10.5 or 12 kb. The Asp718I digest should generate two overlapping ladders, because one fragment is bonded by an Asp718I site in the unique long, while the other is bounded by the end of the $TR_s$. In contrast, only one ladder should be generated by the NotI digest. Comparison of FIG. 14 lane c (NotI) with lane d (Asp718I) does suggest that in lane d a second ladder is superimposed on the first, starting somewhat higher. BamHI cuts close to the repeated region, and a ladder beginning at 3.4 kb is found. HindIII cuts within the repeat and generates a strongly hybridizing 856 bp band, as well as the two flanking HindIII fragments of about 1.1 and 2.5 kb, which each contain a portion of the repeated sequence. The presence of this 856 bp repeat accounted for the occasional observation of very fine submolar bands in ethidium bromide-stained Asp718I digests. It also accounted for the lack, in ethidium bromide-stained gels, of a molar or half-molar quantity Asp718I or BamHI band greater than 10 kb, which was expected to span this region based on analysis of the cosmid clones. Instead, because of the presence of the 856 bp repeat, this hand exists as many submolar bands comprising the ladder. As can be seen in the BamHI digest, there can be thirteen or more repeats of the region. Comparison of the repeat sequence to the sequence submitted to GenBank by Johnson et al. (67) indicated that it corresponded (99% identify) to nucleotides 1140 to 1996 of their sequence, which is a region just upstream of the ILTV ICP4 gene. The relationship of the repeat to the surrounding sequence is depicted in FIG. 15. Restriction digests indicate that the region to the right of the repeat as shown is similar in the two strains; however, the position of the BamHI site indicated to the left of the repeat differs between them.

To identify the remainder of the short repeat from the 856 bp repetitive region to the BamHI fragments used for sequencing the unique short, the 8.0 Kb Asp718I fragment containing part of the short repeat was used as a probe to a second cosmid library of ILTV. One cosmid, clone 2F12, hybridized to the probe. Restriction endonuclease analysis of 2F12 and comparison to the cosmid map indicated that it was not a single contiguous cosmid, but was composed of two large non-contiguous fragments (see FIG. 12). The break in the rightmost fragment was within a repeat of the 856 bp region. This fragment included at least two 856 bp repeats, and extended 4.6 kb though the remainder of the short repeat into the unique short.

Figure 16:
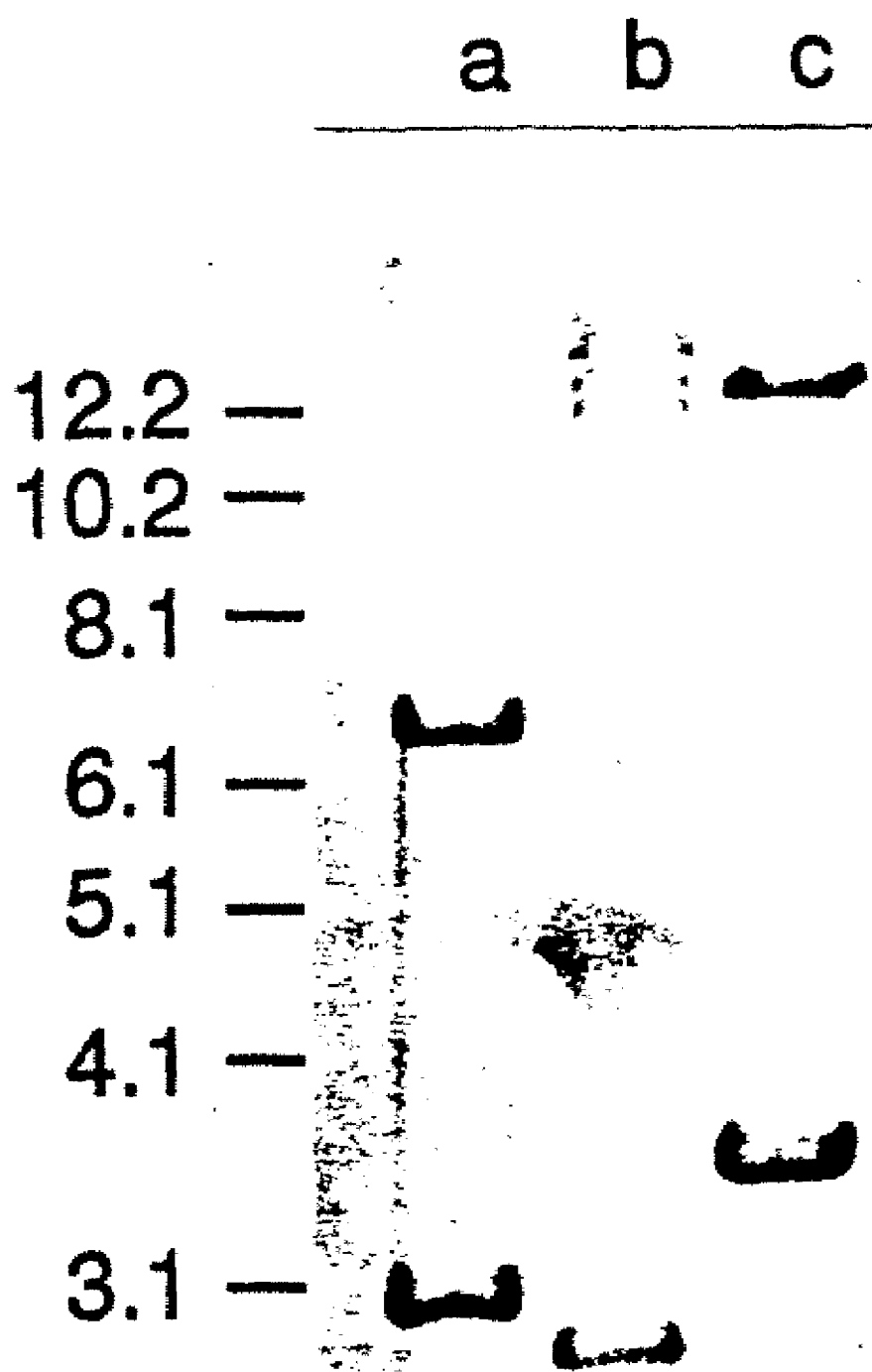
FIG. 16: Southern blot identifying fragments from the internal and terminal repeat that hybridized to a 6.6 kb NotI fragment containing the junction of the unique long and the internal repeat. Genomic ILTV DNA digested with NotI (a), Asp718I (b), and BamHI (c) was probed with the 6.6 kb NotI fragment. Positions of molecular weight markers are indicated.

To identify the end of the $TR_s$, the 6.6 kb NotI fragment spanning the unique long and the short internal repeat ($IR_s$) (P3 in FIG. 2) was used as a probe. It was noted that a 2.9 kb NotI fragment seen in gels stained with ethidium bromide was net represented in the restriction endonuclease map, and considered that it might represent the end of the $TR_s$. Hybridization of a NotI digest of ILTV with P3 indicated that this was indeed the case (FIG. 16). The 2.9 kb NotI bad hybridizes, as does the 6.6 kb bad corresponding to the probe. In the BamHI digest, the predicted 13 kb fragment containing a portion of the $IR_s$ and a 3.5 kb fragment corresponding to the end of the $TR_s$ are evident. In the Asp718I digest, an overlapping 2.7 kb fragment from the unique long hybridizes, and the high molecular weight ladder described previously was seen.

Sequencing of the ILTV unique short and flanking region identified nine open reading frames in the unique region and two (duplicated) in the repeat region as diagrammed in FIG. 13 (SEQ ID NO:59). Comparison of the proteins encoded by these ORFs to the GenBank database (BLAST homology search, National Center for Biological Information. NCBI) demonstrated identity for most of the potential proteins with other known herpesvirus gene products. Table V summarizes the closest homologies found for each gene and gives the probability scores for those homologies as generated by the search program. ORF2 (SEQ ID NO:63), the protein kinase (PK) gene (SEQ ID NO:63), is the most highly conserved of the ILTV ORFs to its herpes homologues. In contrast, the glycoprotein genes are less conserved. It should be noted that portions of the sequences of the ILTV protein kinase, gG, and ORE 5 genes have been published (69, 70 and 81); however, these genes were mapped to the unique long region. A description of each of the nine unique short genes and the two genes in the flanking short repeat follows.

The first open reading frame in the unique short encodes a 229 aa protein showing identity to other herpesvirus US2 proteins (SEQ ID NO:62). Like other US2 genes, it is in the opposite orientation to the remaining ORFs in the unique short. The coding sequence of the gene ends just within the unique short region, and a potential poly-A addition site is found 115 bases downstream in the short repeat. Two possible TATA promoters are found 37 and 70 bases upstream from the initiation codon.

ORF2 encodes a protein kinase with strong identity to many other herpesvirus protein kinases and to cellular protein kinases. The organization of the US2 and PK genes, with their 5' ends close together and their promoters possibly overlapping, is similar to that found in other herpesviruses. Two TATA sequences are present 14 and 49 bases upstream of the PK start codon, and two polyadenylation signals are found, one immediately after the stop codon, and one 50 bases downstream.

ORF3 encodes a 623 aa protein with similarity to the herpes simplex virus UL47 gene (SEQ ID NO:64). The program comparing this protein with other UL47 proteins projects a poor probability score for this homology. However, at least one of the regions of identity between ILTV and HSV UL47 corresponds to a region that is conserved among other herpesvirus UL47 homologues, suggesting that this identity is significant (FIG. 17). Additionally, it should be noted that equally poor probability scores for homology generated by comparisons of the gG or gI genes are also seen for certain homologue pairings, suggesting that these scores are not sufficient for determining homology. It is interesting that the ILTV UL47 gene, normally found in the unique long region of other herpesviruses, appears to have been transposed into the unique short in ILTV.

The fourth open reading frame encodes a 292 aa glycoprotein homologous to PRV gG (SEQ ID NO:65). Four N-linked glycosylation sites with the consensus sequence NXT or NXS are present. The protein has a signal sequence of 26 aa, which could be cleaved at G/AP, but lacks a transmembrane anchor. It is therefore likely that is protein is secreted, similar to other herpesvirus gG homologues. This gene has a consensus TATA sequence 83 bases upstream from the ATG start and has two potential polyadenylation sites 73 and 166 bases downstream from the stop codon.

ORF5 could encode a protein of 985 amino acids (SEQ ID NO:66). A hydrophobic signal sequence is found at the amino terminus, and a hydrophobic sequence is present at the carboxy terminus. Nine glycosylation sites are found, suggesting that this is a glycoprotein. ORF 5 contains an imperfect repeat, consisting of 30 to 36 bp repeated approximately 23 times from amino acid 431 to amino acid 677. The hydrophilic amino acid consensus sequence created by this repeat is FTQTPSTEPET/A. Comparison of ORF 5 with other herpesvirus sequences (Table V) shows similarity to the glycoprotein product from the equine herpesvirus 1 US5 gene (EUS5, 82). The low probability score for this identity arises primarily from the fact that both genes contain threonine-rich repeats. It is not clear whether this reflects homology in form, function, or both. Both the EUS5 and the ILTV ORF 5 genes are large, have similar positions among flanking genes in the unique short, have signal sequences and encode glycoproteins, but other sequence similarities are not seen. It is interesting that the ORF 5 repeat region shows similarity to mucin genes, which also contain threonine rich repeats. The human mucin gene, for example, has the repeat GTQTPTTTPITTTTTVTPTPTPT, where 7 of the first 11 amino acids are identical to the ORF 5 repeat sequence. Again, whether this reflects a similarity in function of the encoded proteins is unclear. A TATA sequence is found 560 bases upstream of the start codon; the nearest consensus polyadenylation signal is at the end of the gI gene. This suggests that the ORF 5 transcript may be coterminal with the gD transcript.

The open reading frame for the gD homologue (ORF 6) (SEQ ID NO:67) overlaps the end of ORF 5. Four in-frame methionines are found within the first 58 amino acids of the open reading frame, and it is not clear which is the actual translational start codon. Because a potential TATA promoter sequence is located only 6-9 bases upstream from the first possible ATG codon, this codon would probably not be within RNA transcribed from this promoter; however, there are several TATA sequences further upstream that may also be used to initiate transcription. The other three potential initiation codons are found at aa 23, 47 and 58 within this ORF. Comparison of the sequences surrounding the four ATGs with the eukaryotic translational initiation consensus sequence A/GCCATGG (71) suggests that the latter two ATG codons may be preferred translational start sites. The protein sequences derived from each of these starts were examined for the presence of eukaryotic signal sequences and signal cleavage sites. A start at aa 58 within the ORF would result in a signal peptide of 26 amino acids with a predicted cleavage site between two alanine residues. This same signal sequence would be positioned much further from the amino terminus and embedded in a more hydrophilic sequence if the other start sites were used. The start of ILTV gD was tentatively assigned to position 58, which would result in a protein 377 amino acids long. Of course, it is possible that more than one initiation codon is used in vivo. Experiments of Zelnik et al. (88) suggest that alternate in-frame ATG codons are used to initiate MDV and HVT gD transcription in vitro, though the in vivo situation was not addressed. Additional experiments on gD transcription and translation in ILTV are necessary to identify its translational start codon.

The ILTV gD homologue has a secretory signal sequence and a transmembrane helix (aa 352-372) at the carboxy terminus. Only one potential glycosylation site is found at position 250-252; this is of the form NPS, and may not be glycosylated due to the proline residue. There is some question, therefore, as to whether processed ILTV gD contains N-linked oligosaccharides. This would be similar to the gD homologue in pseudorabies virus, gp50, which also lacks N-linked glycosylation sites (75). As in other herpesviruses, the gD coding sequence lacks a poly-A addition signal immediately following the gene, and the closest signal is at the end of the gI gene.

The seven open reading frame encodes a protein of 362 aa and is most homologous to varicella zoster virus glycoprotein I (SEQ ID NO:68). The encoded protein shows all the characteristics of related gI glycoproteins, including a signal sequence with a potential cleavage site at positions 22 and 23 between a glycine and an isoleucine, a transmembrane helix at the carboxy terminus from 272-292, and four possible N-linked glycosylation sites. A TATA sequence is present 51 bases upstream from the methionine start codon. Two possible poly-A addition signals are found within the coding sequence for ILTV gI, and may be the signals used by the gD and ORF 5 transcription units upstream.

The gE gene (OK 8) follows the gI. This gene is 499 aa long, and contains four N-linked glycosylation sites (SEQ ID NO:69). A signal sequence of 18 amino acids is present, and there are two and possibly three membrane-associated helices in the carboxy terminal portion of the protein. The gE gene has a TATA box 86 bases upstream of the start codon, and a potential poly-A addition signal just prior to the 3' end of the coding region. This may serve as the polyadenylation site for the gI gene.

The ninth open reading frame extends across the junction of the unique short and the short repeat, and could encode a protein of 260 amino acids (SEQ ID NO:70). This protein has no signal sequence or membrane anchor, but has one possible N-linked glycosylation site. In a search of GenBank, some similarity is found between this protein and BLRF2 of EBV, but the significance of this similarity is unknown. The poly-A addition signal in the short repeat may be utilized by this gene. A potential TATA sequence is found 178 bases upstream of the first ATG of this ORF.

The first open reading frame in the short repeat (SRORF1) (SEQ ID NOs: 61 and 71) encodes a 294 aa protein which displays homology to the gene product of MDV SORF3 (79 and 84) and HVT ORF3 (87). In MDV and HVT, the corresponding gene is found as one copy in the unique short and its function is unknown. No homology has been identified with mammalian herpesviruses; this gene appears to be specific to avian herpesviruses. MDV SORF3 has been deleted by Parcells et al. (74), and does not appear to be absolutely required for infection in chickens.

SRORF2 encodes a protein of 278 amino acids with homology to other herpesvirus US10 genes (SEQ ID NOs:60 and 72). A zinc finger motif, found in the EHV-4 US10, is highly conserved in the ILTV US10 (amino acids 201-218); this suggests that the ILTV US10 gene is a DNA binding protein. Regulatory sequences include a poly-A addition signal 163 bp after the stop codon; it is unclear where the promoter for this gene resides.

Discussion:

The organization of the genes in the unique short region of ILTV is similar to that seen in other herpesviruses. Several genes encoding glycoproteins are present, and the order of these genes is similar to that seen in equine herpesvirus 1, particularly with respect to ORF 5. Similarities to avian herpesviruses are also evident in the presence of the avian-specific gene, SRORF1, and its position relative to US2 and PK, though it differs from HVT and MDV in that it is in the short repeat and is duplicated, also appearing downstream from the ORF 9 gene. The PK gene itself has the most identity to MDV and HVT PK genes; however, other genes are found to be more like their homologues in diverse herpesviruses such as EHV, PRV, and SHV SA8. Unusual characteristics of the ILTV unique short are the inclusion of a gene normally found in the unique long, the UL47 homologue, and the presence of the unique gene. ORF 5, which contains a set of degenerate repeats.

This analysis of the structure of ILTV disagrees with previous reports. Comparison of the sequences described here with those of the Australian ILTV isolate SA-2 indicates that a 32 kd protein described by Kongsuwan et al. (70) is almost identical to the gG in this application, and the sequenced fragment of the g60 protein presented by Kongsuwan et al. (69) is part of the ORF 5 gene in this application. However, they identified the 5 kb Asp718I fragment containing both of these genes as coming from the unique long region of SA-2 (66). Recently, Guo et al. (62) reported the sequence of a region from the USDA challenge strain which they ascribed to the unique short on the basis of comparison to the map presented by Johnson et al. (66). No identity was found between this sequence and the unique short sequence described here. Instead, the sequence described by Guo et al. (62) shows 98% identity to a sequence recently submitted to GenBank by Johnson et al. (67 and 68), which is reported to encode the ICP4 gene of ILTV. The BamHI sites within the ICP4 coding region generate to contiguous fragments of 1.2 and 1.7 kb (see FIG. 15). In the map described here two contiguous BamHI fragments of this size are found within the short repeats (FIG. 12). In addition, the 856 bp repeat element, which is found just upstream of the ICP4 gene (FIG. 15), was mapped in this application within the short repeats. This indicates that the ICP4 gene in the strain used in these studies is present in the $IR_s$ and the $TR_s$. It is possible, but unlikely, that the Australian SA-2 vaccine strain underwent an unusual rearrangement which altered the relationship of the unique long, unique short, and short repeat. However, Guo et al. (62) used the same challenge strain as the one described in this application, and the sequence they reported is not in the unique short, but in the short repeats, similar to the ICP4 genes of other herpesviruses.

The gene encoded by ORF 5 contains threonine rich, degenerate repeats. These are similar in composition and in their repetitive nature to repeats found in mucin genes. This repeated region in mucin is modified by O-linked oligosaccharides and is highly hydrophilic. It is interesting to speculate on what the function of this somewhat similar region might be in infection, if it is expressed in toto in ILTV. At least a portion of this gene is known to be expressed, as Kongsuwan et al. (69) cloned and sequenced a fragment from it by probing a lambda gt11 library with a monoclonal antibody that was known to bind to a 60 kd ILTV protein (g60) on Western blots (86). The relationship of such a 60 kd protein to the predicted 985 aa product from ORF 5 is unknown. Comparison of the application sequence with the complete sequence of the g60 coding region (81) shows a 98.5% homology between the SA-2 strain and the USDA strain. Interestingly, there is an insertion of a block of 10 amino acids in g60 relative to the ORF 5 protein, this difference reflects one additional degenerate repeat sequence in the SA-2 strain.

As mentioned above, Kongsuwan et al. (70) described an ILTV gene that encoded a 32 kd protein with similarity to PRV gG. A comparison of the ILTV gG protein sequence described in this application with their 32 kd protein found 10 amino acid differences in the first 273 residues of the protein. At amino acid 274, a deletion of one base pair in SA-2 relative to the USDA strain created a frame shift, such that 19 additional residues were found in the challenge strain as opposed to 26 in SA-2. A peptide was made from the carboxy terminal sequence elicited antisera in mice which reacted with ILTV gG; this indicates that the sequence described in this application reflects the actual carboxy terminus in the USDA strain. A similar situation was found when the ILTV gD protein described in this application was compared with the ILTV gD sequence submitted to GenBank by Johnson et al. (68). Ten differences were found in the first 419 amino acids, after which a deletion of a base in the SA-2 strain relative to the sequence described in this application caused the predicted carboxy termini to differ, with 15 more amino acids in the USDA strain and 9 in SA-2. These differences could arise from errors introduced during cloning and sequencing of these genes. It is also possible that the carboxy termini of the ILTV gG and gD genes are variable between these strains.

The 856 bp repeat unit identified within the short repeat is just upstream of the ICP4 gene described by Johnson et al. (67), but, from the sequence alone, it does not appear to be repetitive in the SA-2 strain. The BamHI fragment containing this repetitive region is 2848 bp long in SA-2. The smallest repeat, seen faintly in the BamHI ladder of FIG. 14, is 3.4 kb long. This is not quite large enough to include two repeats, and suggests that other alterations between the two strains may exist in this region. A repeat of this sort has not been previously described for this or other ILTV strains, though the submolar nature of the bands may have obscured its presence. The appearance of the ladder is reminiscent of defective interfering particles, but it is not believed that this represents a case. Of defective interfering particles in the viral stock used here. Several reasons for this follow. 1) Defective interfering particles are generally found when viruses are passaged at high multiplicity, and the ILTV viral stocks of his application were passaged at low multiplicity. In fact, viral stocks originating from a single picked plaque exhibited similar ladders when their DNA was subjected to Southern blot analysis, suggesting that a single viral particle containing a set number of repeats could regenerate the full range of the ladder after being grown for a short period of time. 2) If populations of defective interfering particles were present, one might expect to encounter digest fragments that would not be accommodated in the linear viral map (see, for example, 77), yet all but one of the cosmids analyzed make a contiguous map, with Asp718I bands identical to those present in genomic ILTV digests. The exception, 2F12, was unusual in being the only one of several hundred cosmid clones screened which contained part of the unique short. This probably represented an aberrant cloning event and not a widespread phenomenon related to defective viral particles. 3) Defective interfering particles often are present in larger molar amounts than standard viral particles, such that restriction fragments originating from the defective particles are overrepresented. In contrast, the bands of the 856 bp ladder are submolar, and are only rarely visible in ethidium bromide stained gels. 4) Defective interfering particles contain origins of replication. The 856 bp repeat itself does not contain a herpesvirus origin of replication as defined by the consensus sequence of Baumann et al. (59). From these considerations it was concluded that varying numbers of 856 bp units are present in the short repeats of standard viral DNA from the USDA challenge strain of ILTV. Since fragments exist that contain thirteen or more repeats of the region, genomic DNA from ILTV could vary by over 11 kb in the short repeat regions. Repetitive regions have been identified in other herpesviruses; for example, Marek's disease virus contains a 132 bp repetitive sequence in the long repeat regions (61 and 73) and expansion of this repeat is associated with reduction of viral oncogenicity. The presence of the 856 bp tandem repeats in ILTV, in contrast, does not appear to affect viral pathogenicity, since his strain does cause severe clinical disease in chickens. It would be interesting to examine other ILTV strains for the presence of this repeat.

Table V indicates the ORFs of the ILTV unique short and the HSV nomenclature for these genes, in those cases where homology is found. The third column shows the best matches from the Blast homology search (NCBI), and the probability scores assigned by the program for the matches indicated. Smaller numbers indicate less likelihood that the match could occur randomly.

A genomic map of infectious laryngotracheitis virus (ILTV) and a 18,912 bp sequence containing the entire unique short region and a portion of the flanking short repeats is presented. In determining the genomic map, an 856 bp region repeated as many as 13 times was identified within the short repeats. The unique short sequence contains 9 potential open reading frames (ORFs). Six of these ORFs show homology to other known herpesvirus unique short genes. Using the herpes simplex virus nomenclature, these genes are the US2, protein kinase, and glycoproteins G, D, I, and E (SORFs 1, 2, 4, 6, 7, and 8, respectively). Interestingly, an open reading frame with homology to HSV-1 UL47 (SORF 3) is found in the unique short. One very large open reading frame (ORF 5) is present and contains a threonine rich, degenerate repeat sequence. This gene appears to be unique to ILTV among sequenced herpesviruses. Two ORFs were identified within the short repeat region. SRORF1 is homologous to a gene (SORF3) found in the unique short region in both MDV and HVT, and appears to be specific to avian herpesviruses. SRORF2 has homology to HSV US10.

TABLE V

| ORF | HSV Homolog | Best Matches | Blast Score |
|---|---|---|---|
| 1 | US2 | EHV1 EUS1 | $3.1 \times 10^{-13}$ |
| | | EHV4 EUS1 | $5.3 \times 10^{-12}$ |
| | | HSV2 US2 | $6.7 \times 10^{-7}$ |
| 2 | PK | MDV PK | $8.2 \times 10^{-36}$ |
| | | HVT PK | $5.4 \times 10^{-35}$ |
| | | HSV1 PK | $4.1 \times 10^{-30}$ |
| 3 | UL47 | HSV1 UL47 | $6.0 \times 10^{-1}$ |
| | | EHV1 UL47 | $9.9 \times 10^{-1}$ |
| | | MDV UL47 | $9.9 \times 10^{-1}$ |
| 4 | gG | PRV gG | $5.3 \times 10^{-5}$ |
| | | BHV1 gG | $1.7 \times 10^{-2}$ |
| | | EHV1 gG | $6.8 \times 10^{-1}$ |
| 5 | ORF 5 | EHV1 EUS5 | $1.9 \times 10^{-45}$ |
| | | Human mucin | $1.1 \times 10^{-25}$ |
| 6 | gD | MDV gD | $6.8 \times 10^{-4}$ |
| | | PRV g50 | $2.0 \times 10^{-3}$ |
| | | HVT gD | $3.5 \times 10^{-3}$ |
| 7 | gI | VZV gI | $4.2 \times 10^{-2}$ |
| | | HVT gI | $7.9 \times 10^{-2}$ |
| | | SVV gI | $4.3 \times 10^{-1}$ |
| 8 | gE | SHV SA8 gE | $1.7 \times 10^{-6}$ |
| | | HSV1 gE | $1.1 \times 10^{-3}$ |
| | | BHV1 gE | $1.5 \times 10^{-2}$ |
| 9 | ORF 9 | EBV BLRF2 | $5.7 \times 10^{-1}$ |
| SR1 | no HSV | MDV "ORF3" | $4.8 \times 10^{-4}$ |
| | homologue | HVT "ORF3" | $2.6 \times 10^{-1}$ |
| SR2 | US 10 | EHV-4 US10 | $1.2 \times 10^{-1}$ |
| | | HSV-1 US10 | $8.7 \times 10^{-1}$ |
| | | EHV-1 US10 | $8.7 \times 10^{-1}$ |

REFERENCES

1. L. Nicolson, et. al., Virology 179, 378-387 (1990)
2. R. W. Price and A. Kahn, Infection and Immunity, 34, 571-580 (1981).
3. M. P. Riggio, et. al., Journal of Virology 63, 1123-1133 (1989).
4. G. R. Robertson and J. M. Whalley, Nucleic Acids Research 16, 11303-11317 (1988).
5. B. Roizman, et. al., Cold Spring Harbor Conference on New Approaches to Viral Vaccines (September 1983).
6. B. Roizman, et. al., Archives of Virology 123, 425-449 (1992).
7. F. A. Ferrari, et. al., Journal of Bacteriology 161, 556-562 (1985).
8. R. A. Bhat, et. al., Nucleic Acids Research 17, 1159-1176 (1989)
9. The Herpesviruses, Volume 1, B. Roizman, ed., Plenum Press, New York, (1982).
10. Diseases of Poultry, Eighth Edition, M. S. Hofstad, Ed., pp 444-451, Iowa State University Press, 1984.
11. M. C. Wark, et. al., Journal of Biological Standardization 7: 73-80 (1979).
12. S. Davison, et. al., Avian Diseases 33: 18-23 (1989).
13. S. Davison, et. al., Avian Diseases 33: 24-29 (1989).
14. J. R. Andreasen Jr., et. al., Avian Diseases 33: 516-523 (1989).
15. J. R. Andreasen Jr., et. al., Avian Diseases 33; 524-530 (1989).
16. J. S. Guy, et. al., Avian Diseases 34: 106-113 (1990).
17. J. R. Andreasen Jr., et. al., Avian Diseases 34: 185-192 (1990).
18. J. J. York, and K. J. Fahey, Archives of Virology 115: 289-297 (1990).

19. C. S. Hughes, et. al., Archives of Virology 121: 213-218 (1991).
20. T. J. Bagust, et. al., Patent Application WO 91/02053
21. J. S. Guy, et. al. Avian Diseases 35: 348-455 (1991).
22. M. A. Johnson, et. al., Archives of Virology 119: 181-198 (1991).
23. D. A. Leib, et. al., Archives of Virology 93: 287-294 (1987).
24. M. Kotiw, et. al., Veterinary Microbiology 11: 319-330 (1986).
25. J. S. Guy, et. al., Avian Diseases 33: 316-323 (1989).
26. J. R. Andreasen Jr., et. al., Avian Diseases 34: 64-56 (1990).
27. M. M. Binns, et. al., PCT Patent Application WO 90/02802.
28. A. M. Griffin and M. E. G. Boursnell, Journal of General Virology 71 841-850 (1990).
29. D. J. Poulsen, et. al., Virus Genes 5: 335-347 (1991).
30. A. M. Griffin, Journal of General Virology 72: 393-398 (1991)
31. A. M. Griffin. Journal of General Virology 70: 085-3089 (1989).
32. A. M. Griffin, Nucleic Acids Research 18: 3664 (1990).
33. Y. M. Saif, et. al. AVMA 130th Annual Meeting, Jul. 17-21, 1993, Minneapolis, Minn.
34. J. J. York, et. al., Virology 161: 340-347 (1987).
35. J. J. York, et. al., Archives of Virology 115: 147-162 (1990).
36. C. T. Prideaux, et. al., Archives of Virology 123: 181-192 (1992).
37. R. W. Honess, Journal of General Virology 65, 2077-2107 (1984).
38. M. L. Cook & J. G. Stevens, Journal of General Virology 31, 75-80 (1976).
39. S. Joshi, et. al., Journal of Virology 65, 524-5530 (1991).
40. M. Wachsman, et. al., Journal of General Virology 70, 2513-2520 (1989).
41. R. A. Bhat, et. al., Nucleic Acids Research 17, 1159-1176 (1989)
42. T. Manatis, et. al., Molecular Cloning: A Laboratory Manual, Cold Spring Harbor Press, Cold Spring Harbor, N.Y. (1982)
43. J. Sambrook, et. al., Molecular Cloning: A Laboratory Manual, Second Edition, Cold Spring Harbor Press, Cold Spring Harbor, N.Y. (1989).
44. M. A. Innis, et. al., PCR Protocols: A Guide to Methods and Applications, Academic Press, San Diego (1990).
45. C. Chen and Okayama H., Mol. Cell. Biol. 7, 2745-2752 (1987).
46. M. van Zijl, et. al. Journal of Virology 62, 2191-2195 (1988).
47. B. Lomniczi, et. al., Journal of Virology 49 970-979 (1984).
48. D. J. McGeoch, et. al., Journal of Molecular Biology 181, 1-13 (1985).
49. F. A. Ferrari, et, al. Journal of Bacteriology 161, 556-562 (1985).
50. J. M. Sharma and L. G. Raggi, Avian Disease 13, 268-279 (1969).
51. D. H. Kingsley, J. W. Hazel, and C. L. Keeler, Jr., Abstract from the 65th Northeastern Conference on Avian Diseases, Jun. 9-11, 1993. University of Delaware, Newark, Delaware.
52. D. W. Key and E. Nagy, Abstract from the 65th Northeastern Conference on Avian Diseases, Jun. 9-11, 1993. University of Delaware, Newark, Del.
53. M. G. Sheppard, et. al., PCT Patent Application WO 92/03554.
54. T. Honda, et. al., U.S. Pat. No. 4,980,162.
55. Federal Register, Vol. 55, No. 90, pp. 19245-19253
56. T. Ben-Porat, et. al., Virology 154 325-334 (1986).
57. F. Zuckerman, et. al. in Vaccination and Control of Aujeszky's Disease, Ed. J. van Oirschot, Kluwer, London (1989), pp. 107-117.
58. Altschul, S. F., Gish, W., Miller. W., Myers, E. W., and Lipman, D. J. (1990). Basic local alignment search tool. J. Mol. Biol. 215, 403-410.
59. Baumann, R. P., Yalamanchili, V. R. R., and O'Callaghan, D. J. (1989) Functional mapping and DNA sequence of an equine herpesvirus 1 origin of replication. J. Virol. 63, 1275-1283.
60. Dayhoff, M. O., Barker, W. C., and Hunt, L. T. (1983) Establishing homologies in protein sequences. Methods Enzymol 91, 524-545.
61. Fukuchi K., Tanaka, Schierman, L. W., Witter, R. L., and Nonoyama, M. (1985). The structure of Marek disease virus DNA: the presence of unique expansion in nonpathogenic viral DNA. Proc. Nan. Acad. Sci. USA 82, 751-754.
62. Guo, P., Scholz, E., Maloney, B. and Welniak, E. (1994). Construction of recombinant avian infectious laryngotracheitis virus expressing the β-galactosidase gene and DNA sequencing of the insert region. Virology 202, 771-781.
63. Guy, J. S., Bares, H. J., Munger, L. I. and Rose, L. (1989). Restriction endonuclease analysis of infectious laryngotracheitis viruses: Comparison of modified-live vaccine viruses and North Carolina field isolates. Avian Diseases 33, 316-323.
64. Holland, T. C., Sandri-Goldin, R. M., Holland, L. E., Marlin, S. D., Levine, M., and Glorioso, J. C. (1983). Physical mapping of the mutation in an antigenic variant of herpes simplex virus type 1 by use of an immunoreactive plaque assay. J. Virol. 46, 649-652.
65. Hughes, C. S., Williams, R. A., Gaskell, R. M., Jordan. F. T. W., Bradbury, J. M., Bennett, M., and Jones, R. C. (1991). Latency and reactivation of infectious laryngotracheitis vaccine virus. Arch. Virol. 121, 213-218.
66. Johnson, M. A., Prideaux, C. T., Kongsuwan. K., Sheppard, M., and Fahey, K. J. (1991). Gallid herpesvirus 1 (infectious laryngotracheitis virus): cloning and physical maps of the SA-2 strain. Arch. Virol. 119, 181-198.
67. Johnson, M. A., Tyack, S. G., Prideaux, C. T., Kongsuwan, K. and Sheppard, M. (1994). Gallid herpesvirus 1 major immediate early protein (ICP4) gene. GenBank L32139.
68. Johnson, M. A., Tyack, S. G., Prideaux, C. T., Kongsuwan. K. and Sheppard, M. (1994). Gallid herpesvirus 1 glycoprotein D (gD) gene, complete eds. GenBank L31965.
69. Kongsuwan, K., Johnson, M. A., Prideaux, C. T., and Sheppard, M. (1993). Use of lgt11 and monoclonal antibodies to map the gene for the 60,000 dalton glycoprotein of infectious laryngotracheitis virus. Virus Genes 7, 297-303.
70. Kongsuwan, K., Johnson, M. A., Prideaux, C. T., and Sheppard, M. (1993). Identification of an infectious laryngotracheitis virus gene encoding an immunogenic protein with a predicted $M_r$ of 32 kilodaltons. Virus Research 29, 125-140.
71. Kozak, M. (1987). An analysis of 5'-noncoding sequences from 699 vertebrate messenger PNAs. Nucleic Acids Res. 15, 8125-8148.
72. Leib, D. A., Bradbury, J. M., Gaskell, R. M. Hughes, C. S., and Jones, R. C. (1986). Restriction endonuclease patterns of some European and American isolates of avian infectious laryngotracheitis Virus Avian Dis. 30, 835-837.

73. Maotani, K. Kanamori, A. Ikuta, K., Ueda, S., Kato. S., and Hirai S. (1986). Amplification of a tandem direct repeat within inverted repeats of Marek's disease virus DNA during serial in vitro passage. J. Virol. 58, 657-660.
74. Parcells, M. S., Anderson, A. S., Cantello, J. L., and Morgan, R. W. (1994) Characterization of Marek's disease virus insertion and deletion mutants that lack US1 (ICP22 homolog), US10, and/or US2 and neighboring short-component open reading frames. J. Virol. 68, 8239-8253.
75. Petrovskis, E. A., Timmins, J. G., Armentrout, M. A., Marchioli, C. C., Yancey, R. J., Jr., and Post, L. (1986) DNA sequence of the gene for pseudorabies virus gp50, a glycoprotein without N-linked glycosylation. J. Virol. 59, 216-223.
76. Reilly, J. D., and Silva, R. F. (1993). Cosmid library of the turkey herpesvirus genome constructed from nanogram quantities of viral DNA associated with an excess of cellular DNA. J. Virol. Methods 41, 323-331.
77. Rixon, F. J., and Ben-Porat, T. (1979). Structurally evolution of the DNA of pseudorabies-defective viral particles. Virology 97, 151-163.
78. Roizmann, B., Desrosiers, R. C., Fleckenstein, B., Lopez, C., Minson, A. C., and Studdert, M. J. (1992). The family Herpesviridae: an update. Arch. Virol. 123, 425-449.
79. Sakaguchi, M., Urakawa, T., Hirayama, Y., Miki, N., Yamamoto, M., and Hirai, K. (1992) Sequence determination and genetic content of an 8.9 kb restriction fragment in the short unique region and the internal inverted repeat of Marek's disease virus type 1 DNA. Virus Genes 6, 365-378.
80. Sanger, F., Nicklen, S., and Coulson, A. R. (1977). DNA sequencing with chain-terminating inhibitors. Proc. Natl. Acad. Sci., USA 74, 5463-5467.
81. Sheppard, M. G., Prideaux, C., Johnson, M., Fahey, K. J. York, J. J., and Kongsuwan, K. (1992). Infectious laryngotracheitis vaccine. International Patent Publication no. WO92/03554.
82. Telford, E. A., Watson, M. S., McBride, K., and Davison, A. J. (1992). The DNA sequence of equine herpesvirus-1. Virology 189, 304-316.
83. van Zijl, M., Quint, W., Briaire, J., de Rover, T. Gielkens, A., and Berns, A. (1988). Regeneration of herpesviruses from molecularly cloned subgenomic fragments. J. Virol. 62, 2191-2195.
84. Velicer, L. F., Brunovskis, P., and Coussens, P. M. (1992) Marek's disease herpesvirus DNA segment encoding glycoproteins gD, gI and gE. International Patent Publication no. WO92/03547.
85. Wark, M. C. Tannock, G. A. and Pye, D. (1979). The development and evaluation of a cell culture vaccine against infectious laryngotracheitis virus. J. Biological Standardization 7, 73-80.
86. York, J. J., Sonza, S., Brandon, M. R., and Fahey, K. J. (1990). Antigens of infectious laryngotracheitis herpesvirus defined by monoclonal antibodies. Arch. Virol. 115, 147-162.
87. Zelnik, V., Darteil, R., Audonnet, J. D., Smith, G. D., Riviere, M. Pastorek, J., and Ross, L. J. N. (1993) The complete sequence and gene organization of the short unique region of herpesvirus of turkeys. J. Gen. Virol. 74, 2151-2162.
88. Zelnik, V., Ross, N. L. J., and Pastorek, J. (1994). Characterization of proteins encoded by the short unique region of herpesvirus of turkeys by in vitro expression. J. Gen. Virol. 75, 2747-2753.

What is claimed is:

1. An isolated infectious laryngotracheitis virus glycoprotein that comprises amino acid residues 23 to 362 of the amino acid sequence of SEQ ID NO: 7.

2. The isolated glycoprotein of claim 1 that comprises the amino acid sequence of SEQ ID NO: 7.

3. A recombinant infectious laryngotracheitis virus glycoprotein that comprises amino acid residues 23 to 362 of the amino acid sequence of SEQ ID NO: 7, wherein said recombinant infectious laryngotracheitis virus glycoprotein is independent of a recombinant infectious laryngotracheitis virus.

4. The recombinant glycoprotein of claim 1 that comprises the amino acid sequence of SEQ ID NO: 7.

* * * * *

```
                           SEQUENCE LISTING (1) GENERAL INFORMATION:

(iii) NUMBER OF SEQUENCES: 72

(2) INFORMATION FOR SEQ ID NO: 1:

(i) SEQUENCE CHARACTERISTICS:
             (A) LENGTH: 13473 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (ix) FEATURE:
             (A) NAME/KEY: CDS
             (B) LOCATION: 1059..2489

(ix) FEATURE:
             (A) NAME/KEY: CDS
             (B) LOCATION: 2575..4107

(ix) FEATURE:
             (A) NAME/KEY: CDS
             (B) LOCATION: 4113..4445

(ix) FEATURE:
             (A) NAME/KEY: CDS
             (B) LOCATION: 4609..5487

(ix) FEATURE:
```

```
        (A) NAME/KEY: CDS
        (B) LOCATION: 5697..8654

(ix) FEATURE:
        (A) NAME/KEY: CDS
        (B) LOCATION: 9874..10962

(ix) FEATURE:
        (A) NAME/KEY: CDS
        (B) LOCATION: 11159..12658

(ix) FEATURE:
        (A) NAME/KEY: CDS
        (B) LOCATION: 12665..13447

(xi) SEQUENCE DESCRIPTION: SEQ ID NO: 1:
```

| | |
|---|---:|
| CCCGTGCCCC TAAAGGCCGC CGAGAAAGCT AAGTCCAAAT GTGACGTCGG AGGTCTCGAC | 60 |
| ATGGTCGCCA ACCCTCCAAA TGCTACCCGC CGGCCCACGC AACGCGGGCT TTTATAAAGA | 120 |
| TGGCGCGCGA GACAATAACA CTTACTCATC CGCGTACGCG TTTATTATTG TCAATATTTG | 180 |
| TGTGGTTATT ATTACTGCTA CCGCCCTTGT TTCTGCAAGG CCCTCGCCGC GGCCCAGGCC | 240 |
| ACTATTCCGG CAGCGGCCGC CGACGCGGCG AGCGTCGCCG CTAACGTCGG CGCCGCGGGG | 300 |
| AGCGGGGTTT CTTCGACTTA AATAGACTCC CGAGAAAAAA TTTTGGCTGC CGTTCGCCAT | 360 |
| CATCCGAGTC GGAAACACAG TATGCGGCCG AGTTAGGTTT TACTTTTAAA AACTTTACCG | 420 |
| TGCTGTACGG CCAGGGCGTT CTCAGGCTCG AAGGGGCAAG AGTTGTCCAG ACTGATGGGT | 480 |
| GACTCAGAGA CAGCGTTGTC TTGTCTCCGT TTACCAAAAA TATTTCCACT CCTCTCTCAA | 540 |
| AATTTTTACC TCCGGTTTCG GTAATTAGGA AAGTTTTTGG CGCAGGGAGG TTTAAAGCTG | 600 |
| CCATGCATAT GTCAGCGGTA CCCAGCACCC ACAAATGGAA CTCTTTTGCG GCATACGCGC | 660 |
| CAGATGACAA ATGGTAAAAC CCTGCGTCCA AGCCGCTCCA CTCGGGACTT ACTCCAGGCG | 720 |
| GGTCGCCCCC CTCACCGAAC CGAATCACGG GTCTGCACAT CCTGGGAAGG GAAAACAGCT | 780 |
| CCCCGGAAAC TTCGTACAGA GATGCCGGGC GCACGATTAC CGATAATGTA CTCGGACGAT | 840 |
| CGTAACTCGC CATAGTTTTC ACTGCGTGAA CCAATTCTTT CCATCCAGAA TCCGAGAGCT | 900 |
| CAAATCTAGA ATTAGGTAGT TTGTAGTGCG AATCGACCGC AGAAACTATA GTCACTTTTA | 960 |
| CAGGCGCCAT CGCCGCTCAG ACTCCACCCC GCTATGATGT CAGAAATATA ACGCTCTTAT | 1020 |
| TCTAGCAGAG TCAGGCCAAT ATATACAGCT TAGAGAAG ATG CGG TTT CGG CGC | 1073 |
|                                           Met Arg Phe Arg Arg |  |
|                                             1               5 |  |
| ATC TGT TCA CGC TCT AGG GCA GAA AAA CGA AGA AGA ACA ACC GAG AAT | 1121 |
| Ile Cys Ser Arg Ser Arg Ala Glu Lys Arg Arg Arg Thr Thr Glu Asn |  |
|          10                  15                      20 |  |
| CCG CTT ACC TCA AAA CGC GTT TGC GTA TTG GAT AGT TTC TCA CGG ACA | 1169 |
| Pro Leu Thr Ser Lys Arg Val Cys Val Leu Asp Ser Phe Ser Arg Thr |  |
|              25                  30                  35 |  |
| ATG TCA TTG CGC CCC TAT GCA GAA ATT TTG CCG ACC GCG GAA GGC GTC | 1217 |
| Met Ser Leu Arg Pro Tyr Ala Glu Ile Leu Pro Thr Ala Glu Gly Val |  |
|          40                  45                  50 |  |
| GAG CGC CTC GCC GAA CTT GTT AGT GTG ACA ATG ACA GAA CGC GCG GAA | 1265 |
| Glu Arg Leu Ala Glu Leu Val Ser Val Thr Met Thr Glu Arg Ala Glu |  |
|      55                  60                  65 |  |
| CCT GTG ACA GAG AAT ACA GCT GTA AAC AGT ATC CCC CCG GCT AAC GAG | 1313 |
| Pro Val Thr Glu Asn Thr Ala Val Asn Ser Ile Pro Pro Ala Asn Glu |  |
|  70                  75                  80                  85 |  |
| AAC GGG CAG AAC TTC GCA TAT GCA GGC GAT GGG CCC TCG ACT ACT GAA | 1361 |
| Asn Gly Gln Asn Phe Ala Tyr Ala Gly Asp Gly Pro Ser Thr Thr Glu |  |
|              90                  95                  100 |  |

```
AAA GTT GAC GGC TCG CAT ACA GAC TTC GAT GAA GCA TCG AGC GAC TAC      1409
Lys Val Asp Gly Ser His Thr Asp Phe Asp Glu Ala Ser Ser Asp Tyr
            105                 110                 115

GCC GGC CCT GTC CCG CTC GCG CAA ACT AGA TTG AAG CAT TCG GAT GAA      1457
Ala Gly Pro Val Pro Leu Ala Gln Thr Arg Leu Lys His Ser Asp Glu
            120                 125                 130

TTT CTT CAG CAC TTC CGA GTT TTA GAC GAT TTG GTG GAG GGG GCT TAC      1505
Phe Leu Gln His Phe Arg Val Leu Asp Asp Leu Val Glu Gly Ala Tyr
            135                 140                 145

GGG TTT ATC TGC GGC GTC CGT CGC TAC ACC GAG GAA GAG CAA CGT CGA      1553
Gly Phe Ile Cys Gly Val Arg Arg Tyr Thr Glu Glu Glu Gln Arg Arg
150                 155                 160                 165

AGA GGG GTT AAC AGT ACT AAC CAG GGG AAA TCA AAA TGT AAG CGC CTG      1601
Arg Gly Val Asn Ser Thr Asn Gln Gly Lys Ser Lys Cys Lys Arg Leu
                170                 175                 180

ATA GCT AAA TAT GTG AAA AAT GGA ACA AGG GCG GCC TCT CAG CTG GAA      1649
Ile Ala Lys Tyr Val Lys Asn Gly Thr Arg Ala Ala Ser Gln Leu Glu
                185                 190                 195

AAT GAA ATT TTG GTT CTC GGG CGC CTA AAT CAC GAG AAT GTT CTC AAG      1697
Asn Glu Ile Leu Val Leu Gly Arg Leu Asn His Glu Asn Val Leu Lys
            200                 205                 210

ATC CAG GAA ATC CTT CGG TAC CCG GAT AAT ACG TAC ATG TTA ACG CAG      1745
Ile Gln Glu Ile Leu Arg Tyr Pro Asp Asn Thr Tyr Met Leu Thr Gln
            215                 220                 225

AGG TAT CAG TTC GAC TTG TAC AGC TAC ATG TAC GAT GAA GCG TTC GAC      1793
Arg Tyr Gln Phe Asp Leu Tyr Ser Tyr Met Tyr Asp Glu Ala Phe Asp
230                 235                 240                 245

TGG AAA GAC AGT CCA ATG CTT AAA CAG ACT AGA CGC ATC ATG AAG CAG      1841
Trp Lys Asp Ser Pro Met Leu Lys Gln Thr Arg Arg Ile Met Lys Gln
                250                 255                 260

CTC ATG TCA GCG GTC TCG TAT ATC CAT TCA AAG AAA CTG ATT CAC AGG      1889
Leu Met Ser Ala Val Ser Tyr Ile His Ser Lys Lys Leu Ile His Arg
            265                 270                 275

GAC ATC AAA CTC GAA AAT ATT TTC TTA AAC TGC GAC GGC AAG ACA GTG      1937
Asp Ile Lys Leu Glu Asn Ile Phe Leu Asn Cys Asp Gly Lys Thr Val
            280                 285                 290

CTG GGC GAC TTT GGA ACT GTC ACG CCT TTT GAA AAT GAG CGG GAG CCC      1985
Leu Gly Asp Phe Gly Thr Val Thr Pro Phe Glu Asn Glu Arg Glu Pro
            295                 300                 305

TTC GAA TAT GGA TGG GTG GGG ACC GTG GCT ACT AAC TCT CCC GAG ATA      2033
Phe Glu Tyr Gly Trp Val Gly Thr Val Ala Thr Asn Ser Pro Glu Ile
310                 315                 320                 325

CTC GCC AGG GAT TCG TAC TGT GAA ATT ACA GAC ATT TGG AGC TGC GGA      2081
Leu Ala Arg Asp Ser Tyr Cys Glu Ile Thr Asp Ile Trp Ser Cys Gly
                330                 335                 340

GTA GTA TTG CTG GAA ATG GTA AGC CAT GAA TTT TGC CCG ATC GGC GAT      2129
Val Val Leu Leu Glu Met Val Ser His Glu Phe Cys Pro Ile Gly Asp
                345                 350                 355

GGC GGG GGA AAT CCG CAC CAG CAA TTG CTG AAA GTT ATC GAC TCT CTC      2177
Gly Gly Gly Asn Pro His Gln Gln Leu Leu Lys Val Ile Asp Ser Leu
            360                 365                 370

TCA GTT TGT GAT GAA GAG TTC CCA GAC CCC CCG TGT AAT CTG TAC AAT      2225
Ser Val Cys Asp Glu Glu Phe Pro Asp Pro Pro Cys Asn Leu Tyr Asn
375                 380                 385

TAT TTG CAT TAT GCG AGC ATC GAT CGC GCC GGA CAT ACG GTC CCG TCG      2273
Tyr Leu His Tyr Ala Ser Ile Asp Arg Ala Gly His Thr Val Pro Ser
390                 395                 400                 405

CTC ATA CGG AAC CTC CAC CTT CCG GCG GAT GTG GAA TAC CCT CTA GTT      2321
Leu Ile Arg Asn Leu His Leu Pro Ala Asp Val Glu Tyr Pro Leu Val
            410                 415                 420
```

```
AAA ATG CTT ACT TTT GAC TGG CGT TTG AGA CCC AGC GCG GCC GAA GTA      2369
Lys Met Leu Thr Phe Asp Trp Arg Leu Arg Pro Ser Ala Ala Glu Val
            425                 430                 435

TTG GCA ATG CCA CTG TTT TCG GCT GAA GAG GAA CGG ACC ATA ACA ATT      2417
Leu Ala Met Pro Leu Phe Ser Ala Glu Glu Glu Arg Thr Ile Thr Ile
                440                 445                 450

ATT CAT GGA AAA CAT AAA CCC ATC CGA CCC GAA ATC CGT GCG CGG GTG      2465
Ile His Gly Lys His Lys Pro Ile Arg Pro Glu Ile Arg Ala Arg Val
    455                 460                 465

CCA CGG TCC ATG AGT GAA GGT TAATAATAAA GGACGGAGAT AGAGAACTGA         2516
Pro Arg Ser Met Ser Glu Gly
470                 475

AGCGTCAGAT TTTTTTAAAA AAATAAATGA TCGAGAACTT ATGATTTGTC TTTCTTGA      2574

ATG ACC TTG CCC CAT CGA TTA ACG AAA AGA CCT TTC GCG CGT CGA TTC      2622
Met Thr Leu Pro His Arg Leu Thr Lys Arg Pro Phe Ala Arg Arg Phe
  1                   5                  10                  15

TGC TCG GTC TTT GTG ATA CAT TAT AGT GAG ACT AAA CTC GAC CGA TAT      2670
Cys Ser Val Phe Val Ile His Tyr Ser Glu Thr Lys Leu Asp Arg Tyr
                 20                  25                  30

AAC AAG ACA ATG TTA CTC TAT AGA CCG GAC TCA ACC ATG CGG CAT AGC      2718
Asn Lys Thr Met Leu Leu Tyr Arg Pro Asp Ser Thr Met Arg His Ser
             35                  40                  45

GGA GGC GAC GCA AAT CAC AGA GGG ATA AGG CCG AGG CGG AAA TCT ATT      2766
Gly Gly Asp Ala Asn His Arg Gly Ile Arg Pro Arg Arg Lys Ser Ile
 50                  55                  60

GGA GCG TTT AGC GCG CGC GAA AAG ACT GGA AAA CGA AAT GCG CTG ACG      2814
Gly Ala Phe Ser Ala Arg Glu Lys Thr Gly Lys Arg Asn Ala Leu Thr
 65                  70                  75                  80

GAA AGC AGC TCC TCC TCC GAC ATG CTA GAT CCG TTT TCC ACG GAT AAG      2862
Glu Ser Ser Ser Ser Ser Asp Met Leu Asp Pro Phe Ser Thr Asp Lys
                 85                  90                  95

GAA TTT GGC GGT AAG TGG ACG GTA GAC GGA CCT GCC GAC ATT ACT GCC      2910
Glu Phe Gly Gly Lys Trp Thr Val Asp Gly Pro Ala Asp Ile Thr Ala
            100                 105                 110

GAG GTC CTT TCT CAG GCA TGG GAC GTT CTC CAA TTA GTG AAG CAT GAA      2958
Glu Val Leu Ser Gln Ala Trp Asp Val Leu Gln Leu Val Lys His Glu
        115                 120                 125

GAT GCG GAG GAG GAG AGA GTG ACT TAT GAG TCC AAA CCG ACC CCG ATA      3006
Asp Ala Glu Glu Glu Arg Val Thr Tyr Glu Ser Lys Pro Thr Pro Ile
130                 135                 140

CAG CCG TTC AAT GCC TGG CCG GAC GGG CCG AGT TGG AAC GCG CAG GAT      3054
Gln Pro Phe Asn Ala Trp Pro Asp Gly Pro Ser Trp Asn Ala Gln Asp
145                 150                 155                 160

TTT ACT CGA GCG CCA ATA GTT TAT CCC TCT GCG GAG GTA TTG GAC GCA      3102
Phe Thr Arg Ala Pro Ile Val Tyr Pro Ser Ala Glu Val Leu Asp Ala
                165                 170                 175

GAG GCG TTG AAA GTA GGG GCA TTC GTT AGC CGA GTT TTA CAA TGT GTA      3150
Glu Ala Leu Lys Val Gly Ala Phe Val Ser Arg Val Leu Gln Cys Val
            180                 185                 190

CCG TTC ACG CGA TCA AAG AAA AGC GTT ACG GTG CGG GAT GCG CAG TCG      3198
Pro Phe Thr Arg Ser Lys Lys Ser Val Thr Val Arg Asp Ala Gln Ser
        195                 200                 205

TTT TTG GGG GAC TCG TTC TGG AGA ATA ATG CAG AAC GTT TAC ACG GTT      3246
Phe Leu Gly Asp Ser Phe Trp Arg Ile Met Gln Asn Val Tyr Thr Val
    210                 215                 220

TGC TTA CGA CAG CAC ATA ACT CGA CTC AGG CAC CCT TCC AGC AAA AGC      3294
Cys Leu Arg Gln His Ile Thr Arg Leu Arg His Pro Ser Ser Lys Ser
225                 230                 235                 240
```

```
ATT GTT AAC TGC AAC GAC CCT CTA TGG TAC GCC TAC GCG AAT CAA TTT        3342
Ile Val Asn Cys Asn Asp Pro Leu Trp Tyr Ala Tyr Ala Asn Gln Phe
            245                 250                 255

CAC TGG AGA GGA ATG CGC GTG CCG TCG CTT AAA TTA GCC TCT CCC CCG        3390
His Trp Arg Gly Met Arg Val Pro Ser Leu Lys Leu Ala Ser Pro Pro
            260                 265                 270

GAG GAG AAT ATT CAA CAC GGC CCA ATG GCC GCC GTT TTT AGA AAC GCG        3438
Glu Glu Asn Ile Gln His Gly Pro Met Ala Ala Val Phe Arg Asn Ala
            275                 280                 285

GGG GCT GGT CTG TTC CTG TGG CCT GCC ATG CGC GCA GCC TTT GAA GAG        3486
Gly Ala Gly Leu Phe Leu Trp Pro Ala Met Arg Ala Ala Phe Glu Glu
            290                 295                 300

CGC GAC AAG CGA CTG TTA AGA GCA TGC CTG TCT TCA CTC GAT ATC ATG        3534
Arg Asp Lys Arg Leu Leu Arg Ala Cys Leu Ser Ser Leu Asp Ile Met
305             310                 315                 320

GAC GCA GCC GTC CTC GCG TCG TTT CCA TTT TAC TGG CGC GGC GTC CAA        3582
Asp Ala Ala Val Leu Ala Ser Phe Pro Phe Tyr Trp Arg Gly Val Gln
            325                 330                 335

GAC ACC TCG CGC TTC GAG CCT GCG CTG GGC TGT TTG TCA GAG TAC TTT        3630
Asp Thr Ser Arg Phe Glu Pro Ala Leu Gly Cys Leu Ser Glu Tyr Phe
            340                 345                 350

GCA CTA GTG GTG TTA CTG GCC GAG ACG GTC TTA GCG ACC ATG TTC GAC        3678
Ala Leu Val Val Leu Leu Ala Glu Thr Val Leu Ala Thr Met Phe Asp
            355                 360                 365

CAC GCA CTG GTA TTC ATG AGG GCG CTG GCA GAC GGC AAT TTC GAT GAC        3726
His Ala Leu Val Phe Met Arg Ala Leu Ala Asp Gly Asn Phe Asp Asp
            370                 375                 380

TAT GAC GAA ACT AGA TAT ATA GAC CCC GTT AAA AAC GAG TAC CTG AAC        3774
Tyr Asp Glu Thr Arg Tyr Ile Asp Pro Val Lys Asn Glu Tyr Leu Asn
385             390                 395                 400

GGA GCC GAG GGT ACT CTG TTA CGG GGC ATA GTG GCC TCC AAC ACC GCT        3822
Gly Ala Glu Gly Thr Leu Leu Arg Gly Ile Val Ala Ser Asn Thr Ala
            405                 410                 415

CTG GCG GTG GTT TGC GCA AAC ACC TAT TCG ACG ATA AGA AAA CTC CCG        3870
Leu Ala Val Val Cys Ala Asn Thr Tyr Ser Thr Ile Arg Lys Leu Pro
            420                 425                 430

TCC GTG GCA ACT AGC GCG TGC AAT GTT GCC TAC AGG ACC GAA ACG CTG        3918
Ser Val Ala Thr Ser Ala Cys Asn Val Ala Tyr Arg Thr Glu Thr Leu
            435                 440                 445

AAA GCG AGG CGC CCT GGC ATG AGC GAC ATA TAC CGG ATA TTA CAA AAA        3966
Lys Ala Arg Arg Pro Gly Met Ser Asp Ile Tyr Arg Ile Leu Gln Lys
450                 455                 460

GAG TTT TTC TTT TAC ATT GCG TGG CTC CAG AGG GTT GCA ACA CAC GCA        4014
Glu Phe Phe Phe Tyr Ile Ala Trp Leu Gln Arg Val Ala Thr His Ala
465             470                 475                 480

AAT TTC TGT TTA AAC ATT CTG AAG AGA AGC GTG GAT ACG GGC CCC CGC        4062
Asn Phe Cys Leu Asn Ile Leu Lys Arg Ser Val Asp Thr Gly Pro Arg
            485                 490                 495

CAT TTT TGT TCA GGG CCA GCT CGG AGA AGC GGC TGC AGC AGT TAAATAAA      4112
His Phe Cys Ser Gly Pro Ala Arg Arg Ser Gly Cys Ser Ser
            500                 505                 510

ATG CTC TGC CCC CTT CTC GTG CCG ATT CAA TAT GAA GAC TTT TCG AAG        4160
Met Leu Cys Pro Leu Leu Val Pro Ile Gln Tyr Glu Asp Phe Ser Lys
1               5                   10                  15

GCC ATG GGG TCT GAG CTC AAG AGG GAA AAG TTA GAG ACA TTC GTT AAA        4208
Ala Met Gly Ser Glu Leu Lys Arg Glu Lys Leu Glu Thr Phe Val Lys
            20                  25                  30

GCT ATT TCC AGC GAC AGG GAC CCG AGG GGG TCC TTA AGA TTT CTC ATT        4256
Ala Ile Ser Ser Asp Arg Asp Pro Arg Gly Ser Leu Arg Phe Leu Ile
            35                  40                  45
```

-continued

| | |
|---|---|
| TCG GAC CAT GCA AGG GAA ATT ATT GCA GAC GGA GTA CGG TTT AAG CCG<br>Ser Asp His Ala Arg Glu Ile Ile Ala Asp Gly Val Arg Phe Lys Pro<br>50                             55                        60 | 4304 |
| GTG ATA GAC GAG CCG GTT CGG GCT TCA GTT GCG CTG AGT ACC GCT GCC<br>Val Ile Asp Glu Pro Val Arg Ala Ser Val Ala Leu Ser Thr Ala Ala<br>65                          70                        75                        80 | 4352 |
| GCT GGG AAA GTG AAA GCG CGA CGC TTA ACC TCA GTT CGC GCG CCC GTA<br>Ala Gly Lys Val Lys Ala Arg Arg Leu Thr Ser Val Arg Ala Pro Val<br>85                          90                        95 | 4400 |
| CCG CCC GCA GGC GCC GTT TCC GCG CGC CGG AAA TCG GAA ATA TGA TA<br>Pro Pro Ala Gly Ala Val Ser Ala Arg Arg Lys Ser Glu Ile *<br>100                        105                    110 | 4447 |
| AAAATGCTTG GCATTTGCGG GCGAAGAGGC GTGATCTGAA GGGCTCCACA ATGACGTAAC | 4507 |
| TGAGCTACGC ATCCCTATAA AGTGTACSCG CTGACCGCTA GCCCATACAG TGTTACAGGA | 4567 |
| GGGGAGAGAG ACAACTTCAG CTCGAAGTCT GAAGAGACAT C ATG AGC GGC<br>                                                         Met Ser Gly<br>                                                          1 | 4617 |
| TTC AGT AAC ATA GGA TCG ATT GCC ACC GTT TCC CTA GTA TGC TCG CTT<br>Phe Ser Asn Ile Gly Ser Ile Ala Thr Val Ser Leu Val Cys Ser Leu<br>5                          10                        15 | 4665 |
| TTG TGC GCA TCT GTA TTA GGG GCG CCG GTA CTG GAC GGG CTC GAG TCG<br>Leu Cys Ala Ser Val Leu Gly Ala Pro Val Leu Asp Gly Leu Glu Ser<br>20                         25                        30                        35 | 4713 |
| AGC CCT TTC CCG TTC GGG GGC AAA ATT ATA GCC CAG GCG TGC AAC CGC<br>Ser Pro Phe Pro Phe Gly Gly Lys Ile Ile Ala Gln Ala Cys Asn Arg<br>                    40                        45                        50 | 4761 |
| ACC ACG ATT GAG GTG ACG GTC CCG TGG AGC GAC TAC TCT GGT CGC ACC<br>Thr Thr Ile Glu Val Thr Val Pro Trp Ser Asp Tyr Ser Gly Arg Thr<br>                  55                        60                        65 | 4809 |
| GAA GGA GTG TCA GTC GAG GTG AAA TGG TTC TAC GGG AAT AGT AAT CCC<br>Glu Gly Val Ser Val Glu Val Lys Trp Phe Tyr Gly Asn Ser Asn Pro<br>          70                        75                        80 | 4857 |
| GAA AGC TTC GTG TTC GGG GTG GAT AGC GAA ACG GGC AGT GGA CAC GAG<br>Glu Ser Phe Val Phe Gly Val Asp Ser Glu Thr Gly Ser Gly His Glu<br>          85                        90                        95 | 4905 |
| GAC CTG TCT ACG TGC TGG GCT CTA ATC CAT AAT CTG AAC GCG TCT GTG<br>Asp Leu Ser Thr Cys Trp Ala Leu Ile His Asn Leu Asn Ala Ser Val<br>100                        105                    110                    115 | 4953 |
| TGC AGG GCG TCT GAC GCC GGG ATA CCT GAT TTC GAC AAG CAG TGC GAA<br>Cys Arg Ala Ser Asp Ala Gly Ile Pro Asp Phe Asp Lys Gln Cys Glu<br>                    120                    125                    130 | 5001 |
| AAA GTG CAG AGA AGA CTG CGC TCC GGG GTG GAA CTT GGT AGT TAC GTG<br>Lys Val Gln Arg Arg Leu Arg Ser Gly Val Glu Leu Gly Ser Tyr Val<br>                    135                    140                    145 | 5049 |
| TCT GGC AAT GGA TCC CTG GTG CTG TAC CCA GGG ATG TAC GAT GCC GGC<br>Ser Gly Asn Gly Ser Leu Val Leu Tyr Pro Gly Met Tyr Asp Ala Gly<br>                    150                    155                    160 | 5097 |
| ATC TAC GCC TAC CAG CTC TCA GTG GGT GGG AAG GGA TAT ACC GGG TCT<br>Ile Tyr Ala Tyr Gln Leu Ser Val Gly Gly Lys Gly Tyr Thr Gly Ser<br>165                        170                    175 | 5145 |
| GTT TAT CTA GAC GTC GGA CCA AAC CCC GGA TGC CAC GAC CAG TAT GGG<br>Val Tyr Leu Asp Val Gly Pro Asn Pro Gly Cys His Asp Gln Tyr Gly<br>180                        185                    190                    195 | 5193 |
| TAC ACC TAT TAC AGC CTG GCC GAC GAG GCG TCA GAC TTA TCA TCT TAT<br>Tyr Thr Tyr Tyr Ser Leu Ala Asp Glu Ala Ser Asp Leu Ser Ser Tyr<br>                    200                    205                    210 | 5241 |
| GAC GTA GCC TCG CCC GAA CTC GAC GGT CCT ATG GAG GAA GAT TAT TCC<br>Asp Val Ala Ser Pro Glu Leu Asp Gly Pro Met Glu Glu Asp Tyr Ser | 5289 |

-continued

```
                   215                 220                 225
AAT TGT CTA GAC ATG CCC CCG CTA CGC CCA TGG ACA ACC GTT TGT TCG     5337
Asn Cys Leu Asp Met Pro Pro Leu Arg Pro Trp Thr Thr Val Cys Ser
            230                 235                 240

CAT GAC GTC GAG GAG CAG GAA AAC GCC ACG GAC GAG CTT TAC CTA TGG     5385
His Asp Val Glu Glu Gln Glu Asn Ala Thr Asp Glu Leu Tyr Leu Trp
        245                 250                 255

GAC GAG GAA TGC GCC GGT CCG CTG GAC GAG TAC GTC GAC GAA AGG TCA     5433
Asp Glu Glu Cys Ala Gly Pro Leu Asp Glu Tyr Val Asp Glu Arg Ser
260                 265                 270                 275

GAG ACG ATG CCC AGG ATG GTT GTC TTT TCA CCG CCC TCT ACG CTC CAG     5481
Glu Thr Met Pro Arg Met Val Val Phe Ser Pro Pro Ser Thr Leu Gln
                280                 285                 290

CAG TAGCCACCCG AGAGTGTTTT TTGTGAGCGC CCACGCAACA TACCTAACTG          5534
Gln
CTTCATTTCT GATCAATTAT TGCGTATTGA ATAAATAAAC AGTACAAAAG CATCAGGTGT   5594

GGTTTGCGTG TCTGTGCTAA ACCATGGCGT GTGCGGGTGA AACCGTAAAT TACGTGATAA   5654

TAAATAGCAT AGGAGTTGGC GTGCAGCGTA TTTCGCCGAG AG ATG GGG ACA ATG      5708
                                               Met Gly Thr Met
                                                 1

TTA GTG TTG CGC CTT TTC CTA CTT GCA GTA GCG GAC GCG GCG TTG CCG     5756
Leu Val Leu Arg Leu Phe Leu Leu Ala Val Ala Asp Ala Ala Leu Pro
 5                  10                  15                  20

ACC GGC AGA TTC TGC CGA GTT TGG AAG GTG CCT CCG GGA GGA ACC ATC     5804
Thr Gly Arg Phe Cys Arg Val Trp Lys Val Pro Pro Gly Gly Thr Ile
                25                  30                  35

CAA GAG AAC CTG GCG GTG CTC GCG GAA TCG CCG GTC ACG GGA CAC GCG     5852
Gln Glu Asn Leu Ala Val Leu Ala Glu Ser Pro Val Thr Gly His Ala
            40                  45                  50

ACA TAT CCG CCG CCT GAA GGC GCC GTC AGC TTT CAG ATT TTT GCG GAC     5900
Thr Tyr Pro Pro Pro Glu Gly Ala Val Ser Phe Gln Ile Phe Ala Asp
        55                  60                  65

ACC CCT ACT TTG CGC ATT CGC TAC GGG CCT ACG GAG GAC GAA CTT GCA     5948
Thr Pro Thr Leu Arg Ile Arg Tyr Gly Pro Thr Glu Asp Glu Leu Ala
    70                  75                  80

CTG GAG CGC GGG ACG TCC GCC TCA GAC GCG GAC AAC GTG ACA TTT TCG     5996
Leu Glu Arg Gly Thr Ser Ala Ser Asp Ala Asp Asn Val Thr Phe Ser
 85                  90                  95                 100

CTG TCA TAT CGC CCG CGC CCA GAA ATT CAC GGA GCA TAC TTC ACC ATA     6044
Leu Ser Tyr Arg Pro Arg Pro Glu Ile His Gly Ala Tyr Phe Thr Ile
                105                 110                 115

GGG GTA TTC GCT ACT GGC CAG AGC ACG GAA AGC AGC TAT TCG GTC ATC     6092
Gly Val Phe Ala Thr Gly Gln Ser Thr Glu Ser Ser Tyr Ser Val Ile
            120                 125                 130

AGT CGG GTC TTA GTT AAC GCC TCT CTG GAA CGG TCC GTG CGC CTG GAA     6140
Ser Arg Val Leu Val Asn Ala Ser Leu Glu Arg Ser Val Arg Leu Glu
        135                 140                 145

ACG CCG TGC GAT GAA AAT TTT TTG CAG AAC GAG CCT ACA TGG GGC TCG     6188
Thr Pro Cys Asp Glu Asn Phe Leu Gln Asn Glu Pro Thr Trp Gly Ser
    150                 155                 160

AAG CGT TGG TTA GGC CCC CCG TCG CCT TAT GTG CGA GAT AAC GAT GTC     6236
Lys Arg Trp Leu Gly Pro Pro Ser Pro Tyr Val Arg Asp Asn Asp Val
165                 170                 175                 180

GCC GTG TTG ACA AAA GCG CAG TAC ATT GGG GAG TGC TAC TCC AAC TCG     6284
Ala Val Leu Thr Lys Ala Gln Tyr Ile Gly Glu Cys Tyr Ser Asn Ser
                185                 190                 195

GCG GCC CAG ACG GGG CTC ACG TCT CTC AAC ATG ACC TTT TTC TAT TCG     6332
Ala Ala Gln Thr Gly Leu Thr Ser Leu Asn Met Thr Phe Phe Tyr Ser
            200                 205                 210
```

```
CCT AAA AGA ATA GTA AAC GTC ACG TGG ACA ACC GGC GGC CCC TCC CCC      6380
Pro Lys Arg Ile Val Asn Val Thr Trp Thr Thr Gly Gly Pro Ser Pro
        215                 220                 225

TCG CGC ATA ACG GTA TAC TCG TCG CGG GAG AAC GGG CAG CCC GTG TTG      6428
Ser Arg Ile Thr Val Tyr Ser Ser Arg Glu Asn Gly Gln Pro Val Leu
        230                 235                 240

AGG AAC GTT TCT GAC GGG TTC TTG GTT AAG TAC ACT CCC GAC ATT GAC      6476
Arg Asn Val Ser Asp Gly Phe Leu Val Lys Tyr Thr Pro Asp Ile Asp
245                 250                 255                 260

GGC CGG GCC ATG ATA AAC GTT ATT GCC AAT TAT TCG CCG GCG GAC TCC      6524
Gly Arg Ala Met Ile Asn Val Ile Ala Asn Tyr Ser Pro Ala Asp Ser
                265                 270                 275

GGC AGC GTC CTC GCG TTT ACG GCC TTT AGG GAA GGA AAA CTC CCA TCC      6572
Gly Ser Val Leu Ala Phe Thr Ala Phe Arg Glu Gly Lys Leu Pro Ser
            280                 285                 290

GCG ATT CAA CTG CAC CGG ATA GAT ATG TCC GGG ACT GAG CCG CCG GGG      6620
Ala Ile Gln Leu His Arg Ile Asp Met Ser Gly Thr Glu Pro Pro Gly
        295                 300                 305

ACT GAA ACG ACC TTC GAC TGT CAA AAA ATG ATA GAA ACC CCG TAC CGA      6668
Thr Glu Thr Thr Phe Asp Cys Gln Lys Met Ile Glu Thr Pro Tyr Arg
        310                 315                 320

GCG CTC GGG AGC AAT GTT CCC AGG GAC GAC TCT ATC CGT CCG GGG GCC      6716
Ala Leu Gly Ser Asn Val Pro Arg Asp Asp Ser Ile Arg Pro Gly Ala
325                 330                 335                 340

ACT CTG CCT CCG TTC GAT ACC GCA GCA CCT GAT TTC GAT ACA GGT ACT      6764
Thr Leu Pro Pro Phe Asp Thr Ala Ala Pro Asp Phe Asp Thr Gly Thr
                345                 350                 355

TCC CCG ACC CCC ACT ACC GTG CCA GAG CCA GCC ATT ACT ACA CTC ATA      6812
Ser Pro Thr Pro Thr Thr Val Pro Glu Pro Ala Ile Thr Thr Leu Ile
            360                 365                 370

CCG CGC AGC ACT AGC GAT ATG GGA TTC TTC TCC ACG GCA CGT GCT ACC      6860
Pro Arg Ser Thr Ser Asp Met Gly Phe Phe Ser Thr Ala Arg Ala Thr
        375                 380                 385

GGA TCA GAA ACT CTT TCG GTA CCC GTC CAG GAA ACG GAT AGA ACT CTT      6908
Gly Ser Glu Thr Leu Ser Val Pro Val Gln Glu Thr Asp Arg Thr Leu
        390                 395                 400

TCG ACA ACT CCT CTT ACC CTT CCA CTG ACT CCC GGT GAG TCA GAA AAT      6956
Ser Thr Thr Pro Leu Thr Leu Pro Leu Thr Pro Gly Glu Ser Glu Asn
405                 410                 415                 420

ACA CTG TTT CCT ACG ACC GCG CCG GGG ATT TCT ACC GAG ACC CCG AGC      7004
Thr Leu Phe Pro Thr Thr Ala Pro Gly Ile Ser Thr Glu Thr Pro Ser
                425                 430                 435

GCG GCA CAT GAA ACT ACA CAG ACC CAG AGT GCA GAA ACG GTG GTC TTT      7052
Ala Ala His Glu Thr Thr Gln Thr Gln Ser Ala Glu Thr Val Val Phe
            440                 445                 450

ACT CAG AGT CCG AGT ACC GAG TCG GAA ACC GCG CGG TCC CAG AGT CAG      7100
Thr Gln Ser Pro Ser Thr Glu Ser Glu Thr Ala Arg Ser Gln Ser Gln
        455                 460                 465

GAA CCG TGG TAT TTT ACT CAG ACT CCG AGT ACT GAA CAG GCG GCT CTT      7148
Glu Pro Trp Tyr Phe Thr Gln Thr Pro Ser Thr Glu Gln Ala Ala Leu
        470                 475                 480

ACT CAG ACG CAG ATC GCA GAA ACG GAG GCG TTG TTT ACT CAG ACT CCG      7196
Thr Gln Thr Gln Ile Ala Glu Thr Glu Ala Leu Phe Thr Gln Thr Pro
485                 490                 495                 500

AGT GCT GAA CAG ATG ACT TTT ACT CAG ACT CCG GGT GCA GAA ACC GAG      7244
Ser Ala Glu Gln Met Thr Phe Thr Gln Thr Pro Gly Ala Glu Thr Glu
                505                 510                 515

GCA CCT GCC CAG ACC CCG AGC ACG ATA CCC GAG ATA TTT ACT CAG TCT      7292
Ala Pro Ala Gln Thr Pro Ser Thr Ile Pro Glu Ile Phe Thr Gln Ser
```

```
                520              525              530
CGT AGC ACG CCC CCC GAA ACC GCT CGC GCT CCG AGC GCG GCG CCG GAG        7340
Arg Ser Thr Pro Pro Glu Thr Ala Arg Ala Pro Ser Ala Ala Pro Glu
            535              540              545

GTT TTT ACA CAG AGT TCG AGT ACG GTA ACG GAG GTG TTT ACT CAG ACC        7388
Val Phe Thr Gln Ser Ser Ser Thr Val Thr Glu Val Phe Thr Gln Thr
        550              555              560

CCG AGC ACG GTA CCG AAA ACT ACT CTG AGT TCG AGT ACT GAA CCG GCG        7436
Pro Ser Thr Val Pro Lys Thr Thr Leu Ser Ser Ser Thr Glu Pro Ala
565              570              575              580

ATT TTT ACT CGG ACT CAG AGC GCG GGA ACT GAG GCC TTT ACT CAG ACT        7484
Ile Phe Thr Arg Thr Gln Ser Ala Gly Thr Glu Ala Phe Thr Gln Thr
                585              590              595

TCG AGT GCC GAG CCG GAC ACT ATG CGA ACT CAG AGT ACT GAA ACA CAC        7532
Ser Ser Ala Glu Pro Asp Thr Met Arg Thr Gln Ser Thr Glu Thr His
            600              605              610

TTT TTC ACT CAG GCC CCG AGT ACG GTA CCG AAA GCT ACT CAG ACT CCG        7580
Phe Phe Thr Gln Ala Pro Ser Thr Val Pro Lys Ala Thr Gln Thr Pro
        615              620              625

AGT ACA GAG CCG GAG GTG TTG ACT CAG AGT CCG AGT ACC GAA CCT GTG        7628
Ser Thr Glu Pro Glu Val Leu Thr Gln Ser Pro Ser Thr Glu Pro Val
    630              635              640

CCT TTC ACC CGG ACT CTG GGC GCA GAG CCG GAA ATT ACT CAG ACC CCG        7676
Pro Phe Thr Arg Thr Leu Gly Ala Glu Pro Glu Ile Thr Gln Thr Pro
645              650              655              660

AGC GCG GCA CCG GAG GTT TAT ACT CGG AGT TCG AGT ACG ATG CCA GAA        7724
Ser Ala Ala Pro Glu Val Tyr Thr Arg Ser Ser Ser Thr Met Pro Glu
                665              670              675

ACT GCA CAG AGC ACA CCC CTG GCC TCG CAA AAC CCT ACC AGT TCG GGA        7772
Thr Ala Gln Ser Thr Pro Leu Ala Ser Gln Asn Pro Thr Ser Ser Gly
            680              685              690

ACC GGG ACG CAT AAT ACT GAA CCG AGG ACT TAT CCA GTG CAA ACG ACA        7820
Thr Gly Thr His Asn Thr Glu Pro Arg Thr Tyr Pro Val Gln Thr Thr
        695              700              705

CCA CAT ACC CAG AAA CTC TAC ACA GAA AAT AAG ACT TTA TCG TTT CCT        7868
Pro His Thr Gln Lys Leu Tyr Thr Glu Asn Lys Thr Leu Ser Phe Pro
    710              715              720

ACT GTT GTT TCA GAA TTC CAT GAG ATG TCG ACG GCA GAG TCG CAG ACG        7916
Thr Val Val Ser Glu Phe His Glu Met Ser Thr Ala Glu Ser Gln Thr
725              730              735              740

CCC CTA TTG GAC GTC AAA ATT GTA GAG GTG AAG TTT TCA AAC GAT GGC        7964
Pro Leu Leu Asp Val Lys Ile Val Glu Val Lys Phe Ser Asn Asp Gly
                745              750              755

GAA GTA ACG GCG ACT TGC GTT TCC ACC GTC AAA TCT CCC TAT AGG GTA        8012
Glu Val Thr Ala Thr Cys Val Ser Thr Val Lys Ser Pro Tyr Arg Val
            760              765              770

GAA ACT AAT TGG AAA GTA GAC CTC GTA GAT GTA ATG GAT GAA ATT TCT        8060
Glu Thr Asn Trp Lys Val Asp Leu Val Asp Val Met Asp Glu Ile Ser
        775              780              785

GGG AAC AGT CCC GCC GGG GTT TTT AAC AGT AAT GAG AAA TGG CAG AAA        8108
Gly Asn Ser Pro Ala Gly Val Phe Asn Ser Asn Glu Lys Trp Gln Lys
    790              795              800

CAG CTG TAC TAC AGA GTA ACC GAT GGA AGA ACA TCG GTC CAG CTA ATG        8156
Gln Leu Tyr Tyr Arg Val Thr Asp Gly Arg Thr Ser Val Gln Leu Met
805              810              815              820

TGC CTG TCG TGC ACG AGC CAT TCT CCG GAA CCT TAC TGT CTT TTC GAC        8204
Cys Leu Ser Cys Thr Ser His Ser Pro Glu Pro Tyr Cys Leu Phe Asp
                825              830              835

ACG TCT CTT ATA GCG AGG GAA AAA GAT ATC GCG CCA GAG TTA TAC TTT        8252
```

```
                Thr Ser Leu Ile Ala Arg Glu Lys Asp Ile Ala Pro Glu Leu Tyr Phe
                        840                 845                 850

ACC TCT GAT CCG CAA ACG GCA TAC TGC ACA ATA ACT CTG CCG TCC GGC        8300
Thr Ser Asp Pro Gln Thr Ala Tyr Cys Thr Ile Thr Leu Pro Ser Gly
        855                 860                 865

GTT GTT CCG AGA TTC GAA TGG AGC CTT AAT AAT GTT TCA CTG CCG GAA        8348
Val Val Pro Arg Phe Glu Trp Ser Leu Asn Asn Val Ser Leu Pro Glu
        870                 875                 880

TAT TTG ACG GCC ACG ACC GTT GTT TCG CAT ACC GCT GGC CAA AGT ACA        8396
Tyr Leu Thr Ala Thr Thr Val Val Ser His Thr Ala Gly Gln Ser Thr
885                 890                 895                 900

GTG TGG AAG AGC AGC GCG AGA GCA GGC GAG GCG TGG ATT TCT GGC CGG        8444
Val Trp Lys Ser Ser Ala Arg Ala Gly Glu Ala Trp Ile Ser Gly Arg
                905                 910                 915

GGA GGC AAT ATA TAC GAA TGC ACC GTC CTC ATC TCA GAC GGC ACT CGC        8492
Gly Gly Asn Ile Tyr Glu Cys Thr Val Leu Ile Ser Asp Gly Thr Arg
                920                 925                 930

GTT ACT ACG CGA AAG GAG AGG TGC TTA ACA AAC ACA TGG ATT GCG GTG        8540
Val Thr Thr Arg Lys Glu Arg Cys Leu Thr Asn Thr Trp Ile Ala Val
                935                 940                 945

GAA AAC GGT GCT GCT CAG GCG CAG CTG TAT TCA CTC TTT TCT GGA CTT        8588
Glu Asn Gly Ala Ala Gln Ala Gln Leu Tyr Ser Leu Phe Ser Gly Leu
        950                 955                 960

GTG TCA GGA TTA TGC GGG AGC ATA TCT GCT TTG TAC GCA ACG CTA TGG        8636
Val Ser Gly Leu Cys Gly Ser Ile Ser Ala Leu Tyr Ala Thr Leu Trp
965                 970                 975                 980

ACC GCC ATT TAT TTT TGAGGAATGC TTTTTGGACT ATCGTACTGC TTTCTTCCTT        8691
Thr Ala Ile Tyr Phe
                985

CGCTAGCCAG AGCACCGCCG CCGTCACGTA CGACTACATT TTAGGCCGTC GCGCGCTCGA     8751

CGCGCTAACC ATACCGGCGG TTGGCCCGTA TAACAGATAC CTCACTAGGG TATCAAGAGG     8811

CTGCGACGTT GTCGAGCTCA ACCCGATTTC TAACGTGGAC GACATGATAT CGGCGGCCAA     8871

AGAAAAAGAG AAGGGGGGCC CTTTCGAGGC CTCCGTCGTC TGGTTCTACG TGATTAAGGG     8931

CGACGACGGC GAGGACAAGT ACTGTCCAAT CTATAGAAAA GAGTACAGGG AATGTGGCGA     8991

CGTACAACTG CTATCTGAAT GCGCCGTTCA ATCTGCACAG ATGTGGGCAG TGGACTATGT     9051

TCCTAGCACC CTTGTATCGC GAAATGGCGC GGGACTGACT ATATTCTCCC CCACTGCTGC     9111

GCTCTCTGGC CAATACTTGC TGACCCTGAA ATCGGGAGA TTTGCGCAAA CAGCTCTCGT      9171

AACTCTAGAA GTTAACGATC GCTGTTTAAA GATCGGGTCG CAGCTTAACT TTTTACCGTC     9231

GAAATGCTGG ACAACAGAAC AGTATCAGAC TGGATTTCAA GGCGAACACC TTTATCCGAT     9291

CGCAGACACC AATACACGAC ACGCGGACGA CGTATATCGG GGATACGAAG ATATTCTGCA     9351

GCGCTGGAAT AATTTGCTGA GGAAAAAGAA TCCTAGCGCG CCAGACCCTC GTCCAGATAG     9411

CGTCCCGCAA GAAATTCCCG CTGTAACCAA GAAAGCGGAA GGGCGCACCC CGGACGCAGA     9471

AAGCAGCGAA AAGAAGGCCC CTCCAGAAGA CTCGGAGGAC GACATGCAGG CAGAGGCTTC     9531

TGGAGAAAAT CCTGCCGCCC TCCCCGAAGA CGACGAAGTC CCCGAGGACA CCGAGCACGA     9591

TGATCCAAAC TCGGATCCTG ACTATTACAA TGACATGCCC GCCGTGATCC CGGTGGAGGA     9651

GACTACTAAA AGTTCTAATG CCGTCTCCAT GCCCATATTC GCGGCGTTCG TAGCCTGCGC     9711

GGTCGCGCTC GTGGGGCTAC TGGTTTGGAG CATCGTAAAA TGCGCGCGTA GCTAATCGAG     9771

CCTAGAATAG GTGGTTTCTT CCTACATGCC ACGCCTCACG CTCATAATAT AAATCACATG     9831

GAATAGCATA CCAATGCCTA TTCATTGGGA CGTTCGAAAA GC                        9873
```

```
ATG GCA TCG CTA CTT GGA ACT                                           9894
Met Ala Ser Leu Leu Gly Thr
 1               5

CTG GCT CTC CTT GCC GCG ACG CTC GCA CCC TTC GGC GCG ATG GGA ATC       9942
Leu Ala Leu Leu Ala Ala Thr Leu Ala Pro Phe Gly Ala Met Gly Ile
         10                  15                  20

GTG ATC ACT GGA AAT CAC GTC TCC GCC AGG ATT GAC GAC GAT CAC ATC       9990
Val Ile Thr Gly Asn His Val Ser Ala Arg Ile Asp Asp Asp His Ile
     25                  30                  35

GTG ATC GTC GCG CCT CGC CCC GAA GCT ACA ATT CAA CTG CAG CTA TTT      10038
Val Ile Val Ala Pro Arg Pro Glu Ala Thr Ile Gln Leu Gln Leu Phe
 40                  45                  50                  55

TTC ATG CCT GGC CAG AGA CCC CAC AAA CCC TAC TCA GGA ACC GTC CGC      10086
Phe Met Pro Gly Gln Arg Pro His Lys Pro Tyr Ser Gly Thr Val Arg
             60                  65                  70

GTC GCG TTT CGG TCT GAT ATA ACA AAC CAG TGC TAC CAG GAA CTT AGC      10134
Val Ala Phe Arg Ser Asp Ile Thr Asn Gln Cys Tyr Gln Glu Leu Ser
                 75                  80                  85

GAG GAG CGC TTT GAA AAT TGC ACT CAT CGA TCG TCT TCT GTT TTT GTC      10182
Glu Glu Arg Phe Glu Asn Cys Thr His Arg Ser Ser Ser Val Phe Val
             90                  95                 100

GGC TGT AAA GTG ACC GAG TAC ACG TTC TCC GCC TCG AAC AGA CTA ACC      10230
Gly Cys Lys Val Thr Glu Tyr Thr Phe Ser Ala Ser Asn Arg Leu Thr
        105                 110                 115

GGA CCT CCA CAC CCG TTT AAG CTC ACT ATA CGA AAT CCT CGT CCG AAC      10278
Gly Pro Pro His Pro Phe Lys Leu Thr Ile Arg Asn Pro Arg Pro Asn
120                 125                 130                 135

GAC AGC GGG ATG TTC TAC GTA ATT GTT CGG CTA GAC GAC ACC AAA GAA      10326
Asp Ser Gly Met Phe Tyr Val Ile Val Arg Leu Asp Asp Thr Lys Glu
                140                 145                 150

CCC ATT GAC GTC TTC GCG ATC CAA CTA TCG GTG TAT CAA TTC GCG AAC      10374
Pro Ile Asp Val Phe Ala Ile Gln Leu Ser Val Tyr Gln Phe Ala Asn
            155                 160                 165

ACC GCC GCG ACT CGC GGA CTC TAT TCC AAG GCT TCG TGT CGC ACC TTC      10422
Thr Ala Ala Thr Arg Gly Leu Tyr Ser Lys Ala Ser Cys Arg Thr Phe
        170                 175                 180

GGA TTA CCT ACC GTC CAA CTT GAG GCC TAT CTC AGG ACC GAG GAA AGT      10470
Gly Leu Pro Thr Val Gln Leu Glu Ala Tyr Leu Arg Thr Glu Glu Ser
185                 190                 195

TGG CGC AAC TGG CAA GCG TAC GTT GCC ACG GAG GCC ACG ACG ACC AGC      10518
Trp Arg Asn Trp Gln Ala Tyr Val Ala Thr Glu Ala Thr Thr Thr Ser
200                 205                 210                 215

GCC GAG GCG ACA ACC CCG ACG CCC GTC ACT GCA ACC AGC GCC TCC GAA      10566
Ala Glu Ala Thr Thr Pro Thr Pro Val Thr Ala Thr Ser Ala Ser Glu
                220                 225                 230

CTT GAA GCG GAA CAC TTT ACC TTT CCC TGG CTA GAA AAT GGC GTG GAT      10614
Leu Glu Ala Glu His Phe Thr Phe Pro Trp Leu Glu Asn Gly Val Asp
            235                 240                 245

CAT TAC GAA CCG ACA CCC GCA AAC GAA AAT TCA AAC GTT ACT GTC CGT      10662
His Tyr Glu Pro Thr Pro Ala Asn Glu Asn Ser Asn Val Thr Val Arg
        250                 255                 260

CTC GGG ACA ATG AGC CCT ACG CTA ATT GGG GTA ACC GTG GCT GCC GTC      10710
Leu Gly Thr Met Ser Pro Thr Leu Ile Gly Val Thr Val Ala Ala Val
265                 270                 275

GTG AGC GCA ACG ATC GGC CTC GTC ATT GTA ATT TCC ATC GTC ACC AGA      10758
Val Ser Ala Thr Ile Gly Leu Val Ile Val Ile Ser Ile Val Thr Arg
280                 285                 290                 295

AAC ATG TGC ACC CCG CAC CGA AAA TTA GAC ACG GTC TCG CAA GAC GAC      10806
Asn Met Cys Thr Pro His Arg Lys Leu Asp Thr Val Ser Gln Asp Asp
                300                 305                 310
```

```
GAA GAA CGT TCC CAA ACT AGA AGG GAA TCG CGA AAA TTT GGA CCC ATG      10854
Glu Glu Arg Ser Gln Thr Arg Arg Glu Ser Arg Lys Phe Gly Pro Met
            315                 320                 325

GTT GCG TGC GAA ATA AAC AAG GGC GCT GAC CAG GAT AGT GAA CTT GTG      10902
Val Ala Cys Glu Ile Asn Lys Gly Ala Asp Gln Asp Ser Glu Leu Val
            330                 335                 340

GAA CTG GTT GCG ATT GTT AAC CCG TCT GCG CTA AGC TCG CCC GAC TCA      10950
Glu Leu Val Ala Ile Val Asn Pro Ser Ala Leu Ser Ser Pro Asp Ser
        345                 350                 355

ATA AAA ATG TGATTAAGTC TGAATGTGGC TCTCCAATCA TTTCGATTCT              10999
Ile Lys Met
360

CTAATCTCCC AATCCTCTCA AAAGGGGCAG TATCGGACAC GGACTGGGAG GGGCGTACTA    11059

CACGATAGTT ATATGGTACA GCAGAGGCCT CTGAACACTT AGGAGGAGAA TTCAGCCGGG    11119

GAGAGCCCCT GTTGAGTAGG CTTGGGAGCA TATTGCAGG ATG AAC ATG TTA GTG       11173
                                           Met Asn Met Leu Val
                                             1               5

ATA GTT CTC GCC TCT TGT CTT GCG CGC CTA ACT TTT GCG ACG CGA CAC      11221
Ile Val Leu Ala Ser Cys Leu Ala Arg Leu Thr Phe Ala Thr Arg His
                 10                  15                  20

GTC CTC TTT TTG GAA GGC ACT CAG GCT GTC CTC GGG GAA GAT GAT CCC      11269
Val Leu Phe Leu Glu Gly Thr Gln Ala Val Leu Gly Glu Asp Asp Pro
            25                  30                  35

AGA AAC GTT CCG GAA GGG ACT GTA ATC AAA TGG ACA AAA GTC CTG CGG      11317
Arg Asn Val Pro Glu Gly Thr Val Ile Lys Trp Thr Lys Val Leu Arg
         40                  45                  50

AAC GCG TGC AAG ATG AAG GCG GCC GAT GTC TGC TCT TCG CCT AAC TAT      11365
Asn Ala Cys Lys Met Lys Ala Ala Asp Val Cys Ser Ser Pro Asn Tyr
     55                  60                  65

TGC TTT CAT GAT TTA ATT TAC GAC GGA GGA AAG AAA GAC TGC CCG CCC      11413
Cys Phe His Asp Leu Ile Tyr Asp Gly Gly Lys Lys Asp Cys Pro Pro
 70                  75                  80                  85

GCG GGA CCC CTG TCT GCA AAC CTG GTA ATT TTA CTA AAG CGC GGC GAA      11461
Ala Gly Pro Leu Ser Ala Asn Leu Val Ile Leu Leu Lys Arg Gly Glu
                 90                  95                 100

AGC TTC GTC GTG CTG GGT TCT GGG CTA CAC AAC AGC AAT ATA ACT AAT      11509
Ser Phe Val Val Leu Gly Ser Gly Leu His Asn Ser Asn Ile Thr Asn
            105                 110                 115

ATC ATG TGG ACA GAG TAC GGA GGC CTG CTC TTT GAT CCT GTA ACT CGT      11557
Ile Met Trp Thr Glu Tyr Gly Gly Leu Leu Phe Asp Pro Val Thr Arg
        120                 125                 130

TCG GAC GAG GGA ATC TAT TTT CGA CGG ATC TCT CAG CCA GAT CTG GCC      11605
Ser Asp Glu Gly Ile Tyr Phe Arg Arg Ile Ser Gln Pro Asp Leu Ala
    135                 140                 145

ATG GAA ACT ACA TCG TAC AAC GTC AGC GTT CTT TCG CAC GTA GAC GAG      11653
Met Glu Thr Thr Ser Tyr Asn Val Ser Val Leu Ser His Val Asp Glu
150                 155                 160                 165

AAG GCT CCA GCA CCG CAC GAG GTG GAG ATA GAC ACC ATC AAG CCG TCA      11701
Lys Ala Pro Ala Pro His Glu Val Glu Ile Asp Thr Ile Lys Pro Ser
                170                 175                 180

GAG GCC CAC GCG CAC GTG GAA TTA CAA ATG CTG CCG TTT CAT GAA CTC      11749
Glu Ala His Ala His Val Glu Leu Gln Met Leu Pro Phe His Glu Leu
            185                 190                 195

AAC GAC AAC AGC CCC ACC TAT GTG ACC CCT GTT CTT AGA GTC TTC CCA      11797
Asn Asp Asn Ser Pro Thr Tyr Val Thr Pro Val Leu Arg Val Phe Pro
        200                 205                 210

CCG ACC GAG CAC GTA AAA TTT AAC GTT ACG TAT TCG TGG TAT GGG TTT      11845
Pro Thr Glu His Val Lys Phe Asn Val Thr Tyr Ser Trp Tyr Gly Phe
```

-continued

```
            215                 220                 225
GAT GTC AAA GAG GAG TGC GAA GAA GTG AAA CTG TTC GAG CCG TGC GTA    11893
Asp Val Lys Glu Glu Cys Glu Glu Val Lys Leu Phe Glu Pro Cys Val
230             235                 240                 245

TAC CAT CCT ACA GAC GGC AAA TGT CAG TTT CCC GCA ACC AAC CAG AGA    11941
Tyr His Pro Thr Asp Gly Lys Cys Gln Phe Pro Ala Thr Asn Gln Arg
                250                 255                 260

TGC CTC ATA GGA TCT GTC TTG ATG GCG GAA TTC TTG GGC GCG GCC TCT    11989
Cys Leu Ile Gly Ser Val Leu Met Ala Glu Phe Leu Gly Ala Ala Ser
            265                 270                 275

TTG CTG GAT TGT TCC CGC GAT ACT CTA GAA GAC TGC CAC GAA AAT CGC    12037
Leu Leu Asp Cys Ser Arg Asp Thr Leu Glu Asp Cys His Glu Asn Arg
                280                 285                 290

GTG CCG AAC CTA CGG TTC GAT TCG CGA CTC TCC GAG TCA CGC GCA GGC    12085
Val Pro Asn Leu Arg Phe Asp Ser Arg Leu Ser Glu Ser Arg Ala Gly
            295                 300                 305

CTG GTG ATC AGT CCT CTT ATA GCC ATC CCC AAA GTT TTG ATT ATA GTC    12133
Leu Val Ile Ser Pro Leu Ile Ala Ile Pro Lys Val Leu Ile Ile Val
310                 315                 320                 325

GTT TCC GAC GGA GAC ATT TTG GGA TGG AGC TAC ACG GTG CTC GGG AAA    12181
Val Ser Asp Gly Asp Ile Leu Gly Trp Ser Tyr Thr Val Leu Gly Lys
                330                 335                 340

CGT AAC AGT CCG CGC GTA GTA GTC GAA ACG CAC ATG CCC TCG AAG GTC    12229
Arg Asn Ser Pro Arg Val Val Val Glu Thr His Met Pro Ser Lys Val
            345                 350                 355

CCG ATG AAC AAA GTA GTA ATT GGC AGT CCC GGA CCA ATG GAC GAA ACG    12277
Pro Met Asn Lys Val Val Ile Gly Ser Pro Gly Pro Met Asp Glu Thr
                360                 365                 370

GGT AAC TAT AAA ATG TAC TTC GTC GTC GCG GGG GTG GCC GCG ACG TGC    12325
Gly Asn Tyr Lys Met Tyr Phe Val Val Ala Gly Val Ala Ala Thr Cys
            375                 380                 385

GTA ATT CTT ACA TGC GCT CTG CTT GTG GGG AAA AAG AAG TGC CCC GCG    12373
Val Ile Leu Thr Cys Ala Leu Leu Val Gly Lys Lys Lys Cys Pro Ala
390                 395                 400                 405

CAC CAA ATG GGT ACT TTT TCC AAG ACC GAA CCA TTG TAC GCG CCG CTC    12421
His Gln Met Gly Thr Phe Ser Lys Thr Glu Pro Leu Tyr Ala Pro Leu
                410                 415                 420

CCC AAA AAC GAG TTT GAG GCC GGC GGG CTT ACG GAC GAT GAG GAA GTG    12469
Pro Lys Asn Glu Phe Glu Ala Gly Gly Leu Thr Asp Asp Glu Glu Val
            425                 430                 435

ATT TAT GAC GAA GTA TAC GAA CCC CTA TTT CGC GGC TAC TGT AAG CAG    12517
Ile Tyr Asp Glu Val Tyr Glu Pro Leu Phe Arg Gly Tyr Cys Lys Gln
                440                 445                 450

GAA TTC CGC GAA GAT GTG AAT ACC TTT TTC GGT GCG GTC GTG GAG GGA    12565
Glu Phe Arg Glu Asp Val Asn Thr Phe Phe Gly Ala Val Val Glu Gly
455                 460                 465

GAA AGG GCC TTA AAC TTT AAA TCC GCC ATC GCA TCA ATG GCA GAT CGC    12613
Glu Arg Ala Leu Asn Phe Lys Ser Ala Ile Ala Ser Met Ala Asp Arg
470                 475                 480                 485

ATC CTG GCA AAT AAA AGC GGC AGA AGG AAT ATG GAT AGC TAT TAGTTGGTC  12664
Ile Leu Ala Asn Lys Ser Gly Arg Arg Asn Met Asp Ser Tyr
                490                 495                 500

ATG CCT TTT AAG ACC AGA GGG GCC GAA GAC                           12694
Met Pro Phe Lys Thr Arg Gly Ala Glu Asp
 1               5                  10

GCG GCC GCG GGC AAG AAC AGG TTT AAG AAA TCG AGA AAT CGG GAA ATC    12742
Ala Ala Ala Gly Lys Asn Arg Phe Lys Lys Ser Arg Asn Arg Glu Ile
                15                  20                  25

TTA CCG ACC AGA CTG CGT GGC ACC GGT AAG AAA ACT GCC GGA TTG TCC    12790
```

-continued

```
Leu Pro Thr Arg Leu Arg Gly Thr Gly Lys Lys Thr Ala Gly Leu Ser
            30                  35                  40

AAT TAT ACC CAG CCT ATT CCC TGG AAC CCT AAA TTC TGC AGC GCG CGC    12838
Asn Tyr Thr Gln Pro Ile Pro Trp Asn Pro Lys Phe Cys Ser Ala Arg
            45                  50                  55

GGG GAA TCT GAC AAC CAC GCG TGT AAA GAC ACT TTT TAT CGC AGG ACG    12886
Gly Glu Ser Asp Asn His Ala Cys Lys Asp Thr Phe Tyr Arg Arg Thr
 60                  65                  70

TGC TGC GCA TCG CGC TCT ACC GTT TCC AGT CAA CCC GAT TCC CCC CAC    12934
Cys Cys Ala Ser Arg Ser Thr Val Ser Ser Gln Pro Asp Ser Pro His
 75                  80                  85                  90

ACA CCC ATG CCT ACT GAG TAT GGG CGC GTG CCC TCC GCA AAG CGC AAA    12982
Thr Pro Met Pro Thr Glu Tyr Gly Arg Val Pro Ser Ala Lys Arg Lys
                 95                 100                 105

AAA CTA TCA TCT TCA GAC TSS GAG GGC GCG CAC CAA CCC CTA GTA TCC    13030
Lys Leu Ser Ser Ser Asp Xaa Glu Gly Ala His Gln Pro Leu Val Ser
                110                 115                 120

TGT AAA CTT CCG GAT TCT CAA GCA GCA CCG GCG CGA ACC TAT AGT TCT    13078
Cys Lys Leu Pro Asp Ser Gln Ala Ala Pro Ala Arg Thr Tyr Ser Ser
                125                 130                 135

GCG CAA AGA TAT ACT GTT GAC GAG GTT TCG TCG CCA ACT CCG CCA GGC    13126
Ala Gln Arg Tyr Thr Val Asp Glu Val Ser Ser Pro Thr Pro Pro Gly
 140                 145                 150

GTC GAC GCT GTT GCG GAC TTA GAA ACG CGC GCG GAA CTT CCT GGC GCT    13174
Val Asp Ala Val Ala Asp Leu Glu Thr Arg Ala Glu Leu Pro Gly Ala
155                 160                 165                 170

ACG ACG GAA CAA ACG GAA AGT AAA AAT AAG CTC CCC AAC CAA CAA TCG    13222
Thr Thr Glu Gln Thr Glu Ser Lys Asn Lys Leu Pro Asn Gln Gln Ser
                175                 180                 185

CGC CTG AAG CCG AAA CCC ACA AAC GAG CAC GTC GGA GGG GAG CGG TGC    13270
Arg Leu Lys Pro Lys Pro Thr Asn Glu His Val Gly Gly Glu Arg Cys
                190                 195                 200

CCC TCC GAA GGC ACG GTC GAG GCG CCA TCG CTC GGC ATC CTC TCG CGC    13318
Pro Ser Glu Gly Thr Val Glu Ala Pro Ser Leu Gly Ile Leu Ser Arg
                205                 210                 215

GTC GGG GCA GCG ATA GCA AAC GAG CTG GCT CGT ATG CGG AGG GCG TGT    13366
Val Gly Ala Ala Ile Ala Asn Glu Leu Ala Arg Met Arg Arg Ala Cys
220                 225                 230

CTT CCG CTC GCC GCG TCG GCG GCC GCT GCC GGA ATA GTG GCC TGG GCC    13414
Leu Pro Leu Ala Ala Ser Ala Ala Ala Ala Gly Ile Val Ala Trp Ala
235                 240                 245                 250

GCG GCG AGG GCC TTG CAG AAA CAA GGG CGG TAG CAGTAATAATA ACCACACAA  13467
Ala Ala Arg Ala Leu Gln Lys Gln Gly Arg *
                255                 260

ATATTG                                                              13473

(2) INFORMATION FOR SEQ ID NO: 2:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO: 2:

Met Arg Phe Arg Arg Ile Cys Ser Arg Ser Arg Ala Glu Lys Arg Arg
 1               5                  10                  15

Arg Thr Thr Glu Asn Pro Leu Thr Ser Lys Arg Val Cys Val Leu Asp
            20                  25                  30
```

-continued

```
Ser Phe Ser Arg Thr Met Ser Leu Arg Pro Tyr Ala Glu Ile Leu Pro
         35                  40                  45

Thr Ala Glu Gly Val Glu Arg Leu Ala Glu Leu Val Ser Val Thr Met
 50                  55                  60

Thr Glu Arg Ala Glu Pro Val Thr Glu Asn Thr Ala Val Asn Ser Ile
 65                  70                  75                  80

Pro Pro Ala Asn Glu Asn Gly Gln Asn Phe Ala Tyr Ala Gly Asp Gly
                 85                  90                  95

Pro Ser Thr Thr Glu Lys Val Asp Gly Ser His Thr Asp Phe Asp Glu
                100                 105                 110

Ala Ser Ser Asp Tyr Ala Gly Pro Val Pro Leu Ala Gln Thr Arg Leu
            115                 120                 125

Lys His Ser Asp Glu Phe Leu Gln His Phe Arg Val Leu Asp Asp Leu
130                 135                 140

Val Gly Ala Tyr Gly Phe Ile Cys Gly Val Arg Arg Tyr Thr Glu
145                 150                 155                 160

Glu Glu Gln Arg Arg Gly Val Asn Ser Thr Asn Gln Gly Lys Ser
                165                 170                 175

Lys Cys Lys Arg Leu Ile Ala Lys Tyr Val Lys Asn Gly Thr Arg Ala
            180                 185                 190

Ala Ser Gln Leu Glu Asn Glu Ile Leu Val Leu Gly Arg Leu Asn His
        195                 200                 205

Glu Asn Val Leu Lys Ile Gln Glu Ile Leu Arg Tyr Pro Asp Asn Thr
210                 215                 220

Tyr Met Leu Thr Gln Arg Tyr Gln Phe Asp Leu Tyr Ser Tyr Met Tyr
225                 230                 235                 240

Asp Glu Ala Phe Asp Trp Lys Asp Ser Pro Met Leu Lys Gln Thr Arg
                245                 250                 255

Arg Ile Met Lys Gln Leu Met Ser Ala Val Ser Tyr Ile His Ser Lys
            260                 265                 270

Lys Leu Ile His Arg Asp Ile Lys Leu Glu Asn Ile Phe Leu Asn Cys
        275                 280                 285

Asp Gly Lys Thr Val Leu Gly Asp Phe Gly Thr Val Thr Pro Phe Glu
290                 295                 300

Asn Glu Arg Glu Pro Phe Glu Tyr Gly Trp Val Gly Thr Val Ala Thr
305                 310                 315                 320

Asn Ser Pro Glu Ile Leu Ala Arg Asp Ser Tyr Cys Glu Ile Thr Asp
                325                 330                 335

Ile Trp Ser Cys Gly Val Val Leu Leu Glu Met Val Ser His Glu Phe
            340                 345                 350

Cys Pro Ile Gly Asp Gly Gly Asn Pro His Gln Gln Leu Leu Lys
        355                 360                 365

Val Ile Asp Ser Leu Ser Val Cys Asp Glu Glu Phe Pro Asp Pro Pro
370                 375                 380

Cys Asn Leu Tyr Asn Tyr Leu His Tyr Ala Ser Ile Asp Arg Ala Gly
385                 390                 395                 400

His Thr Val Pro Ser Leu Ile Arg Asn Leu His Leu Pro Ala Asp Val
                405                 410                 415

Glu Tyr Pro Leu Val Lys Met Leu Thr Phe Asp Trp Arg Leu Arg Pro
            420                 425                 430

Ser Ala Ala Glu Val Leu Ala Met Pro Leu Phe Ser Ala Glu Glu Glu
        435                 440                 445

Arg Thr Ile Thr Ile Ile His Gly Lys His Lys Pro Ile Arg Pro Glu
```

450                 455                 460
Ile Arg Ala Arg Val Pro Arg Ser Met Ser Glu Gly
465                 470                 475

(2) INFORMATION FOR SEQ ID NO: 3:

(i) SEQUENCE CHARACTERISTICS:
        (A) LENGTH: 510 amino acids
        (B) TYPE: amino acid
        (D) TOPOLOGY: linear (ii) MOLECULE TYPE: protein (xi) SEQUENCE DESCRIPTION: SEQ ID NO: 3:

Met Thr Leu Pro His Arg Leu Thr Lys Arg Pro Phe Ala Arg Phe
1               5                   10                  15

Cys Ser Val Phe Val Ile His Tyr Ser Glu Thr Lys Leu Asp Arg Tyr
                20                  25                  30

Asn Lys Thr Met Leu Leu Tyr Arg Pro Asp Ser Thr Met Arg His Ser
            35                  40                  45

Gly Gly Asp Ala Asn His Arg Gly Ile Arg Pro Arg Arg Lys Ser Ile
        50                  55                  60

Gly Ala Phe Ser Ala Arg Glu Lys Thr Gly Lys Arg Asn Ala Leu Thr
65                  70                  75                  80

Glu Ser Ser Ser Ser Asp Met Leu Asp Pro Phe Ser Thr Asp Lys
                85                  90                  95

Glu Phe Gly Gly Lys Trp Thr Val Asp Gly Pro Ala Asp Ile Thr Ala
            100                 105                 110

Glu Val Leu Ser Gln Ala Trp Asp Val Leu Gln Leu Val Lys His Glu
            115                 120                 125

Asp Ala Glu Glu Glu Arg Val Thr Tyr Glu Ser Lys Pro Thr Pro Ile
        130                 135                 140

Gln Pro Phe Asn Ala Trp Pro Asp Gly Pro Ser Trp Asn Ala Gln Asp
145                 150                 155                 160

Phe Thr Arg Ala Pro Ile Val Tyr Pro Ser Ala Glu Val Leu Asp Ala
                165                 170                 175

Glu Ala Leu Lys Val Gly Ala Phe Val Ser Arg Val Leu Gln Cys Val
            180                 185                 190

Pro Phe Thr Arg Ser Lys Lys Ser Val Thr Val Arg Asp Ala Gln Ser
        195                 200                 205

Phe Leu Gly Asp Ser Phe Trp Arg Ile Met Gln Asn Val Tyr Thr Val
        210                 215                 220

Cys Leu Arg Gln His Ile Thr Arg Leu Arg His Pro Ser Ser Lys Ser
225                 230                 235                 240

Ile Val Asn Cys Asn Asp Pro Leu Trp Tyr Ala Tyr Ala Asn Gln Phe
                245                 250                 255

His Trp Arg Gly Met Arg Val Pro Ser Leu Lys Leu Ala Ser Pro Pro
            260                 265                 270

Glu Glu Asn Ile Gln His Gly Pro Met Ala Ala Val Phe Arg Asn Ala
        275                 280                 285

Gly Ala Gly Leu Phe Leu Trp Pro Ala Met Arg Ala Ala Phe Glu Glu
        290                 295                 300

Arg Asp Lys Arg Leu Leu Arg Ala Cys Leu Ser Ser Leu Asp Ile Met
305                 310                 315                 320

Asp Ala Ala Val Leu Ala Ser Phe Pro Phe Tyr Trp Arg Gly Val Gln
                325                 330                 335

```
Asp Thr Ser Arg Phe Glu Pro Ala Leu Gly Cys Leu Ser Glu Tyr Phe
            340                 345                 350

Ala Leu Val Val Leu Leu Ala Glu Thr Val Leu Ala Thr Met Phe Asp
            355                 360                 365

His Ala Leu Val Phe Met Arg Ala Leu Ala Asp Gly Asn Phe Asp Asp
            370                 375                 380

Tyr Asp Glu Thr Arg Tyr Ile Asp Pro Val Lys Asn Glu Tyr Leu Asn
385                 390                 395                 400

Gly Ala Glu Gly Thr Leu Leu Arg Gly Ile Val Ala Ser Asn Thr Ala
                405                 410                 415

Leu Ala Val Val Cys Ala Asn Thr Tyr Ser Thr Ile Arg Lys Leu Pro
                420                 425                 430

Ser Val Ala Thr Ser Ala Cys Asn Val Ala Tyr Arg Thr Glu Thr Leu
                435                 440                 445

Lys Ala Arg Arg Pro Gly Met Ser Asp Ile Tyr Arg Ile Leu Gln Lys
            450                 455                 460

Glu Phe Phe Phe Tyr Ile Ala Trp Leu Gln Arg Val Ala Thr His Ala
465                 470                 475                 480

Asn Phe Cys Leu Asn Ile Leu Lys Arg Ser Val Asp Thr Gly Pro Arg
                485                 490                 495

His Phe Cys Ser Gly Pro Ala Arg Arg Ser Gly Cys Ser Ser
                500                 505                 510

(2) INFORMATION FOR SEQ ID NO: 4:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO: 4:

Met Leu Cys Pro Leu Leu Val Pro Ile Gln Tyr Glu Asp Phe Ser Lys
1               5                   10                  15

Ala Met Gly Ser Glu Leu Lys Arg Glu Lys Leu Glu Thr Phe Val Lys
            20                  25                  30

Ala Ile Ser Ser Asp Arg Asp Pro Arg Gly Ser Leu Arg Phe Leu Ile
            35                  40                  45

Ser Asp His Ala Arg Glu Ile Ile Ala Asp Gly Val Arg Phe Lys Pro
        50                  55                  60

Val Ile Asp Glu Pro Val Arg Ala Ser Val Ala Leu Ser Thr Ala Ala
65              70                  75                  80

Ala Gly Lys Val Lys Ala Arg Arg Leu Thr Ser Val Arg Ala Pro Val
                85                  90                  95

Pro Pro Ala Gly Ala Val Ser Ala Arg Arg Lys Ser Glu Ile
            100                 105                 110

(2) INFORMATION FOR SEQ ID NO: 5:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO: 5:
```

```
Met Ser Gly Phe Ser Asn Ile Gly Ile Ala Thr Val Ser Leu Val
 1               5                  10                  15

Cys Ser Leu Leu Cys Ala Ser Val Leu Gly Ala Pro Val Leu Asp Gly
                20                  25                  30

Leu Glu Ser Ser Pro Phe Pro Phe Gly Gly Lys Ile Ile Ala Gln Ala
            35                  40                  45

Cys Asn Arg Thr Thr Ile Glu Val Thr Val Pro Trp Ser Asp Tyr Ser
 50                  55                  60

Gly Arg Thr Glu Gly Val Ser Val Glu Val Lys Trp Phe Tyr Gly Asn
 65                  70                  75                  80

Ser Asn Pro Glu Ser Phe Val Phe Gly Val Asp Ser Glu Thr Gly Ser
                85                  90                  95

Gly His Glu Asp Leu Ser Thr Cys Trp Ala Leu Ile His Asn Leu Asn
            100                 105                 110

Ala Ser Val Cys Arg Ala Ser Asp Ala Gly Ile Pro Asp Phe Asp Lys
            115                 120                 125

Gln Cys Glu Lys Val Gln Arg Arg Leu Arg Ser Gly Val Glu Leu Gly
130                 135                 140

Ser Tyr Val Ser Gly Asn Gly Ser Leu Val Leu Tyr Pro Gly Met Tyr
145                 150                 155                 160

Asp Ala Gly Ile Tyr Ala Tyr Gln Leu Ser Val Gly Gly Lys Gly Tyr
                165                 170                 175

Thr Gly Ser Val Tyr Leu Asp Val Gly Pro Asn Pro Gly Cys His Asp
            180                 185                 190

Gln Tyr Gly Tyr Thr Tyr Ser Leu Ala Asp Glu Ala Ser Asp Leu
            195                 200                 205

Ser Ser Tyr Asp Val Ala Ser Pro Glu Leu Asp Gly Pro Met Glu Glu
210                 215                 220

Asp Tyr Ser Asn Cys Leu Asp Met Pro Pro Leu Arg Pro Trp Thr Thr
225                 230                 235                 240

Val Cys Ser His Asp Val Glu Glu Gln Glu Asn Ala Thr Asp Glu Leu
                245                 250                 255

Tyr Leu Trp Asp Glu Glu Cys Ala Gly Pro Leu Asp Glu Tyr Val Asp
            260                 265                 270

Glu Arg Ser Glu Thr Met Pro Arg Met Val Val Phe Ser Pro Pro Ser
            275                 280                 285

Thr Leu Gln Gln
            290

(2) INFORMATION FOR SEQ ID NO: 6:

(i) SEQUENCE CHARACTERISTICS:
        (A) LENGTH: 985 amino acids
        (B) TYPE: amino acid
        (D) TOPOLOGY: linear (ii) MOLECULE TYPE: protein (xi) SEQUENCE DESCRIPTION: SEQ ID NO: 6:

Met Gly Thr Met Leu Val Leu Arg Leu Phe Leu Leu Ala Val Ala Asp
 1               5                  10                  15

Ala Ala Leu Pro Thr Gly Arg Phe Cys Arg Val Trp Lys Val Pro Pro
                20                  25                  30

Gly Gly Thr Ile Gln Glu Asn Leu Ala Val Leu Ala Glu Ser Pro Val
            35                  40                  45

Thr Gly His Ala Thr Tyr Pro Pro Pro Glu Gly Ala Val Ser Phe Gln
```

```
                50                    55                    60
Ile Phe Ala Asp Thr Pro Thr Leu Arg Ile Arg Tyr Gly Pro Thr Glu
 65                  70                  75                  80

Asp Glu Leu Ala Leu Glu Arg Gly Thr Ser Ala Ser Asp Ala Asp Asn
                     85                  90                  95

Val Thr Phe Ser Leu Ser Tyr Arg Pro Arg Pro Glu Ile His Gly Ala
                    100                 105                 110

Tyr Phe Thr Ile Gly Val Phe Ala Thr Gly Gln Ser Thr Glu Ser Ser
                115                 120                 125

Tyr Ser Val Ile Ser Arg Val Leu Val Asn Ala Ser Leu Glu Arg Ser
130                 135                 140

Val Arg Leu Glu Thr Pro Cys Asp Glu Asn Phe Leu Gln Asn Glu Pro
145                 150                 155                 160

Thr Trp Gly Ser Lys Arg Trp Leu Gly Pro Ser Pro Tyr Val Arg
                165                 170                 175

Asp Asn Asp Val Ala Val Leu Thr Lys Ala Gln Tyr Ile Gly Glu Cys
                180                 185                 190

Tyr Ser Asn Ser Ala Ala Gln Thr Gly Leu Thr Ser Leu Asn Met Thr
                195                 200                 205

Phe Phe Tyr Ser Pro Lys Arg Ile Val Asn Val Thr Trp Thr Thr Gly
                210                 215                 220

Gly Pro Ser Pro Ser Arg Ile Thr Val Tyr Ser Ser Arg Glu Asn Gly
225                 230                 235                 240

Gln Pro Val Leu Arg Asn Val Ser Asp Gly Phe Leu Val Lys Tyr Thr
                245                 250                 255

Pro Asp Ile Asp Gly Arg Ala Met Ile Asn Val Ile Ala Asn Tyr Ser
                260                 265                 270

Pro Ala Asp Ser Gly Ser Val Leu Ala Phe Thr Ala Phe Arg Glu Gly
                275                 280                 285

Lys Leu Pro Ser Ala Ile Gln Leu His Arg Ile Asp Met Ser Gly Thr
                290                 295                 300

Glu Pro Pro Gly Thr Glu Thr Thr Phe Asp Cys Gln Lys Met Ile Glu
305                 310                 315                 320

Thr Pro Tyr Arg Ala Leu Gly Ser Asn Val Pro Arg Asp Asp Ser Ile
                325                 330                 335

Arg Pro Gly Ala Thr Leu Pro Pro Phe Asp Thr Ala Ala Pro Asp Phe
                340                 345                 350

Asp Thr Gly Thr Ser Pro Thr Pro Thr Thr Val Pro Glu Pro Ala Ile
                355                 360                 365

Thr Thr Leu Ile Pro Arg Ser Thr Ser Asp Met Gly Phe Phe Ser Thr
370                 375                 380

Ala Arg Ala Thr Gly Ser Glu Thr Leu Ser Val Pro Val Gln Glu Thr
385                 390                 395                 400

Asp Arg Thr Leu Ser Thr Thr Pro Leu Thr Leu Pro Leu Thr Pro Gly
                405                 410                 415

Glu Ser Glu Asn Thr Leu Phe Pro Thr Thr Ala Pro Gly Ile Ser Thr
                420                 425                 430

Glu Thr Pro Ser Ala Ala His Glu Thr Thr Gln Thr Gln Ser Ala Glu
                435                 440                 445

Thr Val Val Phe Thr Gln Ser Pro Thr Glu Ser Glu Thr Ala Arg
                450                 455                 460

Ser Gln Ser Gln Glu Pro Trp Tyr Phe Thr Gln Thr Pro Ser Thr Glu
465                 470                 475                 480
```

```
Gln Ala Ala Leu Thr Gln Thr Gln Ile Ala Glu Thr Glu Ala Leu Phe
                485                 490                 495
Thr Gln Thr Pro Ser Ala Glu Gln Met Thr Phe Thr Gln Thr Pro Gly
                500                 505                 510
Ala Glu Thr Glu Ala Pro Ala Gln Thr Pro Ser Thr Ile Pro Glu Ile
                515                 520                 525
Phe Thr Gln Ser Arg Ser Thr Pro Pro Glu Thr Ala Arg Ala Pro Ser
                530                 535                 540
Ala Ala Pro Glu Val Phe Thr Gln Ser Ser Ser Thr Val Thr Glu Val
545                 550                 555                 560
Phe Thr Gln Thr Pro Ser Thr Val Pro Lys Thr Thr Leu Ser Ser Ser
                565                 570                 575
Thr Glu Pro Ala Ile Phe Thr Arg Thr Gln Ser Ala Gly Thr Glu Ala
                580                 585                 590
Phe Thr Gln Thr Ser Ser Ala Glu Pro Asp Thr Met Arg Thr Gln Ser
                595                 600                 605
Thr Glu Thr His Phe Phe Thr Gln Ala Pro Ser Thr Val Pro Lys Ala
                610                 615                 620
Thr Gln Thr Pro Ser Thr Glu Pro Glu Val Leu Thr Gln Ser Pro Ser
625                 630                 635                 640
Thr Glu Pro Val Pro Phe Thr Arg Thr Leu Gly Ala Glu Pro Glu Ile
                645                 650                 655
Thr Gln Thr Pro Ser Ala Ala Pro Glu Val Tyr Thr Arg Ser Ser Ser
                660                 665                 670
Thr Met Pro Glu Thr Ala Gln Ser Thr Pro Leu Ala Ser Gln Asn Pro
                675                 680                 685
Thr Ser Ser Gly Thr Gly Thr His Asn Thr Glu Pro Arg Thr Tyr Pro
                690                 695                 700
Val Gln Thr Thr Pro His Thr Gln Lys Leu Tyr Thr Glu Asn Lys Thr
705                 710                 715                 720
Leu Ser Phe Pro Thr Val Val Ser Glu Phe His Glu Met Ser Thr Ala
                725                 730                 735
Glu Ser Gln Thr Pro Leu Leu Asp Val Lys Ile Val Glu Val Lys Phe
                740                 745                 750
Ser Asn Asp Gly Glu Val Thr Ala Thr Cys Val Ser Thr Val Lys Ser
                755                 760                 765
Pro Tyr Arg Val Glu Thr Asn Trp Lys Val Asp Leu Val Asp Val Met
                770                 775                 780
Asp Glu Ile Ser Gly Asn Ser Pro Ala Gly Val Phe Asn Ser Asn Glu
785                 790                 795                 800
Lys Trp Gln Lys Gln Leu Tyr Tyr Arg Val Thr Asp Gly Arg Thr Ser
                805                 810                 815
Val Gln Leu Met Cys Leu Ser Cys Thr Ser His Ser Pro Glu Pro Tyr
                820                 825                 830
Cys Leu Phe Asp Thr Ser Leu Ile Ala Arg Glu Lys Asp Ile Ala Pro
                835                 840                 845
Glu Leu Tyr Phe Thr Ser Asp Pro Gln Thr Ala Tyr Cys Thr Ile Thr
                850                 855                 860
Leu Pro Ser Gly Val Val Pro Arg Phe Glu Trp Ser Leu Asn Asn Val
865                 870                 875                 880
Ser Leu Pro Glu Tyr Leu Thr Ala Thr Val Val Ser His Thr Ala
                885                 890                 895
```

```
Gly Gln Ser Thr Val Trp Lys Ser Ser Ala Arg Ala Gly Glu Ala Trp
                900                 905                 910

Ile Ser Gly Arg Gly Gly Asn Ile Tyr Glu Cys Thr Val Leu Ile Ser
            915                 920                 925

Asp Gly Thr Arg Val Thr Thr Arg Lys Glu Arg Cys Leu Thr Asn Thr
        930                 935                 940

Trp Ile Ala Val Glu Asn Gly Ala Ala Gln Ala Gln Leu Tyr Ser Leu
945                 950                 955                 960

Phe Ser Gly Leu Val Ser Gly Leu Cys Gly Ser Ile Ser Ala Leu Tyr
                965                 970                 975

Ala Thr Leu Trp Thr Ala Ile Tyr Phe
                980                 985

(2) INFORMATION FOR SEQ ID NO: 7:

(i) SEQUENCE CHARACTERISTICS:
        (A) LENGTH: 362 amino acids
        (B) TYPE: amino acid
        (D) TOPOLOGY: linear (ii) MOLECULE TYPE: protein (xi) SEQUENCE DESCRIPTION: SEQ ID NO: 7:

Met Ala Ser Leu Leu Gly Thr Leu Ala Leu Leu Ala Ala Thr Leu Ala
 1               5                  10                  15

Pro Phe Gly Ala Met Gly Ile Val Ile Thr Gly Asn His Val Ser Ala
                20                  25                  30

Arg Ile Asp Asp Asp His Ile Val Ile Val Ala Pro Arg Pro Glu Ala
            35                  40                  45

Thr Ile Gln Leu Gln Leu Phe Phe Met Pro Gly Gln Arg Pro His Lys
        50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Val Phe Val Gly Cys Lys Val Thr Glu Tyr Thr Phe
                100                 105                 110

Ser Ala Ser Asn Arg Leu Thr Gly Pro Pro His Pro Phe Lys Leu Thr
            115                 120                 125

Ile Arg Asn Pro Arg Pro Asn Asp Ser Gly Met Phe Tyr Val Ile Val
130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
                165                 170                 175

Lys Ala Ser Cys Arg Thr Phe Gly Leu Pro Thr Val Gln Leu Glu Ala
            180                 185                 190

Tyr Leu Arg Thr Glu Glu Ser Trp Arg Asn Trp Gln Ala Tyr Val Ala
        195                 200                 205

Thr Glu Ala Thr Thr Thr Ser Ala Glu Ala Thr Thr Pro Thr Pro Val
    210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
                245                 250                 255

Asn Ser Asn Val Thr Val Arg Leu Gly Thr Met Ser Pro Thr Leu Ile
```

```
                  260                 265                 270
Gly Val Thr Val Ala Ala Val Val Ser Ala Thr Ile Gly Leu Val Ile
            275                 280                 285
Val Ile Ser Ile Val Thr Arg Asn Met Cys Thr Pro His Arg Lys Leu
        290                 295                 300
Asp Thr Val Ser Gln Asp Asp Glu Glu Arg Ser Gln Thr Arg Arg Glu
305                 310                 315                 320
Ser Arg Lys Phe Gly Pro Met Val Ala Cys Glu Ile Asn Lys Gly Ala
                    325                 330                 335
Asp Gln Asp Ser Glu Leu Val Glu Leu Val Ala Ile Val Asn Pro Ser
                340                 345                 350
Ala Leu Ser Ser Pro Asp Ser Ile Lys Met
            355                 360
```

(2) INFORMATION FOR SEQ ID NO: 8:

(i) SEQUENCE CHARACTERISTICS:
        (A) LENGTH: 499 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Asn Met Leu Val Ile Val Leu Ala Ser Cys Leu Ala Arg Leu Thr
1               5                   10                  15
Phe Ala Thr Arg His Val Leu Phe Leu Glu Gly Thr Gln Ala Val Leu
            20                  25                  30
Gly Glu Asp Asp Pro Arg Asn Val Pro Glu Gly Thr Val Ile Lys Trp
        35                  40                  45
Thr Lys Val Leu Arg Asn Ala Cys Lys Met Lys Ala Ala Asp Val Cys
    50                  55                  60
Ser Ser Pro Asn Tyr Cys Phe His Asp Leu Ile Tyr Asp Gly Gly Lys
65                  70                  75                  80
Lys Asp Cys Pro Pro Ala Gly Pro Leu Ser Ala Asn Leu Val Ile Leu
                85                  90                  95
Leu Lys Arg Gly Glu Ser Phe Val Val Leu Gly Ser Gly Leu His Asn
            100                 105                 110
Ser Asn Ile Thr Asn Ile Met Trp Thr Glu Tyr Gly Gly Leu Leu Phe
        115                 120                 125
Asp Pro Val Thr Arg Ser Asp Glu Gly Ile Tyr Phe Arg Arg Ile Ser
    130                 135                 140
Gln Pro Asp Leu Ala Met Glu Thr Thr Ser Tyr Asn Val Ser Val Leu
145                 150                 155                 160
Ser His Val Asp Glu Lys Ala Pro Ala Pro His Glu Val Glu Ile Asp
                165                 170                 175
Thr Ile Lys Pro Ser Glu Ala His Ala His Val Glu Leu Gln Met Leu
            180                 185                 190
Pro Phe His Glu Leu Asn Asp Asn Ser Pro Thr Tyr Val Thr Pro Val
        195                 200                 205
Leu Arg Val Phe Pro Pro Thr Glu His Val Lys Phe Asn Val Thr Tyr
    210                 215                 220
Ser Trp Tyr Gly Phe Asp Val Lys Glu Glu Cys Glu Glu Val Lys Leu
225                 230                 235                 240
Phe Glu Pro Cys Val Tyr His Pro Thr Asp Gly Lys Cys Gln Phe Pro
                245                 250                 255
```

```
Ala Thr Asn Gln Arg Cys Leu Ile Gly Ser Val Leu Met Ala Glu Phe
            260                 265                 270

Leu Gly Ala Ala Ser Leu Leu Asp Cys Ser Arg Asp Thr Leu Glu Asp
            275                 280                 285

Cys His Glu Asn Arg Val Pro Asn Leu Arg Phe Asp Ser Arg Leu Ser
            290                 295                 300

Glu Ser Arg Ala Gly Leu Val Ile Ser Pro Leu Ile Ala Ile Pro Lys
305                 310                 315                 320

Val Leu Ile Ile Val Ser Asp Gly Asp Ile Leu Gly Trp Ser Tyr
                325                 330                 335

Thr Val Leu Gly Lys Arg Asn Ser Pro Arg Val Val Glu Thr His
            340                 345                 350

Met Pro Ser Lys Val Pro Met Asn Lys Val Val Ile Gly Ser Pro Gly
            355                 360                 365

Pro Met Asp Glu Thr Gly Asn Tyr Lys Met Tyr Phe Val Val Ala Gly
            370                 375                 380

Val Ala Ala Thr Cys Val Ile Leu Thr Cys Ala Leu Leu Val Gly Lys
385                 390                 395                 400

Lys Lys Cys Pro Ala His Gln Met Gly Thr Phe Ser Lys Thr Glu Pro
                405                 410                 415

Leu Tyr Ala Pro Leu Pro Lys Asn Glu Phe Glu Ala Gly Gly Leu Thr
            420                 425                 430

Asp Asp Glu Glu Val Ile Tyr Asp Glu Val Tyr Glu Pro Leu Phe Arg
            435                 440                 445

Gly Tyr Cys Lys Gln Glu Phe Arg Glu Asp Val Asn Thr Phe Phe Gly
            450                 455                 460

Ala Val Val Glu Gly Glu Arg Ala Leu Asn Phe Lys Ser Ala Ile Ala
465                 470                 475                 480

Ser Met Ala Asp Arg Ile Leu Ala Asn Lys Ser Gly Arg Arg Asn Met
                485                 490                 495

Asp Ser Tyr (2) INFORMATION FOR SEQ ID NO: 9:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO: 9:

Met Pro Phe Lys Thr Arg Gly Ala Glu Asp Ala Ala Gly Lys Asn
1               5                   10                  15

Arg Phe Lys Lys Ser Arg Asn Arg Glu Ile Leu Pro Thr Arg Leu Arg
                20                  25                  30

Gly Thr Gly Lys Lys Thr Ala Gly Leu Ser Asn Tyr Thr Gln Pro Ile
            35                  40                  45

Pro Trp Asn Pro Lys Phe Cys Ser Ala Arg Gly Glu Ser Asp Asn His
            50                  55                  60

Ala Cys Lys Asp Thr Phe Tyr Arg Arg Thr Cys Cys Ala Ser Arg Ser
65                  70                  75                  80

Thr Val Ser Ser Gln Pro Asp Ser Pro His Thr Pro Met Pro Thr Glu
                85                  90                  95

Tyr Gly Arg Val Pro Ser Ala Lys Arg Lys Lys Leu Ser Ser Ser Asp
```

-continued

```
                100                 105                 110
Xaa Glu Gly Ala His Gln Pro Leu Val Ser Cys Lys Leu Pro Asp Ser
            115                 120                 125

Gln Ala Ala Pro Ala Arg Thr Tyr Ser Ser Ala Gln Arg Tyr Thr Val
        130                 135                 140

Asp Glu Val Ser Ser Pro Thr Pro Pro Gly Val Asp Ala Val Ala Asp
145                 150                 155                 160

Leu Glu Thr Arg Ala Glu Leu Pro Gly Ala Thr Thr Glu Gln Thr Glu
                165                 170                 175

Ser Lys Asn Lys Leu Pro Asn Gln Gln Ser Arg Leu Lys Pro Lys Pro
            180                 185                 190

Thr Asn Glu His Val Gly Gly Glu Arg Cys Pro Ser Glu Gly Thr Val
        195                 200                 205

Glu Ala Pro Ser Leu Gly Ile Leu Ser Arg Val Gly Ala Ala Ile Ala
    210                 215                 220

Asn Glu Leu Ala Arg Met Arg Arg Ala Cys Leu Pro Leu Ala Ala Ser
225                 230                 235                 240

Ala Ala Ala Ala Gly Ile Val Ala Trp Ala Ala Ala Arg Ala Leu Gln
                245                 250                 255

Lys Gln Gly Arg
            260
```

(2) INFORMATION FOR SEQ ID NO: 10:

(i) SEQUENCE CHARACTERISTICS:
        (A) LENGTH: 1305 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1305

(xi) SEQUENCE DESCRIPTION: SEQ ID NO: 10:

```
ATG CAC CGT CCT CAT CTC AGA CGG CAC TCG CGT TAC TAC GCG AAA GGA      48
Met His Arg Pro His Leu Arg Arg His Ser Arg Tyr Tyr Ala Lys Gly
 1               5                  10                  15

GAG GTG CTT AAC AAA CAC ATG GAT TGC GGT GGA AAA CGG TGC TGC TCA      96
Glu Val Leu Asn Lys His Met Asp Cys Gly Gly Lys Arg Cys Cys Ser
                20                  25                  30

GGC GCA GCT GTA TTC ACT CTT TTC TGG ACT TGT GTC AGG ATT ATG CGG     144
Gly Ala Ala Val Phe Thr Leu Phe Trp Thr Cys Val Arg Ile Met Arg
            35                  40                  45

GAG CAT ATC TGC TTT GTA CGC AAC GCT ATG GAC CGC CAT TTA TTT TTG     192
Glu His Ile Cys Phe Val Arg Asn Ala Met Asp Arg His Leu Phe Leu
    50                  55                  60

AGG AAT GCT TTT TGG ACT ATC GTA CTG CTT TCT TCC TTC GCT AGC CAG     240
Arg Asn Ala Phe Trp Thr Ile Val Leu Leu Ser Ser Phe Ala Ser Gln
65                  70                  75                  80

AGC ACC GCC GCC GTC ACG TAC GAC TAC ATT TTA GGC CGT CGC GCG CTC     288
Ser Thr Ala Ala Val Thr Tyr Asp Tyr Ile Leu Gly Arg Arg Ala Leu
                85                  90                  95

GAC GCG CTA ACC ATA CCG GCG GTT GGC CCG TAT AAC AGA TAC CTC ACT     336
Asp Ala Leu Thr Ile Pro Ala Val Gly Pro Tyr Asn Arg Tyr Leu Thr
```

-continued

```
              100                 105                 110
AGG GTA TCA AGA GGC TGC GAC GTT GTC GAG CTC AAC CCG ATT TCT AAC      384
Arg Val Ser Arg Gly Cys Asp Val Val Glu Leu Asn Pro Ile Ser Asn
            115                 120                 125

GTG GAC GAC ATG ATA TCG GCG GCC AAA GAA AAA GAG AAG GGG GGC CCT      432
Val Asp Asp Met Ile Ser Ala Ala Lys Glu Lys Glu Lys Gly Gly Pro
130                 135                 140

TTC GAG GCC TCC GTC GTC TGG TTC TAC GTG ATT AAG GGC GAC GAC GGC      480
Phe Glu Ala Ser Val Val Trp Phe Tyr Val Ile Lys Gly Asp Asp Gly
145                 150                 155                 160

GAG GAC AAG TAC TGT CCA ATC TAT AGA AAA GAG TAC AGG GAA TGT GGC      528
Glu Asp Lys Tyr Cys Pro Ile Tyr Arg Lys Glu Tyr Arg Glu Cys Gly
                165                 170                 175

GAC GTA CAA CTG CTA TCT GAA TGC GCC GTT CAA TCT GCA CAG ATG TGG      576
Asp Val Gln Leu Leu Ser Glu Cys Ala Val Gln Ser Ala Gln Met Trp
            180                 185                 190

GCA GTG GAC TAT GTT CCT AGC ACC CTT GTA TCG CGA AAT GGC GCG GGA      624
Ala Val Asp Tyr Val Pro Ser Thr Leu Val Ser Arg Asn Gly Ala Gly
        195                 200                 205

CTG ACT ATA TTC TCC CCC ACT GCT GCG CTC TCT GGC CAA TAC TTG CTG      672
Leu Thr Ile Phe Ser Pro Thr Ala Ala Leu Ser Gly Gln Tyr Leu Leu
    210                 215                 220

ACC CTG AAA ATC GGG AGA TTT GCG CAA ACA GCT CTC GTA ACT CTA GAA      720
Thr Leu Lys Ile Gly Arg Phe Ala Gln Thr Ala Leu Val Thr Leu Glu
225                 230                 235                 240

GTT AAC GAT CGC TGT TTA AAG ATC GGG TCG CAG CTT AAC TTT TTA CCG      768
Val Asn Asp Arg Cys Leu Lys Ile Gly Ser Gln Leu Asn Phe Leu Pro
                245                 250                 255

TCG AAA TGC TGG ACA ACA GAA CAG TAT CAG ACT GGA TTT CAA GGC GAA      816
Ser Lys Cys Trp Thr Thr Glu Gln Tyr Gln Thr Gly Phe Gln Gly Glu
            260                 265                 270

CAC CTT TAT CCG ATC GCA GAC ACC AAT ACA CGA CAC GCG GAC GAC GTA      864
His Leu Tyr Pro Ile Ala Asp Thr Asn Thr Arg His Ala Asp Asp Val
        275                 280                 285

TAT CGG GGA TAC GAA GAT ATT CTG CAG CGC TGG AAT AAT TTG CTG AGG      912
Tyr Arg Gly Tyr Glu Asp Ile Leu Gln Arg Trp Asn Asn Leu Leu Arg
    290                 295                 300

AAA AAG AAT CCT AGC GCG CCA GAC CCT CGT CCA GAT AGC GTC CCG CAA      960
Lys Lys Asn Pro Ser Ala Pro Asp Pro Arg Pro Asp Ser Val Pro Gln
305                 310                 315                 320

GAA ATT CCC GCT GTA ACC AAG AAA GCG GAA GGG CGC ACC CCG GAC GCA     1008
Glu Ile Pro Ala Val Thr Lys Lys Ala Glu Gly Arg Thr Pro Asp Ala
                325                 330                 335

GAA AGC AGC GAA AAG AAG GCC CCT CCA GAA GAC TCG GAG GAC GAC ATG     1056
Glu Ser Ser Glu Lys Lys Ala Pro Pro Glu Asp Ser Glu Asp Asp Met
            340                 345                 350

CAG GCA GAG GCT TCT GGA GAA AAT CCT GCC GCC CTC CCC GAA GAC GAC     1104
Gln Ala Glu Ala Ser Gly Glu Asn Pro Ala Ala Leu Pro Glu Asp Asp
        355                 360                 365

GAA GTC CCC GAG GAC ACC GAG CAC GAT GAT CCA AAC TCG GAT CCT GAC     1152
Glu Val Pro Glu Asp Thr Glu His Asp Asp Pro Asn Ser Asp Pro Asp
    370                 375                 380

TAT TAC AAT GAC ATG CCC GCC GTG ATC CCG GTG GAG GAG ACT ACT AAA     1200
Tyr Tyr Asn Asp Met Pro Ala Val Ile Pro Val Glu Glu Thr Thr Lys
385                 390                 395                 400

AGT TCT AAT GCC GTC TCC ATG CCC ATA TTC GCG GCG TTC GTA GCC TGC     1248
Ser Ser Asn Ala Val Ser Met Pro Ile Phe Ala Ala Phe Val Ala Cys
                405                 410                 415

GCG GTC GCG CTC GTG GGG CTA CTG GTT TGG AGC ATC GTA AAA TGC GCG     1296
Ala Val Ala Leu Val Gly Leu Leu Val Trp Ser Ile Val Lys Cys Ala
```

```
Ala Val Ala Leu Val Gly Leu Leu Val Trp Ser Ile Val Lys Cys Ala
            420                 425                 430

CGT AGC TAA                                                              1305
Arg Ser
    435

(2) INFORMATION FOR SEQ ID NO: 11:

(i) SEQUENCE CHARACTERISTICS:
        (A) LENGTH: 434 amino acids
        (B) TYPE: amino acid
        (D) TOPOLOGY: linear (ii) MOLECULE TYPE: protein (xi) SEQUENCE DESCRIPTION: SEQ ID NO: 11:

Met His Arg Pro His Leu Arg Arg His Ser Arg Tyr Tyr Ala Lys Gly
 1               5                  10                  15

Glu Val Leu Asn Lys His Met Asp Cys Gly Gly Lys Arg Cys Cys Ser
                20                  25                  30

Gly Ala Ala Val Phe Thr Leu Phe Trp Thr Cys Val Arg Ile Met Arg
            35                  40                  45

Glu His Ile Cys Phe Val Arg Asn Ala Met Asp Arg His Leu Phe Leu
        50                  55                  60

Arg Asn Ala Phe Trp Thr Ile Val Leu Leu Ser Ser Phe Ala Ser Gln
 65                 70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320
```

-continued

```
Glu Ile Pro Ala Val Thr Lys Lys Ala Glu Gly Arg Thr Pro Asp Ala
            325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
            355                 360                 365

Glu Val Pro Glu Asp Thr Glu His Asp Asp Pro Asn Ser Asp Pro Asp
        370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
            405                 410                 415

Ala Val Ala Leu Val Gly Leu Leu Val Trp Ser Ile Val Lys Cys Ala
            420                 425                 430

Arg Ser
```

(2) INFORMATION FOR SEQ ID NO: 12:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..689

(xi) SEQUENCE DESCRIPTION: SEQ ID NO: 12:

```
ATG GCG CCT GTA AAA GTG ACT ATA GTT TCT GCG GTC GAT TCG CAC TAC        48
Met Ala Pro Val Lys Val Thr Ile Val Ser Ala Val Asp Ser His Tyr
 1               5                  10                  15

AAA CTA CCT AAT TCT AGA TTT GAG CTC TCG GAT TCT GGA TGG AAA GAA        96
Lys Leu Pro Asn Ser Arg Phe Glu Leu Ser Asp Ser Gly Trp Lys Glu
                20                  25                  30

TTG GTT CAC GCA GTG AAA ACT ATG GCG AGT TAC GAT CGT CCG AGT ACA       144
Leu Val His Ala Val Lys Thr Met Ala Ser Tyr Asp Arg Pro Ser Thr
            35                  40                  45

TTA TCG GTA ATC GTG CGC CCG GCA TCT CTG TAC GAA GTT TCC GGG GAG       192
Leu Ser Val Ile Val Arg Pro Ala Ser Leu Tyr Glu Val Ser Gly Glu
        50                  55                  60

CTG TTT TCC CTT CCC AGG ATG TGC AGA CCC GTG ATT CGG TTC GGT GAG       240
Leu Phe Ser Leu Pro Arg Met Cys Arg Pro Val Ile Arg Phe Gly Glu
 65                 70                  75                  80

GGG GGC GAC CCG CCT GGA GTA AGT CCC GAG TGG AGC GGC TTG GAC GCA       288
Gly Gly Asp Pro Pro Gly Val Ser Pro Glu Trp Ser Gly Leu Asp Ala
                85                  90                  95

GGG TTT TAC CAT TTG TCA TCT GGC GCG TAT GCC GCA AAA GAG TTC CAT       336
Gly Phe Tyr His Leu Ser Ser Gly Ala Tyr Ala Ala Lys Glu Phe His
            100                 105                 110

TTG TGG GTG CTG GGT ACC GCT GAC ATA TGC ATG GCA GCT TTA AAC CTC       384
Leu Trp Val Leu Gly Thr Ala Asp Ile Cys Met Ala Ala Leu Asn Leu
        115                 120                 125

CCT GCG CCA AAA ACT TTC CTA ATT ACC GAA ACC GGA GGT AAA AAT TTT       432
Pro Ala Pro Lys Thr Phe Leu Ile Thr Glu Thr Gly Gly Lys Asn Phe
130                 135                 140
```

```
GAG AGA GGA GTG GAA ATA TTT TTG GTA AAC GGA GAC AAG ACA ACG CTG      480
Glu Arg Gly Val Glu Ile Phe Leu Val Asn Gly Asp Lys Thr Thr Leu
145                 150                 155                 160

TCT CTG AGT CAC CCA TCA GTC TGG ACA ACT CTT GCC CCT TCG AGC CTG      528
Ser Leu Ser His Pro Ser Val Trp Thr Thr Leu Ala Pro Ser Ser Leu
                165                 170                 175

AGA ACG CCC TGG CCG TAC AGC ACG GTA AAG TTT TTA AAA GTA AAA CCT      576
Arg Thr Pro Trp Pro Tyr Ser Thr Val Lys Phe Leu Lys Val Lys Pro
            180                 185                 190

AAC TCG GCC GCA TAC TGT GTT TCC GAC TCG GAT GAT GGC GAA CGG CAG      624
Asn Ser Ala Ala Tyr Cys Val Ser Asp Ser Asp Asp Gly Glu Arg Gln
                195                 200                 205

CCA AAA TTT TTT CTC GGG AGT CTA TTT AAG TCG AAG AAA CCC CGC TCC      672
Pro Lys Phe Phe Leu Gly Ser Leu Phe Lys Ser Lys Lys Pro Arg Ser
210                 215                 220

CCG CGG CGC CGA CGT TA G                                             690
Pro Arg Arg Arg Arg
225

(2) INFORMATION FOR SEQ ID NO: 13:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO: 13:

Met Ala Pro Val Lys Val Thr Ile Val Ser Ala Val Asp Ser His Tyr
1               5                   10                  15

Lys Leu Pro Asn Ser Arg Phe Glu Leu Ser Asp Ser Gly Trp Lys Glu
            20                  25                  30

Leu Val His Ala Val Lys Thr Met Ala Ser Tyr Asp Arg Pro Ser Thr
        35                  40                  45

Leu Ser Val Ile Val Arg Pro Ala Ser Leu Tyr Glu Val Ser Gly Glu
    50                  55                  60

Leu Phe Ser Leu Pro Arg Met Cys Arg Pro Val Ile Arg Phe Gly Glu
65                  70                  75                  80

Gly Gly Asp Pro Pro Gly Val Ser Pro Glu Trp Ser Gly Leu Asp Ala
                85                  90                  95

Gly Phe Tyr His Leu Ser Ser Gly Ala Tyr Ala Ala Lys Glu Phe His
            100                 105                 110

Leu Trp Val Leu Gly Thr Ala Asp Ile Cys Met Ala Ala Leu Asn Leu
        115                 120                 125

Pro Ala Pro Lys Thr Phe Leu Ile Thr Glu Thr Gly Gly Lys Asn Phe
    130                 135                 140

Glu Arg Gly Val Glu Ile Phe Leu Val Asn Gly Asp Lys Thr Thr Leu
145                 150                 155                 160

Ser Leu Ser His Pro Ser Val Trp Thr Thr Leu Ala Pro Ser Ser Leu
                165                 170                 175

Arg Thr Pro Trp Pro Tyr Ser Thr Val Lys Phe Leu Lys Val Lys Pro
            180                 185                 190

Asn Ser Ala Ala Tyr Cys Val Ser Asp Ser Asp Asp Gly Glu Arg Gln
        195                 200                 205

Pro Lys Phe Phe Leu Gly Ser Leu Phe Lys Ser Lys Lys Pro Arg Ser
    210                 215                 220
```

Pro Arg Arg Arg Arg
225

(2) INFORMATION FOR SEQ ID NO: 14:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..380

(xi) SEQUENCE DESCRIPTION: SEQ ID NO: 14:

```
ATG CGT AGC TCA GTT ACG TCA TTG TGG AGC CCT TCA GAT CAC GCC TCT        48
Met Arg Ser Ser Val Thr Ser Leu Trp Ser Pro Ser Asp His Ala Ser
 1               5                  10                  15

TCG CCC GCA AAT GCC AAG CAT TTT TAT CAT ATT TCC GAT TTC CGG CGC        96
Ser Pro Ala Asn Ala Lys His Phe Tyr His Ile Ser Asp Phe Arg Arg
            20                  25                  30

GCG GAA ACG GCG CCT GCG GGC GGT ACG GGC GCG CGA ACT GAG GTT AAG       144
Ala Glu Thr Ala Pro Ala Gly Gly Thr Gly Ala Arg Thr Glu Val Lys
        35                  40                  45

CGT CGC GCT TTC ACT TTC CCA GCG GCA GCG GTA CTC AGC GCA ACT GAA       192
Arg Arg Ala Phe Thr Phe Pro Ala Ala Ala Val Leu Ser Ala Thr Glu
 50                  55                  60

GCC CGA ACC GGC TCG TCT ATC ACC GGC TTA AAC CGT ACT CCG TCT GCA       240
Ala Arg Thr Gly Ser Ser Ile Thr Gly Leu Asn Arg Thr Pro Ser Ala
 65                  70                  75                  80

ATA ATT TCC CTT GCA TGG TCC GAA ATG AGA AAT CTT AAG GAC CCC CTC       288
Ile Ile Ser Leu Ala Trp Ser Glu Met Arg Asn Leu Lys Asp Pro Leu
                85                  90                  95

GGG TCC CTG TCG CTG GAA ATA GCT TTA ACG AAT GTC TCT AAC TTT TCC       336
Gly Ser Leu Ser Leu Glu Ile Ala Leu Thr Asn Val Ser Asn Phe Ser
            100                 105                 110

CTC TTG AGC TCA GAC CCC ATG GCC TTC GAA AAG TCT TCA TAT TG            380
Leu Leu Ser Ser Asp Pro Met Ala Phe Glu Lys Ser Ser Tyr
        115                 120                 125

A                                                                      381
```

(2) INFORMATION FOR SEQ ID NO: 15:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Arg Ser Ser Val Thr Ser Leu Trp Ser Pro Ser Asp His Ala Ser
 1               5                  10                  15

Ser Pro Ala Asn Ala Lys His Phe Tyr His Ile Ser Asp Phe Arg Arg
            20                  25                  30

Ala Glu Thr Ala Pro Ala Gly Gly Thr Gly Ala Arg Thr Glu Val Lys
        35                  40                  45
```

```
Arg Arg Ala Phe Thr Phe Pro Ala Ala Ala Val Leu Ser Ala Thr Glu
 50                  55                  60

Ala Arg Thr Gly Ser Ser Ile Thr Gly Leu Asn Arg Thr Pro Ser Ala
 65                  70                  75                  80

Ile Ile Ser Leu Ala Trp Ser Glu Met Arg Asn Leu Lys Asp Pro Leu
                 85                  90                  95

Gly Ser Leu Ser Leu Glu Ile Ala Leu Thr Asn Val Ser Asn Phe Ser
            100                 105                 110

Leu Leu Ser Ser Asp Pro Met Ala Phe Glu Lys Ser Ser Tyr
        115                 120                 125
```

(2) INFORMATION FOR SEQ ID NO: 16:

(i) SEQUENCE CHARACTERISTICS:
  (A) LENGTH: 879 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (ix) FEATURE:
  (A) NAME/KEY: CDS
  (B) LOCATION: 1..878

(xi) SEQUENCE DESCRIPTION: SEQ ID NO: 16:

```
ATG TGG TGT CGT TTG CAC TGG ATA AGT CCT CGG TTC AGT ATT ATG CGT      48
Met Trp Cys Arg Leu His Trp Ile Ser Pro Arg Phe Ser Ile Met Arg
 1               5                  10                  15

CCC GGT TCC CGA ACT GGT AGG GTT TTG CGA GGC CAG GGG TGT GCT CTG      96
Pro Gly Ser Arg Thr Gly Arg Val Leu Arg Gly Gln Gly Cys Ala Leu
                 20                  25                  30

TGC AGT TTC TGG CAT CGT ACT CGA ACT CCG AGT ATA AAC CTC CGG TGC     144
Cys Ser Phe Trp His Arg Thr Arg Thr Pro Ser Ile Asn Leu Arg Cys
             35                  40                  45

CGC GCT CGG GGT CTG AGT AAT TTC CGG CTC TGC GCC CAG AGT CCG GGT     192
Arg Ala Arg Gly Leu Ser Asn Phe Arg Leu Cys Ala Gln Ser Pro Gly
 50                  55                  60

GAA AGG CAC AGG TTC GGT ACT CGG ACT CTG AGT CAA CAC CTC CGG CTC     240
Glu Arg His Arg Phe Gly Thr Arg Thr Leu Ser Gln His Leu Arg Leu
 65                  70                  75                  80

TGT ACT CGG AGT CTG AGT AGC TTT CGG TAC CGT ACT CGG GGC CTG AGT     288
Cys Thr Arg Ser Leu Ser Ser Phe Arg Tyr Arg Thr Arg Gly Leu Ser
                 85                  90                  95

GAA AAA GTG TGT TTC AGT ACT CTG AGT TCG CAT AGT GTC CGG CTC GGC     336
Glu Lys Val Cys Phe Ser Thr Leu Ser Ser His Ser Val Arg Leu Gly
            100                 105                 110

ACT CGA AGT CTG AGT AAA GGC CTC AGT TCC CGC GCT CTG AGT CCG AGT     384
Thr Arg Ser Leu Ser Lys Gly Leu Ser Ser Arg Ala Leu Ser Pro Ser
        115                 120                 125

AAA AAT CGC CGG TTC AGT ACT CGA ACT CAG AGT AGT TTT CGG TAC CGT     432
Lys Asn Arg Arg Phe Ser Thr Arg Thr Gln Ser Ser Phe Arg Tyr Arg
        130                 135                 140

GCT CGG GGT CTG AGT AAA CAC CTC CGT TAC CGT ACT CGA ACT CTG TGT     480
Ala Arg Gly Leu Ser Lys His Leu Arg Tyr Arg Thr Arg Thr Leu Cys
145                 150                 155                 160

AAA AAC CTC CGG CGC CGC GCT CGG AGC GCG AGC GGT TTC GGG GGG CGT     528
Lys Asn Leu Arg Arg Arg Ala Arg Ser Ala Ser Gly Phe Gly Gly Arg
                165                 170                 175
```

```
GCT ACG AGA CTG AGT AAA TAT CTC GGG TAT CGT GCT CGG GGT CTG GGC        576
Ala Thr Arg Leu Ser Lys Tyr Leu Gly Tyr Arg Ala Arg Gly Leu Gly
            180                 185                 190

AGG TGC CTC GGT TTC TGC ACC CGG AGT CTG AGT AAA AGT CAT CTG TTC        624
Arg Cys Leu Gly Phe Cys Thr Arg Ser Leu Ser Lys Ser His Leu Phe
            195                 200                 205

AGC ACT CGG AGT CTG AGT AAA CAA CGC CTC CGT TTC TGC GAT CTG CGT        672
Ser Thr Arg Ser Leu Ser Lys Gln Arg Leu Arg Phe Cys Asp Leu Arg
            210                 215                 220

CTG AGT AAG AGC CGC CTG TTC AGT ACT CGG AGT CTG AGT AAA ATA CCA        720
Leu Ser Lys Ser Arg Leu Phe Ser Thr Arg Ser Leu Ser Lys Ile Pro
225                 230                 235                 240

CGG TTC CTG ACT CTG GGA CCG CGC GGT TTC CGA CTC GGT ACT CGG ACT        768
Arg Phe Leu Thr Leu Gly Pro Arg Gly Phe Arg Leu Gly Thr Arg Thr
                245                 250                 255

CTG AGT AAA GAC CAC CGT TTC TGC ACT CTG GGT CTG TGT AGT TTC ATG        816
Leu Ser Lys Asp His Arg Phe Cys Thr Leu Gly Leu Cys Ser Phe Met
                260                 265                 270

TGC CGC GCT CGG GGT CTC GGT AGA AAT CCC CGG CGC GGT CGT AGG AAA        864
Cys Arg Ala Arg Gly Leu Gly Arg Asn Pro Arg Arg Gly Arg Arg Lys
                275                 280                 285

CAG TGT ATT TTC TG A                                                    879
Gln Cys Ile Phe
    290
```

(2) INFORMATION FOR SEQ ID NO: 17:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Trp Cys Arg Leu His Trp Ile Ser Pro Arg Phe Ser Ile Met Arg
  1               5                  10                  15

Pro Gly Ser Arg Thr Gly Arg Val Leu Arg Gly Gln Gly Cys Ala Leu
                 20                  25                  30

Cys Ser Phe Trp His Arg Thr Thr Pro Ser Ile Asn Leu Arg Cys
             35                  40                  45

Arg Ala Arg Gly Leu Ser Asn Phe Arg Leu Cys Ala Gln Ser Pro Gly
         50                  55                  60

Glu Arg His Arg Phe Gly Thr Arg Thr Leu Ser Gln His Leu Arg Leu
 65                  70                  75                  80

Cys Thr Arg Ser Leu Ser Phe Arg Tyr Arg Thr Arg Gly Leu Ser
                 85                  90                  95

Glu Lys Val Cys Phe Ser Thr Leu Ser Ser His Ser Val Arg Leu Gly
             100                 105                 110

Thr Arg Ser Leu Ser Lys Gly Leu Ser Ser Arg Ala Leu Ser Pro Ser
         115                 120                 125

Lys Asn Arg Arg Phe Ser Thr Arg Thr Gln Ser Ser Phe Arg Tyr Arg
         130                 135                 140

Ala Arg Gly Leu Ser Lys His Leu Arg Tyr Arg Thr Arg Thr Leu Cys
145                 150                 155                 160

Lys Asn Leu Arg Arg Arg Ala Arg Ser Ala Ser Gly Phe Gly Gly Arg
                 165                 170                 175

Ala Thr Arg Leu Ser Lys Tyr Leu Gly Tyr Arg Ala Arg Gly Leu Gly
```

```
                    180                 185                 190
Arg Cys Leu Gly Phe Cys Thr Arg Ser Leu Ser Lys Ser His Leu Phe
            195                 200                 205
Ser Thr Arg Ser Leu Ser Lys Gln Arg Leu Arg Phe Cys Asp Leu Arg
        210                 215                 220
Leu Ser Lys Ser Arg Leu Phe Ser Thr Arg Ser Leu Ser Lys Ile Pro
225                 230                 235                 240
Arg Phe Leu Thr Leu Gly Pro Arg Gly Phe Arg Leu Gly Thr Arg Thr
                245                 250                 255
Leu Ser Lys Asp His Arg Phe Cys Thr Leu Gly Leu Cys Ser Phe Met
            260                 265                 270
Cys Arg Ala Arg Gly Leu Gly Arg Asn Pro Arg Arg Gly Arg Arg Lys
        275                 280                 285
Gln Cys Ile Phe
    290

(2) INFORMATION FOR SEQ ID NO: 18:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..533

(xi) SEQUENCE DESCRIPTION: SEQ ID NO: 18:

ATG CTC CCA AGC CTA CTC AAC AGG GGC TCT CCC CGG CTG AAT TCT CCT      48
Met Leu Pro Ser Leu Leu Asn Arg Gly Ser Pro Arg Leu Asn Ser Pro
 1               5                  10                  15

CCT AAG TGT TCA GAG GCC TCT GCT GTA CCA TAT AAC TAT CGT GTA GTA      96
Pro Lys Cys Ser Glu Ala Ser Ala Val Pro Tyr Asn Tyr Arg Val Val
                20                  25                  30

CGC CCC TCC CAG TCC GTG TCC GAT ACT GCC CCT TTT GAG AGG ATT GGG     144
Arg Pro Ser Gln Ser Val Ser Asp Thr Ala Pro Phe Glu Arg Ile Gly
            35                  40                  45

AGA TTA GAG AAT CGA AAT GAT TGG AGA GCC ACA TTC AGA CTT AAT CAC     192
Arg Leu Glu Asn Arg Asn Asp Trp Arg Ala Thr Phe Arg Leu Asn His
        50                  55                  60

ATT TTT ATT GAG TCG GGC GAG CTT AGC GCA GAC GGG TTA ACA ATC GCA     240
Ile Phe Ile Glu Ser Gly Glu Leu Ser Ala Asp Gly Leu Thr Ile Ala
 65                 70                  75                  80

ACC AGT TCC ACA AGT TCA CTA TCC TGG TCA GCG CCC TTG TTT ATT TCG     288
Thr Ser Ser Thr Ser Ser Leu Ser Trp Ser Ala Pro Leu Phe Ile Ser
                85                  90                  95

CAC GCA ACC ATG GGT CCA AAT TTT CGC GAT TCC CTT CTA GTT TGG GAA     336
His Ala Thr Met Gly Pro Asn Phe Arg Asp Ser Leu Leu Val Trp Glu
            100                 105                 110

CGT TCT TCG TCG TCT TGC GAG ACC GTG TCT AAT TTT CGG TGC GGG GTG     384
Arg Ser Ser Ser Ser Cys Glu Thr Val Ser Asn Phe Arg Cys Gly Val
        115                 120                 125

CAC ATG TTT CTG GTG ACG ATG GAA ATT ACA ATG ACG AGG CCA ATC GTT     432
His Met Phe Leu Val Thr Met Glu Ile Thr Met Thr Arg Pro Ile Val
            130                 135                 140
```

```
GCG CTC ACG ACG GCA GCC ACG GTT ACC CCA ATT AGC GTA GGG CTC ATT      480
Ala Leu Thr Thr Ala Ala Thr Val Thr Pro Ile Ser Val Gly Leu Ile
145                 150                 155                 160

GTC CCG AGA CGG ACA GTA ACG TTT GAA TTT TCG TTT GCG GGT GTC GGT      528
Val Pro Arg Arg Thr Val Thr Phe Glu Phe Ser Phe Ala Gly Val Gly
                165                 170                 175

TCG TA A                                                              534
Ser
```

(2) INFORMATION FOR SEQ ID NO: 19:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO: 19:

```
Met Leu Pro Ser Leu Leu Asn Arg Gly Ser Pro Arg Leu Asn Ser Pro
1               5                   10                  15

Pro Lys Cys Ser Glu Ala Ser Ala Val Pro Tyr Asn Tyr Arg Val Val
                20                  25                  30

Arg Pro Ser Gln Ser Val Ser Asp Thr Ala Pro Phe Glu Arg Ile Gly
                35                  40                  45

Arg Leu Glu Asn Arg Asn Asp Trp Arg Ala Thr Phe Arg Leu Asn His
                50                  55                  60

Ile Phe Ile Glu Ser Gly Glu Leu Ser Ala Asp Gly Leu Thr Ile Ala
65                  70                  75                  80

Thr Ser Ser Thr Ser Ser Leu Ser Trp Ser Ala Pro Leu Phe Ile Ser
                85                  90                  95

His Ala Thr Met Gly Pro Asn Phe Arg Asp Ser Leu Leu Val Trp Glu
                100                 105                 110

Arg Ser Ser Ser Ser Cys Glu Thr Val Ser Asn Phe Arg Cys Gly Val
                115                 120                 125

His Met Phe Leu Val Thr Met Glu Ile Thr Met Thr Arg Pro Ile Val
                130                 135                 140

Ala Leu Thr Thr Ala Ala Thr Val Thr Pro Ile Ser Val Gly Leu Ile
145                 150                 155                 160

Val Pro Arg Arg Thr Val Thr Phe Glu Phe Ser Phe Ala Gly Val Gly
                165                 170                 175

Ser
```

(2) INFORMATION FOR SEQ ID NO: 20:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

```
GAATTCGAGC TCGGTACCCG GATAATACGT ACATGTTAAC GCAGAGGT                  48
```

(2) INFORMATION FOR SEQ ID NO: 21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 21:

```
GCTGACCGCT AGTCGACCTG CAGTGAATAA TAAAAT                              36
```

(2) INFORMATION FOR SEQ ID NO: 22:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

```
TGTCCGTCGA GATCCTCTAG AGTCGACGAA AGGTCAGAGA CGATGCCC                 48
```

(2) INFORMATION FOR SEQ ID NO: 23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

```
CGGATCAGAA ACTCTTTCGG TACCCGGGAT CCTCTAGA                            38
```

(2) INFORMATION FOR SEQ ID NO: 24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

```
GAATACAAGC TTAGATGCAT ATTTACTCGA GCC                                 33
```

(2) INFORMATION FOR SEQ ID NO: 25:

(i) SEQUENCE CHARACTERISTICS:

(A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 25:

GGTTTGGCGG AGCGGATATG ATCTCGACCT GCAGTGAATA ATAAAATGTG T          51

(2) INFORMATION FOR SEQ ID NO: 26:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 26:

TGTCCGTCGA GATCCTCTAG AGTCGAGATC AGCAAAATGT TCACGGGG              48

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 27:

AAGCTTGGCG TAATCATG                                               18

(2) INFORMATION FOR SEQ ID NO: 28:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 28:

GGAATTCGAG CTCGGTACCT CGTGGCGAGC GCAGGCGGC                        39

(2) INFORMATION FOR SEQ ID NO: 29:

(i) SEQUENCE CHARACTERISTICS:
        (A) LENGTH: 51 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 29:

GGCCGAGTTA GGTTTTACTT TTCTAGAGGA TCCCCTCGAC GTCTGGGGCG C            51

(2) INFORMATION FOR SEQ ID NO: 30:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 30:

TTGCTGCGTT CCCGGGGATC CTCTAGAATT AGGTAGTTTG TAGTGCGA                48

(2) INFORMATION FOR SEQ ID NO: 31:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 31:

TCAAGATCCA GGAAATCCTT CGGTACCGAG CTCGAATTCG TA                      42

(2) INFORMATION FOR SEQ ID NO: 32:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

GAATTCGAGC TCGGTACCGA AAGCTACTCA GAC                                33

(2) INFORMATION FOR SEQ ID NO: 33:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

CGCAAACAGC TCTCGTAACT CTAGAAGTTA ACGATCGCTG TT                42

(2) INFORMATION FOR SEQ ID NO: 34:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

GAATAGCATA CCAATGCCTA TTCATTGGGA CTCGACTCTA GAGGATCCCC GGGAACG    57

(2) INFORMATION FOR SEQ ID NO: 35:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

TCGAGGGGAT CCTCTAGAGT CGAGGGACCC ATGGTTGCGT GC                42

(2) INFORMATION FOR SEQ ID NO: 36:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

TTTACTAAAG CGCGGCGAAA GCTTCGTCGT GCTGGGTTCT GG                42

(2) INFORMATION FOR SEQ ID NO: 37:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

AAGCTTGGCG TAATCATGGT C                                              21

(2) INFORMATION FOR SEQ ID NO: 38:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 38:

GGAATTCGAG CTCGGTACCC GGATAATACG TACATGTTAA CGCAGAGG                  48

(2) INFORMATION FOR SEQ ID NO: 39:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

ATCTATTGGA GCGTTTAGCG CGCGTCGACG AAAGGTCAGA GACGA                     45

(2) INFORMATION FOR SEQ ID NO: 40:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:

CTGCTTCATT TCTGATCCCC GGGAACG                                        27

(2) INFORMATION FOR SEQ ID NO: 41:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:

ACCACCCCCG CGCCCCAGAC GTCGAGGGGA TCAATTATTG CGTATTGAAT A        51

(2) INFORMATION FOR SEQ ID NO: 42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:

ATCAGAAACT CTTTCGGTAC CGAGCTCGAA TTC                            33

(2) INFORMATION FOR SEQ ID NO: 43:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:

GAATTCGAGC TCGGTACCCG ATAATACGT ACATGTTAAC GCAGAGGT             48

(2) INFORMATION FOR SEQ ID NO: 44:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

GCTGACCGCT AGTCGACTCT AGAGGATCCC CTC                            33

(2) INFORMATION FOR SEQ ID NO: 45:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 45:

CGTTCCCGGG GATCCTCTAG AGTCGACGGC AGAGTCGCAG AC                  42

(2) INFORMATION FOR SEQ ID NO: 46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 46:

```
TGATCCAAAC TCGGATCCTC TAGAGTCGAC                                      30
```

(2) INFORMATION FOR SEQ ID NO: 47:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

```
AAGCTTGGGC TGCAGGTCGA CTCTAGAGGA TCCCCTCGAC GTCTGGGG                  48
```

(2) INFORMATION FOR SEQ ID NO: 48:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

```
CACACCTTTG CGCATCTCCA CAGCTCAACA ATGAATTCCA TGTTACGTCC TGTAGAAACC     60
```

(2) INFORMATION FOR SEQ ID NO: 49:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

```
CAGGGAGGCA ACAATGAAT CAACAACTCT CCCGGGAGAT GGGGGAGGCT AACTGAAACA      60
```

(2) INFORMATION FOR SEQ ID NO: 50:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

TGCTGCGTTC CCGGGGATCC TCTAGAGTCG ACCTGCAGCC CAAGC                45

(2) INFORMATION FOR SEQ ID NO: 51:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

TCTAGAGTCG ACCTGCAGTG AATAATAAAA TGTGTGTTTG TCCGAAAT              48

(2) INFORMATION FOR SEQ ID NO: 52:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

CTCCATAGAA GACACCGGGA CCATGGATCC CGTCGTTTTA CAACG                45

(2) INFORMATION FOR SEQ ID NO: 53:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

TCGGCGGAAA TCCAGCTGAG CGCCGGTCGC TACCATTACC AGTTGGTCTG GTGTCAAAAA     60
GATCTAGAAT AAGCTAGAGG ATCGATCCCC TATGGCGATC ATCAG                    105

(2) INFORMATION FOR SEQ ID NO: 54:

(i) SEQUENCE CHARACTERISTICS:

(A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

CCGTCGAGAT CCTCTAGAGT CGACCTGCAG GTCGAC                                      36

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO: 55:

CCTAGCACCC TTGTATCGCG                                                        20

(2) INFORMATION FOR SEQ ID NO: 56:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO: 56:

CGCCTCGAGT CCCAATGAAT AGGCATTGG                                              29

(2) INFORMATION FOR SEQ ID NO: 57:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO: 57:

CGCCTCGAGG ACCCATGGTT GCGTGCG                                                27

(2) INFORMATION FOR SEQ ID NO: 58:

(i) SEQUENCE CHARACTERISTICS:
        (A) LENGTH: 20 base pairs
        (B) TYPE: nucleic acid
        (C) STRANDEDNESS: single -continued

```
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO: 58:

CTCGTCCGAA CGAGTTACAG                                                    20

(2) INFORMATION FOR SEQ ID NO: 59:

(i) SEQUENCE CHARACTERISTICS:
         (A) LENGTH: 18913 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: N (iv) ANTI-SENSE: N (ix) FEATURE:
         (A) NAME/KEY: CDS
         (B) LOCATION: 697..1533
         (D) OTHER INFORMATION:

(ix) FEATURE:
         (A) NAME/KEY: CDS
         (B) LOCATION: complement (1900..2784)
         (D) OTHER INFORMATION:

(ix) FEATURE:
         (A) NAME/KEY: CDS
         (B) LOCATION: complement (2916..3605)
         (D) OTHER INFORMATION:

(ix) FEATURE:
         (A) NAME/KEY: CDS
         (B) LOCATION: 3694..5124
         (D) OTHER INFORMATION:

(ix) FEATURE:
         (A) NAME/KEY: CDS
         (B) LOCATION: 5210..7081
         (D) OTHER INFORMATION:

(ix) FEATURE:
         (A) NAME/KEY: CDS
         (B) LOCATION: 7245..8123
         (D) OTHER INFORMATION:

(ix) FEATURE:
         (A) NAME/KEY: CDS
         (B) LOCATION: 8333..11290
         (D) OTHER INFORMATION:

(ix) FEATURE:
         (A) NAME/KEY: CDS
         (B) LOCATION: 11098..12402
         (D) OTHER INFORMATION:

(ix) FEATURE:
         (A) NAME/KEY: CDS
         (B) LOCATION: 12510..13598
         (D) OTHER INFORMATION:

(ix) FEATURE:
         (A) NAME/KEY: CDS
         (B) LOCATION: 13792..15291
         (D) OTHER INFORMATION:

(ix) FEATURE:
         (A) NAME/KEY: CDS
```

(B) LOCATION: 15298..16080
(D) OTHER INFORMATION:

(ix) FEATURE:
  (A) NAME/KEY: CDS
  (B) LOCATION: 16129..17013
  (D) OTHER INFORMATION:

(ix) FEATURE:
  (A) NAME/KEY: CDS
  (B) LOCATION: complement (17380..18216)
  (D) OTHER INFORMATION:

(xi) SEQUENCE DESCRIPTION: SEQ ID NO: 59:

```
GGATCCCGAA GAGCTCTCCC AGAAGTTTTT CTTTTCGGAC GTATCGGAGG ACGAAGAACC      60

GGCACGCGGG AGGAGCTGGA GCGACCCGGA GTCGGAGGAA GAGCAGCCTG GGTGCCGGGG     120

AGTGGACTTG GGCGAGGAGG ACACGGGACA CAGCTCCACC GAGTCAGAGC CCACGCAATC     180

TGACTTAGAC TTTATTGACG ACAGCTCTCC GGCGCCGCCG CCATTTGCTA TCCCCCGCGT     240

CCGTGCGTTA TTGCGGTGCG CGGCACCCGC AAAGACCCAC GGAAGGCTTC GGCCGCCAGG     300

GCGGGTAGGC GCACTCTTAA AAGACGGAGG TTGTCATTTT CTTCTTCCTC TGACGAGGAA     360

TCCGAGGAGA GAAGTAAAAA AGAAGAAGCG GCCTCGACCC CTGCACGGCG ACGCAAGGCC     420

GAGGCCTCGA CGAGCAGATA GAGGAGACGC GGGGCAGAAC CTCCCCCTCC CTCCCACCCC     480

CCTACTCTGG ACATTTATTG CCCGCTCGAT CCATTCTCAT CCAGAACTTC TTTCCCGCTC     540

AGCCTTCACG CAGAAGCGGA CGCGCGCCCC TTTGCGACCG CCGGACATCC CGCCGCCCCC     600

CCCCCTTCAC GCCCGGCGCA ATCCGTAGCC GTCCAACTCG GCCCAGCACA ACCGCAGTAG     660

ACCGCCCGGA CCGCTCTCCT CTAGACACAT CCCTAA ATG GAA AAC ATG CTC GAC      714
                                        Met Glu Asn Met Leu Asp
                                          1               5

GGG TGC TAC CCG CTG GCG CTG ATG GAC AGC GAT CAC ATT ACT GCG CAC      762
Gly Cys Tyr Pro Leu Ala Leu Met Asp Ser Asp His Ile Thr Ala His
         10                  15                  20

GCG GTA CCT CGT GGC GAG CGC AGG CGG CAA GGT GCC GCT GTC GCC TCG      810
Ala Val Pro Arg Gly Glu Arg Arg Arg Gln Gly Ala Ala Val Ala Ser
     25                  30                  35

TCG GAG TCG GCC GAC TCG GTA GAC CCG TGC ATT CGG ATC GCC TCG CGG      858
Ser Glu Ser Ala Asp Ser Val Asp Pro Cys Ile Arg Ile Ala Ser Arg
 40                  45                  50

CTC TGG CGC GAG TTA GTC GAG ATA TCG TCC GAA CTC AAG GAC GGT TAC      906
Leu Trp Arg Glu Leu Val Glu Ile Ser Ser Glu Leu Lys Asp Gly Tyr
 55                  60                  65                  70

GGA GAG TTC ACG TCA GCG AGA GAC CGC CGC AAC GCG CTG ATT GCT GCC      954
Gly Glu Phe Thr Ser Ala Arg Asp Arg Arg Asn Ala Leu Ile Ala Ala
             75                  80                  85

AAC GAA CGG CTA CGT TCG GCT TTT CTG GGG GCC AGC CGG GCG ACG CGC     1002
Asn Glu Arg Leu Arg Ser Ala Phe Leu Gly Ala Ser Arg Ala Thr Arg
         90                  95                 100

GGC CTA GGT TTG AGG CCG CGG TGG GCG TCG ACG GAG AGC GTC GCC AAC     1050
Gly Leu Gly Leu Arg Pro Arg Trp Ala Ser Thr Glu Ser Val Ala Asn
     105                 110                 115

TCC CCC ACT GAC CCG AAT AAC GGC AAC GGG TTG GGA GAA TTA GAG GAG     1098
Ser Pro Thr Asp Pro Asn Asn Gly Asn Gly Leu Gly Glu Leu Glu Glu
120                 125                 130

GCA ATG GAA GGG ATC GAG GGC GAT TTC TGG CTC GAC TCT CTG GAC GGT     1146
Ala Met Glu Gly Ile Glu Gly Asp Phe Trp Leu Asp Ser Leu Asp Gly
135                 140                 145                 150

GAC CGC TTC GAG GAC GAG AGC CGT ACC ATG CAG AGC GAG AAT ATG CGT     1194
Asp Arg Phe Glu Asp Glu Ser Arg Thr Met Gln Ser Glu Asn Met Arg
```

```
                    155                 160                  165
TTC GTG ATC GAG AAA GAA CTG TTA TCC TGG CTG TCC CGA CAC CTG CCG      1242
Phe Val Ile Glu Lys Glu Leu Leu Ser Trp Leu Ser Arg His Leu Pro
                170                 175                 180

GCC GAC CTC GCG TCC GCC GAG CGA GAG ACC TCC CGG TCT CTC CTG GCG      1290
Ala Asp Leu Ala Ser Ala Glu Arg Glu Thr Ser Arg Ser Leu Leu Ala
                185                 190                 195

GCC GGG CAC TGG TGC TGC TTG TGG CAC CCT CGG CCG TGC CGC GAA GCG      1338
Ala Gly His Trp Cys Cys Leu Trp His Pro Arg Pro Cys Arg Glu Ala
                200                 205                 210

TGT TTG TAC GAC TCG ATT TAC GTG CAG AGT CTT TTC TGC GTC GGG ACG      1386
Cys Leu Tyr Asp Ser Ile Tyr Val Gln Ser Leu Phe Cys Val Gly Thr
215                 220                 225                 230

GGG AGA GTC CCG CAA TCG GAG ATG CGC CGT CGC GAA TAC CTG GCC GCC      1434
Gly Arg Val Pro Gln Ser Glu Met Arg Arg Arg Glu Tyr Leu Ala Ala
                235                 240                 245

TTG CGC GCC GGC GCG GCT GCC GCC AAC TCT CCC GAA GTG AGC GCC TCG      1482
Leu Arg Ala Gly Ala Ala Ala Ala Asn Ser Pro Glu Val Ser Ala Ser
                250                 255                 260

ATC TTT GCG AGG GAC GCT GGA ATC GCG CTG GCG CTG GCG CGG CGC CGT      1530
Ile Phe Ala Arg Asp Ala Gly Ile Ala Leu Ala Leu Ala Arg Arg Arg
                265                 270                 275

TGA CGGGAGAATG ACGCCCTCTA GCGGCTTCCT TACCTCCGCG TCCCTGACAA           1583

CCTCGCGGGT TTTTACACTG TCCTCCGTCC ACTCTCCCCC CTCACCCACT CCGCGGCAGC    1643

GAAACACAAC CCCCCCCCCC CCCCAGAAAC GAGCGACACG CGAGCGCTGC GAAATAAATA    1703

AAGTAATATT ATTGTGTGTT TTTCACGTTG TTGCAATCGA GAGGCCGTTT GTCTGTCTGT    1763

GTCTGTGCGG AGCTAGGCTT TCCCGGGCGG CCCCGTTCCA CCGTTCGGTT AGGCCGGTGG    1823

CGACGGGACA TAGAGAAAGA TAGAGCGCGC GCCCTGGCGG CGAGAGGGTG TTGCGGGGGT    1883

AAATGGGACC CTGAGCTCAC CATTTTGGCG GGGGATTGCA CGGGTAACAA AAAGCTCTCT    1943

CGCACATAAT GATTTCCCTT AAACAGTGGC TGTAAAAGCT TCTTCGACT GGGACGCGCA     2003

CGTCCGGAGA CATGATCTTA TCGGTAGCTA CACAGTTCAT GAGGTGGGCC ACGAACGCGC    2063

GGATCGAGTT TTGGGAACCT TCGGGGAGGT CTTCCGGGAG GGTGAAGTTT GACAGAGGCA    2123

GCGCTATCAC CAGGAGGCTC CGCACCATCT CCATGCCTAT CCTTATCGCC GCGAGTCCGG    2183

CGGCCGGCGC GCTGCTCTGG TTATTCCAGT GCGCGGACCG CGAGTGCGCC CCTCCCCGGG    2243

CTCTGATATA GAGCACCGGC AGCTCGACGG CGGCGGAGAA AAAAGAAAGA ATGTCCGGCC    2303

CAATGACTGG AACTTTGGGC ACGTCTCTTA TTTCCCACGC GGCGGCCCGG GGAATCTGCT    2363

TGCCCCAGAC CTTGCTTTCC AACTCCCCGT TCGGCCCCCC AACTAACTCC GACAGCGCGG    2423

TCCACAGTCC TACCGCCGCT GCGACGGCGC GCTTAGCCGC GGGCGCTATT CGCGGGTCGT    2483

GCGCCGTGAT ATCTTCGGCG ACCTGCAGAC TGCCCAGCCT TTCCTTCCCT TCAAAATACG    2543

CGCGGGCGGC CTGTACGATC ACCGCGGCCA GATCGGGCCA AAAGAAAATA TCGCAACTCT    2603

GCGACGCCCG CCAGAATCTC CCTCCGGGCA GGTCCGTGCC CCTAAAGGCC GCCGAGAAAG    2663

CTAAGTCCAA ATGTGACGTC GGAGGTCTCG ACATGGTCGC CAACCCTCCA ATGCTACCC     2723

GCCGGCCCAC GCAACGCGGG CTTTTATAAA GATGGCGCGC GAGACAATAA CACTTACTCA    2783

TCCGCGTACG CGTTTATTAT TGTCAATATT TGTGTGGTTA TTATTACTGC TACCGCCCTT    2843

GTTTCTGCAA GGCCCTCGCC GCGGCCCAGG CCACTATTCC GGCAGCGGCC GCCGACGCGG    2903

CGAGCGTCGC CGCTAACGTC GGCGCCGCGG GGAGCGGGGT TCTTCGACT TAAATAGACT     2963

CCCGAGAAAA AATTTTGGCT GCCGTTCGCC ATCATCCGAG TCGGAAACAC AGTATGCGGC    3023
```

```
CGAGTTAGGT TTTACTTTTA AAAACTTTAC CGTGCTGTAC GGCCAGGGCG TTCTCAGGCT    3083

CGAAGGGGCA AGAGTTGTCC AGACTGATGG GTGACTCAGA GACAGCGTTG TCTTGTCTCC    3143

GTTTACCAAA AATATTTCCA CTCCTCTCTC AAAATTTTTA CCTCCGGTTT CGGTAATTAG    3203

GAAAGTTTTT GGCGCAGGGA GGTTTAAAGC TGCCATGCAT ATGTCAGCGG TACCCAGCAC    3263

CCACAAATGG AACTCTTTTG CGGCATACGC GCCAGATGAC AAATGGTAAA ACCCTGCGTC    3323

CAAGCCGCTC CACTCGGGAC TTACTCCAGG CGGGTCGCCC CCCTCACCGA ACCGAATCAC    3383

GGGTCTGCAC ATCCTGGGAA GGGAAAACAG CTCCCCGGAA ACTTCGTACA GAGATGCCGG    3443

GCGCACGATT ACCGATAATG TACTCGGACG ATCGTAACTC GCCATAGTTT TCACTGCGTG    3503

AACCAATTCT TTCCATCCAG AATCCGAGAG CTCAAATCTA GAATTAGGTA GTTTGTAGTG    3563

CGAATCGACC GCAGAAACTA TAGTCACTTT TACAGGCGCC ATCGCCGCTCAG             3615

ACTCCACCCC GCTATGATGT CAGAAATATA ACGCTCTTAT TCTAGCAGAG TCAGGCCAAT    3675

ATATACAGCT TAGAGAAG ATG CGG TTT CGG CGC ATC TGT TCA CGC TCT AGG      3726
                    Met Arg Phe Arg Arg Ile Cys Ser Arg Ser Arg
                     1               5                      10

GCA GAA AAA CGA AGA AGA ACA ACC GAG AAT CCG CTT ACC TCA AAA CGC      3774
Ala Glu Lys Arg Arg Arg Thr Thr Glu Asn Pro Leu Thr Ser Lys Arg
              15                  20                  25

GTT TGC GTA TTG GAT AGT TTC TCA CGG ACA ATG TCA TTG CGC CCC TAT      3822
Val Cys Val Leu Asp Ser Phe Ser Arg Thr Met Ser Leu Arg Pro Tyr
             30                  35                  40

GCA GAA ATT TTG CCG ACC GCG GAA GGC GTC GAG CGC CTC GCC GAA CTT      3870
Ala Glu Ile Leu Pro Thr Ala Glu Gly Val Glu Arg Leu Ala Glu Leu
         45                  50                  55

GTT AGT GTG ACA ATG ACA GAA CGC GCG GAA CCT GTG ACA GAG AAT ACA      3918
Val Ser Val Thr Met Thr Glu Arg Ala Glu Pro Val Thr Glu Asn Thr
     60                  65                  70                  75

GCT GTA AAC AGT ATC CCC CCG GCT AAC GAG AAC GGG CAG AAC TTC GCA      3966
Ala Val Asn Ser Ile Pro Pro Ala Asn Glu Asn Gly Gln Asn Phe Ala
                 80                  85                  90

TAT GCA GGC GAT GGG CCC TCG ACT ACT GAA AAA GTT GAC GGC TCG CAT      4014
Tyr Ala Gly Asp Gly Pro Ser Thr Thr Glu Lys Val Asp Gly Ser His
             95                 100                 105

ACA GAC TTC GAT GAA GCA TCG AGC GAC TAC GCC GGC CCT GTC CCG CTC      4062
Thr Asp Phe Asp Glu Ala Ser Ser Asp Tyr Ala Gly Pro Val Pro Leu
        110                 115                 120

GCG CAA ACT AGA TTG AAG CAT TCG GAT GAA TTT CTT CAG CAC TTC CGA      4110
Ala Gln Thr Arg Leu Lys His Ser Asp Glu Phe Leu Gln His Phe Arg
    125                 130                 135

GTT TTA GAC GAT TTG GTG GAG GGG GCT TAC GGG TTT ATC TGC GAC GTC      4158
Val Leu Asp Asp Leu Val Glu Gly Ala Tyr Gly Phe Ile Cys Asp Val
140                 145                 150                 155

CGT CGC TAC ACC GAG GAA GAG CAA CGT CGA AGA GGG GTT AAC AGT ACT      4206
Arg Arg Tyr Thr Glu Glu Glu Gln Arg Arg Arg Gly Val Asn Ser Thr
                160                 165                 170

AAC CAG GGG AAA TCA AAA TGT AAG CGC CTG ATA GCT AAA TAT GTG AAA      4254
Asn Gln Gly Lys Ser Lys Cys Lys Arg Leu Ile Ala Lys Tyr Val Lys
            175                 180                 185

AAT GGA ACA AGG GCG GCC TCT CAG CTG GAA AAT GAA ATT TTG GTT CTC      4302
Asn Gly Thr Arg Ala Ala Ser Gln Leu Glu Asn Glu Ile Leu Val Leu
        190                 195                 200

GGG CGC CTA AAT CAC GAG AAT GTT CTC AAG ATC CAG GAA ATC CTT CGG      4350
Gly Arg Leu Asn His Glu Asn Val Leu Lys Ile Gln Glu Ile Leu Arg
    205                 210                 215
```

-continued

```
TAC CCG GAT AAT ACG TAC ATG TTA ACG CAG AGG TAT CAG TTC GAC TTG      4398
Tyr Pro Asp Asn Thr Tyr Met Leu Thr Gln Arg Tyr Gln Phe Asp Leu
220                 225                 230                 235

TAC AGC TAC ATG TAC GAT GAA GCG TTC GAC TGG AAA GAC AGT CCA ATG      4446
Tyr Ser Tyr Met Tyr Asp Glu Ala Phe Asp Trp Lys Asp Ser Pro Met
                240                 245                 250

CTT AAA CAG ACT AGA CGC ATC ATG AAG CAG CTC ATG TCA GCG GTC TCG      4494
Leu Lys Gln Thr Arg Arg Ile Met Lys Gln Leu Met Ser Ala Val Ser
                255                 260                 265

TAT ATC CAT TCA AAG AAA CTG ATT CAC AGG GAC ATC AAA CTC GAA AAT      4542
Tyr Ile His Ser Lys Lys Leu Ile His Arg Asp Ile Lys Leu Glu Asn
                270                 275                 280

ATT TTC TTA AAC TGC GAC GGC AAG ACA GTG CTG GGC GAC TTT GGA ACT      4590
Ile Phe Leu Asn Cys Asp Gly Lys Thr Val Leu Gly Asp Phe Gly Thr
285                 290                 295

GTC ACG CCT TTT GAA AAT GAG CGG GAG CCC TTC GAA TAT GGA TGG GTG      4638
Val Thr Pro Phe Glu Asn Glu Arg Glu Pro Phe Glu Tyr Gly Trp Val
300                 305                 310                 315

GGG ACC GTG GCT ACT AAC TCT CCC GAG ATA CTC GCC AGG GAT TCG TAC      4686
Gly Thr Val Ala Thr Asn Ser Pro Glu Ile Leu Ala Arg Asp Ser Tyr
                320                 325                 330

TGT GAA ATT ACA GAC ATT TGG AGC TGC GGA GTA GTA TTG CTG GAA ATG      4734
Cys Glu Ile Thr Asp Ile Trp Ser Cys Gly Val Val Leu Leu Glu Met
                335                 340                 345

GTA AGC CAT GAA TTT TGC CCG ATC GGC GAT GGC GGG GGA AAT CCG CAC      4782
Val Ser His Glu Phe Cys Pro Ile Gly Asp Gly Gly Gly Asn Pro His
                350                 355                 360

CAG CAA TTG CTG AAA GTT ATC GAC TCT CTC TCA GTT TGT GAT GAA GAG      4830
Gln Gln Leu Leu Lys Val Ile Asp Ser Leu Ser Val Cys Asp Glu Glu
365                 370                 375

TTC CCA GAC CCC CCG TGT AAT CTG TAC AAT TAT TTG CAT TAT GCG AGC      4878
Phe Pro Asp Pro Pro Cys Asn Leu Tyr Asn Tyr Leu His Tyr Ala Ser
380                 385                 390                 395

ATC GAT CGC GCC GGA CAT ACG GTC CCG TCG CTC ATA CGG AAC CTC CAC      4926
Ile Asp Arg Ala Gly His Thr Val Pro Ser Leu Ile Arg Asn Leu His
                400                 405                 410

CTT CCG GCG GAT GTG GAA TAC CCT CTA GTT AAA ATG CTT ACT TTT GAC      4974
Leu Pro Ala Asp Val Glu Tyr Pro Leu Val Lys Met Leu Thr Phe Asp
                415                 420                 425

TGG CGT TTG AGA CCC AGC GCG GCC GAA GTA TTG GCA ATG CCA CTG TTT      5022
Trp Arg Leu Arg Pro Ser Ala Ala Glu Val Leu Ala Met Pro Leu Phe
                430                 435                 440

TCG GCT GAA GAG GAA CGG ACC ATA ACA ATT ATT CAT GGA AAA CAT AAA      5070
Ser Ala Glu Glu Glu Arg Thr Ile Thr Ile Ile His Gly Lys His Lys
445                 450                 455

CCC ATC CGA CCC GAA ATC CGT GCG CGG GTG CCA CGG TCC ATG AGT GAA      5118
Pro Ile Arg Pro Glu Ile Arg Ala Arg Val Pro Arg Ser Met Ser Glu
460                 465                 470                 475

GGT TAA TAATAAAGGA CGGAGATAGA GAACTGAAGC GTCAGATTTT TTTAAAAAAA      5174
Gly

TAAATGATCG AGAACTTATG ATTTGTCTTT CTTGA ATG ACC TTG CCC CAT CGA      5227
                                      Met Thr Leu Pro His Arg
                                      1                   5

TTA ACG AAA AGA CCT TTC GCG CGT CGA TTC TGC TCG GTC TTT GTG ATA      5275
Leu Thr Lys Arg Pro Phe Ala Arg Arg Phe Cys Ser Val Phe Val Ile
                10                  15                  20

CAT TAT AGT GAG ACT AAA CTC GAC CGA TAT AAC AAG ACA ATG TTA CTC      5323
His Tyr Ser Glu Thr Lys Leu Asp Arg Tyr Asn Lys Thr Met Leu Leu
                25                  30                  35
```

-continued

| | |
|---|---|
| TAT AGA CCG GAC TCA ACC ATG CGG CAT AGC GGA GGC GAC GCA AAT CAC<br>Tyr Arg Pro Asp Ser Thr Met Arg His Ser Gly Gly Asp Ala Asn His<br>40                           45                         50 | 5371 |
| AGA GGG ATA AGG CCG AGG CGG AAA TCT ATT GGA GCG TTT AGC GCG CGC<br>Arg Gly Ile Arg Pro Arg Arg Lys Ser Ile Gly Ala Phe Ser Ala Arg<br>55                         60                      65                  70 | 5419 |
| GAA AAG ACT GGA AAA CGA AAT GCG CTG ACG GAA AGC AGC TCC TCC TCC<br>Glu Lys Thr Gly Lys Arg Asn Ala Leu Thr Glu Ser Ser Ser Ser Ser<br>               75                      80                   85 | 5467 |
| GAC ATG CTA GAT CCG TTT TCC ACG GAT AAG GAA TTT GGC GGT AAG TGG<br>Asp Met Leu Asp Pro Phe Ser Thr Asp Lys Glu Phe Gly Gly Lys Trp<br>              90                     95                     100 | 5515 |
| ACG GTA GAC GGA CCT GCC GAC ATT ACT GCC GAG GTC CTT TCT CAG GCA<br>Thr Val Asp Gly Pro Ala Asp Ile Thr Ala Glu Val Leu Ser Gln Ala<br>105                      110                   115 | 5563 |
| TGG GAC GTT CTC CAA TTA GTG AAG CAT GAA GAT GCG GAG GAG GAG AGA<br>Trp Asp Val Leu Gln Leu Val Lys His Glu Asp Ala Glu Glu Glu Arg<br>120                      125                   130 | 5611 |
| GTG ACT TAT GAG TCC AAA CCG ACC CCG ATA CAG CCG TTC AAT GCC TGG<br>Val Thr Tyr Glu Ser Lys Pro Thr Pro Ile Gln Pro Phe Asn Ala Trp<br>135                      140                   145                  150 | 5659 |
| CCG GAC GGG CCG AGT TGG AAC GCG CAG GAT TTT ACT CGA GCG CCA ATA<br>Pro Asp Gly Pro Ser Trp Asn Ala Gln Asp Phe Thr Arg Ala Pro Ile<br>                      155                   160                  165 | 5707 |
| GTT TAT CCC TCT GCG GAG GTA TTG GAC GCA GAG GCG TTG AAA GTA GGG<br>Val Tyr Pro Ser Ala Glu Val Leu Asp Ala Glu Ala Leu Lys Val Gly<br>                    170                   175                  180 | 5755 |
| GCA TTC GTT AGC CGA GTT TTA CAA TGT GTA CCG TTC ACG CGA TCA AAG<br>Ala Phe Val Ser Arg Val Leu Gln Cys Val Pro Phe Thr Arg Ser Lys<br>                    185                   190                  195 | 5803 |
| AAA AGC GTT ACG GTG CGG GAT GCG CAG TCG TTT TTG GGG GAC TCG TTC<br>Lys Ser Val Thr Val Arg Asp Ala Gln Ser Phe Leu Gly Asp Ser Phe<br>200                      205                   210 | 5851 |
| TGG AGA ATA ATG CAG AAC GTT TAC ACG GTT GTC TTA CGA CAG CAC ATA<br>Trp Arg Ile Met Gln Asn Val Tyr Thr Val Val Leu Arg Gln His Ile<br>215                      220                   225                  230 | 5899 |
| ACT CGA CTC AGG CAC CCT TCC AGC AAA AGC ATT GTT AAC TGC AAC GAC<br>Thr Arg Leu Arg His Pro Ser Ser Lys Ser Ile Val Asn Cys Asn Asp<br>                    235                   240                  245 | 5947 |
| CCT CTA TGG TAC GCC TAC GCG AAT CAA TTT CAC TGG AGA GGA ATG CGC<br>Pro Leu Trp Tyr Ala Tyr Ala Asn Gln Phe His Trp Arg Gly Met Arg<br>                    250                   255                  260 | 5995 |
| GTG CCG TCG CTT AAA TTA GCC TCT CCC CCG GAG GAG AAT ATT CAA CAC<br>Val Pro Ser Leu Lys Leu Ala Ser Pro Pro Glu Glu Asn Ile Gln His<br>265                      270                   275 | 6043 |
| GGC CCA ATG GCC GCC GTT TTT AGA AAC GCG GGG GCT GGT CTG TTC CTG<br>Gly Pro Met Ala Ala Val Phe Arg Asn Ala Gly Ala Gly Leu Phe Leu<br>280                      285                   290 | 6091 |
| TGG CCT GCC ATG CGC GCA GCC TTT GAA GAG CGC GAC AAG CGA CTG TTA<br>Trp Pro Ala Met Arg Ala Ala Phe Glu Glu Arg Asp Lys Arg Leu Leu<br>295                      300                   305                  310 | 6139 |
| AGA GCA TGC CTG TCT TCA CTC GAT ATC ATG GAC GCA GCC GTC CTC GCG<br>Arg Ala Cys Leu Ser Ser Leu Asp Ile Met Asp Ala Ala Val Leu Ala<br>                    315                   320                  325 | 6187 |
| TCG TTT CCA TTT TAC TGG CGC GGC GTC CAA GAC ACC TCG CGC TTC GAG<br>Ser Phe Pro Phe Tyr Trp Arg Gly Val Gln Asp Thr Ser Arg Phe Glu<br>                    330                   335                  340 | 6235 |
| CCT GCG CTG GGC TGT TTG TCA GAG TAC TTT GCA CTA GTG GTG TTA CTG<br>Pro Ala Leu Gly Cys Leu Ser Glu Tyr Phe Ala Leu Val Val Leu Leu<br>345                      350                   355 | 6283 |

-continued

```
GCC GAG ACG GTC TTA GCG ACC ATG TTC GAC CAC GCA CTG GTA TTC ATG    6331
Ala Glu Thr Val Leu Ala Thr Met Phe Asp His Ala Leu Val Phe Met
    360             365             370

AGG GCG CTG GCA GAC GGC AAT TTC GAT GAC TAT GAC GAA ACT AGA TAT    6379
Arg Ala Leu Ala Asp Gly Asn Phe Asp Asp Tyr Asp Glu Thr Arg Tyr
375             380             385             390

ATA GAC CCC GTT AAA AAC GAG TAC CTG AAC GGA GCC GAG GGT ACT CTG    6427
Ile Asp Pro Val Lys Asn Glu Tyr Leu Asn Gly Ala Glu Gly Thr Leu
            395             400             405

TTA CGG GGC ATA GTG GCC TCC AAC ACC GCT CTG GCG GTG GTT TGC GCA    6475
Leu Arg Gly Ile Val Ala Ser Asn Thr Ala Leu Ala Val Val Cys Ala
        410             415             420

AAC ACC TAT TCG ACG ATA AGA AAA CTC CCG TCC GTG GCA ACT AGC GCG    6523
Asn Thr Tyr Ser Thr Ile Arg Lys Leu Pro Ser Val Ala Thr Ser Ala
                425             430             435

TGC AAT GTT GCC TAC AGG ACC GAA ACG CTG AAA GCG AGG CGC CCT GGC    6571
Cys Asn Val Ala Tyr Arg Thr Glu Thr Leu Lys Ala Arg Arg Pro Gly
    440             445             450

ATG AGC GAC ATA TAC CGG ATA TTA CAA AAA GAG TTT TTC TTT TAC ATT    6619
Met Ser Asp Ile Tyr Arg Ile Leu Gln Lys Glu Phe Phe Phe Tyr Ile
455             460             465             470

GCG TGG CTC CAG AGG GTT GCA ACA CAC GCA AAT TTC TGT TTA AAC ATT    6667
Ala Trp Leu Gln Arg Val Ala Thr His Ala Asn Phe Cys Leu Asn Ile
            475             480             485

CTG AAG AGA AGC GTG GAT ACG GGG GCC CCG CCA TTT TTG TTC AGG GCC    6715
Leu Lys Arg Ser Val Asp Thr Gly Ala Pro Pro Phe Leu Phe Arg Ala
        490             495             500

AGC TCG GAG AAG CGG CTG CAG CAG TTA AAT AAA ATG CTC TGC CCC CTT    6763
Ser Ser Glu Lys Arg Leu Gln Gln Leu Asn Lys Met Leu Cys Pro Leu
                505             510             515

CTC GTG CCG ATT CAA TAT GAA GAC TTT TCG AAG GCC ATG GGG TCT GAG    6811
Leu Val Pro Ile Gln Tyr Glu Asp Phe Ser Lys Ala Met Gly Ser Glu
    520             525             530

CTC AAG AGG GAA AAG TTA GAG ACA TTC GTT AAA GCT ATT TCC AGC GAC    6859
Leu Lys Arg Glu Lys Leu Glu Thr Phe Val Lys Ala Ile Ser Ser Asp
535             540             545             550

AGG GAC CCG AGG GGG TCC TTA AGA TTT CTC ATT TCG GAC CAT GCA AGG    6907
Arg Asp Pro Arg Gly Ser Leu Arg Phe Leu Ile Ser Asp His Ala Arg
            555             560             565

GAA ATT ATT GCA GAC GGA GTA CGG TTT AAG CCG GTG ATA GAC GAG CCG    6955
Glu Ile Ile Ala Asp Gly Val Arg Phe Lys Pro Val Ile Asp Glu Pro
        570             575             580

GTT CGG GCT TCA GTT GCG CTG AGT ACC GCT GCC GCT GGG AAA GTG AAA    7003
Val Arg Ala Ser Val Ala Leu Ser Thr Ala Ala Ala Gly Lys Val Lys
                585             590             595

GCG CGA CGC TTA ACC TCA GTT CGC GCG CCC GTA CCG GGC GCA GGC GCC    7051
Ala Arg Arg Leu Thr Ser Val Arg Ala Pro Val Pro Gly Ala Gly Ala
    600             605             610

GTT TCC GCG CGC CGG AAA TCG GAA ATA TGA TAAAAATGCT TGGCATTTGC      7101
Val Ser Ala Arg Arg Lys Ser Glu Ile  .
615             620

GGGCGAAGAG GCGTGATCTG AAGGGCTCCA CAATGACGTA ACTGAGCTAC GCATCCCTAT  7161

AAAGTGTACC CGCTGACCGC TAGCCCATAC AGTGTTACAG GAGGGGAGAG AGACAACTTC  7221

AGCTCGAAGT CTGAAGAGAC ATC ATG AGC GGC TTC AGT AAC ATA GGA TCG     7271
                         Met Ser Gly Phe Ser Asn Ile Gly Ser
                          1               5

ATT GCC ACC GTT TCC CTA GTA TGC TCG CTT TTG TGC GCA TCT GTA TTA   7319
Ile Ala Thr Val Ser Leu Val Cys Ser Leu Leu Cys Ala Ser Val Leu
```

-continued

```
          10                  15                  20                  25
GGG GCG CCG GTA CTG GAC GGG CTC GAG TCG AGC CCT TTC CCG TTC GGG         7367
Gly Ala Pro Val Leu Asp Gly Leu Glu Ser Ser Pro Phe Pro Phe Gly
                    30                  35                  40

GGC AAA ATT ATA GCC CAG GCG TGC AAC CGC ACC ACG ATT GAG GTG ACG         7415
Gly Lys Ile Ile Ala Gln Ala Cys Asn Arg Thr Thr Ile Glu Val Thr
                45                  50                  55

GTC CCG TGG AGC GAC TAC TCT GGT CGC ACC GAA GGA GTG TCA GTC GAG         7463
Val Pro Trp Ser Asp Tyr Ser Gly Arg Thr Glu Gly Val Ser Val Glu
            60                  65                  70

GTG AAA TGG TTC TAC GGG AAT AGT AAT CCC GAA AGC TTC GTG TTC GGG         7511
Val Lys Trp Phe Tyr Gly Asn Ser Asn Pro Glu Ser Phe Val Phe Gly
        75                  80                  85

GTG GAT AGC GAA ACG GGC AGT GGA CAC GAG GAC CTG TCT ACG TGC TGG         7559
Val Asp Ser Glu Thr Gly Ser Gly His Glu Asp Leu Ser Thr Cys Trp
 90                  95                 100                 105

GCT CTA ATC CAT AAT CTG AAC GCG TCT GTG TGC AGG GCG TCT GAC GCC         7607
Ala Leu Ile His Asn Leu Asn Ala Ser Val Cys Arg Ala Ser Asp Ala
                   110                 115                 120

GGG ATA CCT GAT TTC GAC AAG CAG TGC GAA AAA GTG CAG AGA AGA CTG         7655
Gly Ile Pro Asp Phe Asp Lys Gln Cys Glu Lys Val Gln Arg Arg Leu
               125                 130                 135

CGC TCC GGG GTG GAA CTT GGT AGT TAC GTG TCT GGC AAT GGA TCC CTG         7703
Arg Ser Gly Val Glu Leu Gly Ser Tyr Val Ser Gly Asn Gly Ser Leu
           140                 145                 150

GTG CTG TAC CCA GGG ATG TAC GAT GCC GGC ATC TAC GCC TAC CAG CTC         7751
Val Leu Tyr Pro Gly Met Tyr Asp Ala Gly Ile Tyr Ala Tyr Gln Leu
       155                 160                 165

TCA GTG GGT GGG AAG GGA TAT ACC GGG TCT GTT TAT CTA GAC GTC GGA         7799
Ser Val Gly Gly Lys Gly Tyr Thr Gly Ser Val Tyr Leu Asp Val Gly
170                 175                 180                 185

CCA AAC CCC GGA TGC CAC GAC CAG TAT GGG TAC ACC TAT TAC AGC CTG         7847
Pro Asn Pro Gly Cys His Asp Gln Tyr Gly Tyr Thr Tyr Tyr Ser Leu
                   190                 195                 200

GCC GAC GAG GCG TCA GAC TTA TCA TCT TAT GAC GTA GCC TCG CCC GAA         7895
Ala Asp Glu Ala Ser Asp Leu Ser Ser Tyr Asp Val Ala Ser Pro Glu
               205                 210                 215

CTC GAC GGT CCT ATG GAG GAA GAT TAT TCC AAT TGT CTA GAC ATG CCC         7943
Leu Asp Gly Pro Met Glu Glu Asp Tyr Ser Asn Cys Leu Asp Met Pro
           220                 225                 230

CCG CTA CGC CCA TGG ACA ACC GTT TGT TCG CAT GAC GTC GAG GAG CAG         7991
Pro Leu Arg Pro Trp Thr Thr Val Cys Ser His Asp Val Glu Glu Gln
       235                 240                 245

GAA AAC GCC ACG GAC GAG CTT TAC CTA TGG GAC GAG GAA TGC GCC GGT         8039
Glu Asn Ala Thr Asp Glu Leu Tyr Leu Trp Asp Glu Glu Cys Ala Gly
250                 255                 260                 265

CCG CTG GAC GAG TAC GTC GAC GAA AGG TCA GAG ACG ATG CCC AGG ATG         8087
Pro Leu Asp Glu Tyr Val Asp Glu Arg Ser Glu Thr Met Pro Arg Met
                   270                 275                 280

GTT GTC TTT TCA CCG CCC TCT ACG CTC CAG CAG TAG CCACCCGAGA             8133
Val Val Phe Ser Pro Pro Ser Thr Leu Gln Gln  .
               285                 290

GTGTTTTTTG TGAGCGCCCA CGCAACATAC CTAACTGCTT CATTTCTGAT CAATTATTGC       8193

GTATTGAATA AATAAACAGT ACAAAAGCAT CAGGTGTGGT TTGCGTGTCT GTGCTAAACC       8253

ATGGCGTGTG CGGGTGAAAC CGTAAATTAC GTGATAATAA ATAGCATAGG AGTTGGCGTG       8313

CAGCGTATTT CGCCGAGAGA TGGGGACAAT GTTAGTGTTG CGCCTTTTCC TACTTGCAGT       8373

AGCGGACGCG GCGTTGCCGA CCGGCAGATT CTGCCGAGTT TGGAAGGTGC CTCCGGGAGG       8433
```

```
AACCATCCAA GAGAACCTGG CGGTGCTCGC GGAATCGCCG GTCACGGGAC ACGCGACATA    8493

TCCGCCGCCT GAAGGCGCCG TCAGCTTTCA GATTTTTGCG GACACCCCTA CTTTGCGCAT    8553

TCGCTACGGC GCTACGGAGG ACGAACTTGC ACTGGAGCGC GGGACGTCCG CCTCAGACGC    8613

GGACAACGTG ACATTTTCGC TGTCATATCG CCCGCGCCCA GAAATTCACG GAGCATACTT    8673

CACCATAGGG GTATTCGCTA CTGGCCAGAG CACGGAAAGC AGCTATTCGG TCATCAGTCG    8733

GGTCTTAGTT AACGCCTCTC TGGAACGGTC CGTGCGCCTG GAAACGCCGT GCGATGAAAA    8793

TTTTTTGCAG AACGAGCCTA CATGGGGCTC GAAGCGTTGG TTAGGCCCCC CGTCGCCTTA    8853

TGTGCGAGAT AACGATGTCG CCGTGTTGAC AAAAGCGCAG TACATTGGGG AGTGCTACTC    8913

CAACTCGGCG GCCCAGACGG GGCTCACGTC TCTCAACATG ACCTTTTTCT ATTCGCCTAA    8973

AAGAATAGTA AACGTCACGT GGACAACCGG CGGCCCCTCC CCCTCGCGCA TAACGGTATA    9033

CTCGTCGCGG GAGAACGGGC AGCCCGTGTT GAGGAACGTT TCTGACGGGT CTTGGTTAA    9093

GTACACTCCC GACATTGACG GCCGGGCCAT GATAAACGTT ATTGCCAATT ATTCGCCGGC    9153

GGACTCCGGC AGCGTCCTCG CGTTTACGGC CTTTAGGGAA GGAAAACTCC CATCCGCGAT    9213

TCAACTGCAC CGGATAGATA TGTCCGGGAC TGAGCCGCCG GGGACTGAAA CGACCTTCGA    9273

CTGTCAAAAA ATGATAGAAA CCCCGTACCG AGCGCTCGGG AGCAATGTTC CCAGGGACGA    9333

CTCTATCCGT CCGGGGGCCA CTCTGCCTCC GTTCGATACC GCAGCACCTG ATTTCGATAC    9393

AGGTACTTCC CCGACCCCCA CTACCGTGCC AGAGCCAGCC ATTACTACAC TCATACCGCG    9453

CAGCACTAGC GATATGGGAT TCTTCTCCAC GGCACGTGCT ACCGGATCAG AAACTCTTTC    9513

GGTACCCGTC CAGGAAACGG ATAGAACTCT TTCGACAACT CCTCTTACCC TTCCACTGAC    9573

TCCCGGTGAG TCAGAAAATA CACTGTTTCC TACGACCGCG CCGGGGATTT CTACCGAGAC    9633

CCCGAGCGCG GCACATGAAA CTACACAGAC CCAGAGTGCA GAAACGGTGG TCTTTACTCA    9693

GAGTCCGAGT ACCGAGTCGG AAACCGCGCG GTCCCGAGT CAGGAACCGT GGTATTTTAC     9753

TCAGACTCCG AGTACTGAAC AGGCGGCTCT TACTCAGACG CAGATCGCAG AAACGGAGGC    9813

GTTGTTTACT CAGACTCCGA GTGCTGAACA GATGACTTTT ACTCAGACTC CGGGTGCAGA    9873

AACCGAGGCA CCTGCCCAGA CCCCGAGCAC GATACCCGAG ATATTTACTC AGTCTCGTAG    9933

CACGCCCCCC GAAACCGCTC GCGCTCCGAG CGCGGCGCCG GAGGTTTTTA CACAGAGTTC    9993

GAGTACGGTA ACGGAGGTGT TTACTCAGAC CCCGAGCACG GTACCGAAAA CTACTCTGAG   10053

TTCGAGTACT GAACCGGCGA TTTTTACTCG GACTCAGAGC GCGGGAACTG AGGCCTTTAC   10113

TCAGACTTCG AGTGCCGAGC CGGACACTAT GCGAACTCAG AGTACTGAAA CACACTTTTT   10173

CACTCAGGCC CCGAGTACGG TACCGAAAGC TACTCAGACT CCGAGTACAG AGCCGGAGGT   10233

GTTGACTCAG AGTCCGAGTA CCGAACCTGT GCCTTTCACC CGGACTCTGG GCGCAGAGCC   10293

GGAAATTACT CAGACCCCGA GCGCGGCACC GGAGGTTTAT ACTCGGAGTT CGAGTACGAT   10353

GCCAGAAACT GCACAGAGCA CACCCCTGGC CTCGCAAAAC CCTACCAGTT CGGGAACCGG   10413

GACGCATAAT ACTGAACCGA GGACTTATCC AGTGCAAACG ACACCACATA CCCAGAAACT   10473

CTACACAGAA AATAAGACTT TATCGTTTCC TACTGTTGTT TCAGAATTCC ATGAGATGTC   10533

GACGGCAGAG TCGCAGACGC CCCTATTGGA CGTCAAAATT GTAGAGGTGA AGTTTTCAAA   10593

CGATGGCGAA GTAACGGCGA CTTGCGTTTC CACCGTCAAA TCTCCCTATA GGGTAGAAAC   10653

TAATTGGAAA GTAGACCTCG TAGATGTAAT GGATGAAATT TCTGGGAACA GTCCCGCCGG   10713

GGTTTTTAAC AGTAATGAGA AATGGCAGAA ACAGCTGTAC TACAGAGTAA CCGATGGAAG   10773
```

```
AACATCGGTC CAGCTAATGT GCCTGTCGTG CACGAGCCAT TCTCCGGAAC CTTACTGTCT    10833
TTTCGACACG TCTCTTATAG CGAGGGAAAA AGATATCGCG CCAGAGTTAT ACTTTACCTC    10893
TGATCCGCAA ACGGCATACT GCACAATAAC TCTGCCGTCC GGCGTTGTTC CGAGATTCGA    10953
ATGGAGCCTT AATAATGTTT CACTGCCGGA ATATTTGACG GCCACGACCG TTGTTTCGCA    11013
TACCGCTGGC CAAAGTACAG TGTGGAAGAG CAGCGCGAGA GCAGGCGAGG CGTGGATTTC    11073
TGGCCGGGGA GGCAATATAT ACGAATGCAC CGTCCTCATC TCAGACGGCA CTCGCGTTAC    11133
TACGCGAAAG GAGAGGTGCT TAACAAACAC ATGGATTGCG GTGGAAAACG GTGCTGCTCA    11193
GGCGCAGCTG TATTCACTCT TTTCTGGACT TGTGTCAGGA TTATGCGGGA GCATATCTGC    11253
TTTGTACGCA ACGCTATGGA CCGCCATTTA TTTTTGAGGA ATGCTTTTTG GACTATCGTA    11313
CTGCTTTCTT CCTTCGCTAG CCAGAGCACC GCCGCCGTCA CGTACGACTA CATTTTAGGC    11373
CGTCGCGCGC TCGACGCGCT AACCATACCG GCGGTTGGCC CGTATAACAG ATACCTCACT    11433
AGGGTATCAA GAGGCTGCGA CGTTGTCGAG CTCAACCCGA TTTCTAACGT GGACGACATG    11493
ATATCGGCGG CCAAAGAAAA AGAGAAGGGG GGCCCTTTCG AGGCCTCCGT CGTCTGGTTC    11553
TACGTGATTA AGGGCGACGA CGGCGAGGAC AAGTACTGTC CAATCTATAG AAAAGAGTAC    11613
AGGGAATGTG GCGACGTACA ACTGCTATCT GAATGCGCCG TTCAATCTGC ACAGATGTGG    11673
GCAGTGGACT ATGTTCCTAG CACCCTTGTA TCGCGAAATG GCGCGGGACT GACTATATTC    11733
TCCCCCACTG CTGCGCTCTC TGGCCAATAC TTGCTGACCC TGAAAATCGG GAGATTTGCG    11793
CAAACAGCTC TCGTAACTCT AGAAGTTAAC GATCGCTGTT TAAAGATCGG GTCGCAGCTT    11853
AACTTTTTAC CGTCGAAATG CTGGACAACA GAACAGTATC AGACTGGATT TCAAGGCGAA    11913
CACCTTTATC CGATCGCAGA CACCAATACA CGACACGCGG ACGACGTATA TCGGGGATAC    11973
GAAGATATTC TGCAGCGCTG GAATAATTTG CTGAGGAAAA GAATCCTAG CGCGCCAGAC    12033
CCTCGTCCAG ATAGCGTCCC GCAAGAAATT CCCGCTGTAA CCAAGAAAGC GGAAGGGCGC    12093
ACCCCGGACG CAGAAAGCAG CGAAAAGAAG GCCCCTCCAG AAGACTCGGA GGACGACATG    12153
CAGGCAGAGG CTTCTGGAGA AAATCCTGCC GCCCTCCCCG AAGACGACGA AGTCCCCGAG    12213
GACACCGAGC ACGATGATCC AAACTCGGAT CCTGACTATT ACAATGACAT GCCCGCCGTG    12273
ATCCCGGTGG AGGAGACTAC TAAAAGTTCT AATGCCGTCT CCATGCCCAT ATTCGCGGCG    12333
TTCGTAGCCT GCGCGGTCGC GCTCGTGGGG CTACTGGTTT GGAGCATCGT AAAATGCGCG    12393
CGTAGCTAAT CGAGCCTAGA ATAGGTGGTT CTTCCTACA TGCCACGCCT CACGCTCATA     12453
AATATAAATC ACATGGAATA GCATACCAAT GCCTATTCAT TGGGACGTTC GAAAAGC       12510
```

```
ATG GCA TCG CTA CTT GGA ACT CTG GCT CTC CTT GCC GCG ACG             12552
Met Ala Ser Leu Leu Gly Thr Leu Ala Leu Leu Ala Ala Thr
1               5                  10

CTC GCA CCC TTC GGC GCG ATG GGA ATC GTG ATC ACT GGA AAT CAC GTC    12600
Leu Ala Pro Phe Gly Ala Met Gly Ile Val Ile Thr Gly Asn His Val
 15                  20                  25                  30

TCC GCC AGG ATT GAC GAC GAT CAC ATC GTG ATC GTC GCG CCT CGC CCC    12648
Ser Ala Arg Ile Asp Asp Asp His Ile Val Ile Val Ala Pro Arg Pro
                 35                  40                  45

GAA GCT ACA ATT CAA CTG CAG CTA TTT TTC ATG CCT GGC CAG AGA CCC    12696
Glu Ala Thr Ile Gln Leu Gln Leu Phe Phe Met Pro Gly Gln Arg Pro
                 50                  55                  60

CAC AAA CCC TAC TCA GGA ACC GTC CGC GTC GCG TTT CGG TCT GAT ATA    12744
His Lys Pro Tyr Ser Gly Thr Val Arg Val Ala Phe Arg Ser Asp Ile
             65                  70                  75

ACA AAC CAG TGC TAC CAG GAA CTT AGC GAG GAG CGC TTT GAA AAT TGC    12792
```

```
                                                                -continued

Thr Asn Gln Cys Tyr Gln Glu Leu Ser Glu Glu Arg Phe Glu Asn Cys
    80              85                  90
ACT CAT CGA TCG TCT TCT GTT TTT GTC GGC TGT AAA GTG ACC GAG TAC   12840
Thr His Arg Ser Ser Ser Val Phe Val Gly Cys Lys Val Thr Glu Tyr
 95          100                 105                 110
ACG TTC TCC GCC TCG AAC AGA CTA ACC GGA CCT CCA CAC CCG TTT AAG   12888
Thr Phe Ser Ala Ser Asn Arg Leu Thr Gly Pro Pro His Pro Phe Lys
                 115                 120                 125
CTC ACT ATA CGA AAT CCT CGT CCG AAC GAC AGC GGG ATG TTC TAC GTA   12936
Leu Thr Ile Arg Asn Pro Arg Pro Asn Asp Ser Gly Met Phe Tyr Val
             130                 135                 140
ATT GTT CGG CTA GAC GAC ACC AAA GAA CCC ATT GAC GTC TTC GCG ATC   12984
Ile Val Arg Leu Asp Asp Thr Lys Glu Pro Ile Asp Val Phe Ala Ile
         145                 150                 155
CAA CTA TCG GTG TAT CAA TTC GCG AAC ACC GCC GCG ACT CGC GGA CTC   13032
Gln Leu Ser Val Tyr Gln Phe Ala Asn Thr Ala Ala Thr Arg Gly Leu
     160                 165                 170
TAT TCC AAG GCT TCG TGT CGC ACC TTC GGA TTA CCT ACC GTC CAA CTT   13080
Tyr Ser Lys Ala Ser Cys Arg Thr Phe Gly Leu Pro Thr Val Gln Leu
175                 180                 185                 190
GAG GCC TAT CTC AGG ACC GAG GAA AGT TGG CGC AAC TGG CAA GCG TAC   13128
Glu Ala Tyr Leu Arg Thr Glu Glu Ser Trp Arg Asn Trp Gln Ala Tyr
                195                 200                 205
GTT GCC ACG GAG GCC ACG ACG ACC AGC GCC GAG GCG ACA ACC CCG ACG   13176
Val Ala Thr Glu Ala Thr Thr Thr Ser Ala Glu Ala Thr Thr Pro Thr
            210                 215                 220
CCC GTC ACT GCA ACC AGC GCC TCC GAA CTT GAA GCG GAA CAC TTT ACC   13224
Pro Val Thr Ala Thr Ser Ala Ser Glu Leu Glu Ala Glu His Phe Thr
        225                 230                 235
TTT CCC TGG CTA GAA AAT GGC GTG GAT CAT TAC GAA CCG ACA CCC GCA   13272
Phe Pro Trp Leu Glu Asn Gly Val Asp His Tyr Glu Pro Thr Pro Ala
    240                 245                 250
AAC GAA AAT TCA AAC GTT ACT GTC CGT CTC GGG ACA ATG AGC CCT ACG   13320
Asn Glu Asn Ser Asn Val Thr Val Arg Leu Gly Thr Met Ser Pro Thr
255                 260                 265                 270
CTA ATT GGG GTA ACC GTG GCT GCC GTC GTG AGC GCA ACG ATC GGC CTC   13368
Leu Ile Gly Val Thr Val Ala Ala Val Val Ser Ala Thr Ile Gly Leu
                275                 280                 285
GTC ATT GTA ATT TCC ATC GTC ACC AGA AAC ATG TGC ACC CCG CAC CGA   13416
Val Ile Val Ile Ser Ile Val Thr Arg Asn Met Cys Thr Pro His Arg
            290                 295                 300
AAA TTA GAC ACG GTC TCG CAA GAC GAC GAA GAA CGT TCC CAA ACT AGA   13464
Lys Leu Asp Thr Val Ser Gln Asp Asp Glu Glu Arg Ser Gln Thr Arg
        305                 310                 315
AGG GAA TCG CGA AAA TTT GGA CCC ATG GTT GCG TGC GAA ATA AAC AAG   13512
Arg Glu Ser Arg Lys Phe Gly Pro Met Val Ala Cys Glu Ile Asn Lys
    320                 325                 330
GGG GCT GAC CAG GAT AGT GAA CTT GTG GAA CTG GTT GCG ATT GTT AAC   13560
Gly Ala Asp Gln Asp Ser Glu Leu Val Glu Leu Val Ala Ile Val Asn
335                 340                 345                 350
CCG TCT GCG CTA AGC TCG CCC GAC TCA ATA AAA ATG TGA TTAAGTCTGA    13609
Pro Ser Ala Leu Ser Ser Pro Asp Ser Ile Lys Met  .
                355                 360
ATGTGGCTCT CCAATCATTT CGATTCTCTA ATCTCCCAAT CCTCTCAAAA GGGGCAGTAT  13669

CGGACACGGA CTGGGAGGGG CGTACACGAT AGTTATATGG TACAGCAGAG GCCTCTGAAC  13729

ACTTAGGAGG AGAATTCAGC CGGGGAGAGC CCCTGTTGAG TAGGCTTGGG AGCATATTGC  13789

AGG ATG AAC ATG TTA GTG ATA GTT CTC GCC TCT TGT CTT GCG CGC CTA   13837
    Met Asn Met Leu Val Ile Val Leu Ala Ser Cys Leu Ala Arg Leu
```

```
                    1               5                   10                  15
ACT TTT GCG ACG CGA CAC GTC CTC TTT TTG GAA GGC ACT CAG GCT GTC        13885
Thr Phe Ala Thr Arg His Val Leu Phe Leu Glu Gly Thr Gln Ala Val
                        20                  25                  30

CTC GGG GAA GAT GAT CCC AGA AAC GTT CCG GAA GGG ACT GTA ATC AAA        13933
Leu Gly Glu Asp Asp Pro Arg Asn Val Pro Glu Gly Thr Val Ile Lys
                35                  40                  45

TGG ACA AAA GTC CTG CGG AAC GCG TGC AAG ATG AAG GCG GCC GAT GTC        13981
Trp Thr Lys Val Leu Arg Asn Ala Cys Lys Met Lys Ala Ala Asp Val
            50                  55                  60

TGC TCT TCG CCT AAC TAT TGC TTT CAT GAT TTA ATT TAC GAC GGA GGA        14029
Cys Ser Ser Pro Asn Tyr Cys Phe His Asp Leu Ile Tyr Asp Gly Gly
        65                  70                  75

AAG AAA GAC TGC CCG CCC GCG GGA CCC CTG TCT GCA AAC CTG GTA ATT        14077
Lys Lys Asp Cys Pro Pro Ala Gly Pro Leu Ser Ala Asn Leu Val Ile
    80                  85                  90                  95

TTA CTA AAG CGC GGC GAA AGC TTC GTC GTG CTG GGT TCT GGG CTA CAC        14125
Leu Leu Lys Arg Gly Glu Ser Phe Val Val Leu Gly Ser Gly Leu His
                    100                 105                 110

AAC AGC AAT ATA ACT AAT ATC ATG TGG ACA GAG TAC GGA GGC CTG CTC        14173
Asn Ser Asn Ile Thr Asn Ile Met Trp Thr Glu Tyr Gly Gly Leu Leu
                115                 120                 125

TTT GAT CCT GTA ACT CGT TCG GAC GAG GGA ATC TAT TTT CGA CGG ATC        14221
Phe Asp Pro Val Thr Arg Ser Asp Glu Gly Ile Tyr Phe Arg Arg Ile
            130                 135                 140

TCT CAG CCA GAT CTG GCC ATG GAA ACT ACA TCG TAC AAC GTC AGC GTT        14269
Ser Gln Pro Asp Leu Ala Met Glu Thr Thr Ser Tyr Asn Val Ser Val
        145                 150                 155

CTT TCG CAC GTA GAC GAG AAG GCT CCA GCA CCG CAC GAG GTG GAG ATA        14317
Leu Ser His Val Asp Glu Lys Ala Pro Ala Pro His Glu Val Glu Ile
160                 165                 170                 175

GAC ACC ATC AAG CCG TCA GAG GCC CAC GCG CAC GTG GAA TTA CAA ATG        14365
Asp Thr Ile Lys Pro Ser Glu Ala His Ala His Val Glu Leu Gln Met
                    180                 185                 190

CTG CCG TTT CAT GAA CTC AAC GAC AAC AGC CCC ACC TAT GTG ACC CCT        14413
Leu Pro Phe His Glu Leu Asn Asp Asn Ser Pro Thr Tyr Val Thr Pro
                195                 200                 205

GTT CTT AGA GTC TTC CCA CCG ACC GAG CAC GTA AAA TTT AAC GTT ACG        14461
Val Leu Arg Val Phe Pro Pro Thr Glu His Val Lys Phe Asn Val Thr
            210                 215                 220

TAT TCG TGG TAT GGG TTT GAT GTC AAA GAG GAG TGC GAA GAA GTG AAA        14509
Tyr Ser Trp Tyr Gly Phe Asp Val Lys Glu Glu Cys Glu Glu Val Lys
        225                 230                 235

CTG TTC GAG CCG TGC GTA TAC CAT CCT ACA GAC GGC AAA TGT CAG TTT        14557
Leu Phe Glu Pro Cys Val Tyr His Pro Thr Asp Gly Lys Cys Gln Phe
240                 245                 250                 255

CCC GCA ACC AAC CAG AGA TGC CTC ATA GGA TCT GTC TTG ATG GCG GAA        14605
Pro Ala Thr Asn Gln Arg Cys Leu Ile Gly Ser Val Leu Met Ala Glu
                    260                 265                 270

TTC TTG GGC GCG GCC TCT TTG CTG GAT TGT TCC CGC GAT ACT CTA GAA        14653
Phe Leu Gly Ala Ala Ser Leu Leu Asp Cys Ser Arg Asp Thr Leu Glu
                275                 280                 285

GAC TGC CAC GAA AAT CGC GTG CCG AAC CTA CGG TTC GAT TCG CGA CTC        14701
Asp Cys His Glu Asn Arg Val Pro Asn Leu Arg Phe Asp Ser Arg Leu
            290                 295                 300

TCC GAG TCA CGC GCA GGC CTG GTG ATC AGT CCT CTT ATA GCC ATC CCC        14749
Ser Glu Ser Arg Ala Gly Leu Val Ile Ser Pro Leu Ile Ala Ile Pro
        305                 310                 315

AAA GTT TTG ATT ATA GTC GTT TCC GAC GGA GAC ATT TTG GGA TGG AGC        14797
```

```
Lys Val Leu Ile Ile Val Val Ser Asp Gly Asp Ile Leu Gly Trp Ser
320                 325                 330                 335

TAC ACG GTG CTC GGG AAA CGT AAC AGT CCG CGC GTA GTA GTC GAA ACG    14845
Tyr Thr Val Leu Gly Lys Arg Asn Ser Pro Arg Val Val Val Glu Thr
                340                 345                 350

CAC ATG CCC TCG AAG GTC CCG ATG AAC AAA GTA GTA ATT GGC AGT CCC    14893
His Met Pro Ser Lys Val Pro Met Asn Lys Val Val Ile Gly Ser Pro
                355                 360                 365

GGA CCA ATG GAC GAA ACG GGT AAC TAT AAA ATG TAC TTC GTC GTC GCG    14941
Gly Pro Met Asp Glu Thr Gly Asn Tyr Lys Met Tyr Phe Val Val Ala
                370                 375                 380

GGG GTG GCC GCG ACG TGC GTA ATT CTT ACA TGC GCT CTG CTT GTG GGG    14989
Gly Val Ala Ala Thr Cys Val Ile Leu Thr Cys Ala Leu Leu Val Gly
                385                 390                 395

AAA AAG AAG TGC CCC GCG CAC CAA ATG GGT ACT TTT TCC AAG ACC GAA    15037
Lys Lys Lys Cys Pro Ala His Gln Met Gly Thr Phe Ser Lys Thr Glu
400                 405                 410                 415

CCA TTG TAC GCG CCG CTC CCC AAA AAC GAG TTT GAG GCC GGC GGG CTT    15085
Pro Leu Tyr Ala Pro Leu Pro Lys Asn Glu Phe Glu Ala Gly Gly Leu
                420                 425                 430

ACG GAC GAT GAG GAA GTG ATT TAT GAC GAA GTA TAC GAA CCC CTA TTT    15133
Thr Asp Asp Glu Glu Val Ile Tyr Asp Glu Val Tyr Glu Pro Leu Phe
                435                 440                 445

CGC GGC TAC TGT AAG CAG GAA TTC CGC GAA GAT GTG AAT ACC TTT TTC    15181
Arg Gly Tyr Cys Lys Gln Glu Phe Arg Glu Asp Val Asn Thr Phe Phe
                450                 455                 460

GGT GCG GTC GTG GAG GGA GAA AGG GCC TTA AAC TTT AAA TCC GCC ATC    15229
Gly Ala Val Val Glu Gly Glu Arg Ala Leu Asn Phe Lys Ser Ala Ile
465                 470                 475

GCA TCA ATG GCA GAT CGC ATC CTG GCA AAT AAA AGC GGC AGA AGG AAT    15277
Ala Ser Met Ala Asp Arg Ile Leu Ala Asn Lys Ser Gly Arg Arg Asn
480                 485                 490                 495

ATG GAT AGC TAT TAG TTGGTC ATG CCT TTT AAG ACC AGA GGG GCC GAA    15325
Met Asp Ser Tyr  .         Met Pro Phe Lys Thr Arg Gly Ala Glu
                500          1               5

GAC GCG GCC GCG GGC AAG AAC AGG TTT AAG AAA TCG AGA AAT CGG GAA    15373
Asp Ala Ala Ala Gly Lys Asn Arg Phe Lys Lys Ser Arg Asn Arg Glu
10                  15                  20                  25

ATC TTA CCG ACC AGA CTG CGT GGC ACC GGT AAG AAA ACT GCC GGA TTG    15421
Ile Leu Pro Thr Arg Leu Arg Gly Thr Gly Lys Lys Thr Ala Gly Leu
                30                  35                  40

TCC AAT TAT ACC CAG CCT ATT CCC TGG AAC CCT AAA TTC TGC AGC GCG    15469
Ser Asn Tyr Thr Gln Pro Ile Pro Trp Asn Pro Lys Phe Cys Ser Ala
                45                  50                  55

CGC GGG GAA TCT GAC AAC CAC GCG TGT AAA GAC ACT TTT TAT CGC AGG    15517
Arg Gly Glu Ser Asp Asn His Ala Cys Lys Asp Thr Phe Tyr Arg Arg
                60                  65                  70

ACG TGC TGC GCA TCG CGC TCT ACC GTT TCC AGT CAA CCC GAT TCC CCC    15565
Thr Cys Cys Ala Ser Arg Ser Thr Val Ser Ser Gln Pro Asp Ser Pro
75                  80                  85

CAC ACA CCC ATG CCT ACT GAG TAT GGG CGC GTG CCC TCC GCA AAG CGC    15613
His Thr Pro Met Pro Thr Glu Tyr Gly Arg Val Pro Ser Ala Lys Arg
90                  95                  100                 105

AAA AAA CTA TCA TCT TCA GAC TGC GAG GGC GCG CAC CAA CCC CTA GTA    15661
Lys Lys Leu Ser Ser Ser Asp Cys Glu Gly Ala His Gln Pro Leu Val
                110                 115                 120

TCC TGT AAA CTT CCG GAT TCT CAA GCA GCA CCG GCG CGA ACC TAT AGT    15709
Ser Cys Lys Leu Pro Asp Ser Gln Ala Ala Pro Ala Arg Thr Tyr Ser
                125                 130                 135
```

| | | |
|---|---|---|
| TCT GCG CAA AGA TAT ACT GTT GAC GAG GTT TCG TCG CCA ACT CCG CCA<br>Ser Ala Gln Arg Tyr Thr Val Asp Glu Val Ser Ser Pro Thr Pro Pro<br>140 145 150 | 15757 | |
| GGC GTC GAC GCT GTT GCG GAC TTA GAA ACG CGC GCG GAA CTT CCT GGC<br>Gly Val Asp Ala Val Ala Asp Leu Glu Thr Arg Ala Glu Leu Pro Gly<br>155 160 165 | 15805 | |
| GCT ACG ACG GAA CAA ACG GAA AGT AAA AAT AAG CTC CCC AAC CAA CAA<br>Ala Thr Thr Glu Gln Thr Glu Ser Lys Asn Lys Leu Pro Asn Gln Gln<br>170 175 180 185 | 15853 | |
| TCG CGC CTG AAG CCG AAA CCC ACA AAC GAG CAC GTC GGA GGG GAG CGG<br>Ser Arg Leu Lys Pro Lys Pro Thr Asn Glu His Val Gly Gly Glu Arg<br>190 195 200 | 15901 | |
| TGC CCC TCC GAA GGC ACG GTC GAG GCG CCA TCG CTC GGC ATC CTC TCG<br>Cys Pro Ser Glu Gly Thr Val Glu Ala Pro Ser Leu Gly Ile Leu Ser<br>205 210 215 | 15949 | |
| CGC GTC GGG GCA GCG ATA GCA AAC GAG CTG GCT CGT ATG CGG AGG GCG<br>Arg Val Gly Ala Ala Ile Ala Asn Glu Leu Ala Arg Met Arg Arg Ala<br>220 225 230 | 15997 | |
| TGT CTT CCG CTC GCC GCG TCG GCG GCC GCT GCC GGA ATA GTG GCC TGG<br>Cys Leu Pro Leu Ala Ala Ser Ala Ala Ala Ala Gly Ile Val Ala Trp<br>235 240 245 | 16045 | |
| GCC GCG GCG AGG GCC TTG CAG AAA CAA GGG CGG TAG CAGTAATAAT<br>Ala Ala Ala Arg Ala Leu Gln Lys Gln Gly Arg .<br>250 255 260 | 16091 | |
| AACCACACAA ATATTGACAA TAATAAACGC GTACGCGG ATG AGT AAG TGT TAT<br>Met Ser Lys Cys Tyr<br>1 5 | 16144 | |
| TGT CTC GCG CGC CAT CTT TAT AAA AGC CCG CGT TGC GTG GGC CGG CGG<br>Cys Leu Ala Arg His Leu Tyr Lys Ser Pro Arg Cys Val Gly Arg Arg<br>10 15 20 | 16192 | |
| GTA GCA TTT GGA GGG TTG GCG ACC ATG TCG AGA CCT CCG ACG TCA CAT<br>Val Ala Phe Gly Gly Leu Ala Thr Met Ser Arg Pro Pro Thr Ser His<br>25 30 35 | 16240 | |
| TTG GAC TTA GCT TTC TCG GCG GCC TTT AGG GGC ACG GAC CTG CCC GGA<br>Leu Asp Leu Ala Phe Ser Ala Ala Phe Arg Gly Thr Asp Leu Pro Gly<br>40 45 50 | 16288 | |
| GGG AGA TTC TGG CGG GCG TCG CAG AGT TGC GAT ATT TTC TTT TGG CCC<br>Gly Arg Phe Trp Arg Ala Ser Gln Ser Cys Asp Ile Phe Phe Trp Pro<br>55 60 65 | 16336 | |
| GAT CTG GCC GCG GTG ATC GTA CAG GCC GCC CGC GCG TAT TTT GAA GGG<br>Asp Leu Ala Ala Val Ile Val Gln Ala Ala Arg Ala Tyr Phe Glu Gly<br>70 75 80 85 | 16384 | |
| AAG GAA AGG CTG GGC AGT CTG CAG GTC GCC GAA GAT ATC ACG GCG CAC<br>Lys Glu Arg Leu Gly Ser Leu Gln Val Ala Glu Asp Ile Thr Ala His<br>90 95 100 | 16432 | |
| GAC CCG CGA ATA GCG CCC GCG GCT AAG CGC GCC GTC GCA GCG GCG GTA<br>Asp Pro Arg Ile Ala Pro Ala Ala Lys Arg Ala Val Ala Ala Ala Val<br>105 110 115 | 16480 | |
| GGA CTG TGG ACC GCG CTG TCG GAG TTA GTT GGG GGG CCG AAC GGG GAG<br>Gly Leu Trp Thr Ala Leu Ser Glu Leu Val Gly Gly Pro Asn Gly Glu<br>120 125 130 | 16528 | |
| TTG GAA AGC AAG GTC TGG GGC AAG CAG ATT CCC CGG GCC GCC GCG TGG<br>Leu Glu Ser Lys Val Trp Gly Lys Gln Ile Pro Arg Ala Ala Ala Trp<br>135 140 145 | 16576 | |
| GAA ATA AGA GAC GTG CCC AAA GTT CCA GTC ATT GGG CCG GAC ATT CTT<br>Glu Ile Arg Asp Val Pro Lys Val Pro Val Ile Gly Pro Asp Ile Leu<br>150 155 160 165 | 16624 | |
| TCT TTT TTC TCC GCC GCC GTC GAG CTG CCG GTG CTC TAT ATC AGA GCC<br>Ser Phe Phe Ser Ala Ala Val Glu Leu Pro Val Leu Tyr Ile Arg Ala<br>170 175 180 | 16672 | |

```
CGG GGA GGG GCG CAC TCG CGG TCC GCG CAC TGG AAT AAC CAG AGC AGC        16720
Arg Gly Gly Ala His Ser Arg Ser Ala His Trp Asn Asn Gln Ser Ser
            185                 190                 195

GCG CCG GCC GCC GGA CTC GCG GCG ATA AGG ATA GGC ATG GAG ATG GTG        16768
Ala Pro Ala Ala Gly Leu Ala Ala Ile Arg Ile Gly Met Glu Met Val
            200                 205                 210

CGG AGC CTC CTG GTG ATA GCG CTG CCT CTG TCA AAC TTC ACC CTC CCG        16816
Arg Ser Leu Leu Val Ile Ala Leu Pro Leu Ser Asn Phe Thr Leu Pro
        215                 220                 225

GAA GAC CTC CCC GAA GGT TCC CAA AAC TCG ATC CGC GCG TTC GTG GCC        16864
Glu Asp Leu Pro Glu Gly Ser Gln Asn Ser Ile Arg Ala Phe Val Ala
230                 235                 240                 245

CAC CTC ATG AAC TGT GTA GCT ACC GAT AAG ATC ATG TCT CCG GAC GTG        16912
His Leu Met Asn Cys Val Ala Thr Asp Lys Ile Met Ser Pro Asp Val
            250                 255                 260

CGC GTC CCA GTC GAA GAA AGC TTT TAC AGC CAC TGT TTA AGG GAA ATC        16960
Arg Val Pro Val Glu Glu Ser Phe Tyr Ser His Cys Leu Arg Glu Ile
            265                 270                 275

ATT ATG TGC GAG AGA GCT TTT TGT TAC CCG TGC AAT CCC CCG CCA AAA        17008
Ile Met Cys Glu Arg Ala Phe Cys Tyr Pro Cys Asn Pro Pro Pro Lys
            280                 285                 290

TGG TGA GCTCAGGGTC CCATTTACCC CCGCAACACC CTCTCGCCGC CAGGGCGCGC         17064
Trp
295

GCTCTATCTT TCTCTATGTC CCGTCGCCAC CGGCCTAACC GAACGGTGGA ACGGGGCCGC      17124

CCGGGAAAGC CTAGCTCCGC ACAGACACAG ACAGACAAAC GGCCTCTCGA TTGCAACAAC      17184

GTGAAAAACA CACAATAATA TTACTTTATT TATTTCGCAG CGCTCGCGTG TCGCTCGTTT      17244

CTGGGGGGGG GGGGGGGTTG TGTTTCGCTG CCGCGGAGTG GGTGAGGGGG GAGAGTGGAC      17304

GGAGGACAGT GTAAAAACCC GCGAGGTTGT CAGGGACGCG GAGGTAAGGA AGCCGCTAGA      17364

GGGCGTCATT CTCCCGTCAA CGGCGCCGCG CCAGCGCCAG CGCGATTCCA GCGTCCCTCG      17424

CAAAGATCGA GGCGCTCACT TCGGGAGAGT TGGCGGCAGC CGCGCCGGCG CGCAAGGCGG      17484

CCAGGTATTC GCGACGGCGC ATCTCCGATT GCGGGACTCT CCCCGTCCCG ACGCAGAAAA      17544

GACTCTGCAC GTAAATCGAG TCGTACAAAC ACGCTTCGCG GCACGGCCGA GGGTGCCACA      17604

AGCAGCACCA GTGCCCGGCC GCCAGGAGAG ACCGGGAGGT CTCTCGCTCG GCGGACGCGA      17664

GGTCGGCCGG CAGGTGTCGG GACAGCCAGG ATAACAGTTC TTTCTCGATC ACGAAACGCA      17724

TATTCTCGCT CTGCATGGTA CGGCTCTCGT CCTCGAAGCG GTCACCGTCC AGAGAGTCGA      17784

GCCAGAAATC GCCCTCGATC CCTTCCATTG CCTCCTCTAA TTCTCCCAAC CCGTTGCCGT      17844

TATTCGGGTC AGTGGGGAG TTGGCGACGC TCTCCGTCGA CGCCCACCGC GGCCTCAAAC       17904

CTAGGCCGCG CGTCGCCCGG CTGGCCCCCA GAAAAGCCGA ACGTAGCCGT TCGTTGGCAG      17964

CAATCAGCGC GTTGCGGCGG TCTCTCGCTG ACGTGAACTC TCCGTAACCG TCCTTGAGTT      18024

CGGACGATAT CTCGACTAAC TCGCGCCAGA GCCGCGAGGC GATCCGAATG CACGGGTCTA      18084

CCGAGTCGGC CGACTCCGAC GAGGCGACAG CGGCACCTTG CCGCCTGCGC TCGCCACGAG      18144

GTACCGCGTG CGCAGTAATG TGATCGCTGT CCATCAGCGC CAGCGGGTAG CACCCGTCGA      18204

GCATGTTTTC CATTTAGGGA TGTGTCTAGA GGAGAGCGGT CCGGGCGGTC TACTGCGGTT      18264

GTGCTGGGCC GAGTTGGACG GCTACGGATT GCGCCGGGCG TGAAGGGGGG GGGCGGCGG      18324

GATGTCCGGC GGTCGCAAAG GGGCGCGCGT CCGCTTCTGC GTGAAGGCTG AGCGGGAAAG     18384

AAGTTCTGGA TGAGAATGGA TCGAGCGGGC AATAAATGTC CAGAGTAGGG GGGTGGGAGG     18444
```

```
GAGGGGGAGG TTCTGCCCCG CGTCTCCTCT ATCTGCTCGT CGAGGCCTCG GCCTTGCGTC      18504

GCCGTGCAGG GGTCGAGGCC GCTTCTTCTT TTTTACTTCT CTCCTCGGAT TCCTCGTCAG      18564

AGGAAGAAGA AAATGACAAC CTCCGTCTTT TAAGAGTGCG CCTACCCGCC CTGGCGGCCG      18624

AAGCCTTCCG TGGGTCTTTG CGGGTGCCGC GCACCGCAAT AACGCACGGA CGCGGGGGAT      18684

AGCAAATGGC GGCGGCGCCG GAGAGCTGTC GTCAATAAAG TCTAAGTCAG ATTGCGTGGG      18744

CTCTGACTCG GTGGAGCTGT GTCCCGTGTC CTCCTCGCCC AAGTCCACTC CCCGGCACCC      18804

AGGCTGCTCT TCCTCCGACT CCGGGTCGCT CCAGCTCCTC CCGCGTGCCG GTTCTTCGTC      18864

CTCCGATACG TCCGAAAAGA AAACTTCTG  GGAGAGCTCT TCGGGATCC                  18913
```

(2) INFORMATION FOR SEQ ID NO: 60:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO: 60:

```
Met Glu Asn Met Leu Asp Gly Cys Tyr Pro Leu Ala Leu Met Asp Ser
 1               5                  10                  15

Asp His Ile Thr Ala His Ala Val Pro Arg Gly Glu Arg Arg Gln
             20                  25                  30

Gly Ala Ala Val Ala Ser Ser Glu Ser Ala Asp Ser Val Asp Pro Cys
             35                  40                  45

Ile Arg Ile Ala Ser Arg Leu Trp Arg Glu Leu Val Glu Ile Ser Ser
 50                  55                  60

Glu Leu Lys Asp Gly Tyr Gly Glu Phe Thr Ser Ala Arg Asp Arg Arg
 65                  70                  75                  80

Asn Ala Leu Ile Ala Ala Asn Glu Arg Leu Arg Ser Ala Phe Leu Gly
                 85                  90                  95

Ala Ser Arg Ala Thr Arg Gly Leu Gly Leu Arg Pro Arg Trp Ala Ser
                100                 105                 110

Thr Glu Ser Val Ala Asn Ser Pro Thr Asp Pro Asn Asn Gly Asn Gly
            115                 120                 125

Leu Gly Glu Leu Glu Ala Met Glu Gly Ile Glu Gly Asp Phe Trp
        130                 135                 140

Leu Asp Ser Leu Asp Gly Asp Arg Phe Glu Asp Glu Ser Arg Thr Met
145                 150                 155                 160

Gln Ser Glu Asn Met Arg Phe Val Ile Glu Lys Glu Leu Leu Ser Trp
                165                 170                 175

Leu Ser Arg His Leu Pro Ala Asp Leu Ala Ser Ala Glu Arg Glu Thr
            180                 185                 190

Ser Arg Ser Leu Leu Ala Ala Gly His Trp Cys Cys Leu Trp His Pro
        195                 200                 205

Arg Pro Cys Arg Glu Ala Cys Leu Tyr Asp Ser Ile Tyr Val Gln Ser
    210                 215                 220

Leu Phe Cys Val Gly Thr Gly Arg Val Pro Gln Ser Glu Met Arg Arg
225                 230                 235                 240

Arg Glu Tyr Leu Ala Ala Leu Arg Ala Gly Ala Ala Ala Asn Ser
                245                 250                 255

Pro Glu Val Ser Ala Ser Ile Phe Ala Arg Asp Ala Gly Ile Ala Leu
            260                 265                 270
```

```
Ala Leu Ala Arg Arg Arg
        275
```

(2) INFORMATION FOR SEQ ID NO: 61:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO: 61:

```
Met Ser Lys Cys Tyr Cys Leu Ala Arg His Leu Tyr Lys Ser Pro Arg
 1               5                  10                  15

Cys Val Gly Arg Arg Val Ala Phe Gly Gly Leu Ala Thr Met Ser Arg
                20                  25                  30

Pro Pro Thr Ser His Leu Asp Leu Ala Phe Ser Ala Ala Phe Arg Gly
            35                  40                  45

Thr Asp Leu Pro Gly Gly Arg Phe Trp Arg Ala Ser Gln Ser Cys Asp
        50                  55                  60

Ile Phe Phe Trp Pro Asp Leu Ala Ala Val Ile Val Gln Ala Ala Arg
 65                 70                  75                  80

Ala Tyr Phe Glu Gly Lys Glu Arg Leu Gly Ser Leu Gln Val Ala Glu
                85                  90                  95

Asp Ile Thr Ala His Asp Pro Arg Ile Ala Pro Ala Ala Lys Arg Ala
            100                 105                 110

Val Ala Ala Val Gly Leu Trp Thr Ala Leu Ser Glu Leu Val Gly
        115                 120                 125

Gly Pro Asn Gly Glu Leu Glu Ser Lys Val Trp Gly Lys Gln Ile Pro
    130                 135                 140

Arg Ala Ala Ala Trp Glu Ile Arg Asp Val Pro Lys Val Pro Val Ile
145                 150                 155                 160

Gly Pro Asp Ile Leu Ser Phe Phe Ser Ala Ala Val Glu Leu Pro Val
                165                 170                 175

Leu Tyr Ile Arg Ala Arg Gly Gly Ala His Ser Arg Ser Ala His Trp
            180                 185                 190

Asn Asn Gln Ser Ser Ala Pro Ala Ala Gly Leu Ala Ala Ile Arg Ile
        195                 200                 205

Gly Met Glu Met Val Arg Ser Leu Leu Val Ile Ala Leu Pro Leu Ser
    210                 215                 220

Asn Phe Thr Leu Pro Glu Asp Leu Pro Glu Gly Ser Gln Asn Ser Ile
225                 230                 235                 240

Arg Ala Phe Val Ala His Leu Met Asn Cys Val Ala Thr Asp Lys Ile
                245                 250                 255

Met Ser Pro Asp Val Arg Val Pro Val Glu Glu Ser Phe Tyr Ser His
            260                 265                 270

Cys Leu Arg Glu Ile Ile Met Cys Glu Arg Ala Phe Cys Tyr Pro Cys
        275                 280                 285

Asn Pro Pro Pro Lys Trp
    290
```

(2) INFORMATION FOR SEQ ID NO: 62:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO: 62:

```
Met Ala Pro Val Lys Val Thr Ile Val Ser Ala Val Asp Ser His Tyr
1               5                   10                  15

Lys Leu Pro Asn Ser Arg Phe Glu Leu Ser Asp Ser Gly Trp Lys Glu
                20                  25                  30

Leu Val His Ala Val Lys Thr Met Ala Ser Tyr Asp Arg Pro Ser Thr
            35                  40                  45

Leu Ser Val Ile Val Arg Pro Ala Ser Leu Tyr Glu Val Ser Gly Glu
        50                  55                  60

Leu Phe Ser Leu Pro Arg Met Cys Arg Pro Val Ile Arg Phe Gly Glu
65                  70                  75                  80

Gly Gly Asp Pro Pro Gly Val Ser Pro Glu Trp Ser Gly Leu Asp Ala
                85                  90                  95

Gly Phe Tyr His Leu Ser Ser Gly Ala Tyr Ala Ala Lys Glu Phe His
            100                 105                 110

Leu Trp Val Leu Gly Thr Ala Asp Ile Cys Met Ala Ala Leu Asn Leu
        115                 120                 125

Pro Ala Pro Lys Thr Phe Leu Ile Thr Glu Thr Gly Gly Lys Asn Phe
130                 135                 140

Glu Arg Gly Val Glu Ile Phe Leu Val Asn Gly Asp Lys Thr Thr Leu
145                 150                 155                 160

Ser Leu Ser His Pro Ser Val Trp Thr Thr Leu Ala Pro Ser Ser Leu
                165                 170                 175

Arg Thr Pro Trp Pro Tyr Ser Thr Val Lys Phe Leu Lys Val Lys Pro
            180                 185                 190

Asn Ser Ala Ala Tyr Cys Val Ser Asp Ser Asp Asp Gly Glu Arg Gln
        195                 200                 205

Pro Lys Phe Phe Leu Gly Ser Leu Phe Lys Ser Lys Lys Pro Arg Ser
210                 215                 220

Pro Arg Arg Arg Arg
225
```

(2) INFORMATION FOR SEQ ID NO: 63:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO: 63:

```
Met Arg Phe Arg Arg Ile Cys Ser Arg Ser Arg Ala Glu Lys Arg Arg
1               5                   10                  15

Arg Thr Thr Glu Asn Pro Leu Thr Ser Lys Arg Val Cys Val Leu Asp
                20                  25                  30

Ser Phe Ser Arg Thr Met Ser Leu Arg Pro Tyr Ala Glu Ile Leu Pro
            35                  40                  45

Thr Ala Glu Gly Val Glu Arg Leu Ala Glu Leu Val Ser Val Thr Met
        50                  55                  60

Thr Glu Arg Ala Glu Pro Val Thr Glu Asn Thr Ala Val Asn Ser Ile
65                  70                  75                  80

Pro Pro Ala Asn Glu Asn Gly Gln Asn Phe Ala Tyr Ala Gly Asp Gly
                85                  90                  95
```

```
Pro Ser Thr Thr Glu Lys Val Asp Gly Ser His Thr Asp Phe Asp Glu
            100                 105                 110

Ala Ser Ser Asp Tyr Ala Gly Pro Val Pro Leu Ala Gln Thr Arg Leu
        115                 120                 125

Lys His Ser Asp Glu Phe Leu Gln His Phe Arg Val Leu Asp Asp Leu
    130                 135                 140

Val Glu Gly Ala Tyr Gly Phe Ile Cys Asp Val Arg Arg Tyr Thr Glu
145                 150                 155                 160

Glu Glu Gln Arg Arg Arg Gly Val Asn Ser Thr Asn Gln Gly Lys Ser
                165                 170                 175

Lys Cys Lys Arg Leu Ile Ala Lys Tyr Val Lys Asn Gly Thr Arg Ala
            180                 185                 190

Ala Ser Gln Leu Glu Asn Glu Ile Leu Val Leu Gly Arg Leu Asn His
        195                 200                 205

Glu Asn Val Leu Lys Ile Gln Glu Ile Leu Arg Tyr Pro Asp Asn Thr
    210                 215                 220

Tyr Met Leu Thr Gln Arg Tyr Gln Phe Asp Leu Tyr Ser Tyr Met Tyr
225                 230                 235                 240

Asp Glu Ala Phe Asp Trp Lys Asp Ser Pro Met Leu Lys Gln Thr Arg
                245                 250                 255

Arg Ile Met Lys Gln Leu Met Ser Ala Val Ser Tyr Ile His Ser Lys
            260                 265                 270

Lys Leu Ile His Arg Asp Ile Lys Leu Glu Asn Ile Phe Leu Asn Cys
        275                 280                 285

Asp Gly Lys Thr Val Leu Gly Asp Phe Gly Thr Val Thr Pro Phe Glu
    290                 295                 300

Asn Glu Arg Glu Pro Phe Glu Tyr Gly Trp Val Gly Thr Val Ala Thr
305                 310                 315                 320

Asn Ser Pro Glu Ile Leu Ala Arg Asp Ser Tyr Cys Glu Ile Thr Asp
                325                 330                 335

Ile Trp Ser Cys Gly Val Val Leu Glu Met Val Ser His Glu Phe
            340                 345                 350

Cys Pro Ile Gly Asp Gly Gly Asn Pro His Gln Gln Leu Leu Lys
        355                 360                 365

Val Ile Asp Ser Leu Ser Val Cys Asp Glu Glu Phe Pro Asp Pro
    370                 375                 380

Cys Asn Leu Tyr Asn Tyr Leu His Tyr Ala Ser Ile Asp Arg Ala Gly
385                 390                 395                 400

His Thr Val Pro Ser Leu Ile Arg Asn Leu His Leu Pro Ala Asp Val
                405                 410                 415

Glu Tyr Pro Leu Val Lys Met Leu Thr Phe Asp Trp Arg Leu Arg Pro
            420                 425                 430

Ser Ala Ala Glu Val Leu Ala Met Pro Leu Phe Ser Ala Glu Glu
        435                 440                 445

Arg Thr Ile Thr Ile Ile His Gly Lys His Lys Pro Ile Arg Pro Glu
    450                 455                 460

Ile Arg Ala Arg Val Pro Arg Ser Met Ser Glu Gly
465                 470                 475

(2) INFORMATION FOR SEQ ID NO: 64:

(i) SEQUENCE CHARACTERISTICS:
        (A) LENGTH: 623 amino acids
        (B) TYPE: amino acid
```

(D) TOPOLOGY: linear (ii) MOLECULE TYPE: protein (xi) SEQUENCE DESCRIPTION: SEQ ID NO: 64:

```
Met Thr Leu Pro His Arg Leu Thr Lys Arg Pro Phe Ala Arg Arg Phe
 1               5                  10                  15

Cys Ser Val Phe Val Ile His Tyr Ser Glu Thr Lys Leu Asp Arg Tyr
                20                  25                  30

Asn Lys Thr Met Leu Leu Tyr Arg Pro Asp Ser Thr Met Arg His Ser
            35                  40                  45

Gly Gly Asp Ala Asn His Arg Gly Ile Arg Pro Arg Arg Lys Ser Ile
    50                  55                  60

Gly Ala Phe Ser Ala Arg Glu Lys Thr Gly Lys Arg Asn Ala Leu Thr
65                  70                  75                  80

Glu Ser Ser Ser Ser Asp Met Leu Asp Pro Phe Ser Thr Asp Lys
                85                  90                  95

Glu Phe Gly Gly Lys Trp Thr Val Asp Gly Pro Ala Asp Ile Thr Ala
                100                 105                 110

Glu Val Leu Ser Gln Ala Trp Asp Val Leu Gln Leu Val Lys His Glu
            115                 120                 125

Asp Ala Glu Glu Glu Arg Val Thr Tyr Glu Ser Lys Pro Thr Pro Ile
130                 135                 140

Gln Pro Phe Asn Ala Trp Pro Asp Gly Pro Ser Trp Asn Ala Gln Asp
145                 150                 155                 160

Phe Thr Arg Ala Pro Ile Val Tyr Pro Ser Ala Glu Val Leu Asp Ala
                165                 170                 175

Glu Ala Leu Lys Val Gly Ala Phe Val Ser Arg Val Leu Gln Cys Val
            180                 185                 190

Pro Phe Thr Arg Ser Lys Lys Ser Val Thr Val Arg Asp Ala Gln Ser
            195                 200                 205

Phe Leu Gly Asp Ser Phe Trp Arg Ile Met Gln Asn Val Tyr Thr Val
210                 215                 220

Val Leu Arg Gln His Ile Thr Arg Leu Arg His Pro Ser Ser Lys Ser
225                 230                 235                 240

Ile Val Asn Cys Asn Asp Pro Leu Trp Tyr Ala Tyr Ala Asn Gln Phe
                245                 250                 255

His Trp Arg Gly Met Arg Val Pro Ser Leu Lys Leu Ala Ser Pro Pro
            260                 265                 270

Glu Glu Asn Ile Gln His Gly Pro Met Ala Ala Val Phe Arg Asn Ala
            275                 280                 285

Gly Ala Gly Leu Phe Leu Trp Pro Ala Met Arg Ala Ala Phe Glu Glu
290                 295                 300

Arg Asp Lys Arg Leu Leu Arg Ala Cys Leu Ser Ser Leu Asp Ile Met
305                 310                 315                 320

Asp Ala Ala Val Leu Ala Ser Phe Pro Phe Tyr Trp Arg Gly Val Gln
                325                 330                 335

Asp Thr Ser Arg Phe Glu Pro Ala Leu Gly Cys Leu Ser Glu Tyr Phe
            340                 345                 350

Ala Leu Val Val Leu Leu Ala Glu Thr Val Leu Ala Thr Met Phe Asp
            355                 360                 365

His Ala Leu Val Phe Met Arg Ala Leu Ala Asp Gly Asn Phe Asp Asp
370                 375                 380

Tyr Asp Glu Thr Arg Tyr Ile Asp Pro Val Lys Asn Glu Tyr Leu Asn
```

```
385                 390                 395                 400
Gly Ala Glu Gly Thr Leu Leu Arg Gly Ile Val Ala Ser Asn Thr Ala
                405                 410                 415
Leu Ala Val Val Cys Ala Asn Thr Tyr Ser Thr Ile Arg Lys Leu Pro
                420                 425                 430
Ser Val Ala Thr Ser Ala Cys Asn Val Ala Tyr Arg Thr Glu Thr Leu
                435                 440                 445
Lys Ala Arg Arg Pro Gly Met Ser Asp Ile Tyr Arg Ile Leu Gln Lys
                450                 455                 460
Glu Phe Phe Tyr Ile Ala Trp Leu Gln Arg Val Ala Thr His Ala
465                 470                 475                 480
Asn Phe Cys Leu Asn Ile Leu Lys Arg Ser Val Asp Thr Gly Ala Pro
                485                 490                 495
Pro Phe Leu Phe Arg Ala Ser Ser Glu Lys Arg Leu Gln Gln Leu Asn
                500                 505                 510
Lys Met Leu Cys Pro Leu Leu Val Pro Ile Gln Tyr Glu Asp Phe Ser
                515                 520                 525
Lys Ala Met Gly Ser Glu Leu Lys Arg Glu Lys Leu Glu Thr Phe Val
                530                 535                 540
Lys Ala Ile Ser Ser Asp Arg Asp Pro Arg Gly Ser Leu Arg Phe Leu
545                 550                 555                 560
Ile Ser Asp His Ala Arg Glu Ile Ile Ala Asp Gly Val Arg Phe Lys
                565                 570                 575
Pro Val Ile Asp Glu Pro Val Arg Ala Ser Val Ala Leu Ser Thr Ala
                580                 585                 590
Ala Ala Gly Lys Val Lys Ala Arg Arg Leu Thr Ser Val Arg Ala Pro
                595                 600                 605
Val Pro Gly Ala Gly Ala Val Ser Ala Arg Arg Lys Ser Glu Ile
                610                 615                 620

(2) INFORMATION FOR SEQ ID NO: 65:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO: 65:

Met Ser Gly Phe Ser Asn Ile Gly Ser Ile Ala Thr Val Ser Leu Val
1               5                   10                  15
Cys Ser Leu Leu Cys Ala Ser Val Leu Gly Ala Pro Val Leu Asp Gly
                20                  25                  30
Leu Glu Ser Ser Pro Phe Pro Phe Gly Gly Lys Ile Ile Ala Gln Ala
                35                  40                  45
Cys Asn Arg Thr Thr Ile Glu Val Thr Val Pro Trp Ser Asp Tyr Ser
                50                  55                  60
Gly Arg Thr Glu Gly Val Ser Val Glu Val Lys Trp Phe Tyr Gly Asn
65                  70                  75                  80
Ser Asn Pro Glu Ser Phe Val Phe Gly Val Asp Ser Glu Thr Gly Ser
                85                  90                  95
Gly His Glu Asp Leu Ser Thr Cys Trp Ala Leu Ile His Asn Leu Asn
                100                 105                 110
Ala Ser Val Cys Arg Ala Ser Asp Ala Gly Ile Pro Asp Phe Asp Lys
                115                 120                 125
```

```
Gln Cys Glu Lys Val Gln Arg Arg Leu Arg Ser Gly Val Glu Leu Gly
        130                 135                 140

Ser Tyr Val Ser Gly Asn Gly Ser Leu Val Leu Tyr Pro Gly Met Tyr
145                 150                 155                 160

Asp Ala Gly Ile Tyr Ala Tyr Gln Leu Ser Val Gly Lys Gly Tyr
                165                 170                 175

Thr Gly Ser Val Tyr Leu Asp Val Gly Pro Asn Pro Gly Cys His Asp
            180                 185                 190

Gln Tyr Gly Tyr Thr Tyr Tyr Ser Leu Ala Asp Glu Ala Ser Asp Leu
        195                 200                 205

Ser Ser Tyr Asp Val Ala Ser Pro Glu Leu Asp Gly Pro Met Glu Glu
    210                 215                 220

Asp Tyr Ser Asn Cys Leu Asp Met Pro Pro Leu Arg Pro Trp Thr Thr
225                 230                 235                 240

Val Cys Ser His Asp Val Glu Glu Gln Glu Asn Ala Thr Asp Glu Leu
                245                 250                 255

Tyr Leu Trp Asp Glu Glu Cys Ala Gly Pro Leu Asp Glu Tyr Val Asp
            260                 265                 270

Glu Arg Ser Glu Thr Met Pro Arg Met Val Val Phe Ser Pro Pro Ser
        275                 280                 285

Thr Leu Gln Gln
    290

(2) INFORMATION FOR SEQ ID NO: 66:

(i) SEQUENCE CHARACTERISTICS:
        (A) LENGTH: 985 amino acids
        (B) TYPE: amino acid
        (D) TOPOLOGY: linear (ii) MOLECULE TYPE: protein (xi) SEQUENCE DESCRIPTION: SEQ ID NO: 66:

Met Gly Thr Met Leu Val Leu Arg Leu Phe Leu Leu Ala Val Ala Asp
1               5                   10                  15

Ala Ala Leu Pro Thr Gly Arg Phe Cys Arg Val Trp Lys Val Pro Pro
                20                  25                  30

Gly Gly Thr Ile Gln Glu Asn Leu Ala Val Leu Ala Glu Ser Pro Val
            35                  40                  45

Thr Gly His Ala Thr Tyr Pro Pro Glu Gly Ala Val Ser Phe Gln
    50                  55                  60

Ile Phe Ala Asp Thr Pro Thr Leu Arg Ile Arg Tyr Gly Ala Thr Glu
65                  70                  75                  80

Asp Glu Leu Ala Leu Glu Arg Gly Thr Ser Ala Ser Asp Ala Asp Asn
                85                  90                  95

Val Thr Phe Ser Leu Ser Tyr Arg Pro Arg Pro Glu Ile His Gly Ala
                100                 105                 110

Tyr Phe Thr Ile Gly Val Phe Ala Thr Gly Gln Ser Thr Glu Ser Ser
            115                 120                 125

Tyr Ser Val Ile Ser Arg Val Leu Val Asn Ala Ser Leu Glu Arg Ser
        130                 135                 140

Val Arg Leu Glu Thr Pro Cys Asp Glu Asn Phe Leu Gln Asn Glu Pro
145                 150                 155                 160

Thr Trp Gly Ser Lys Arg Trp Leu Gly Pro Pro Ser Pro Tyr Val Arg
                165                 170                 175
```

-continued

```
Asp Asn Asp Val Ala Val Leu Thr Lys Ala Gln Tyr Ile Gly Glu Cys
            180                 185                 190

Tyr Ser Asn Ser Ala Ala Gln Thr Gly Leu Thr Ser Leu Asn Met Thr
        195                 200                 205

Phe Phe Tyr Ser Pro Lys Arg Ile Val Asn Val Thr Trp Thr Thr Gly
210                 215                 220

Gly Pro Ser Pro Ser Arg Ile Thr Val Tyr Ser Ser Arg Glu Asn Gly
225                 230                 235                 240

Gln Pro Val Leu Arg Asn Val Ser Asp Gly Phe Leu Val Lys Tyr Thr
                245                 250                 255

Pro Asp Ile Asp Gly Arg Ala Met Ile Asn Val Ile Ala Asn Tyr Ser
            260                 265                 270

Pro Ala Asp Ser Gly Ser Val Leu Ala Phe Thr Ala Phe Arg Glu Gly
        275                 280                 285

Lys Leu Pro Ser Ala Ile Gln Leu His Arg Ile Asp Met Ser Gly Thr
290                 295                 300

Glu Pro Pro Gly Thr Glu Thr Thr Phe Asp Cys Gln Lys Met Ile Glu
305                 310                 315                 320

Thr Pro Tyr Arg Ala Leu Gly Ser Asn Val Pro Arg Asp Asp Ser Ile
                325                 330                 335

Arg Pro Gly Ala Thr Leu Pro Pro Phe Asp Thr Ala Ala Pro Asp Phe
            340                 345                 350

Asp Thr Gly Thr Ser Pro Thr Pro Thr Thr Val Pro Glu Pro Ala Ile
        355                 360                 365

Thr Thr Leu Ile Pro Arg Ser Thr Ser Asp Met Gly Phe Phe Ser Thr
370                 375                 380

Ala Arg Ala Thr Gly Ser Glu Thr Leu Ser Val Pro Val Gln Glu Thr
385                 390                 395                 400

Asp Arg Thr Leu Ser Thr Thr Pro Leu Thr Leu Pro Leu Thr Pro Gly
                405                 410                 415

Glu Ser Glu Asn Thr Leu Phe Pro Thr Thr Ala Pro Gly Ile Ser Thr
            420                 425                 430

Glu Thr Pro Ser Ala Ala His Glu Thr Thr Gln Thr Gln Ser Ala Glu
        435                 440                 445

Thr Val Val Phe Thr Gln Ser Pro Ser Thr Glu Ser Glu Thr Ala Arg
450                 455                 460

Ser Gln Ser Gln Glu Pro Trp Tyr Phe Thr Gln Thr Pro Ser Thr Glu
465                 470                 475                 480

Gln Ala Ala Leu Thr Gln Thr Gln Ile Ala Glu Thr Glu Ala Leu Phe
                485                 490                 495

Thr Gln Thr Pro Ser Ala Glu Gln Met Thr Phe Thr Gln Thr Pro Gly
            500                 505                 510

Ala Glu Thr Glu Ala Pro Ala Gln Thr Pro Ser Thr Ile Pro Glu Ile
        515                 520                 525

Phe Thr Gln Ser Arg Ser Thr Pro Pro Glu Thr Ala Arg Ala Pro Ser
530                 535                 540

Ala Ala Pro Glu Val Phe Thr Gln Ser Ser Ser Thr Val Thr Glu Val
545                 550                 555                 560

Phe Thr Gln Thr Pro Ser Thr Val Pro Lys Thr Thr Leu Ser Ser Ser
                565                 570                 575

Thr Glu Pro Ala Ile Phe Thr Arg Thr Gln Ser Ala Gly Thr Glu Ala
            580                 585                 590

Phe Thr Gln Thr Ser Ser Ala Glu Pro Asp Thr Met Arg Thr Gln Ser
```

-continued

```
                595                 600                 605
Thr Glu Thr His Phe Phe Thr Gln Ala Pro Ser Thr Val Pro Lys Ala
        610                 615                 620

Thr Gln Thr Pro Ser Thr Glu Pro Glu Val Leu Thr Gln Ser Pro Ser
625                 630                 635                 640

Thr Glu Pro Val Pro Phe Thr Arg Thr Leu Gly Ala Glu Pro Glu Ile
                645                 650                 655

Thr Gln Thr Pro Ser Ala Ala Pro Glu Val Tyr Thr Arg Ser Ser Ser
        660                 665                 670

Thr Met Pro Glu Thr Ala Gln Ser Thr Pro Leu Ala Ser Gln Asn Pro
        675                 680                 685

Thr Ser Ser Gly Thr Gly Thr His Asn Thr Glu Pro Arg Thr Tyr Pro
        690                 695                 700

Val Gln Thr Thr Pro His Thr Gln Lys Leu Tyr Thr Glu Asn Lys Thr
705                 710                 715                 720

Leu Ser Phe Pro Thr Val Val Ser Glu Phe His Glu Met Ser Thr Ala
                725                 730                 735

Glu Ser Gln Thr Pro Leu Leu Asp Val Lys Ile Val Glu Val Lys Phe
                740                 745                 750

Ser Asn Asp Gly Glu Val Thr Ala Thr Cys Val Ser Thr Val Lys Ser
        755                 760                 765

Pro Tyr Arg Val Glu Thr Asn Trp Lys Val Asp Leu Val Asp Val Met
        770                 775                 780

Asp Glu Ile Ser Gly Asn Ser Pro Ala Gly Val Phe Asn Ser Asn Glu
785                 790                 795                 800

Lys Trp Gln Lys Gln Leu Tyr Tyr Arg Val Thr Asp Gly Arg Thr Ser
                805                 810                 815

Val Gln Leu Met Cys Leu Ser Cys Thr Ser His Ser Pro Glu Pro Tyr
                820                 825                 830

Cys Leu Phe Asp Thr Ser Leu Ile Ala Arg Glu Lys Asp Ile Ala Pro
        835                 840                 845

Glu Leu Tyr Phe Thr Ser Asp Pro Gln Thr Ala Tyr Cys Thr Ile Thr
        850                 855                 860

Leu Pro Ser Gly Val Val Pro Arg Phe Glu Trp Ser Leu Asn Asn Val
865                 870                 875                 880

Ser Leu Pro Glu Tyr Leu Thr Ala Thr Val Val Ser His Thr Ala
                885                 890                 895

Gly Gln Ser Thr Val Trp Lys Ser Ser Ala Arg Ala Gly Glu Ala Trp
        900                 905                 910

Ile Ser Gly Arg Gly Gly Asn Ile Tyr Glu Cys Thr Val Leu Ile Ser
        915                 920                 925

Asp Gly Thr Arg Val Thr Thr Arg Lys Glu Arg Cys Leu Thr Asn Thr
        930                 935                 940

Trp Ile Ala Val Glu Asn Gly Ala Ala Gln Ala Gln Leu Tyr Ser Leu
945                 950                 955                 960

Phe Ser Gly Leu Val Ser Gly Leu Cys Gly Ser Ile Ser Ala Leu Tyr
                965                 970                 975

Ala Thr Leu Trp Thr Ala Ile Tyr Phe
                980                 985
```

(2) INFORMATION FOR SEQ ID NO: 67:

(i) SEQUENCE CHARACTERISTICS:
        (A) LENGTH: 434 amino acids (B) TYPE: amino acid
        (D) TOPOLOGY: linear (ii) MOLECULE TYPE: protein (xi) SEQUENCE DESCRIPTION: SEQ ID NO: 67:

Met His Arg Pro His Leu Arg Arg His Ser Arg Tyr Tyr Ala Lys Gly
  1               5                  10                  15

Glu Val Leu Asn Lys His Met Asp Cys Gly Gly Lys Arg Cys Cys Ser
                 20                  25                  30

Gly Ala Ala Val Phe Thr Leu Phe Trp Thr Cys Val Arg Ile Met Arg
             35                  40                  45

Glu His Ile Cys Phe Val Arg Asn Ala Met Asp Arg His Leu Phe Leu
         50                  55                  60

Arg Asn Ala Phe Trp Thr Ile Val Leu Leu Ser Ser Phe Ala Ser Gln
 65                  70                  75                  80

Ser Thr Ala Ala Val Thr Tyr Asp Tyr Ile Leu Gly Arg Arg Ala Leu
                 85                  90                  95

Asp Ala Leu Thr Ile Pro Ala Val Gly Pro Tyr Asn Arg Tyr Leu Thr
                100                 105                 110

Arg Val Ser Arg Gly Cys Asp Val Val Glu Leu Asn Pro Ile Ser Asn
                115                 120                 125

Val Asp Asp Met Ile Ser Ala Ala Lys Glu Lys Glu Lys Gly Gly Pro
130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
                180                 185                 190

Ala Val Asp Tyr Val Pro Ser Thr Leu Val Ser Arg Asn Gly Ala Gly
                195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
                260                 265                 270

His Leu Tyr Pro Ile Ala Asp Thr Asn Thr Arg His Ala Asp Asp Val
    275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
                340                 345                 350

Gln Ala Glu Ala Ser Gly Glu Asn Pro Ala Ala Leu Pro Glu Asp Asp
                355                 360                 365

Glu Val Pro Glu Asp Thr Glu His Asp Pro Asn Ser Asp Pro Asp
                370                 375                 380

-continued

```
Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
                420                 425                 430

Arg Ser
```

(2) INFORMATION FOR SEQ ID NO: 68:

(i) SEQUENCE CHARACTERISTICS:
        (A) LENGTH: 362 amino acids
        (B) TYPE: amino acid
        (D) TOPOLOGY: linear (ii) MOLECULE TYPE: protein (xi) SEQUENCE DESCRIPTION: SEQ ID NO: 68:

```
Met Ala Ser Leu Leu Gly Thr Leu Ala Leu Ala Ala Thr Leu Ala
1               5                   10                  15

Pro Phe Gly Ala Met Gly Ile Val Ile Thr Gly Asn His Val Ser Ala
                20                  25                  30

Arg Ile Asp Asp His Ile Val Ile Ala Pro Arg Pro Glu Ala
        35                  40                  45

Thr Ile Gln Leu Gln Leu Phe Phe Met Pro Gly Gln Arg Pro His Lys
        50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Ser Val Phe Val Gly Cys Lys Val Thr Glu Tyr Thr Phe
                100                 105                 110

Ser Ala Ser Asn Arg Leu Thr Gly Pro Pro His Pro Phe Lys Leu Thr
                115                 120                 125

Ile Arg Asn Pro Arg Pro Asn Asp Ser Gly Met Phe Tyr Val Ile Val
130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
                165                 170                 175

Lys Ala Ser Cys Arg Thr Phe Gly Leu Pro Thr Val Gln Leu Glu Ala
                180                 185                 190

Tyr Leu Arg Thr Glu Glu Ser Trp Arg Asn Trp Gln Ala Tyr Val Ala
                195                 200                 205

Thr Glu Ala Thr Thr Thr Ser Ala Glu Ala Thr Thr Pro Thr Pro Val
                210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
                245                 250                 255

Asn Ser Asn Val Thr Val Arg Leu Gly Thr Met Ser Pro Thr Leu Ile
                260                 265                 270

Gly Val Thr Val Ala Ala Val Val Ser Ala Thr Ile Gly Leu Val Ile
                275                 280                 285

Val Ile Ser Ile Val Thr Arg Asn Met Cys Thr Pro His Arg Lys Leu
290                 295                 300
```

```
Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
                325                 330                 335

Asp Gln Asp Ser Glu Leu Val Glu Leu Val Ala Ile Val Asn Pro Ser
                340                 345                 350

Ala Leu Ser Ser Pro Asp Ser Ile Lys Met
            355                 360

(2) INFORMATION FOR SEQ ID NO: 69:

(i) SEQUENCE CHARACTERISTICS:
        (A) LENGTH: 499 amino acids
        (B) TYPE: amino acid
        (D) TOPOLOGY: linear (ii) MOLECULE TYPE: protein (xi) SEQUENCE DESCRIPTION: SEQ ID NO: 69:

Met Asn Met Leu Val Ile Val Leu Ala Ser Cys Leu Ala Arg Leu Thr
1               5                   10                  15

Phe Ala Thr Arg His Val Leu Phe Leu Glu Gly Thr Gln Ala Val Leu
                20                  25                  30

Gly Glu Asp Asp Pro Arg Asn Val Pro Glu Gly Thr Val Ile Lys Trp
            35                  40                  45

Thr Lys Val Leu Arg Asn Ala Cys Lys Met Lys Ala Ala Asp Val Cys
    50                  55                  60

Ser Ser Pro Asn Tyr Cys Phe His Asp Leu Ile Tyr Asp Gly Gly Lys
65                  70                  75                  80

Lys Asp Cys Pro Pro Ala Gly Pro Leu Ser Ala Asn Leu Val Ile Leu
                85                  90                  95

Leu Lys Arg Gly Glu Ser Phe Val Val Leu Gly Ser Gly Leu His Asn
            100                 105                 110

Ser Asn Ile Thr Asn Ile Met Trp Thr Glu Tyr Gly Gly Leu Leu Phe
            115                 120                 125

Asp Pro Val Thr Arg Ser Asp Glu Gly Ile Tyr Phe Arg Arg Ile Ser
    130                 135                 140

Gln Pro Asp Leu Ala Met Glu Thr Thr Ser Tyr Asn Val Ser Val Leu
145                 150                 155                 160

Ser His Val Asp Glu Lys Ala Pro Ala Pro His Glu Val Glu Ile Asp
                165                 170                 175

Thr Ile Lys Pro Ser Glu Ala His Ala His Val Glu Leu Gln Met Leu
            180                 185                 190

Pro Phe His Glu Leu Asn Asp Asn Ser Pro Thr Tyr Val Thr Pro Val
            195                 200                 205

Leu Arg Val Phe Pro Pro Thr Glu His Val Lys Phe Asn Val Thr Tyr
    210                 215                 220

Ser Trp Tyr Gly Phe Asp Val Lys Glu Glu Cys Glu Glu Val Lys Leu
225                 230                 235                 240

Phe Glu Pro Cys Val Tyr His Pro Thr Asp Gly Lys Cys Gln Phe Pro
                245                 250                 255

Ala Thr Asn Gln Arg Cys Leu Ile Gly Ser Val Leu Met Ala Glu Phe
            260                 265                 270

Leu Gly Ala Ala Ser Leu Leu Asp Cys Ser Arg Asp Thr Leu Glu Asp
            275                 280                 285
```

-continued

```
Cys His Glu Asn Arg Val Pro Asn Leu Arg Phe Asp Ser Arg Leu Ser
    290                 295                 300

Glu Ser Arg Ala Gly Leu Val Ile Ser Pro Leu Ile Ala Ile Pro Lys
305                 310                 315                 320

Val Leu Ile Ile Val Val Ser Asp Gly Asp Ile Leu Gly Trp Ser Tyr
                325                 330                 335

Thr Val Leu Gly Lys Arg Asn Ser Pro Arg Val Val Glu Thr His
            340                 345                 350

Met Pro Ser Lys Val Pro Met Asn Lys Val Val Ile Gly Ser Pro Gly
            355                 360                 365

Pro Met Asp Glu Thr Gly Asn Tyr Lys Met Tyr Phe Val Ala Gly
    370                 375                 380

Val Ala Ala Thr Cys Val Ile Leu Thr Cys Ala Leu Leu Val Gly Lys
385                 390                 395                 400

Lys Lys Cys Pro Ala His Gln Met Gly Thr Phe Ser Lys Thr Glu Pro
                405                 410                 415

Leu Tyr Ala Pro Leu Pro Lys Asn Glu Phe Glu Ala Gly Gly Leu Thr
            420                 425                 430

Asp Asp Glu Glu Val Ile Tyr Asp Glu Val Tyr Glu Pro Leu Phe Arg
            435                 440                 445

Gly Tyr Cys Lys Gln Glu Phe Arg Glu Asp Val Asn Thr Phe Phe Gly
450                 455                 460

Ala Val Val Glu Gly Glu Arg Ala Leu Asn Phe Lys Ser Ala Ile Ala
465                 470                 475                 480

Ser Met Ala Asp Arg Ile Leu Ala Asn Lys Ser Gly Arg Arg Asn Met
                485                 490                 495

Asp Ser Tyr
```

(2) INFORMATION FOR SEQ ID NO: 70:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO: 70:

```
Met Pro Phe Lys Thr Arg Gly Ala Glu Asp Ala Ala Gly Lys Asn
 1               5                  10                  15

Arg Phe Lys Ser Arg Asn Arg Glu Ile Leu Pro Thr Arg Leu Arg
                20                  25                  30

Gly Thr Gly Lys Lys Thr Ala Gly Leu Ser Asn Tyr Thr Gln Pro Ile
            35                  40                  45

Pro Trp Asn Pro Lys Phe Cys Ser Ala Arg Gly Glu Ser Asp Asn His
    50                  55                  60

Ala Cys Lys Asp Thr Phe Tyr Arg Arg Thr Cys Cys Ala Ser Arg Ser
65                  70                  75                  80

Thr Val Ser Ser Gln Pro Asp Ser Pro His Thr Pro Met Pro Thr Glu
                85                  90                  95

Tyr Gly Arg Val Pro Ser Ala Lys Arg Lys Leu Ser Ser Ser Asp
            100                 105                 110

Cys Glu Gly Ala His Gln Pro Leu Val Ser Cys Lys Leu Pro Asp Ser
            115                 120                 125

Gln Ala Ala Pro Ala Arg Thr Tyr Ser Ser Ala Gln Arg Tyr Thr Val
    130                 135                 140
```

```
Asp Glu Val Ser Ser Pro Thr Pro Gly Val Asp Ala Val Ala Asp
145                 150                 155                 160

Leu Glu Thr Arg Ala Glu Leu Pro Gly Ala Thr Thr Glu Gln Thr Glu
                165                 170                 175

Ser Lys Asn Lys Leu Pro Asn Gln Gln Ser Arg Leu Lys Pro Lys Pro
                180                 185                 190

Thr Asn Glu His Val Gly Gly Glu Arg Cys Pro Ser Glu Gly Thr Val
                195                 200                 205

Glu Ala Pro Ser Leu Gly Ile Leu Ser Arg Val Gly Ala Ala Ile Ala
        210                 215                 220

Asn Glu Leu Ala Arg Met Arg Arg Ala Cys Leu Pro Leu Ala Ala Ser
225                 230                 235                 240

Ala Ala Ala Ala Gly Ile Val Ala Trp Ala Ala Arg Ala Leu Gln
                245                 250                 255

Lys Gln Gly Arg
                260

(2) INFORMATION FOR SEQ ID NO: 71:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO: 71:

Met Ser Lys Cys Tyr Cys Leu Ala Arg His Leu Tyr Lys Ser Pro Arg
1               5                   10                  15

Cys Val Gly Arg Arg Val Ala Phe Gly Gly Leu Ala Thr Met Ser Arg
                20                  25                  30

Pro Pro Thr Ser His Leu Asp Leu Ala Phe Ser Ala Ala Phe Arg Gly
                35                  40                  45

Thr Asp Leu Pro Gly Gly Arg Phe Trp Arg Ala Ser Gln Ser Cys Asp
        50                  55                  60

Ile Phe Phe Trp Pro Asp Leu Ala Val Ile Val Gln Ala Ala Arg
65                  70                  75                  80

Ala Tyr Phe Glu Gly Lys Glu Arg Leu Gly Ser Leu Gln Val Ala Glu
                85                  90                  95

Asp Ile Thr Ala His Asp Pro Arg Ile Ala Pro Ala Ala Lys Arg Ala
                100                 105                 110

Val Ala Ala Val Gly Leu Trp Thr Ala Leu Ser Glu Leu Val Gly
        115                 120                 125

Gly Pro Asn Gly Glu Leu Glu Ser Lys Val Trp Gly Lys Gln Ile Pro
        130                 135                 140

Arg Ala Ala Ala Trp Glu Ile Arg Asp Val Pro Lys Val Pro Val Ile
145                 150                 155                 160

Gly Pro Asp Ile Leu Ser Phe Phe Ser Ala Ala Val Glu Leu Pro Val
                165                 170                 175

Leu Tyr Ile Arg Ala Arg Gly Gly Ala His Ser Arg Ser Ala His Trp
                180                 185                 190

Asn Asn Gln Ser Ser Ala Pro Ala Ala Gly Leu Ala Ala Ile Arg Ile
                195                 200                 205

Gly Met Glu Met Val Arg Ser Leu Leu Val Ile Ala Leu Pro Leu Ser
        210                 215                 220
```

```
Asn Phe Thr Leu Pro Glu Asp Leu Pro Glu Gly Ser Gln Asn Ser Ile
225                 230                 235                 240

Arg Ala Phe Val Ala His Leu Met Asn Cys Val Ala Thr Asp Lys Ile
            245                 250                 255

Met Ser Pro Asp Val Arg Val Pro Val Glu Glu Ser Phe Tyr Ser His
            260                 265                 270

Cys Leu Arg Glu Ile Ile Met Cys Glu Arg Ala Phe Cys Tyr Pro Cys
            275                 280                 285

Asn Pro Pro Lys Trp
            290
```

(2) INFORMATION FOR SEQ ID NO: 72:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO: 72:

```
Met Glu Asn Met Leu Asp Gly Cys Tyr Pro Leu Ala Leu Met Asp Ser
1               5                   10                  15

Asp His Ile Thr Ala His Ala Val Pro Arg Gly Glu Arg Arg Arg Gln
            20                  25                  30

Gly Ala Val Ala Ser Ser Glu Ser Ala Asp Ser Val Asp Pro Cys
            35                  40                  45

Ile Arg Ile Ala Ser Arg Leu Trp Arg Glu Leu Val Glu Ile Ser Ser
    50                  55                  60

Glu Leu Lys Asp Gly Tyr Gly Glu Phe Thr Ser Ala Arg Asp Arg Arg
65                  70                  75                  80

Asn Ala Leu Ile Ala Ala Asn Glu Arg Leu Arg Ser Ala Phe Leu Gly
                85                  90                  95

Ala Ser Arg Ala Thr Arg Gly Leu Gly Leu Arg Pro Arg Trp Ala Ser
            100                 105                 110

Thr Glu Ser Val Ala Asn Ser Pro Thr Asp Pro Asn Asn Gly Asn Gly
            115                 120                 125

Leu Gly Glu Leu Glu Glu Ala Met Glu Gly Ile Glu Gly Asp Phe Trp
130                 135                 140

Leu Asp Ser Leu Asp Gly Asp Arg Phe Glu Asp Glu Ser Arg Thr Met
145                 150                 155                 160

Gln Ser Glu Asn Met Arg Phe Val Ile Glu Lys Glu Leu Leu Ser Trp
                165                 170                 175

Leu Ser Arg His Leu Pro Ala Asp Leu Ala Ser Ala Glu Arg Glu Thr
            180                 185                 190

Ser Arg Ser Leu Leu Ala Ala Gly His Trp Cys Cys Leu Trp His Pro
            195                 200                 205

Arg Pro Cys Arg Glu Ala Cys Leu Tyr Asp Ser Ile Tyr Val Gln Ser
    210                 215                 220

Leu Phe Cys Val Gly Thr Gly Arg Val Pro Gln Ser Glu Met Arg Arg
225                 230                 235                 240

Arg Glu Tyr Leu Ala Ala Leu Arg Ala Gly Ala Ala Ala Asn Ser
                245                 250                 255

Pro Glu Val Ser Ala Ser Ile Phe Ala Arg Asp Ala Gly Ile Ala Leu
            260                 265                 270
```

```
-continued

Ala Leu Ala Arg Arg Arg
    275
```